US012665049B2

(12) United States Patent
Mourao et al.

(10) Patent No.: US 12,665,049 B2
(45) Date of Patent: Jun. 23, 2026

(54) SYSTEMS AND METHODS FOR SYNTHETIC REGULATORY SEQUENCE DESIGN OR PRODUCTION

(71) Applicant: ASKBIO INC., Research Triangle Park, NC (US)

(72) Inventors: Kira Mourao, Midlothian (GB); Michael L. Roberts, Midlothian (GB); Ross Fraser, Midlothian (GB)

(73) Assignee: ASKBIO, INC., Research Triangle Park (NC)

( * ) Notice: Subject to any disclaimer, the term of this patent is extended or adjusted under 35 U.S.C. 154(b) by 1014 days.

(21) Appl. No.: 17/792,832

(22) PCT Filed: Jan. 15, 2021

(86) PCT No.: PCT/US2021/013557
§ 371 (c)(1),
(2) Date: Jul. 14, 2022

(87) PCT Pub. No.: WO2021/146508
PCT Pub. Date: Jul. 22, 2021

(65) Prior Publication Data
US 2023/0056396 A1      Feb. 23, 2023

Related U.S. Application Data

(60) Provisional application No. 63/022,937, filed on May 11, 2020, provisional application No. 62/962,336, filed on Jan. 17, 2020.

(51) Int. Cl.
*G16B 20/00*      (2019.01)
*G16B 40/20*      (2019.01)

(52) U.S. Cl.
CPC ............. *G16B 20/00* (2019.02); *G16B 40/20* (2019.02)

(58) Field of Classification Search
CPC ............................... G16B 20/00; G16B 40/20
See application file for complete search history.

(56) References Cited

U.S. PATENT DOCUMENTS 4,945,050 A * 7/1990 Sanford ............. C12N 15/8207
435/459
5,240,855 A * 8/1993 Tomes ............... C12N 15/8207
89/1.14

(Continued)

FOREIGN PATENT DOCUMENTS

WO        2016183348 A1    11/2016

OTHER PUBLICATIONS

Azofeifa, 2018, pp. 34-344.*

(Continued)

*Primary Examiner* — Michael I Ezewoko
(74) *Attorney, Agent, or Firm* — Nixon Peabody LLP; Ronald I. Eisenstein; Alissa R. Young

(57) ABSTRACT

The technology described herein is directed to systems and methods for synthetic regulatory sequence design or production. In several aspects described herein are methods of designing and optionally synthesizing shortened or otherwise modified polynucleotide sequences from polynucleotide sequences with transcriptional regulatory functionality. In other aspects described herein are isolated nucleic acid modules and viral vectors, comprising said shortened or otherwise modified polynucleotide as designed or synthesized herein.

18 Claims, 36 Drawing Sheets

Specification includes a Sequence Listing.

(56) References Cited

U.S. PATENT DOCUMENTS

| | | | | |
|---|---|---|---|---|
| 5,316,931 A * | 5/1994 | Donson | C12N 9/00 | 800/317.3 |
| 5,322,783 A * | 6/1994 | Tomes | C12N 15/8201 | 435/426 |
| 5,324,646 A * | 6/1994 | Buising | A01H 4/008 | 435/470 |
| 5,380,831 A * | 1/1995 | Adang | C12N 15/8216 | 435/91.1 |
| 5,405,765 A * | 4/1995 | Vasil | C12N 15/8277 | 800/293 |
| 5,436,391 A * | 7/1995 | Fujimoto | C07K 14/325 | 435/320.1 |
| 5,478,745 A | 12/1995 | Samulski et al. | | |
| 5,563,055 A * | 10/1996 | Townsend | C12N 15/8205 | 800/294 |
| 5,589,367 A * | 12/1996 | Donson | C12N 9/18 | 435/320.1 |
| 5,605,793 A * | 2/1997 | Stemmer | C07K 14/43595 | 435/6.16 |
| 5,622,856 A | 4/1997 | Natsoulis | | |
| 5,658,776 A | 8/1997 | Flotte et al. | | |
| 5,736,369 A * | 4/1998 | Bowen | C12N 15/8207 | 435/430 |
| 5,837,458 A * | 11/1998 | Minshull | C12N 15/1027 | 435/6.14 |
| 5,866,785 A * | 2/1999 | Donson | C12N 9/84 | 435/235.1 |
| 5,872,005 A | 2/1999 | Wang et al. | | |
| 5,879,918 A * | 3/1999 | Tomes | C12M 35/04 | 435/459 |
| 5,886,244 A * | 3/1999 | Tomes | C12N 15/8207 | 800/278 |
| 5,889,190 A * | 3/1999 | Donson | C12N 15/8216 | 435/235.1 |
| 5,889,191 A * | 3/1999 | Turpen | C12N 15/8203 | 435/235.1 |
| 5,932,782 A * | 8/1999 | Bidney | C12N 15/8205 | 800/294 |
| 5,981,840 A * | 11/1999 | Zhao | C12N 15/8205 | 800/278 |
| 6,072,050 A * | 6/2000 | Bowen | C12N 15/8216 | 800/278 |
| 6,096,722 A * | 8/2000 | Bennett | C12N 15/1138 | 435/375 |
| 6,156,303 A | 12/2000 | Russell et al. | | |
| 6,440,742 B1 | 8/2002 | Maass et al. | | |
| 6,521,225 B1 | 2/2003 | Srivastava et al. | | |
| 6,632,670 B1 | 10/2003 | Wadsworth et al. | | |
| 6,645,765 B1 * | 11/2003 | Anderson | C12N 15/8216 | 435/320.1 |
| 6,670,127 B2 * | 12/2003 | Evans | C12N 15/66 | 435/6.16 |
| 6,943,019 B2 | 9/2005 | Wilson et al. | | |
| 6,958,214 B2 * | 10/2005 | Braun | C07K 14/003 | 435/325 |
| 7,063,947 B2 * | 6/2006 | Hahm | C12N 15/85 | 435/320.1 |
| 7,629,322 B2 | 12/2009 | Kleinschmidt et al. | | |
| 7,645,919 B2 * | 1/2010 | Anderson | C12N 15/8227 | 800/290 |
| 8,007,780 B2 | 8/2011 | Arbetman et al. | | |
| 8,278,434 B2 * | 10/2012 | Cook | C12N 15/8222 | 435/320.1 |
| 8,378,171 B2 * | 2/2013 | Conner | C12N 15/8231 | 800/298 |
| 8,481,506 B2 * | 7/2013 | Bentwich | C12N 15/113 | 536/24.5 |
| 8,968,999 B2 * | 3/2015 | Gibson | C12N 15/10 | 536/23.1 |
| 9,169,494 B2 | 10/2015 | Hewitt et al. | | |
| 9,234,213 B2 * | 1/2016 | Wu | C12N 9/22 | |
| 9,441,206 B2 | 9/2016 | Grieger et al. | | |
| 9,447,423 B2 * | 9/2016 | Elich | C12N 15/8286 | |
| 9,550,990 B2 * | 1/2017 | Griffey | C12N 15/113 | |
| 10,041,074 B2 * | 8/2018 | Ozsolak | A61K 31/7088 | |
| 10,383,935 B2 * | 8/2019 | Langlois | A61K 39/12 | |
| 11,352,619 B2 * | 6/2022 | Vladar | C12N 15/1027 | |
| 12,018,251 B2 * | 6/2024 | Vladar | C12N 15/1027 | |
| 12,146,186 B2 * | 11/2024 | Dekker | C12Q 1/6837 | |
| 12,188,028 B1 * | 1/2025 | Davis | C12N 15/8216 | |
| 12,234,506 B2 * | 2/2025 | Akilesh | A61K 40/11 | |
| 2002/0009736 A1 * | 1/2002 | Wang | C12Q 1/6809 | 435/6.16 |
| 2002/0040130 A1 * | 4/2002 | Braun | C07K 14/003 | 435/325 |
| 2003/0138782 A1 | 7/2003 | Evans | | |
| 2003/0144799 A1 * | 7/2003 | Nowotny | C12Q 1/6883 | 435/6.13 |
| 2004/0126800 A1 * | 7/2004 | Nowotny | C12Q 1/6883 | 435/6.13 |
| 2004/0175727 A1 * | 9/2004 | Draghia-Akli | C12N 15/1086 | 435/7.1 |
| 2005/0266447 A1 * | 12/2005 | Duvick | C12Q 1/6897 | 435/6.12 |
| 2005/0266567 A1 | 12/2005 | Atkinson et al. | | |
| 2005/0287122 A1 | 12/2005 | Bartlett et al. | | |
| 2006/0003358 A1 * | 1/2006 | Braun | C07K 14/003 | 435/6.16 |
| 2006/0085138 A1 * | 4/2006 | Klingenhoff | G16B 20/00 | 702/20 |
| 2006/0166206 A1 * | 7/2006 | Urnov | C12Q 1/6837 | 435/6.12 |
| 2007/0122817 A1 * | 5/2007 | Church | C12Q 1/6844 | 435/6.16 |
| 2007/0141570 A1 * | 6/2007 | Braun | G01N 33/6893 | 435/7.1 |
| 2007/0161031 A1 * | 7/2007 | Trinklein | C12N 15/1086 | 435/325 |
| 2007/0226830 A1 * | 9/2007 | Pennell | C12N 15/823 | 536/23.6 |
| 2009/0018031 A1 * | 1/2009 | Trinklein | C12N 15/1089 | 506/10 |
| 2009/0298910 A1 * | 12/2009 | Griffey | C12N 15/111 | 435/375 |
| 2009/0317801 A1 * | 12/2009 | Van Den Boom | C12Q 1/6886 | 435/6.12 |
| 2010/0037344 A1 * | 2/2010 | Cook | C12N 15/8222 | 800/278 |
| 2010/0251424 A1 * | 9/2010 | Conner | C07K 14/415 | 536/25.4 |
| 2011/0172127 A1 * | 7/2011 | Jacobson | C12Q 1/6844 | 506/26 |
| 2012/0088677 A1 * | 4/2012 | Urnov | C12N 15/1034 | 506/26 |
| 2013/0005590 A1 * | 1/2013 | Lou | G16B 35/10 | 435/254.2 |
| 2013/0116931 A1 * | 5/2013 | Karczewski | G16B 40/20 | 702/19 |
| 2013/0117883 A1 * | 5/2013 | Elich | C07H 21/00 | 800/278 |
| 2014/0273037 A1 * | 9/2014 | Wu | C12N 15/907 | 435/8 |
| 2014/0273226 A1 | 9/2014 | Wu | | |
| 2014/0274729 A1 * | 9/2014 | Kurn | B01J 19/0046 | 506/26 |
| 2015/0232858 A1 * | 8/2015 | Ozsolak | C12N 15/1137 | 435/375 |
| 2015/0262082 A1 * | 9/2015 | Vaske | G16H 50/50 | 706/13 |
| 2016/0215316 A1 * | 7/2016 | Pedersen | C12N 15/1031 | |
| 2016/0292355 A1 | 10/2016 | Lou et al. | | |
| 2017/0130245 A1 | 5/2017 | Kotin et al. | | |
| 2018/0073028 A1 | 3/2018 | Mirsky et al. | | |
| 2018/0177863 A1 * | 6/2018 | Langlois | C12N 15/113 | |
| 2018/0365375 A1 | 12/2018 | Flygare et al. | | |
| 2018/0373838 A1 * | 12/2018 | Karczewski | G16B 99/00 | |
| 2020/0283756 A1 * | 9/2020 | Vladar | C12N 15/1058 | |
| 2020/0283798 A1 * | 9/2020 | Minshull | G01N 33/48 | |
| 2021/0040547 A1 * | 2/2021 | Dekker | C12Q 1/68 | |

(56)                References Cited

U.S. PATENT DOCUMENTS

| | | | | |
|---|---|---|---|---|
| 2021/0074378 | A1* | 3/2021 | Zhou | G16B 40/20 |
| 2021/0332354 | A1* | 10/2021 | Shah | C12Q 1/6876 |
| 2022/0310275 | A1* | 9/2022 | Senapathy | G16B 45/00 |
| 2022/0348902 | A1* | 11/2022 | Vladar | C12N 15/1031 |
| 2023/0056396 | A1* | 2/2023 | Mourao | G16B 40/20 |
| 2025/0182843 | A1* | 6/2025 | Troyanskaya | G16B 40/20 |

OTHER PUBLICATIONS

Danko, Nat Methods, 2015, pp. 1-20.*
Deshpande, Methods Emzymol, 2019, pp. 1-29.*
Ghandi, Computational Biology, 2014, pp. 1-15.*
Martinez, NIH, 2013, pp. 1-19.*
Rubin, Communications Biology, 2021, pp. 1-15.*
Wang, Genome Research, 2019, pp. 293-303.*
Pundhir_Nucleic_Acids_Research__2016_pp. 4037_4051.*
Ji_Elsevier_2010_2363-2374.*
Abe et al. "Algorithmic learning theory." Proceedings of 12th Intl. Conf. Algorithmic Learning Theory (2001).
Agrawal et al. "Cell-cycle kinetics and VSV-G pseudotyped retrovirus-mediated gene transfer in blood-derived CD34+ cells." Experimental hematology 24.6 (1996): 738-747.
Altschul et al. "Significance of nucleotide sequence alignments: a method for random sequence permutation that preserves dinucleotide and codon usage." Molecular biology and evolution 2.6 (1985): 526-538.
Beaucage et al. "Advances in the synthesis of oligonucleotides by the phosphoramidite approach." Tetrahedron 48.12 (1992): 2223-2311.
Ben-Hur et al. "Support vector clustering." Journal of machine learning research Dec. 2, 2001: 125-137.
Boyle et al. "High-resolution mapping and characterization of open chromatin across the genome." Cell 132.2 (2008): 311-322.
Buenrostro et al. "ATAC-seq: a method for assaying chromatin accessibility genome-wide." Current protocols in molecular biology 109.1 (2015): 21-29.
Buenrostro et al. "Transposition of native chromatin for multimodal regulatory analysis and personal epigenomics." Nature methods 10.12 (2013): 1213-1218.
Caruthers. "The chemical synthesis of DNA/RNA: our gift to science." Journal of biological chemistry 288.2 (2013): 1420-1427.
Cortes et al."Support-vector networks." Machine learning 20.3 (1995): 273-297.
Crawford et al. "Genome-wide mapping of DNase hypersensitive sites using massively parallel signature sequencing (MPSS)." Genome research 16.1 (2006): 123-131.
Cusanovich et al. "A single-cell atlas of in vivo mammalian chromatin accessibility." Cell 174.5 (2018): 1309-1324.
Ghandi et al. "Enhanced regulatory sequence prediction using gapped k-mer features." PLoS computational biology 10.7 (2014): 1-15.
Ghandi et al. "gkmSVM: an R package for gapped-kmer SVM." Bioinformatics 32.14 (2016): 2205-2207.
Giresi et al. "FAIRE (Formaldehyde-Assisted Isolation of Regulatory Elements) isolates active regulatory elements from human chromatin." Genome research 17.6 (2007): 877-885.
Goodman et al. "Recombinant adeno-associated virus-mediated gene transfer into hematopoietic progenitor cells." Blood 84.5 (1994):1492-1500.
Hunt et al. "Improving analysis of transcription factor binding sites within ChIP-Seq data based on topological motif enrichment." BMC genomics 15.1 (2014): 1-19.

Jiang et al. "uShuffle: a useful tool for shuffling biological sequences while preserving the k-let counts." BMC bioinformatics 9.1 (2008): 1-11.
Johnson et al. "Genome-wide mapping of in vivo protein-DNA interactions." Science 316.5830 (2007): 1497-1502.
Khardon et al. "Efficiency versus convergence of boolean kernels for on-line learning algorithms." Journal of Artificial Intelligence Research 24 (2005): 341-356.
Khardon et al. "Maximum margin algorithms with Boolean kernels." Journal of Machine Learning Research 6 (2005): 1405-1429.
Leconte et al. "Discovery, characterization, and optimization of an unnatural base pair for expansion of the genetic alphabet." Journal of the American Chemical Society 130.7 (2008): 2336-2343.
Lee et al. "A method to predict the impact of regulatory variants from DNA sequence." Nature genetics 47.8 (2015): 955-961.
Leslie et al. "Fast string kernels using inexact matching for protein sequences." Journal of Machine Learning Research 5.9 (2004): 1435-1455.
Li et al. "Synthetic muscle promoters: activities exceeding naturally occurring regulatory sequences." Nature biotechnology 17.3 (1999): 241-245.
Li et al. "Large-scale analysis of transcriptional cis-regulatory modules reveals both common features and distinct subclasses." Genome biology 8 (2007): 1-16.
Madrigal et al. "Current bioinformatic approaches to identify DNase I hypersensitive sites and genomic footprints from DNase-seq data." Frontiers in genetics 3: article 230 (2012).
Malyshev et al. "Efficient and sequence-independent replication of DNA containing a third base pair establishes a functional six-letter genetic alphabet." Proceedings of the National Academy of Sciences 109.30 (2012): 12005-12010.
Martin et al. "A new access to 2'-O-alkylated ribonucleosides and propertoes of 2'-O-alykylated oligoribonucleotides." Helv. Chim. Acta, 78 (1995): 486-504.
Miller et al. "Redesign of retrovirus packaging cell lines to avoid recombination leading to helper virus production." Molecular and Cellular Biology 6.8 (1986): 2895-2902.
Mitani et al. "Transduction of human bone marrow by adenoviral vector." Human Gene Therapy 5.8 (1994): 941-948.
Mourão et al. "Learning STRIPS operators from noisy and incomplete observations." Proceedings of the Twenty Eighth Conference on Uncertainty in Artificial Intelligence: (2012): 614-623.
Naldini et al. "In vivo gene delivery and stable transduction of nondividing cells by a lentiviral vector." Science 272. 5259 (1996): 263-267.
Pajoro et al. "Profiling Nucleosome Occupancy by MNase-seq: Experimental Protocol and Computational Analysis" Methods Mol Biol. 1675 (2018): 167-181.
Pastan et al. "A retrovirus carrying an MDR1 cDNA confers multidrug resistance and polarized expression of P-glycoprotein in MDCK cells." Proceedings of the National Academy of Sciences 85.12 (1988): 4486-4490.
Sadohara. "Learning of boolean functions using support vector machines." International Conference on Algorithmic Learning Theory: (2001): 106-118.
Wang et al. "Correlation between DNase I hypersensitive site distribution and gene expression in HeLa S3 cells." Plos One 7.8 (2012): 1-12.
Choi et al. "Optimization of AAV expression cassettes to improve packaging capacity and transgene expression in neurons", Molecular Brain 7.17 (2014).
Colella et al. "Emerging Issues in AAV-Mediated In Vivo Gene Therapy," Mol Ther Methods Clin Dev. 8: 87-104 (2017).

* cited by examiner

SEQ ID NO. 41

GCAACTGCAGATGTGTGACCATCGGCTAGCTGATCTTC

| Kmers around base | Model score |
|---|---|
| SEQ ID 42: GATGTGTGAC | 1.371 |
| SEQ ID 43: ATGTGTGACC | 1.019 |
| SEQ ID 44: TGTGTGACCA | 0.944 |
| SEQ ID 45: GTGTGACCAT | 0.523 |
| SEQ ID 46: TGTGACCATC | 0.003 |
| SEQ ID 47: GTGACCATCG | -0.015 |
| SEQ ID 48: TGACCATCGC | -1.437 |
| SEQ ID 49: GACCATCGCT | -0.011 |
| SEQ ID 50: ACCATCGCTA | 0.325 |
| SEQ ID 51: CCATCGCTAG | 0.276 |

Average for base:          2.998

*FIG. 3*

SYSTEMS AND METHODS FOR SYNTHETIC REGULATORY SEQUENCE DESIGN OR PRODUCTION

CROSS-REFERENCE TO RELATED APPLICATIONS

This application is a 35 U.S.C. § 371 National Phase Entry Application of International Patent Application No. PCT/US2021/013557 filed on Jan. 15, 2021, which designated the U.S., and which claims benefit under 35 U.S.C. § 119(e) of U.S. Provisional Application No. 62/962,336 filed Jan. 17, 2020, and U.S. Provisional Application No. 63/022,937 filed May 11, 2020, the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Jan. 15, 2021, is named 046192-096620WOPT_SL.txt and is 30,864 bytes in size.

TECHNICAL FIELD

The technology described herein relates to systems and methods for synthetic regulatory sequence design or production.

BACKGROUND

Regulatable gene expression is desirable in many circumstances, where it is beneficial or necessary to control the expression levels of an expression product. For example, in gene therapy it is desirable to induce expression of a therapeutic product (e.g. a therapeutic protein) at the desired level during a definite time and/or at a preferred location of treatment, such as a specific tissue or cell type.

Gene expression programs that drive development, differentiation, and many physiological processes are in large part encoded by DNA and RNA sequence elements that recruit regulatory proteins and their co-factors to specific genomic loci or genes under specific conditions. Despite significant research efforts, the relationship between the nucleic acid sequence and the function of these regulatory elements, such as cis-regulatory elements, remains poorly understood. This limited understanding of these regulatory elements is an impediment to a variety of fields, including synthetic biology, medical genetics, and evolutionary biology. Furthermore, existing methods cannot accurately predict active enhancer or promoter candidates in specific tissue or cells types. Thus, more efficient approaches to design synthetic regulatory elements are needed.

SUMMARY

The technology described herein is directed to systems and methods for synthetic regulatory sequence design or production. In several aspects described herein are methods of designing and optionally synthesizing modified (e.g., shortened, replaced, mutated) polynucleotide molecules from polynucleotide sequences, optionally having a known transcriptional regulatory functionality. Such methods comprise processing the polynucleotide sequence into a set of sequence elements; processing the set of sequence elements with a machine learning model (e.g., support vector machine (SVM) comprising a gapped k-mer kernel or k-DNF k-mer kernel); identifying regulatory and non-regulatory regions of the polynucleotide; and designing a shortened (or otherwise modified) polynucleotide sequence, wherein at least one non-regulatory region is removed or replaced in the polynucleotide sequence.

There are a number of reasons one would want to shorten regulatory sequences while either increasing or retaining some or all of the activity, as a non-limiting example AAV-based gene therapies. AAV is a relatively small virus: the packing limit of the therapeutic payload is approximately 4.5kb for the ssDNA AAV version (approximately 2.25 kb for the self-complementary AAV version). When considering AAV design, there is significant pressure to reduce the size of all the elements of the expression cassette; often the therapeutic gene alone takes up the majority of the space, and therefore every base is at a premium.

In terms of retaining or increasing expression, the consensus within the gene therapy field has previously been that it is preferable to administer a smaller dose of very highly active AAV particles expressing sufficient therapeutic protein to reach the therapeutic window. This is because infecting patients with larger doses of AAV can interfere with the therapy itself (e.g., the cells can start to silence the AAV) and cause side effects.

More recently, that view has been challenged, which is in part why having a range of expression strengths is also considered beneficial. This is especially true in situations where finer-grained gene control is required, e.g. gene circuits. Like all of the above, such shortened or otherwise modified regulatory sequences have general application beyond gene therapy.

Thus, the methods and systems described herein allow the identification of synthetic regulatory sequences exhibiting optimal expression in a desired cell or tissue type and/or optimal size, for example a shortened regulatory sequence length that can meet length constraints as dictated by viral vectors. Such methods and systems allow the design or production of isolated nucleic acid compositions or viral vectors with tissue or cell-specific expression. Accordingly, further described herein are isolated nucleic acid modules and viral vectors, comprising said shortened (or otherwise modified) polynucleotide as described herein.

Accordingly, in one aspect described herein is a method of designing or synthesizing a synthetic polynucleotide with transcriptional regulatory functionality, the method comprising: (a) receiving a set of genetic data comprising a regulatory polynucleotide sequence, optionally having a known transcriptional regulatory functionality; (b) processing the set of genetic data into a set of sequence elements that each comprise a portion of the polynucleotide sequence; (c) processing the set of sequence elements with a machine learning model to determine a transcriptional regulatory score associated with each of the set of sequence elements; (d) identifying at least one sequence element of the set of sequence elements comprising a transcriptional regulatory score below a threshold as a non-regulatory sequence element; (e) designing a modified polynucleotide molecule based on the determined transcriptional regulatory scores and/or identified non-regulatory sequence elements; and (f) optionally synthesizing the modified polynucleotide molecule.

In some embodiments of any of the aspects, each of the set of sequence elements is a k-mer fragment of the polynucleotide sequence.

In some embodiments of any of the aspects, each of the k-mer fragments comprises a gapped k-mer fragment.

3

In some embodiments of any of the aspects, the gapped k-mer fragment comprises a 10 nucleotide-long fragment comprising 4 gaps.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, the machine learning model is trained using a second set of genetic data comprising a second set of sequence elements that comprise portions of transcriptional regulatory elements and non-regulatory elements.

In some embodiments of any of the aspects, the modified polynucleotide sequence is designed based on the polynucleotide sequence with the at least one non-regulatory sequence element removed.

In some embodiments of any of the aspects, the modified polynucleotide sequence is designed based on the polynucleotide sequence with the at least one non-regulatory sequence element replaced.

In some embodiments of any of the aspects, the modified polynucleotide sequence is designed based on at least one mutation of nucleotide position(s) to alter a transcriptional regulatory score.

In some embodiments of any of the aspects, synthesizing the shortened modified polynucleotide molecule comprises de novo DNA synthesis In some embodiments of any of the aspects, the known transcriptional regulatory functionality comprises transcriptional activation and/or transcriptional repression.

In some embodiments of any of the aspects, the known transcriptional regulatory functionality is in any given cell or tissue type.

In some embodiments of any of the aspects, the known transcriptional regulatory functionality is in liver cells, cardiac muscle cells, and/or skeletal muscle cells.

In some embodiments of any of the aspects, the known transcriptional regulatory functionality comprises promoter activity.

In some embodiments of any of the aspects, promoter activity comprises a level of expression of a particular set of genes.

In another aspect, described herein is an isolated nucleic acid module comprising a polynucleotide that was synthesized using a process comprising: (a) receiving a set of genetic data comprising a regulatory polynucleotide sequence, optionally having a known transcriptional regulatory functionality; (b) processing the set of genetic data into a set of sequence elements that each comprise a portion of the polynucleotide sequence; (c) processing the set of sequence elements with a machine learning model to determine a transcriptional regulatory score associated with each of the set of sequence elements; (d) identifying at least one sequence element of the set of sequence elements comprising a transcriptional regulatory score below a threshold as a non-regulatory sequence element; (e) designing a modified polynucleotide molecule based on the determined transcriptional regulatory scores and/or identified non-regulatory sequence elements; and (f) synthesizing the modified polynucleotide molecule.

In some embodiments of any of the aspects, each of the set of sequence elements is a k-mer fragment of the polynucleotide sequence.

In some embodiments of any of the aspects, each of the k-mer fragments comprises a gapped k-mer fragment.

In some embodiments of any of the aspects, the gapped k-mer fragment comprises a 10 nucleotide-long fragment comprising 4 gaps.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, the machine learning model is trained using a second set of genetic data comprising a second set of sequence elements that comprise portions of transcriptional regulatory elements and non-regulatory elements.

In some embodiments of any of the aspects, synthesizing the modified polynucleotide molecule comprises de novo DNA synthesis.

In some embodiments of any of the aspects, the known transcriptional regulatory functionality comprises transcriptional activation and/or transcriptional repression.

In some embodiments of any of the aspects, the known transcriptional regulatory functionality is in any given cell or tissue type.

In some embodiments of any of the aspects, the known transcriptional regulatory functionality is in liver cells, cardiac muscle cells, and/or skeletal muscle cells.

In some embodiments of any of the aspects, the known transcriptional regulatory functionality comprises promoter activity.

In some embodiments of any of the aspects, promoter activity comprises a level of expression of a particular set of genes.

In some embodiments of any of the aspects, the modified polynucleotide sequence is designed based on the polynucleotide sequence with the at least one non-regulatory sequence element removed.

In some embodiments of any of the aspects, the modified polynucleotide sequence is designed based on the polynucleotide sequence with the at least one non-regulatory sequence element replaced.

In some embodiments of any of the aspects, the modified polynucleotide sequence is designed based on at least one mutation of nucleotide position(s) to alter a transcriptional regulatory score.

In another aspect, described herein is a method of designing or synthesizing a synthetic polynucleotide with transcriptional regulatory functionality, the method comprising: (a) receiving a set of genetic data comprising a regulatory polynucleotide sequence, optionally having a known transcriptional regulatory functionality; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (g) optionally synthesizing the modified polynucleotide molecule.

In some embodiments of any of the aspects, each of the k-mer fragments comprises a gapped k-mer fragment.

In some embodiments of any of the aspects, the gapped k-mer fragment comprises a 10 nucleotide-long fragment comprising 4 gaps.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, the machine learning model is trained using a second set of genetic data comprising a second set of sequence elements that comprise portions of transcriptional regulatory elements and non-regulatory elements.

In some embodiments of any of the aspects, synthesizing the modified polynucleotide molecule comprises de novo DNA synthesis.

In some embodiments of any of the aspects, the known transcriptional regulatory functionality comprises transcriptional activation and/or transcriptional repression.

In some embodiments of any of the aspects, the known transcriptional regulatory functionality is in any given cell or tissue type.

In some embodiments of any of the aspects, the known transcriptional regulatory functionality is in liver cells, cardiac muscle cells, and/or skeletal muscle cells.

In some embodiments of any of the aspects, the known transcriptional regulatory functionality comprises promoter activity.

In some embodiments of any of the aspects, promoter activity comprises a level of expression of a particular set of genes.

In another aspect, described herein is a method of designing or synthesizing a polynucleotide sequence with transcriptional regulatory functionality that is altered in size without losing transcriptional regulatory functionality comprising: (a) using a machine to process a set of genetic data comprising polynucleotide sequences to identify putative promoter sequences or putative enhancer sequences; (b) processing the set of putative promoter sequences with a machine learning model to determine a transcriptional regulatory score associated with each of the nucleotides within the putative promoter sequences to identify peaks and troughs based upon the scores provided to each nucleotide within the putative promoter sequences; (c) identifying at least one member of the set of putative promoter sequences where there is a trough of at least 20 nucleotides between peaks, wherein the scores for members of the trough is below a pre-determined threshold; and (d) optionally synthesizing a shortened polynucleotide molecule, wherein at least 10% of the nucleotides within a trough has been removed as compared to the selected identified putative promoter sequence of step (c).

In some embodiments of any of the aspects, the nucleotide sequences are scored using k-mer methodology.

In some embodiments of any of the aspects, at least one trough within a putative promoter sequence are identified.

In some embodiments of any of the aspects, at least one trough is removed.

In some embodiments of any of the aspects, the transcriptional regulatory functionality of the shortened polynucleotide molecule is compared against the parent putative promoter sequence and is at least 35% that of the parent putative promoter sequence.

In another aspect, described herein is a method of designing or synthesizing a synthetic polynucleotide with transcriptional regulatory functionality, the method comprising: (a) receiving a set of genetic data comprising a regulatory polynucleotide sequence, optionally having a known transcriptional regulatory functionality; (b) processing the polynucleotide sequence into a first set of sequence elements, wherein the first set of sequence elements comprises at least one subset of sequence elements corresponding to all k-mer fragments comprising a selected nucleotide position of the polynucleotide sequence; (c) training a machine learning model using a second set of sequence elements that comprise portions of transcriptional regulatory elements and non-regulatory elements; (d) generating a third set of sequence elements comprising all k-mer fragments of the same length as the k-mer fragments of the first set of sequence elements; (e) processing the third set of sequence elements with the machine learning model to determine a transcriptional regulatory score associated with each sequence element of the third set of sequence elements, wherein the transcriptional regulatory score is stored in a database referenced to a k-mer fragment; (f) determining the transcriptional regulatory score of each k-mer fragment in a subset by assigning the transcriptional regulatory score of the matching k-mer fragment from the database; (g) determining the transcriptional regulatory score of at least one nucleotide position comprising averaging all transcriptional regulatory scores of all k-mer fragments in the corresponding subset; (h) identifying at least one region of nucleotide positions comprising transcriptional regulatory scores at or above a threshold as a regulatory sequence element; (i) identifying at least one region of nucleotide positions that is not a regulatory sequence element as a non-regulatory sequence element; (j) designing a modified polynucleotide molecule based on the determined transcriptional regulatory scores and/or identified non-regulatory sequence elements; and (k) optionally synthesizing the modified polynucleotide molecule.

In some embodiments of any of the aspects, each of the k-mer fragments of the first set of sequence elements comprises a gapped k-mer fragment.

In some embodiments of any of the aspects, each gapped k-mer fragment of the first set of sequence elements comprises a 10 nucleotide-long fragment comprising 4 gaps.

In some embodiments of any of the aspects, processing the polynucleotide sequence of step (b) comprises processing the polynucleotide sequence into subsets of sequence elements.

In some embodiments of any of the aspects, processing the polynucleotide sequence into subsets of sequence elements comprises selecting a nucleotide position of the polynucleotide sequence and generating all k-mer fragments comprising the nucleotide position.

In some embodiments of any of the aspects, a subset of sequence elements is produced for each nucleotide position of the polynucleotide sequence.

In some embodiments of any of the aspects, the first set of sequence elements comprises at least two subsets of sequence elements.

In some embodiments of any of the aspects, the first set of sequence elements comprises a subset of sequence elements corresponding to each nucleotide position of the polynucleotide sequence.

In some embodiments of any of the aspects, the portions of transcriptional regulatory elements of the second set of sequence elements comprise regions identified as accessible chromatin.

In some embodiments of any of the aspects, the regions identified as accessible chromatin comprise regions detected by DNase I hypersensitive site (DHS) assay, Assay for Transposase-Accessible Chromatin using sequencing (ATAC-seq), or other chromatin accessibility detection methods.

In some embodiments of any of the aspects, the portions of transcriptional regulatory elements of the second set of sequence elements do not comprise promoter regions or are not within 2 kilobases of a transcriptional start site (TSS).

In some embodiments of any of the aspects, the portions of transcriptional regulatory elements of the second set of sequence elements do not comprise regions detected by DHS assay in greater than 30% of human ENCODE cell lines.

In some embodiments of any of the aspects, the portions of non-regulatory elements of the second set of sequence elements comprises shuffled sequences of the portions of transcriptional regulatory elements of the second set of sequence elements.

In some embodiments of any of the aspects, the portions of transcriptional regulatory elements and non-regulatory elements of the second set of sequence elements are adjusted to 250 to 750 base pairs long.

In some embodiments of any of the aspects, the portions of transcriptional regulatory elements comprise a similar GC content and/or similar nucleotide repeat composition as the portions of non-regulatory elements of the second set of sequence elements.

In some embodiments of any of the aspects, the machine learning model is configured to return a transcriptional regulatory score.

In some embodiments of any of the aspects, the transcriptional regulatory score comprises a positive or negative value, corresponding to the degree of confidence the model has that the sequence element is in a group comprising the portions of transcriptional regulatory elements or non-regulatory sequence elements of the second set of sequence elements.

In some embodiments of any of the aspects, a transcriptional regulatory score is determined for each nucleotide position corresponding to each subset of sequence elements.

In some embodiments of any of the aspects, the transcriptional regulatory score for each nucleotide position of the polynucleotide sequence is plotted.

In some embodiments of any of the aspects, the threshold is the average of all transcriptional regulatory scores for each k-mer fragment of the third set of sequence elements plus a variable value.

In some embodiments of any of the aspects, the variable value is at least 1.2 times the standard deviation of the transcriptional regulatory score for each k-mer fragment of the third set of sequence elements.

In some embodiments of any of the aspects, the regulatory sequence element is at least as long as one k-mer fragment of the first set of sequence elements.

In some embodiments of any of the aspects, the regulatory sequence element is at least 10 nucleotides long.

In some embodiments of any of the aspects, the non-regulatory sequence element is at least as long as one k-mer fragment of the first set of sequence elements.

In some embodiments of any of the aspects, the non-regulatory sequence element is at least 10 nucleotides long.

In some embodiments of any of the aspects, the method further comprises after step (i), re-processing a modified polynucleotide sequence using the machine learning model, wherein the modified polynucleotide sequence comprises the polynucleotide sequence with the at least one non-regulatory sequence element removed.

In some embodiments of any of the aspects, wherein re-processing the modified polynucleotide sequence comprises repeating steps b, f, g, h, and i as described herein using the modified polynucleotide sequence in place of the polynucleotide sequence.

In some embodiments of any of the aspects, the modified polynucleotide molecule based on the modified polynucleotide sequence is synthesized if, after the step of re-processing, the length of the at least one regulatory sequence element identified is at least the same length as the corresponding regulatory sequence element identified in the parent polynucleotide sequence.

In some embodiments of any of the aspects, the modified polynucleotide molecule based on the modified polynucleotide sequence is not synthesized if, after the step of re-processing, the length of the at least one regulatory sequence element identified is less than the length of the regulatory sequence element identified in the parent polynucleotide sequence.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, synthesizing the modified polynucleotide molecule comprises de novo DNA synthesis.

In some embodiments of any of the aspects, the known transcriptional regulatory functionality comprises transcriptional activation and/or transcriptional repression.

In some embodiments of any of the aspects, the known transcriptional regulatory functionality is in any given cell or tissue type.

In some embodiments of any of the aspects, the known transcriptional regulatory functionality is in liver cells, cardiac muscle cells, and/or skeletal muscle cells.

In some embodiments of any of the aspects, the known transcriptional regulatory functionality comprises promoter activity.

In some embodiments of any of the aspects, promoter activity comprises a level of expression of a particular set of genes.

In another aspect, described herein is a method of designing or synthesizing a viral vector comprising a synthetic polynucleotide with transcriptional regulatory functionality, the method comprising: (a) receiving a set of genetic data comprising a regulatory polynucleotide sequence, optionally having a known transcriptional regulatory activity; (b) identifying an enhancer portion of the polynucleotide sequence using a machine learning model based on k-mers; (c)

processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (g) optionally synthesizing a viral vector comprising the modified polynucleotide molecule.

In some embodiments of any of the aspects, the viral vector is an AAV vector.

In some embodiments of any of the aspects, the modified polynucleotide molecule is no more than 100 nucleotides long.

In some embodiments of any of the aspects, the transcriptional regulatory functionality of the modified polynucleotide molecule is compared against the parent polynucleotide molecule and is at least 10% that of the parent polynucleotide molecule.

In some embodiments of any of the aspects, each of the k-mer fragments comprises a gapped k-mer fragment.

In some embodiments of any of the aspects, the gapped k-mer fragment comprises a 10 nucleotide-long fragment comprising 4 gaps.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, the machine learning model is trained using a second set of genetic data comprising a second set of sequence elements that comprise portions of transcriptional regulatory elements and non-regulatory elements.

In some embodiments of any of the aspects, synthesizing the modified polynucleotide molecule comprises de novo DNA synthesis.

In some embodiments of any of the aspects, the known transcriptional regulatory functionality comprises transcriptional activation and/or transcriptional repression.

In some embodiments of any of the aspects, the known transcriptional regulatory functionality is in any given cell or tissue type.

In some embodiments of any of the aspects, the known transcriptional regulatory functionality is in liver cells, cardiac muscle cells, and/or skeletal muscle cells.

In some embodiments of any of the aspects, the known transcriptional regulatory functionality comprises promoter activity.

In some embodiments of any of the aspects, promoter activity comprises a level of expression of a particular set of genes.

In some embodiments of any of the aspects, the modified polynucleotide sequence is designed based on the polynucleotide sequence with the at least one non-regulatory sequence element removed.

In some embodiments of any of the aspects, the modified polynucleotide sequence is designed based on the polynucleotide sequence with the at least one non-regulatory sequence element replaced.

In some embodiments of any of the aspects, the modified polynucleotide sequence is designed based on at least one mutation of nucleotide position(s) corresponding to a transcriptional regulatory score below the pre-determined threshold.

In another aspect, described herein is a viral vector comprising a modified polynucleotide that was synthesized using a process comprising: (a) receiving a set of genetic data comprising a regulatory polynucleotide sequence, optionally having a known transcriptional regulatory activity; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (g) synthesizing a viral vector comprising the modified polynucleotide molecule.

In some embodiments of any of the aspects, the viral vector is an AAV vector.

In some embodiments of any of the aspects, the modified polynucleotide molecule is no more than 100 nucleotides long.

In some embodiments of any of the aspects, the transcriptional regulatory functionality of the modified polynucleotide molecule is compared against the parent polynucleotide molecule and is at least 10% that of the parent polynucleotide molecule.

In some embodiments of any of the aspects, each of the k-mer fragments comprises a gapped k-mer fragment.

In some embodiments of any of the aspects, the gapped k-mer fragment comprises a 10 nucleotide-long fragment comprising 4 gaps.

In some embodiments of any of the aspects, the machine learning model is a support vector machine.

In some embodiments of any of the aspects, the set of sequence elements are input into the support vector machine.

In some embodiments of any of the aspects, the support vector machine comprises a gapped k-mer kernel.

In some embodiments of any of the aspects, the support vector machine comprises a k-DNF k-mer kernel.

In some embodiments of any of the aspects, the machine learning model is trained using a second set of genetic data comprising a second set of sequence elements that comprise portions of transcriptional regulatory elements and non-regulatory elements.

In some embodiments of any of the aspects, synthesizing the modified polynucleotide molecule comprises de novo DNA synthesis.

In some embodiments of any of the aspects, the transcriptional regulatory functionality comprises transcriptional activation and/or transcriptional repression.

11

In some embodiments of any of the aspects, the transcriptional regulatory functionality is in any given cell or tissue type.

In some embodiments of any of the aspects, the transcriptional regulatory functionality is in liver cells, cardiac muscle cells, and/or skeletal muscle cells.

In some embodiments of any of the aspects, the transcriptional regulatory functionality comprises promoter activity.

In some embodiments of any of the aspects, promoter activity comprises a level of expression of a particular set of genes.

In some embodiments of any of the aspects, the modified polynucleotide sequence is designed based on the polynucleotide sequence with the at least one non-regulatory sequence element removed.

In some embodiments of any of the aspects, the modified polynucleotide sequence is designed based on the polynucleotide sequence with the at least one non-regulatory sequence element replaced.

In some embodiments of any of the aspects, the modified polynucleotide sequence is designed based on at least one mutation of nucleotide position(s) corresponding to a transcriptional regulatory score below the pre-determined threshold.

In some embodiments of any of the aspects, the modified polynucleotide sequence is designed based on one mutation of a nucleotide position.

BRIEF DESCRIPTION OF THE DRAWINGS

FIG. 3 is a schematic showing calculation of a model score for a specific position (highlighted "C") in the sequence. SEQ ID NOs: 41-51 are also indicated in grey.

FIG. 4A is a graph showing the SVM scores for the enhancer sequence. FIG. 4B is a graph showing the model scores for the enhancer sequence. The grey line is the profile for the actual sequence (see e.g., FIG. 4A). Each point is the score at that position if the base was mutated to each of the other 3 bases. FIG. 4C is a graph showing an analysis of the peak predictions of the enhancer sequence. The six peaks correspond in order to (1) a HNF-4 group; (2) HNF-1 like factors, ZNF333, and DRI1; (3) NFAT-related factors and TCF-7-related factors; (4) NF-1A; (5) TEF-1-related factors; and (6) C/EBP group and FOX factors. The boxed region corresponds to the core or (minimal) promoter region.

FIG. 5A is a plot of SVM scores. For example, the boxed regions (e.g., positions 1-22, 66-170, or 263-319) represent troughs with low scores that can be deleted or replaced. FIG. 5B is a bar graph showing the results of the deletion of specific regions. The far left (light grey) bar shows the activity of the original promoter sequence, and the remaining (dark grey) bars represent the new sequences (e.g., deletion of region 1-22; deletion of region 66-170; replacement of region 66-170; and deletion of region 262-319). Note the increase in promoter activity that can be seen after deletion of a low-score region compared to the activity of the original promoter sequencer.

Figure 6:
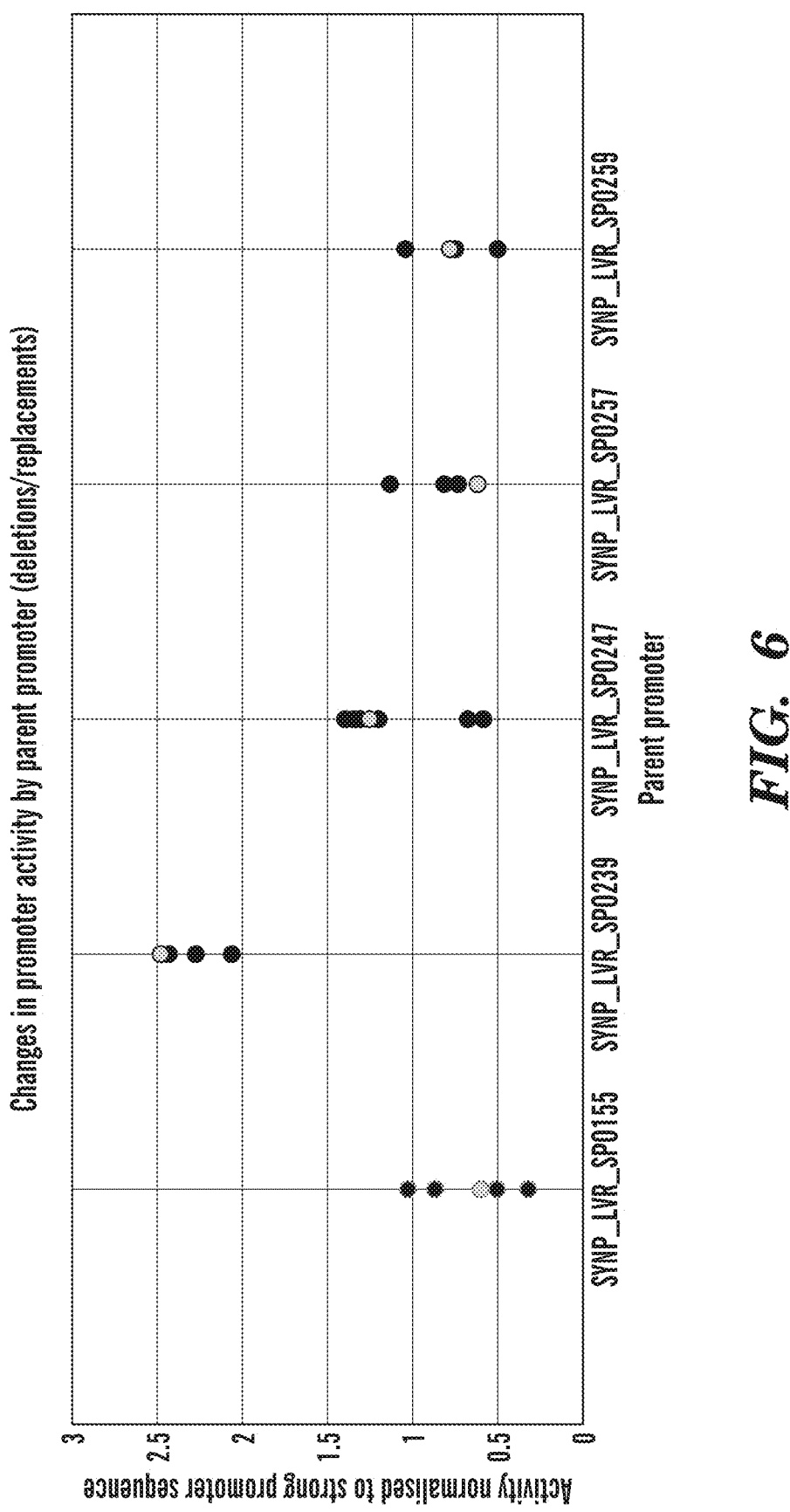

FIG. 6 is a dot plot showing changes in promoter activity by deletion or replacement of part of the parent promoters. Parent promoters tested include SYNP_LVR_SP0155, SYNP_LVR_SP0239, SYNP_LVR_SP0247, SYNP_LVR_SP0257, and SYNP_LVR_SP0259. The light grey dot for each represents the activity of the parent promoter, and the remaining (dark grey) dots represent the activity of promoter with deleted or replaced regions.

Figure 7A:
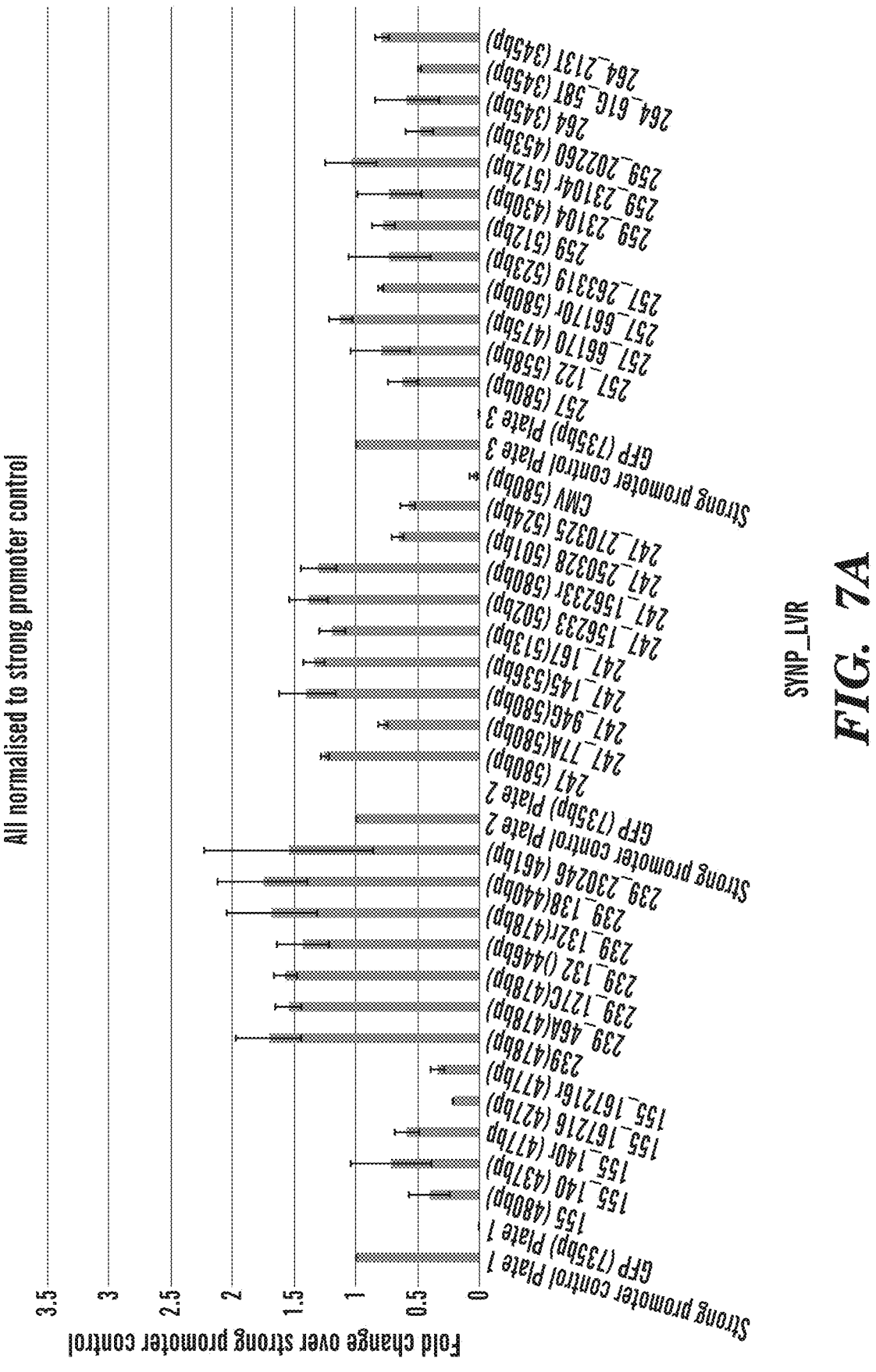
Figure 7B:
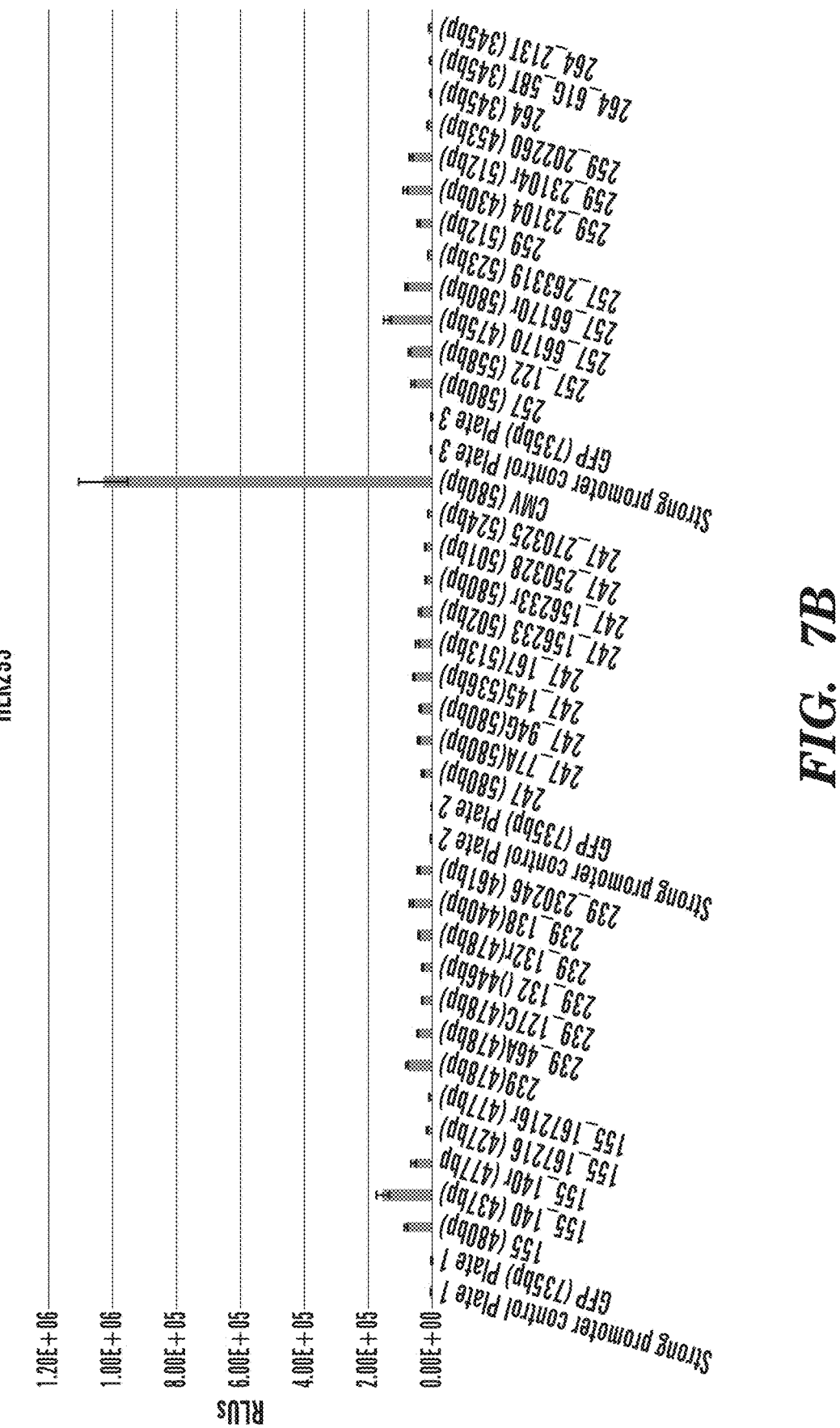

FIG. 7A-7B is a series of bar graphs showing the full set of promoter results from FIG. 6. FIG. 7A shows the fold change over a strong promoter control, as indicated by the horizontal line, in Huh7 liver cells. FIG. 7B shows the relative luciferase units (RLUs) in HEK293 kidney cells, showing the specificity of the promoters to the liver. Note that only the constitutive CMV promoter demonstrated significant activity in the HEK293 kidney cells.

Figure 8:
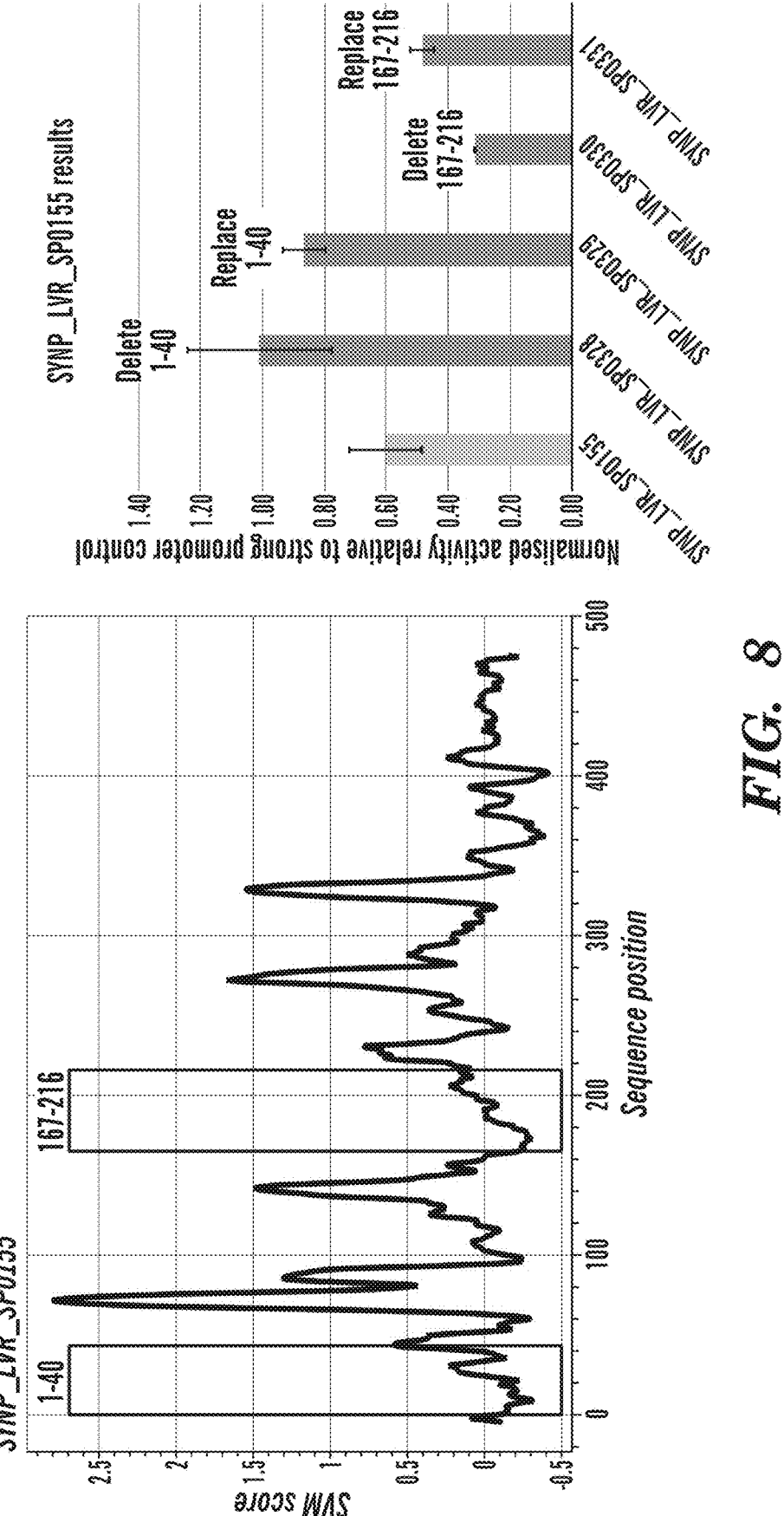

FIG. 8 is a series of graphs showing the SYNP_LVR_SP0155 results.

Figure 9:
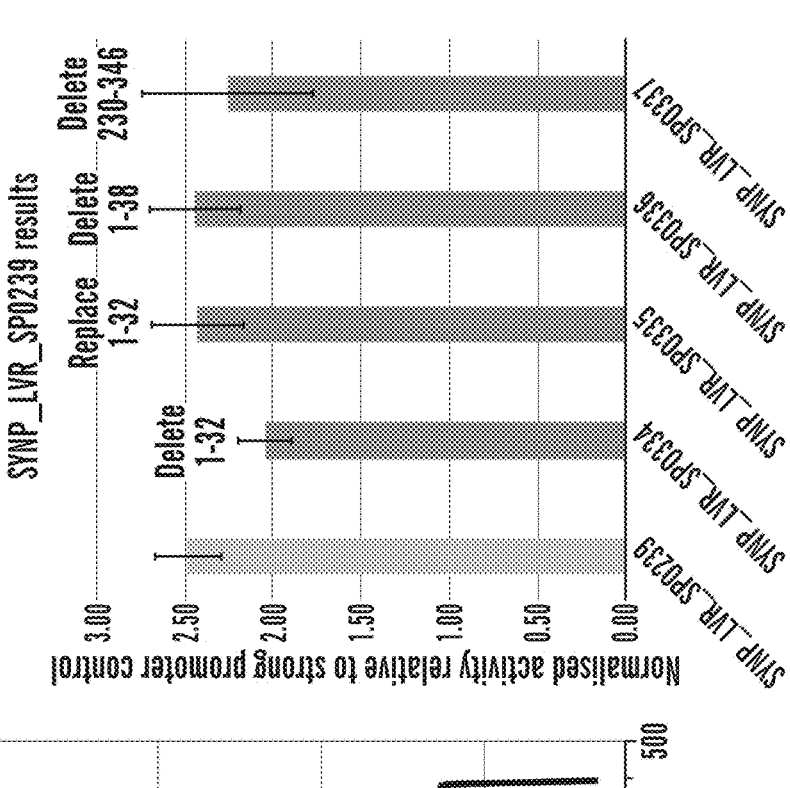
Figure 9:
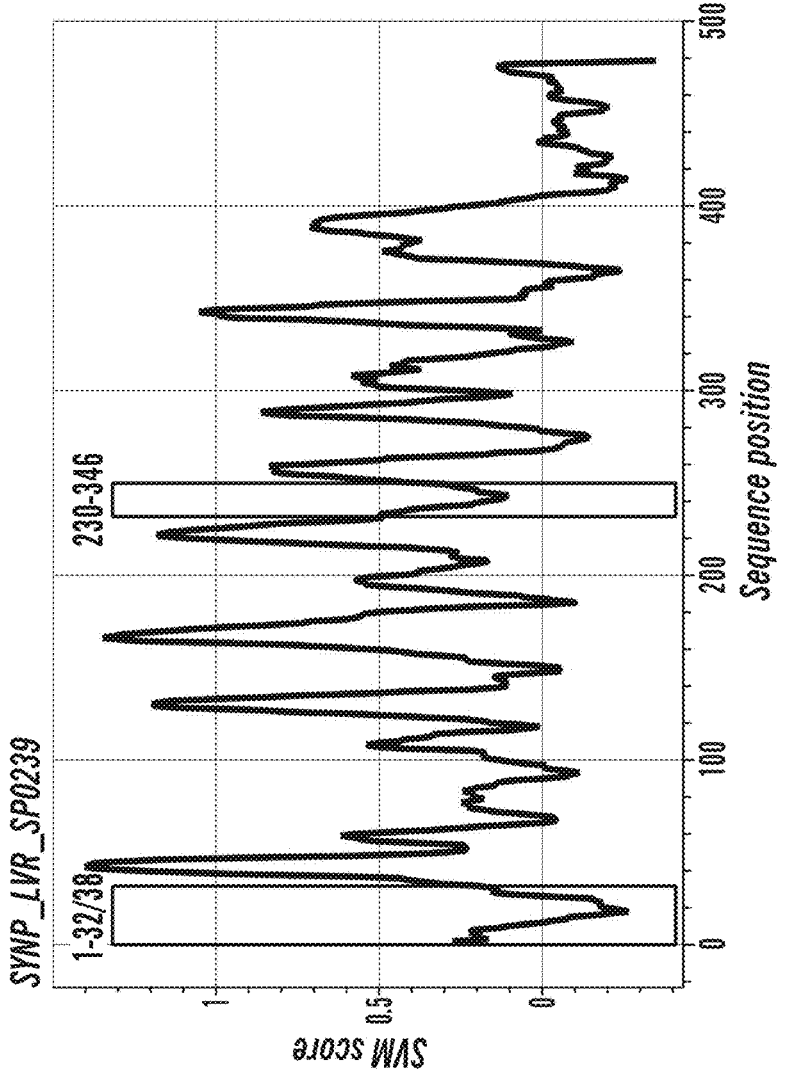

FIG. 9 is a series of graphs showing the SYNP_LVR_SP0239 results.

Figure 10:
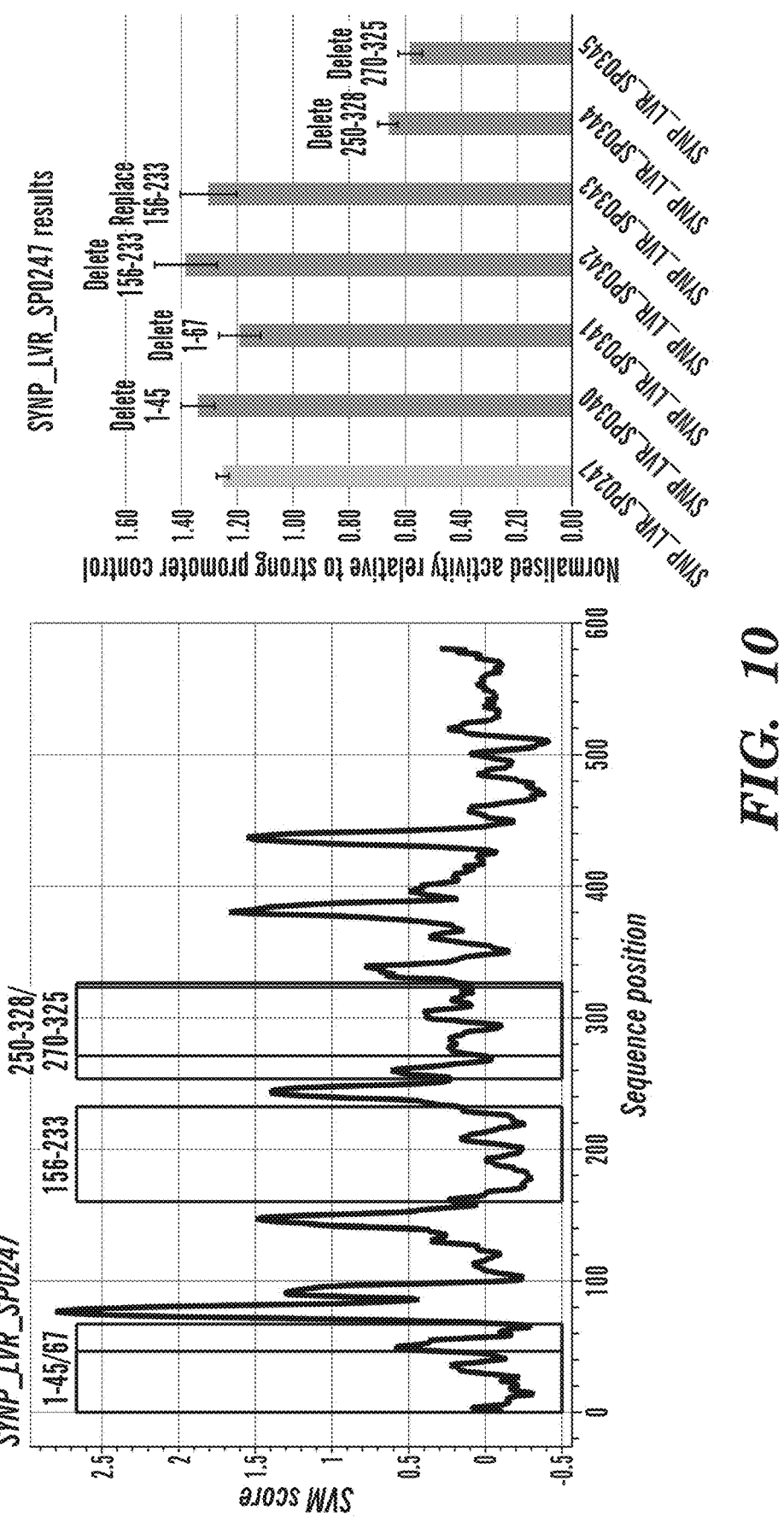

FIG. 10 is a series of graphs showing the SYNP_LVR_SP0247 results.

Figure 11:
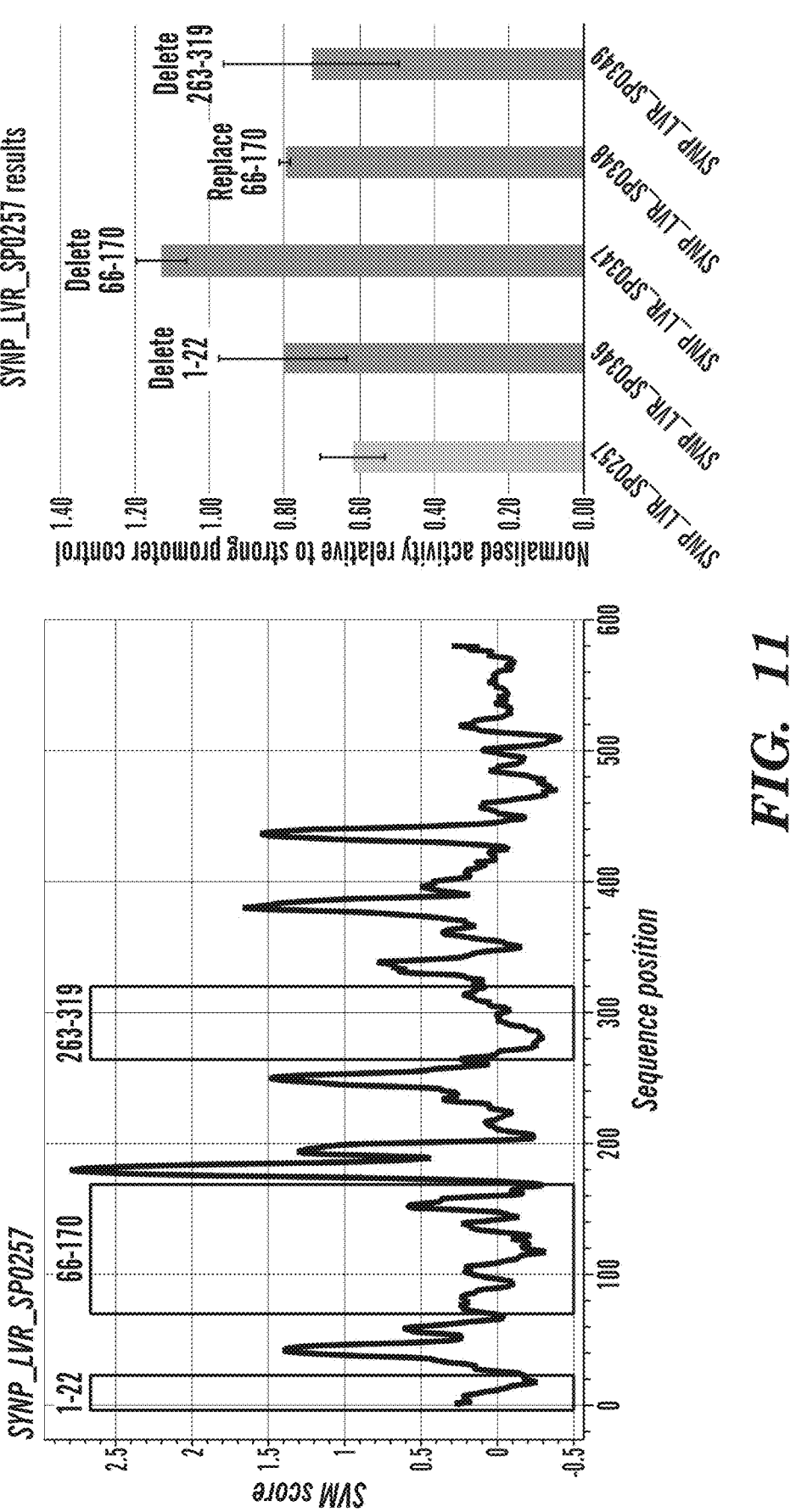

FIG. 11 is a series of graphs showing the SYNP_LVR_SP0257 results.

Figure 12:
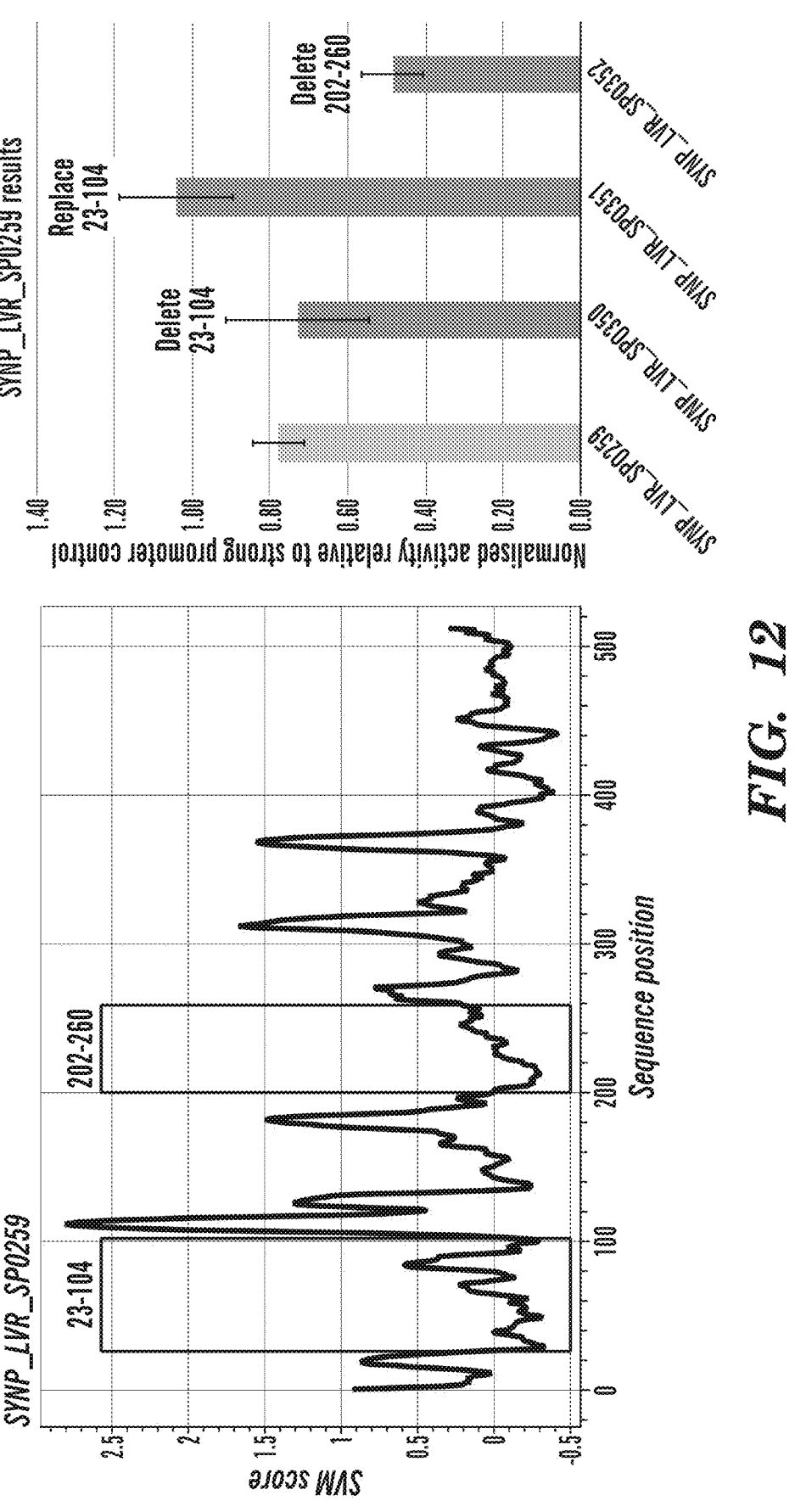

FIG. 12 is a series of graphs showing the SYNP_LVR_SP0259 results.

Figure 13A:
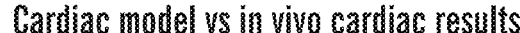
Figure 13A:
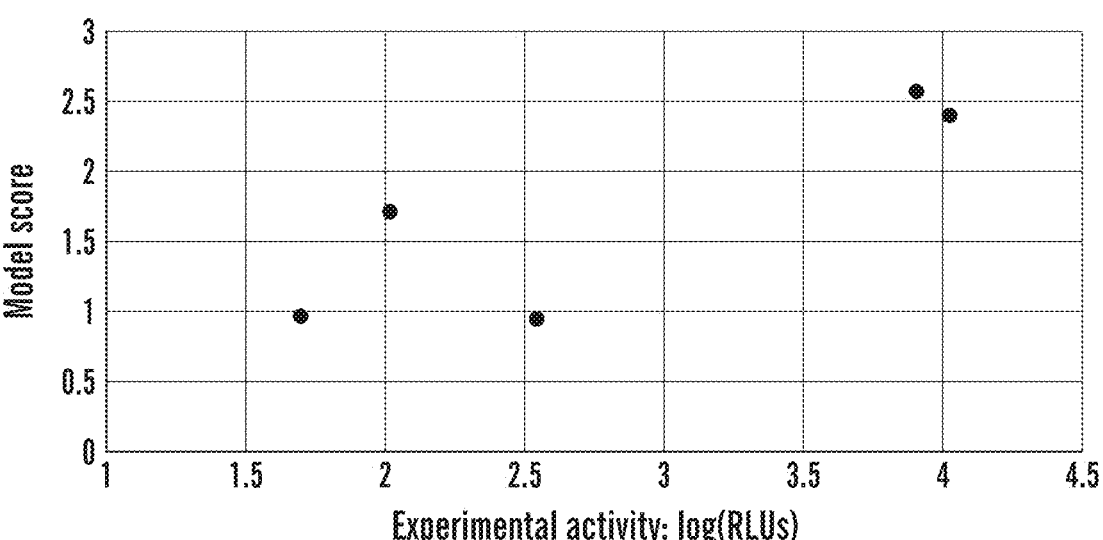
Figure 13B:
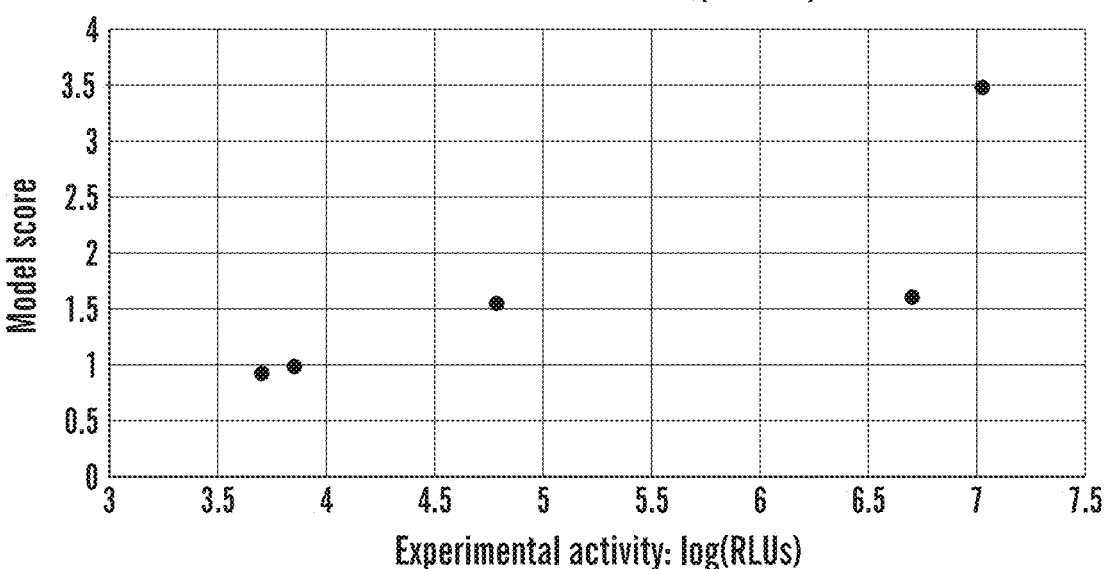

FIG. 13A-13B is a series of scatterplots showing that in vivo muscle model results. FIG. 13A shows a scatterplot of the cardiac model scores vs. in vivo cardiac results for five sequences. Single-cell mouse ATAC-seq data of cardiac muscle (see e.g., Cusanovich et al. A Single-Cell Atlas of In Vivo Mammalian Chromatin Accessibility, Cell. 2018 Aug. 23, 174(5):1309-1324.e18) was analyzed using the methods as described herein. Briefly, 2500 positive example sequences (e.g., 500 bp) from Cusanovich et al. and 2500 matched background sequences were used to train the cardiac model. Five sequences tested by the model were then tested in vivo in cardiac tissue. Note the positive correlation between the model score and the experimental activity (expressed in log(RLUs)). FIG. 13B shows a scatterplot of the skeletal muscle model scores vs. in vivo quadriceps results for the same five sequences as FIG. 13A. Human DHS (DNase I hypersensitive site) data from the psoas muscle (see e.g., Lee et al. 2015, A method to predict the impact of regulatory variants from DNA sequence. Nat Genet. 2015 Aug, 47(8):955-61; Ghandi et al. 2014 Enhanced Regulatory Sequence Prediction Using Gapped k-mer Features. PLoS Comput Biol 10: e1003711; and Ghandi et al. 2016. gkmSVM: an R package for gapped-kmer SVM. Bioinformatics 32: 2205-2207) was analyzed using the methods as described herein. Briefly, 10,000 positive example sequences (e.g., 500 bp) from Lee et al. and 10,000 matched background sequences from Lee et al. were used to train the skeletal muscle model. The five sequences (see e.g., FIG. 13A) were then tested in vivo in cardiac tissue. Note the positive correlation between the model score and the experimental activity (expressed in log(RLUs)).

Figure 14:
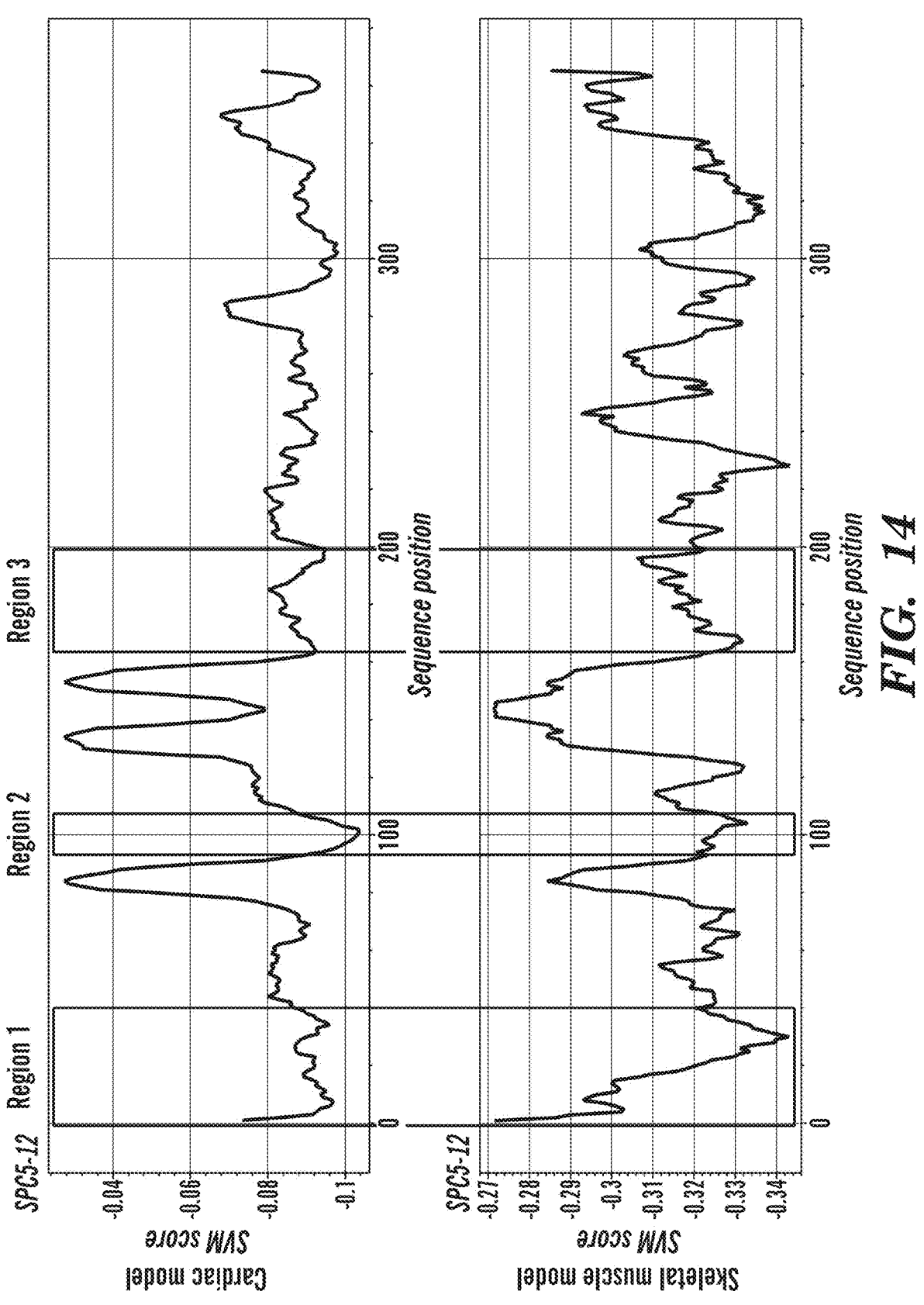

FIG. 14 shows a series of graphs showing the identification of non-regulatory sites in the SPc5-12 promoter. FIG. 14 is a series of graphs showing non-regulatory regions of the SPc5-12 promoter as determined using the cardiac muscle model (top) or skeletal muscle model (bottom).

Figure 15:
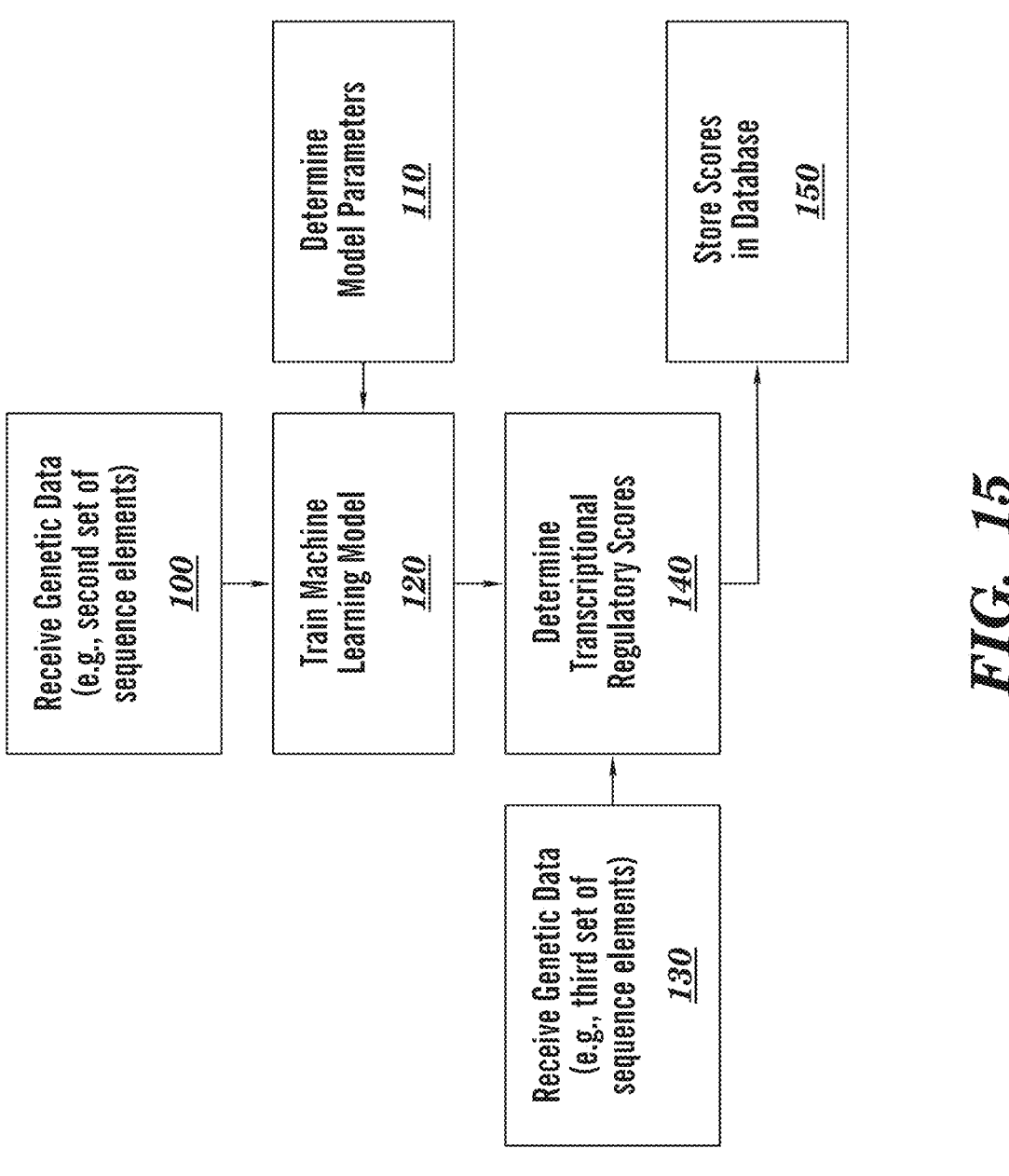

FIG. 15 is a flowchart showing an example process for setting up a Machine Learning Model.

Figure 16:
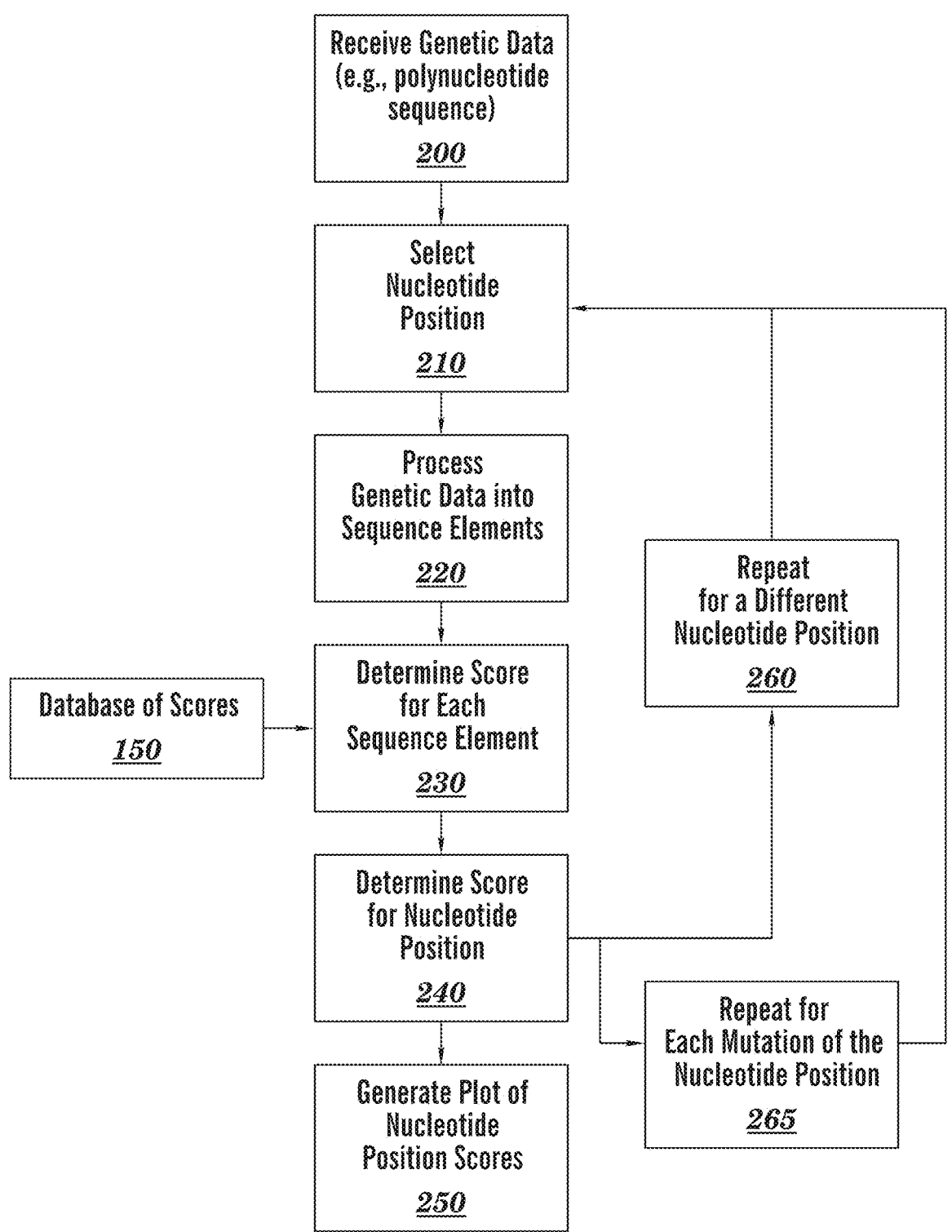

FIG. 16 is a flowchart showing an example process for determining scores for a sequence.

Figure 17A:
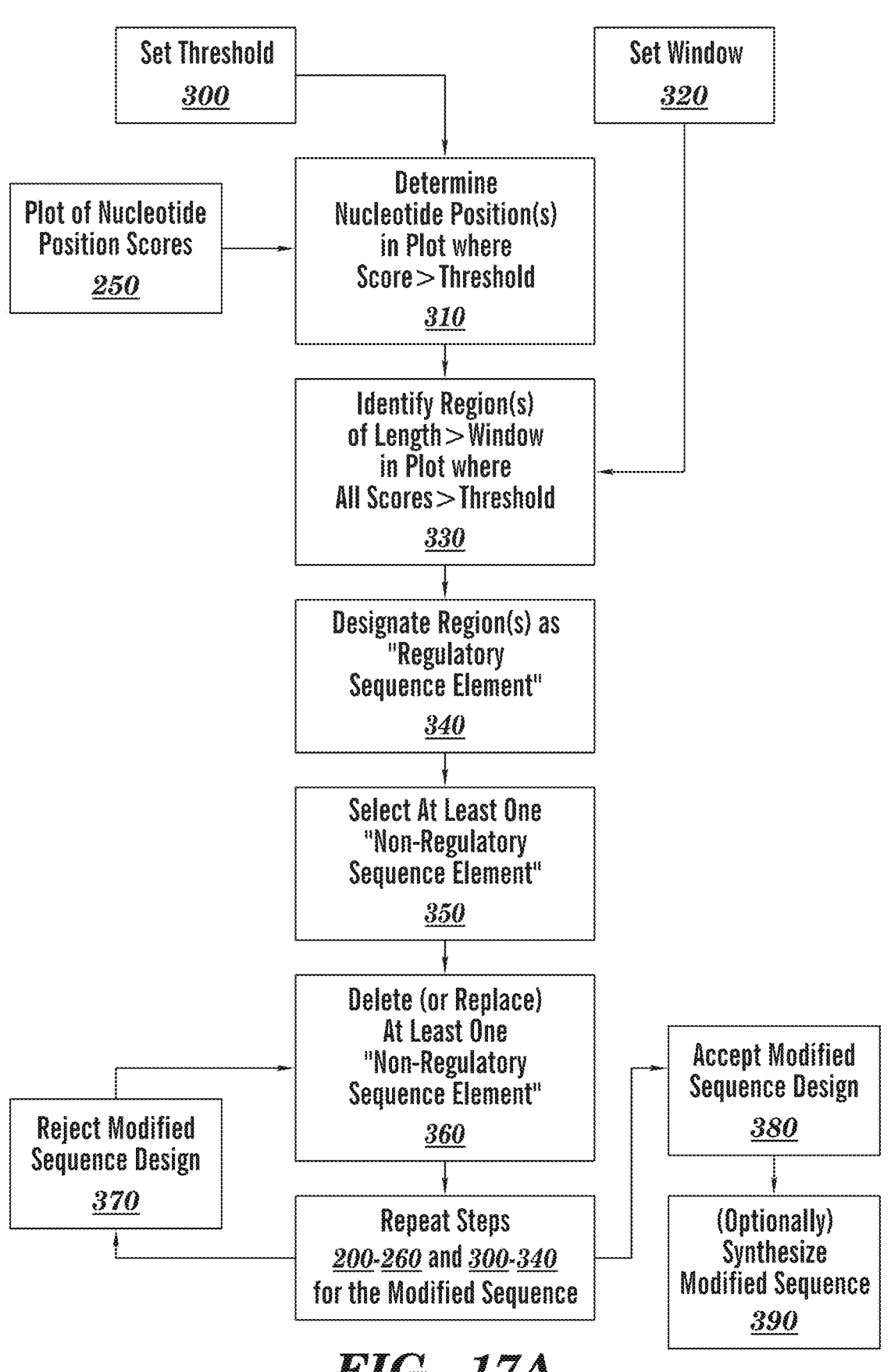
Figure 17B:
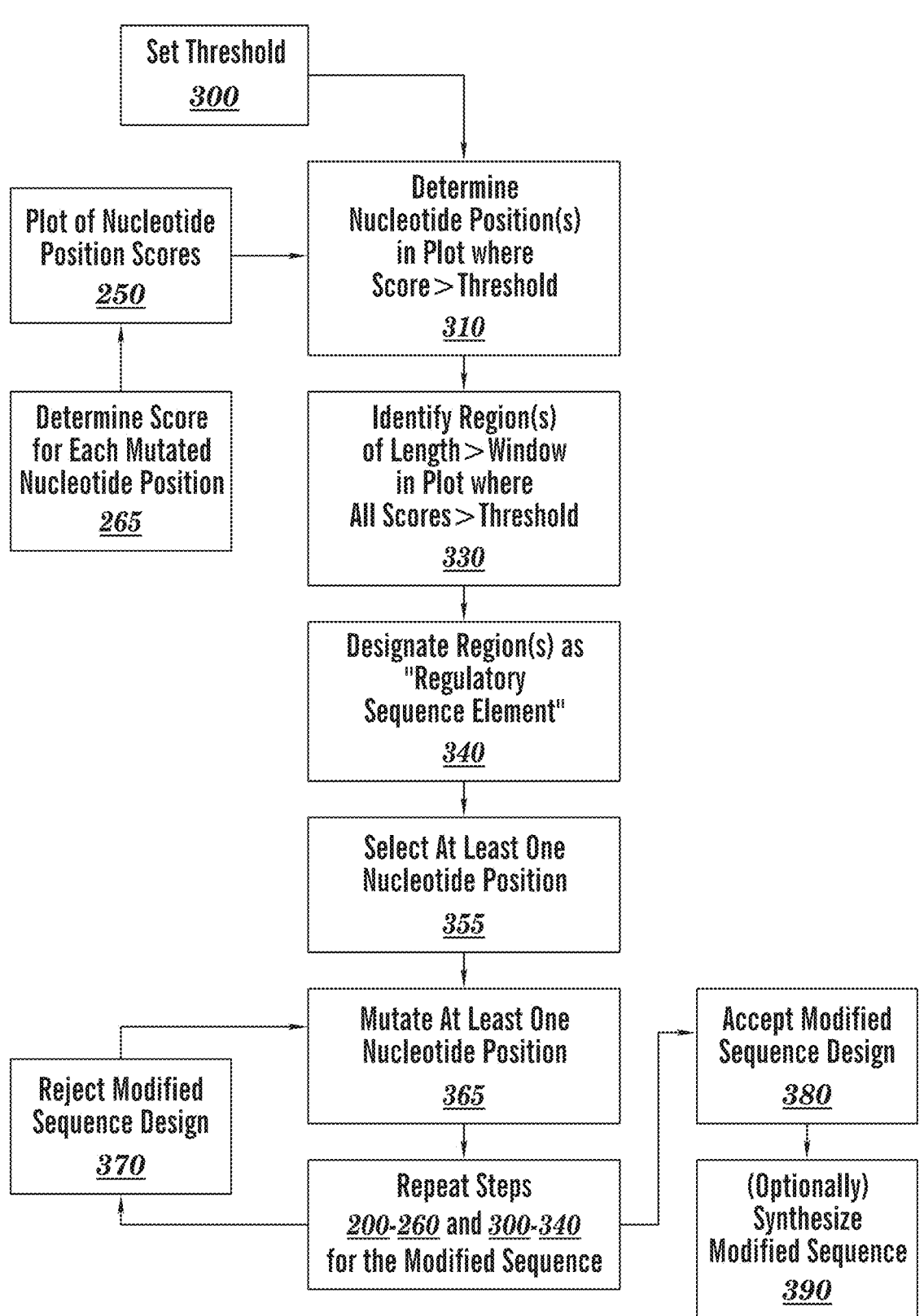

FIG. 17A-17B are flowcharts showing example processes for identifying functional and non-functional regions of a sequence.

Figure 18:
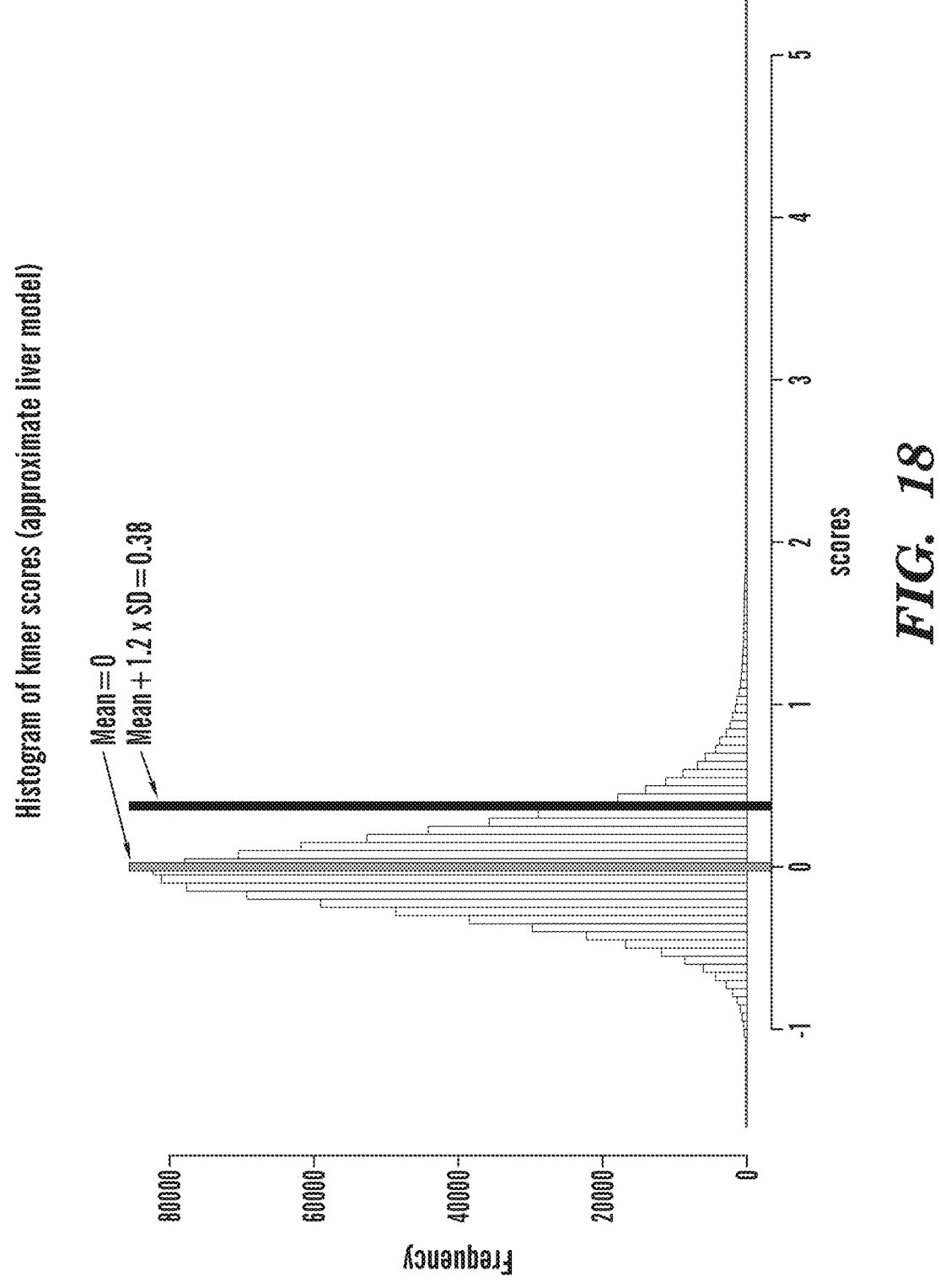

FIG. 18 is a bar graph showing a histogram of k-mer scores from the approximate liver model. The vertical (grey) line to the left shows the mean of the scores (mean=0). The vertical (black) line to the right shows the threshold value for the score (threshold=mean+1.2*SD=0.38).

Figure 19:
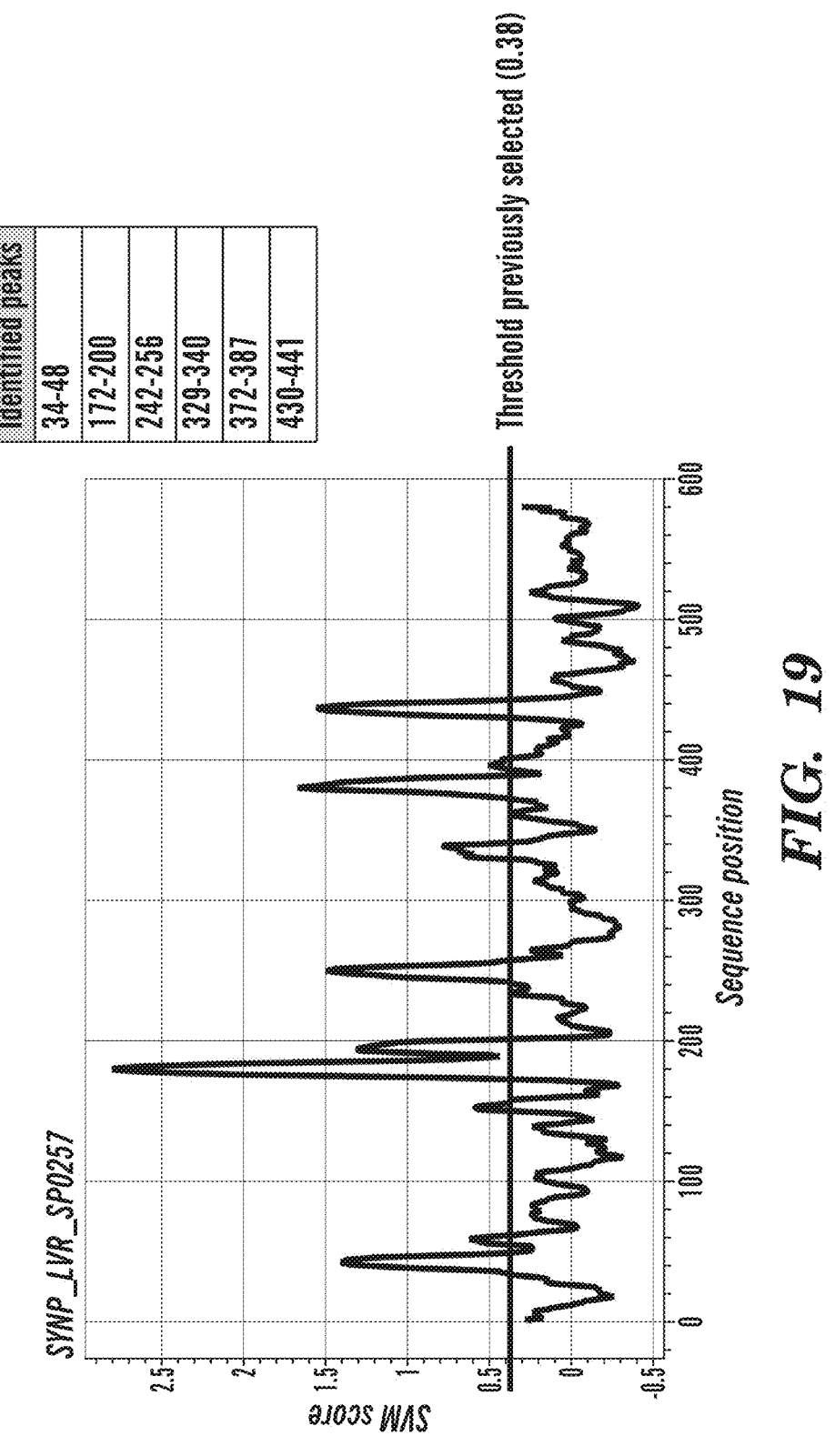

FIG. 19 is a plot showing the model scores of each position in a sequence (SYNP_LVR_SP0257) as determined by the approximate liver model. The threshold, shown as a black horizontal, was previously determined to be 0.38.

Figure 20:
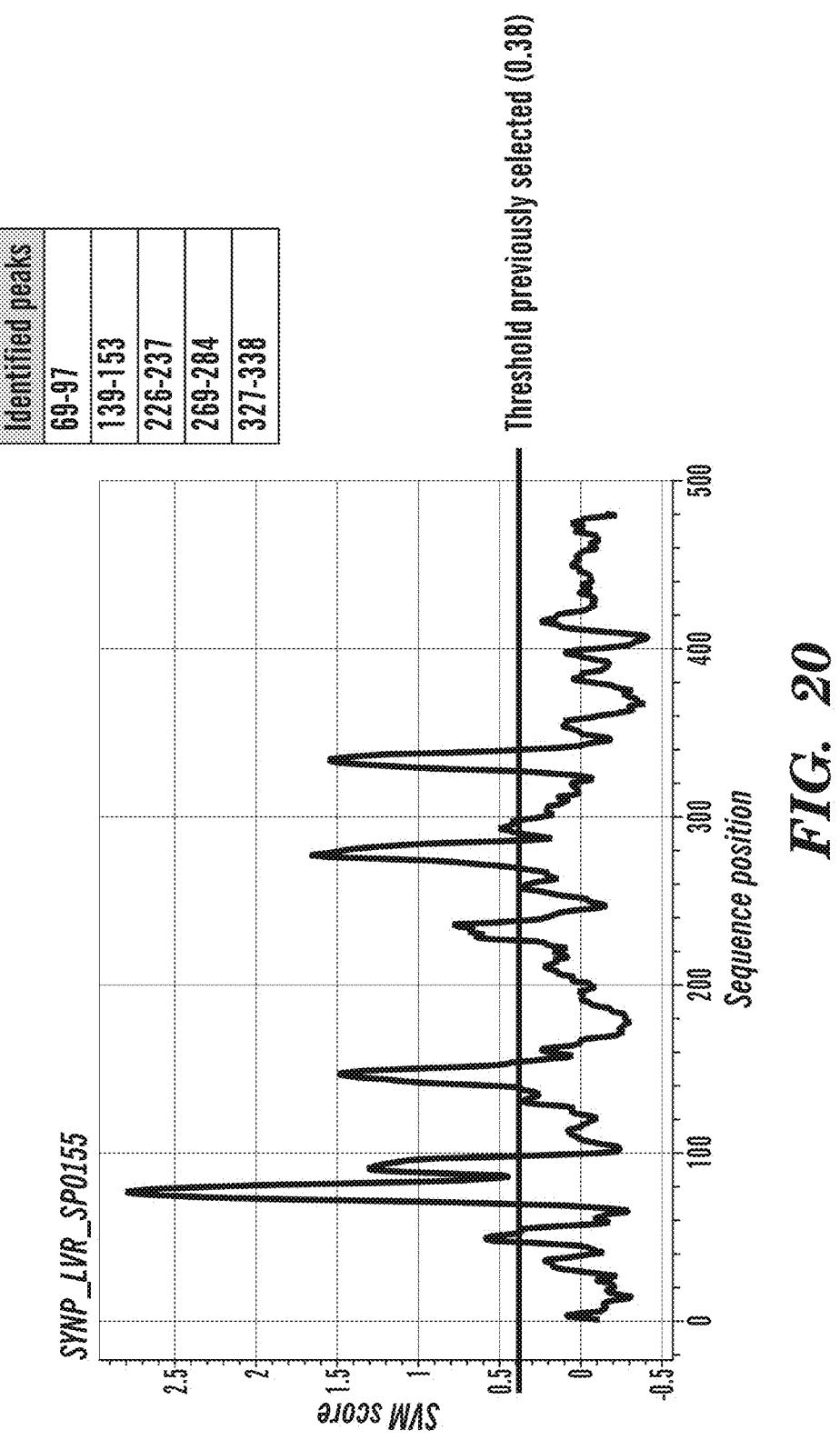

FIG. 20 is a plot showing the model scores of each position in a sequence (SYNP_LVR_SP0155) as determined by the approximate liver model. The threshold, shown as a black horizontal, was previously determined to be 0.38.

Figure 21:
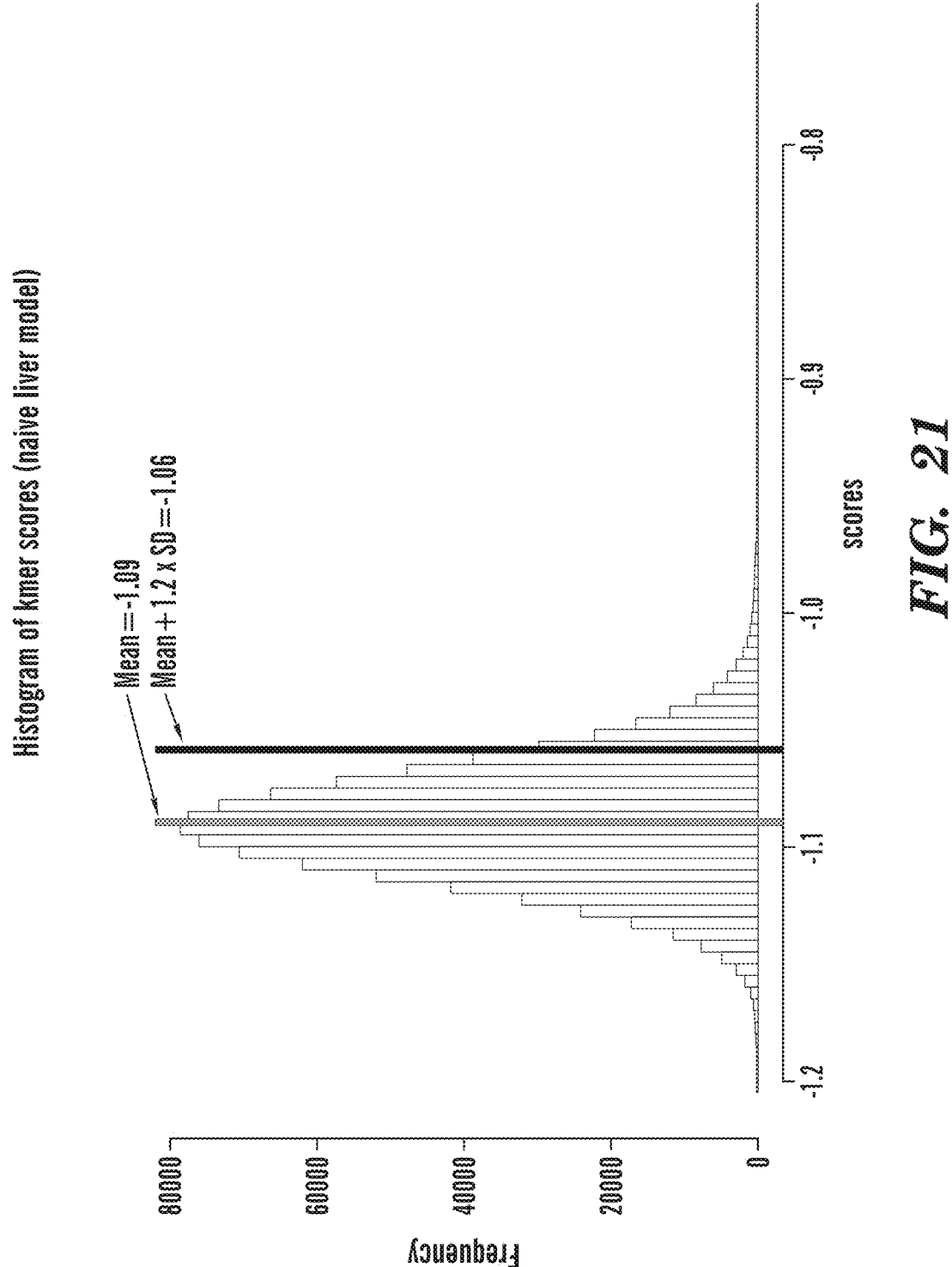

FIG. 21 is a bar graph showing a histogram of k-mer scores from the naive liver model. The vertical (grey) line to the left shows the mean of the scores (mean=−1.09). The vertical (black) line to the right shows the threshold value for the score (threshold=mean+1.2*SD=−1.06).

Figure 22:
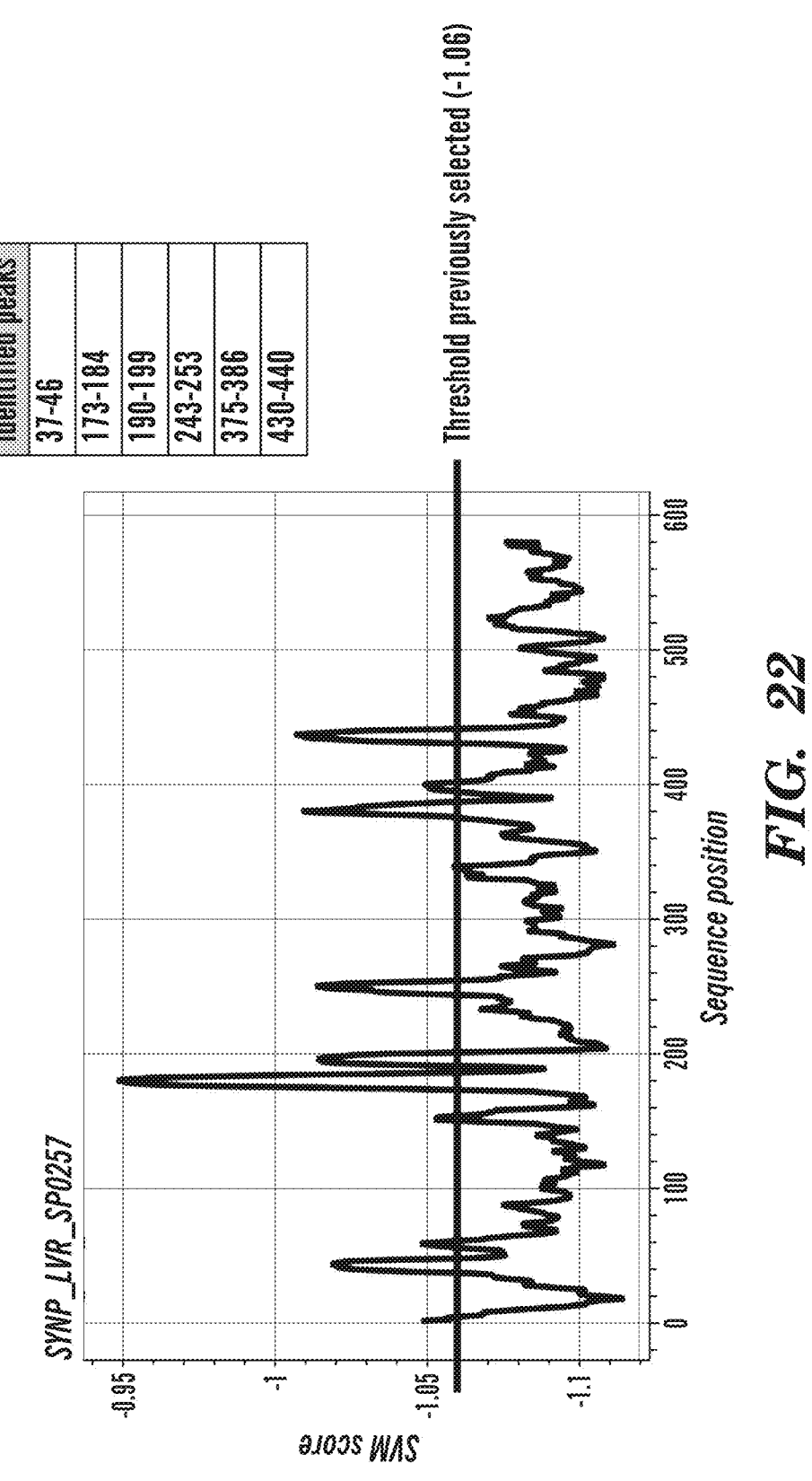

FIG. 22 is a plot showing the model scores of each position in a sequence (SYNP_LVR_SP0257) as determined by the naive liver model. The threshold, shown as a black horizontal, was previously determined to be −1.06.

Figure 23:
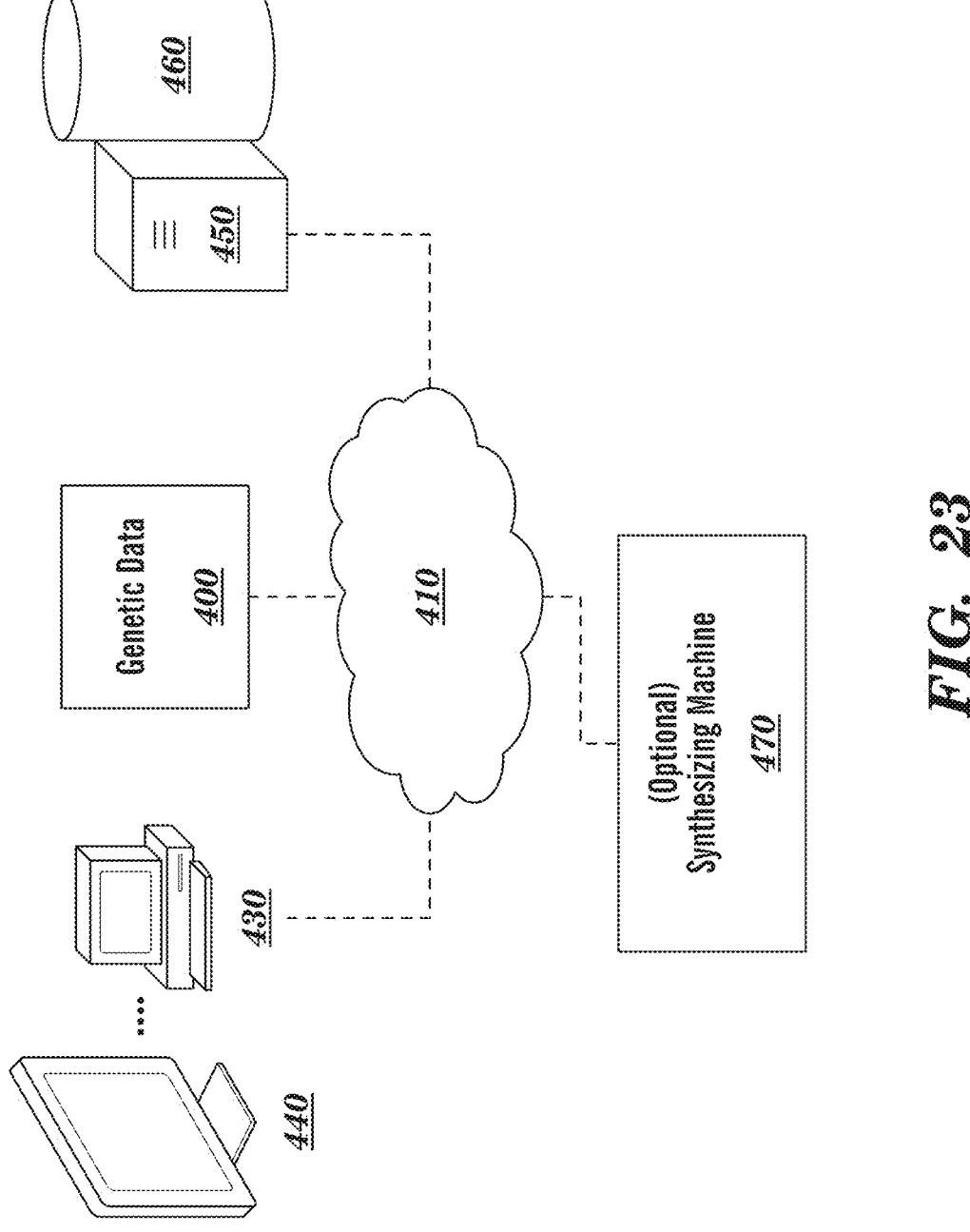

FIG. 23 depicts an example of an overview of a system according to some embodiments of the present disclosure.

Figure 24:
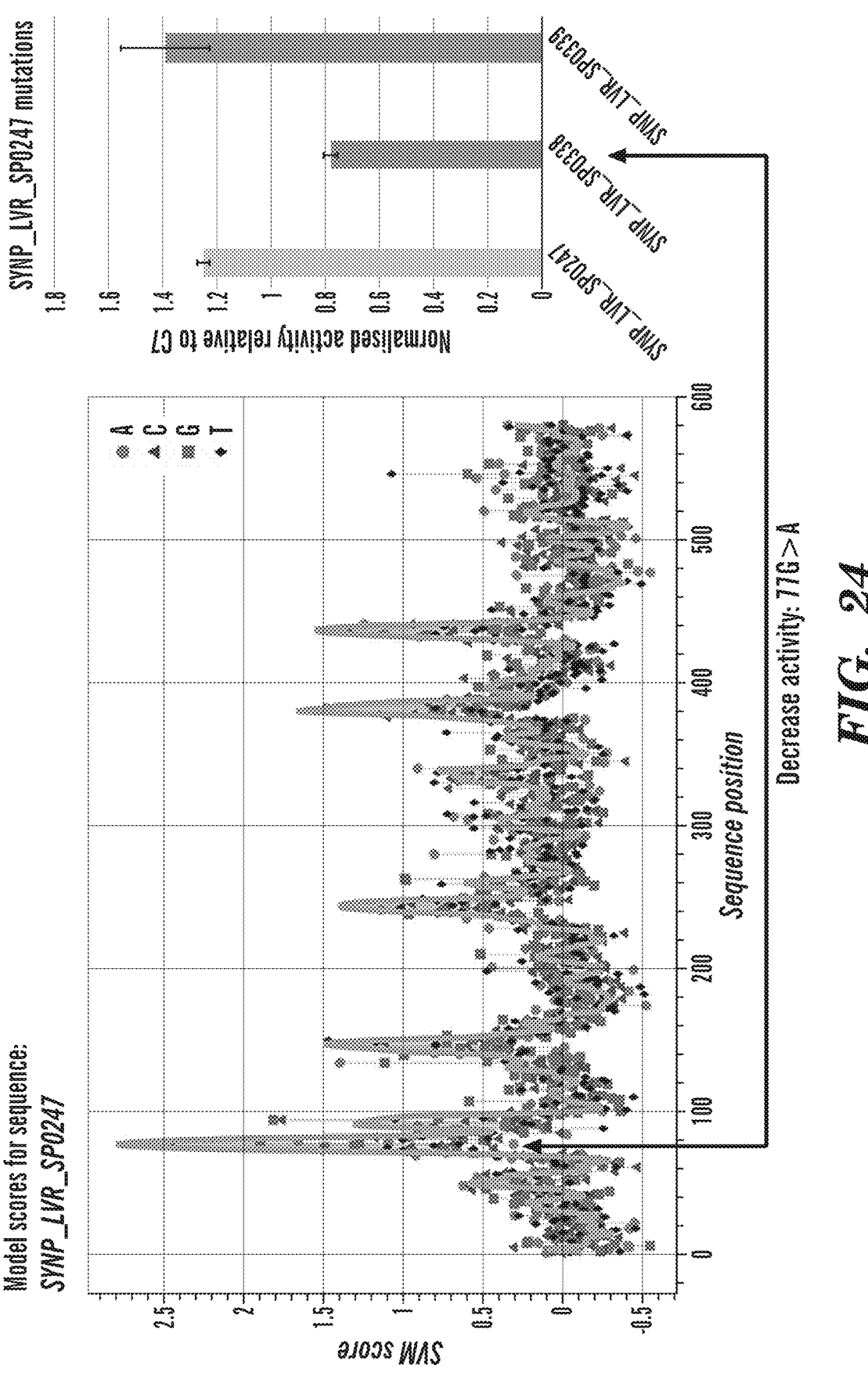

FIG. 24 (left panel) depicts a plot showing model scores of each position in a sequence (SYNP_LVR_SP0247). FIG. 24 (right panel) depicts a bar graph showing the impact on promoter activity of making the single base pair substitutions depicted in the plot in the left panel of FIG. 24.

Figure 25:
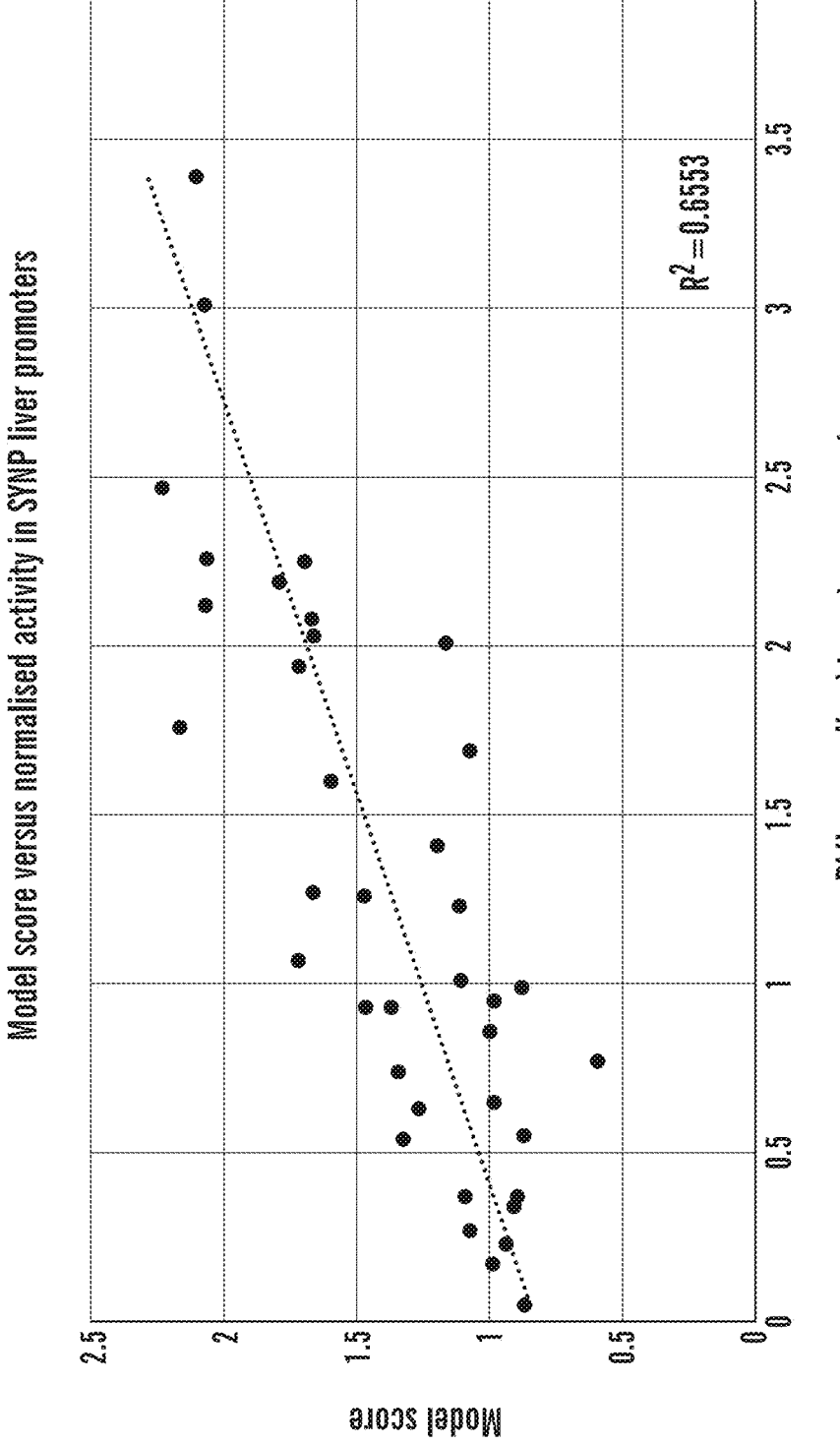

FIG. 25 is a scatter plot showing the model score versus normalized activity in SYNP liver promoters.

Figure 26:
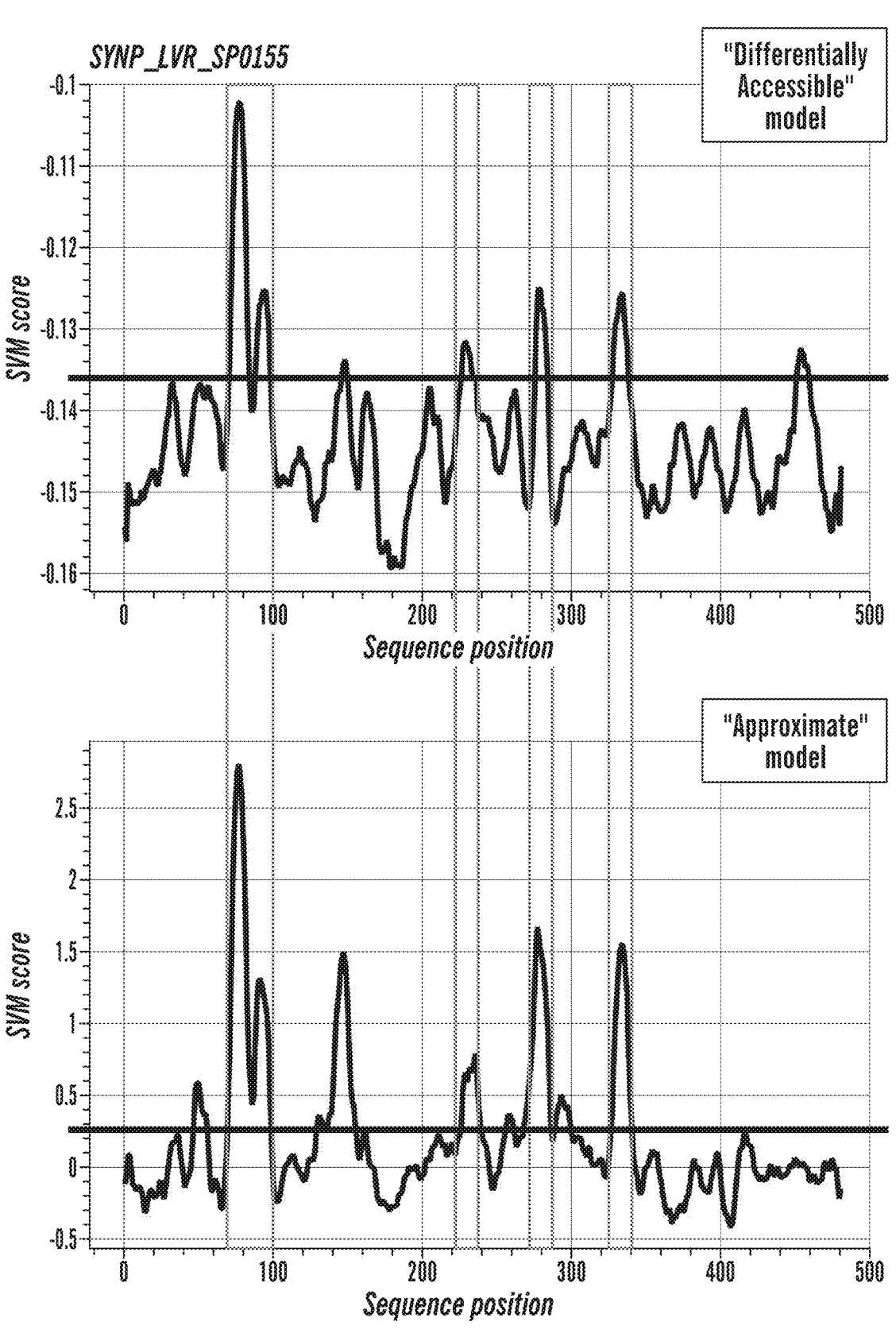

FIG. 26 is a series of line graphs showing the SVM scores for the "Differentially Accessible" model and the "Approximate" model for SYNP_LV_SP0155. Gray boxes show the regions identified as active by both models.

Figure 27:
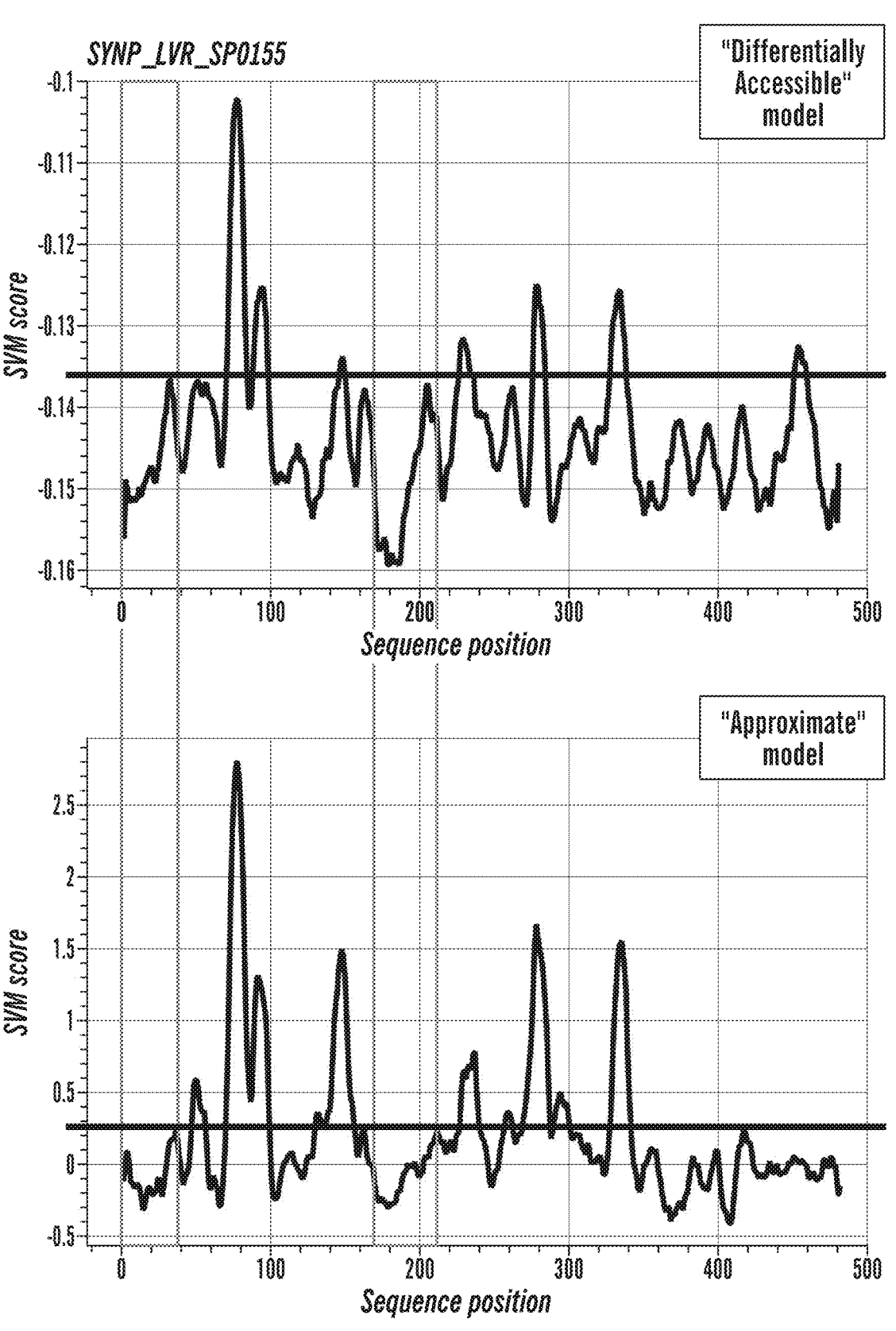

FIG. 27 is a series of line graphs showing the SVM scores for the "Differentially Accessible" model and the "Approximate" model for SYNP_LV_SP0155. Gray boxes show the regions identified as inactive by both models.

Figure 28:
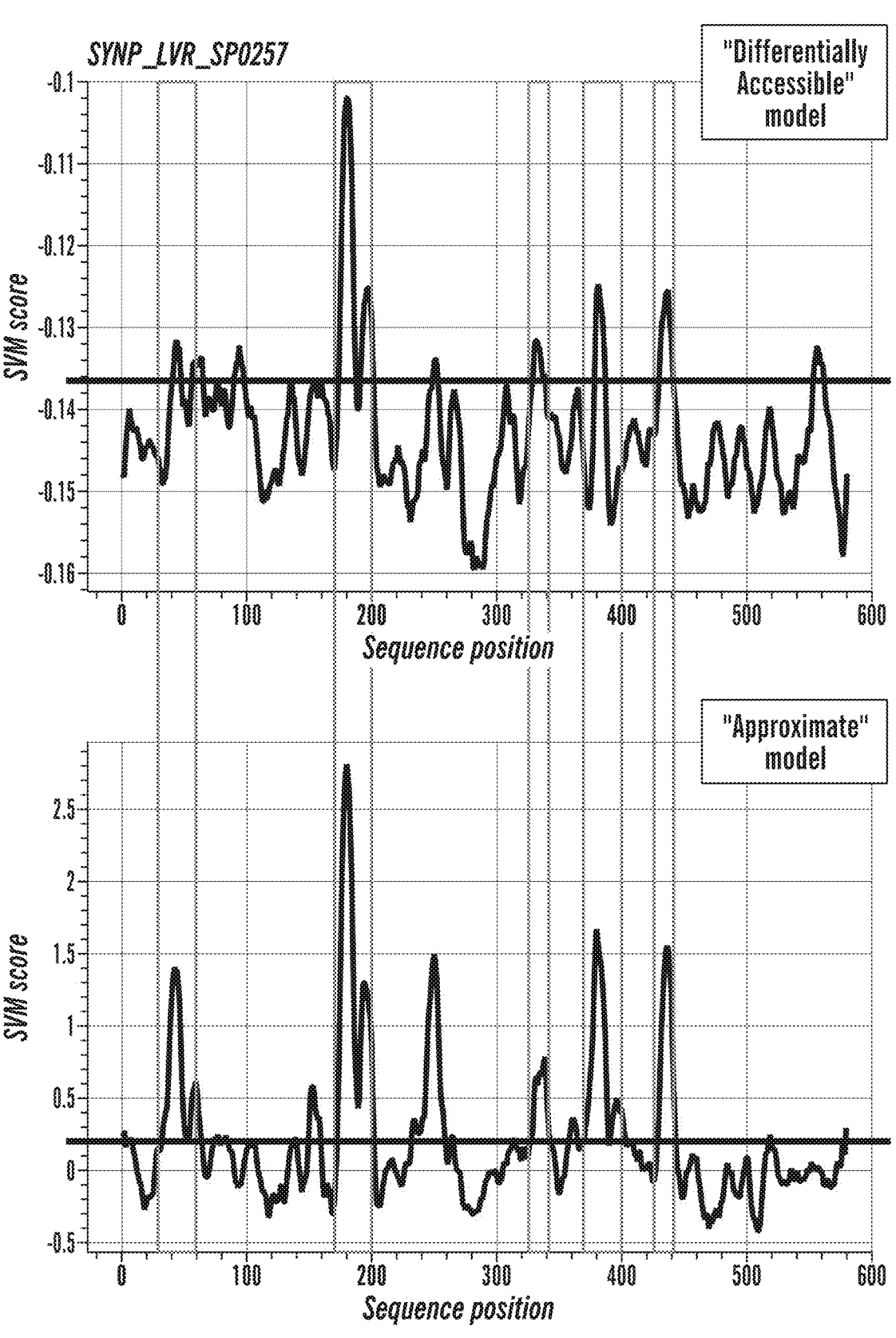

FIG. 28 is a series of line graphs showing the SVM scores for the "Differentially Accessible" model and the "Approximate" model for SYNP_LV_SP0257. Gray boxes show the regions identified as active by both models.

Figure 29:
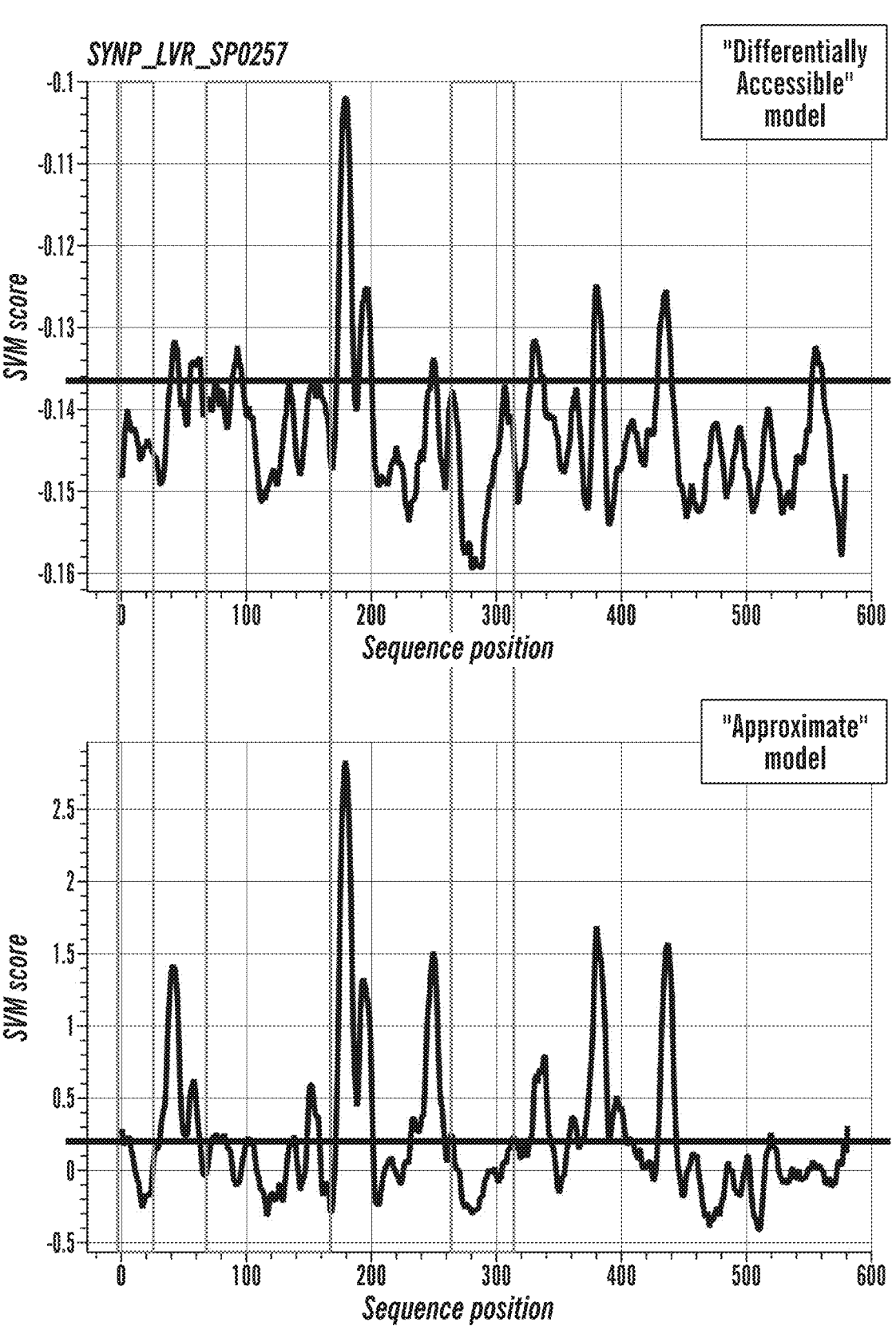

FIG. 29 is a series of line graphs showing the SVM scores for the "Differentially Accessible" model and the "Approximate" model for SYNP_LV_SP0257. Gray boxes show the regions identified as inactive by both models.

Figure 30:
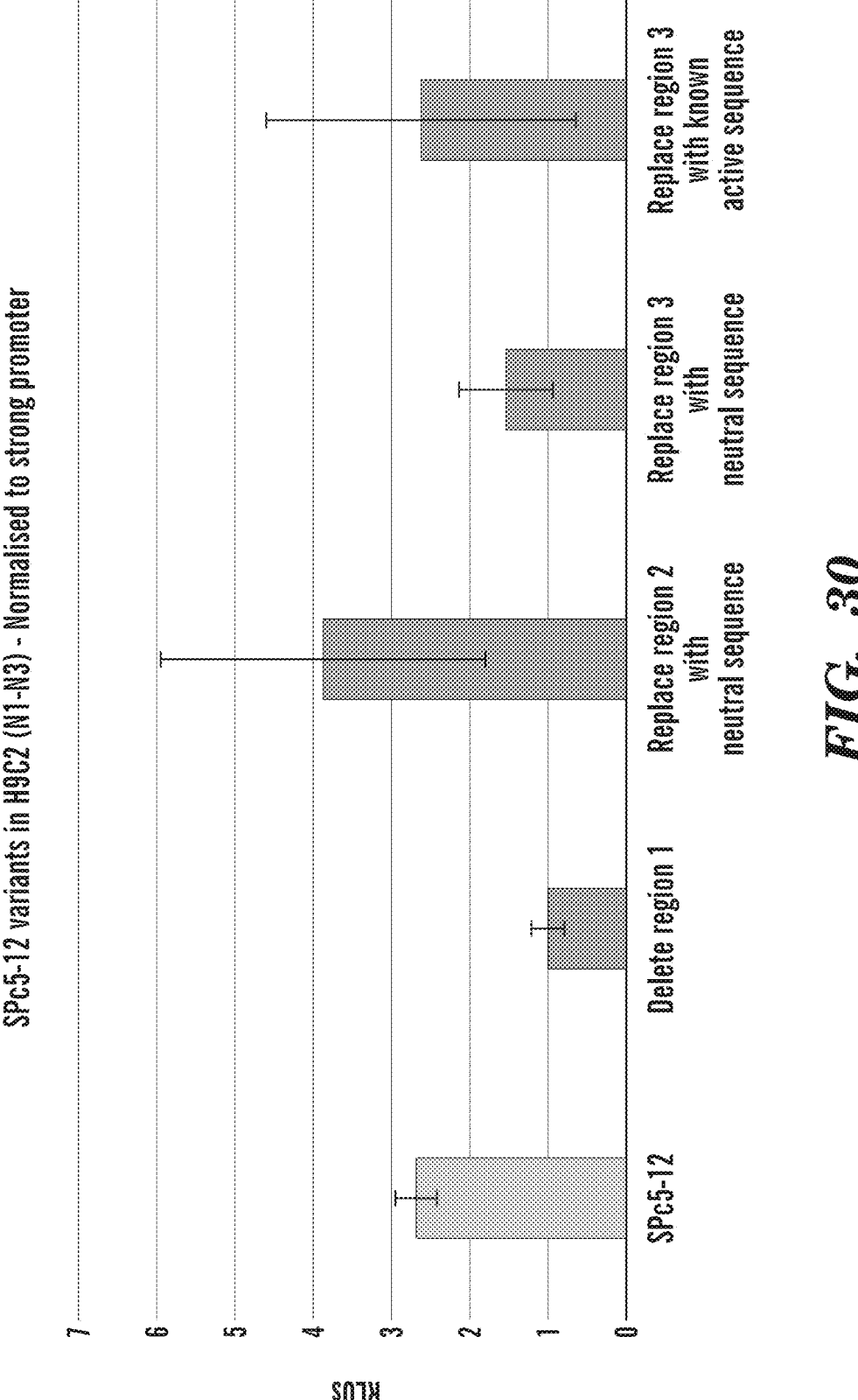

FIG. 30 is a bar graph showing the activity of SPc5-12 variants in H9C2 heart cells.

Figure 31:
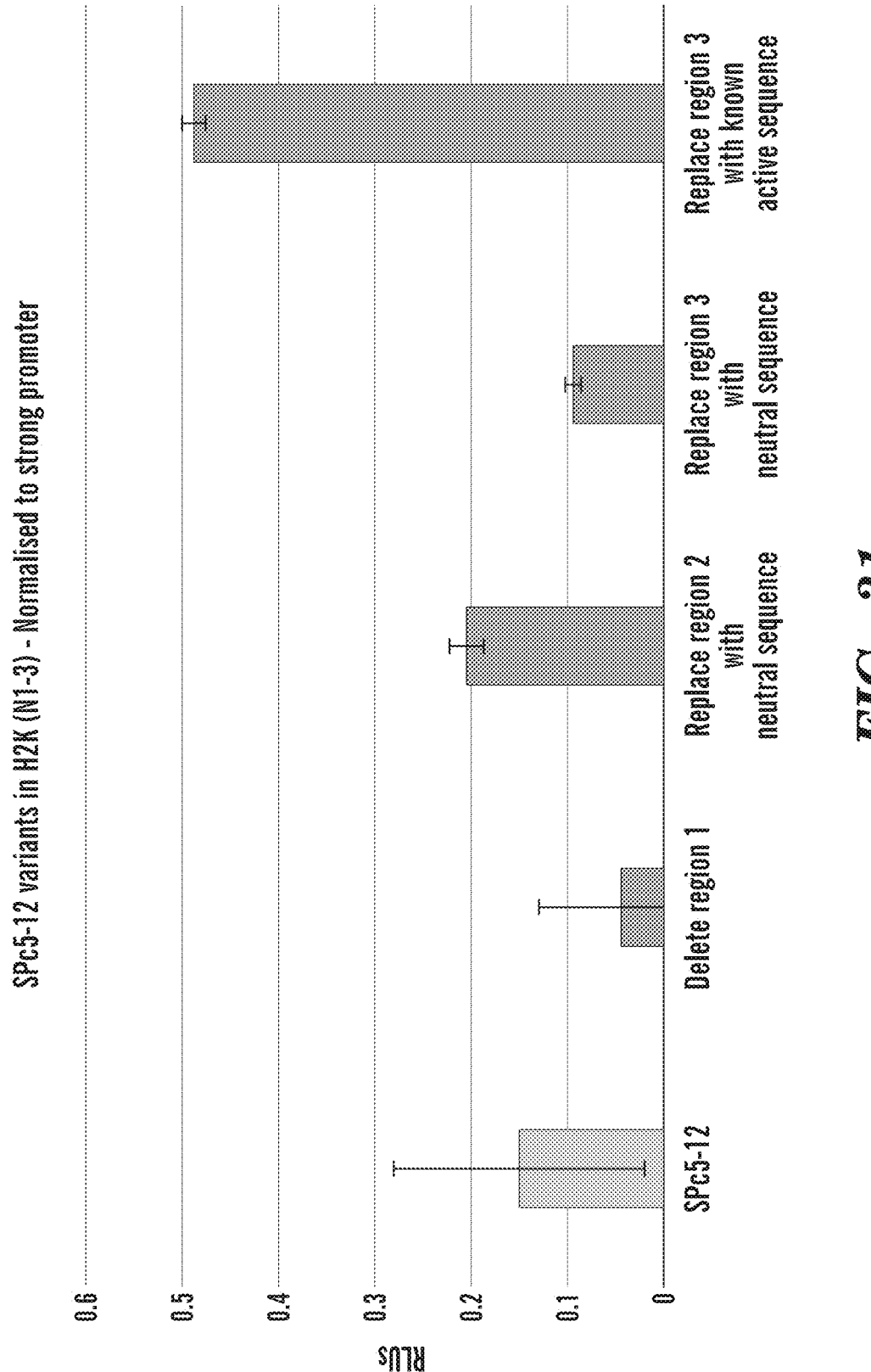

FIG. 31 is a bar graph showing the activity of SPc5-12 variants in H2K skeletal muscle cells.

DETAILED DESCRIPTION

The technology described herein is directed to systems and methods for synthetic regulatory sequence design or production. In several aspects described herein are methods of designing and optionally synthesizing shortened (or otherwise modified) polynucleotide sequences from polynucleotide sequences, optionally having known transcriptional regulatory functionality.

There are a number of reasons one would want to shorten regulatory sequences while either increasing or retaining some or all of the activity, as a non-limiting example AAV-based gene therapies. AAV is a relatively small virus: the packing limit of the therapeutic payload is approximately 4.5kb for the ssDNA AAV version (approximately 2.25 kb for the self-complementary AAV version). When considering AAV design, there is significant pressure to reduce the size of all the elements of the expression cassette; often the therapeutic gene alone takes up the majority of the space, and therefore every base is at a premium.

In terms of retaining or increasing expression, the consensus within the gene therapy field has previously been that it is preferable to administer a smaller dose of very highly active AAV particles expressing sufficient therapeutic protein to reach the therapeutic window. This is because infecting patients with larger doses of AAV can interfere with the therapy itself (e.g., the cells can start to silence the AAV) and cause side effects.

More recently, that view has been challenged, which is in part why having a range of expression strengths is also considered beneficial. This is especially true in situations where finer-grained gene control is required, e.g. gene circuits. Like all of the above, such shortened or otherwise modified regulatory sequences have general application beyond gene therapy.

Thus, the methods and systems described herein allow the design or production of nucleic acid compositions or viral vectors with tissue or cell-specific expression. Accordingly, further described herein, are isolated nucleic acid modules and viral vectors, comprising said shortened (or otherwise modified) polynucleotide as designed or synthesized herein.

Methods of Designing or Synthesizing a Synthetic Polynucleotide

In one aspect, described herein is a method of designing a synthetic polynucleotide with transcriptional regulatory functionality, the method comprising: (a) receiving a set of genetic data comprising a regulatory polynucleotide sequence, optionally having a known transcriptional regulatory functionality; (b) processing the set of genetic data into a set of sequence elements that each comprise a portion of the polynucleotide sequence; (c) processing the set of sequence elements with a machine learning model to determine a transcriptional regulatory score associated with each of the set of sequence elements; (d) identifying at least one sequence element of the set of sequence elements comprising a transcriptional regulatory score below a threshold as a non-regulatory sequence element; and (e) designing a modified polynucleotide molecule based on the determined transcriptional regulatory scores and/or identified non-regulatory sequence elements. In some embodiments of any of the aspects, the designed modified polynucleotide molecule is synthesized.

In another aspect, described herein is a method of synthesizing a synthetic polynucleotide with transcriptional regulatory functionality, the method comprising: (a) receiving a set of genetic data comprising a regulatory polynucleotide sequence, optionally having a known transcriptional regulatory functionality; (b) processing the set of genetic data into a set of sequence elements that each comprise a portion of the polynucleotide sequence; (c) processing the set of sequence elements with a machine learning model to determine a transcriptional regulatory score associated with each of the set of sequence elements; (d) identifying at least one sequence element of the set of sequence elements comprising a transcriptional regulatory score below a threshold as a non-regulatory sequence element; (e) designing a modified polynucleotide molecule based on the determined transcriptional regulatory scores and/or identified non-regulatory sequence elements; and (f) synthesizing the modified polynucleotide molecule.

In yet another aspect, described herein is a method of designing a synthetic polynucleotide with transcriptional regulatory functionality, the method comprising: (a) receiving a set of genetic data comprising a regulatory polynucleotide sequence, optionally having a known transcriptional regulatory functionality; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; and (f) designing a modified polynucleotide molecule based on the determined transcriptional regulatory scores and/or identified non-regulatory sequence elements. In some embodiments of any of the aspects, the designed modified polynucleotide molecule is synthesized.

In yet another aspect, described herein is a method of synthesizing a synthetic polynucleotide with transcriptional regulatory functionality, the method comprising: (a) receiving a set of genetic data comprising a regulatory polynucleotide sequence, optionally having a known transcriptional regulatory functionality; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (f) synthesizing the modified polynucleotide molecule.

In another aspect, described herein is a method of designing a synthetic polynucleotide with transcriptional regulatory functionality, the method comprising: (a) receiving a set of genetic data comprising a regulatory polynucleotide sequence, optionally having a known transcriptional regulatory functionality; (b) processing the polynucleotide sequence into a first set of sequence elements, wherein the first set of sequence elements comprises at least one subset of sequence elements corresponding to all k-mer fragments comprising a selected nucleotide position of the polynucleotide sequence; (c) training a machine learning model using a second set of sequence elements that comprise portions of transcriptional regulatory elements and non-regulatory elements; (d) generating a third set of sequence elements comprising all k-mer fragments of the same length as the k-mer fragments of the first set of sequence elements; (e) processing the third set of sequence elements with the machine learning model to determine a transcriptional regulatory score associated with each sequence element of the third set of sequence elements, wherein the transcriptional regulatory score is stored in a database referenced to a k-mer fragment; (f) determining the transcriptional regulatory score of each k-mer fragment in a subset by assigning the transcriptional regulatory score of the matching k-mer fragment from the database; (g) determining the transcriptional regulatory score of at least one nucleotide position comprising averaging all transcriptional regulatory scores of all k-mers fragments in the corresponding subset; (h) identifying at least one region of nucleotide positions comprising transcriptional regulatory scores at or above a threshold as a regulatory sequence element; (i) identifying at least one region of nucleotide positions that is not a regulatory sequence element as a non-regulatory sequence element; and (j) designing a modified polynucleotide molecule based on the determined transcriptional regulatory scores and/or identified non-regulatory sequence elements. In some embodiments of any of the aspects, the designed modified polynucleotide molecule is synthesized.

In another aspect, described herein is a method of synthesizing a synthetic polynucleotide with transcriptional regulatory functionality, the method comprising: (a) receiving a set of genetic data comprising a regulatory polynucleotide sequence, optionally having a known transcriptional regulatory functionality; (b) processing the polynucleotide sequence into a first set of sequence elements, wherein the first set of sequence elements comprises at least one subset of sequence elements corresponding to all k-mer fragments comprising a selected nucleotide position of the polynucleotide sequence; (c) training a machine learning model using a second set of sequence elements that comprise portions of transcriptional regulatory elements and non-regulatory elements; (d) generating a third set of sequence elements comprising all k-mer fragments of the same length as the k-mer fragments of the first set of sequence elements; (e) processing the third set of sequence elements with the machine learning model to determine a transcriptional regulatory score associated with each sequence element of the third set of sequence elements, wherein the transcriptional regulatory score is stored in a database referenced to a k-mer fragment; (f) determining the transcriptional regulatory score of each k-mer fragment in a subset by assigning the transcriptional regulatory score of the matching k-mer fragment from the database; (g) determining the transcriptional regulatory score of at least one nucleotide position comprising averaging all transcriptional regulatory scores of all k-mers fragments in the corresponding subset; (h) identifying at least one region of nucleotide positions comprising transcriptional regulatory scores at or above a threshold as a regulatory sequence element; (i) identifying at least one region of nucleotide positions that is not a regulatory sequence element as a non-regulatory sequence element; (j) designing a modified polynucleotide molecule based on the determined transcriptional regulatory scores and/or identified non-regulatory sequence elements; and (k) synthesizing the modified polynucleotide molecule.

FIG. 15-17 illustrate an example of a method for designing 380 or optionally synthesizing 390 a modified (e.g., shortened, replaced, mutated) polynucleotide sequence. FIG. 15 illustrates an example of a method to generate 150 a database of transcriptional regulatory scores. First, genetic data (e.g., the second set of sequence elements as described herein) is received 100. The genetic data received 100 can comprise portions of transcriptional regulatory elements and non-regulatory elements, as described further herein. The parameters of a machine learning model are then determined 110. In some embodiments of any of the aspects, said parameters can comprise the parameters of the machine learning model itself (e.g., SVM) and/or the parameters of a kernel (e.g., gapped k-mer kernel, k-DNF k-mer kernel) comprised by the machine learning model. In some embodiments of any of the aspects, determining the model parameters can comprise training the model with various different combinations of parameter values and selecting the parameter values resulting in the best and/or preferred output. After determining the (e.g., preferred) parameters of the machine learning model, the machine learning model is then trained 120 using the input genetic data 100 and the determined model parameters 110. Next, another set of genetic data (e.g., the third set of sequence elements as described herein) is received 130 or alternatively generated, as described herein. The trained machine learning model 120 outputs 140 a transcriptional regulatory score for input 130 of genetic data. The output 140 scores are stored 150 in a database (see e.g., FIG. 15).

FIG. 16 illustrates an example of a method to generate 250 a plot of nucleotide position scores using the 150 database of scores. First, genetic data (e.g., a polynucleotide sequence as described herein) is received 200. Then, a nucleotide position in the genetic data is selected 210. Next, the genetic data is processed 220 into sequence elements (e.g., a subset of sequence elements of the first set of sequence elements as described herein). Using 150 the database of scores, a score is determined 230 for each sequence element. Next, a score is determined 240 for the nucleotide position. Then, the score for the nucleotide position is plotted 250. The process is repeated 260 for a different nucleotide position in the genetic data. In some embodiments of any of the aspects, the process is repeated 265 for each mutation (e.g., A, G, T, C) of the nucleotide position. Then, each subsequent score is added 250 to the plot (see e.g., FIG. 16).

FIG. 17A-17B illustrate examples of a method for designing 380 or optionally synthesizing 390 a modified polynucleotide sequence using the generated 250 plot. FIG. 17A illustrates an example of a method for designing 380 or optionally synthesizing 390 a modified (e.g., shortened or replaced) polynucleotide sequence. First, a threshold is set 300, and a window is set 320. Using the 250 plot of nucleotide position scores, the nucleotide position(s) having a score greater than the threshold 300 are determined 310. Next, the region(s) having a length greater than the window 320 and where all scores are determined 310 to be greater than the threshold are identified 330. Such region(s) are designated 340 as "regulatory sequence element." Next, at least one "non-regulatory sequence element" (e.g., not a regulatory sequence element 340; e.g., below the threshold 300) is selected 350. The at least one selected 350 non-regulatory sequence element is deleted or replaced 360. Then, steps 200-260 and 300-340 are repeated using the modified (e.g., shortened or replaced) sequence as the 200 genetic data input. If the regulatory sequence elements identified 340 in the modified (e.g., shortened or replaced) sequence are shorter than the original regulatory sequence elements identified 340 in the parent sequence, then the modified (e.g., shortened or replaced) sequence design is rejected 370. If the sequence is rejected 370, then a different set of non-regulatory elements are deleted or replaced 360. If the regulatory sequence elements identified 340 in the modified (e.g., shortened or replaced) sequence are the same length or longer than the regulatory sequence elements identified 340 in the parent (i.e., original) sequence, then the modified (e.g., shortened or replaced) sequence design is accepted 380. If the sequence design is accepted 380, then the designed sequence can optionally be synthesized 390.

FIG. 17B illustrates an example of a method for designing 380 or optionally synthesizing 390 a modified (e.g., mutated) polynucleotide sequence. First, a threshold is set 300, and a window is set 320. Using the 250 plot of nucleotide position scores, which includes the determined 265 scores for each mutated nucleotide position, the nucleotide position(s) having a score greater than the threshold 300 are determined 310. Next, the region(s) having a length greater than the window 320 and where all scores are determined 310 to be greater than the threshold are identified 330. Such region(s) are designated 340 as "regulatory sequence element." Next, at least one nucleotide position is selected 355. The at least one selected 355 nucleotide position is mutated 365. Then, steps 200-260 and 300-340 are repeated using the modified (e.g., mutated) sequence as the 200 genetic data input. If the regulatory sequence elements identified 340 in the modified (e.g., mutated) sequence are shorter than the regulatory sequence elements identified 340 in the parent (i.e., original) sequence, then the modified (e.g., mutated) sequence design is rejected 370. If the sequence is rejected 370, then a different nucleotide position(s) is mutated 365. If the regulatory sequence elements identified 340 in the modified (e.g., mutated) sequence are the same length or longer than the regulatory sequence elements identified 340 in the parent (i.e., original) sequence, then the modified (e.g., mutated) sequence design is accepted 380. If the sequence design is accepted 380, then the designed sequence can optionally be synthesized 390.

In some embodiments of any of the aspects, a method for designing 380 or optionally synthesizing 390 a mutated polynucleotide sequence does not necessarily comprise rerunning the model (e.g., repeating steps 200-260 and 300-340 for the modified sequence). In some embodiments of any of the aspects, the effects of individual mutations can be determined from the plot itself. Accordingly, in some embodiments of any of the aspects, the mutation method comprises identifying at least one nucleotide position with a higher mutated score than the original sequence using the methods as described herein; the nucleotide position can be in regulatory sequence element or in a non-regulatory sequence element. In some embodiments of any of the aspects, mutating at a specific nucleotide position can lead to a chain of mutation steps, wherein each change produces a new plot with a new suggested mutation(s) within the same peak. Such a method of mutating and replotting is repeated until the model converges or does not result in mutation predictions with a higher score than the current nucleotide. In some embodiments of any of the aspects, the mutation process can comprise replacing a larger sequence section (e.g., 10 bp-30 bp) with mutations, wherein the score of each nucleotide position is maintained at, around, or above the threshold.

Polynucleotide Sequence

In some embodiments of any of the aspects, methods of designing or synthesizing a synthetic polynucleotide with transcriptional regulatory functionality comprise receiving a set of genetic data. In some embodiments of any of the aspects, the set of genetic data comprises a regulatory polynucleotide sequence, optionally having a known transcriptional regulatory functionality. As used herein, the term "polynucleotide" refers to a nucleic acid comprising multiple nucleotide monomers covalently bonded in a chain. In some embodiments of any of the aspects, the polynucleotide is at least 13 nucleotides long. In some embodiments of any of the aspects, the polynucleotide is at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 250, at least 300, at least 350, at least 400, at least 450, at least 500, at least 550, at least 600, at least 650, at least 700, at least 750, at least 800, at least 850, at least 900, at least 950, or at least 1000 nucleotides long.

As used herein the term "transcriptional regulatory function" refers to the control of the conversion of genomic DNA to RNA. As used herein the term "known transcriptional regulatory function" indicates that the function is known in the art and/or can be readily identified by a skilled practitioner. In some embodiments of any of the aspects, the known transcriptional regulatory functionality is detected by a method as described herein. In some embodiments of any of the aspects, the known transcriptional regulatory functionality comprises transcriptional activation, i.e., an increase compared to baseline in the conversion of genomic DNA to RNA of a particular gene or set of genes of interest. In some embodiments of any of the aspects, the known transcriptional regulatory functionality comprises transcriptional repression, i.e., a decrease compared to baseline in the conversion of genomic DNA to RNA of a particular gene or set of genes of interest.

In some embodiments of any of the aspects, the known transcriptional regulatory functionality comprises promoter activity. In some embodiments of any of the aspects, the known transcriptional regulatory functionality comprises enhancer activity. In some embodiments of any of the aspects, promoter activity comprises a level of expression of a particular gene or a particular set of genes. As used herein, the term promoter activity is understood to comprise the activity of enhancers, CREs, core promoter, etc.

In some embodiments of any of the aspects, a regulatory polynucleotide sequence, optionally having a known transcriptional regulatory functionality comprises a cis-regulatory element. In some embodiments of any of the aspects, the polynucleotide sequence with a known transcriptional regulatory functionality is selected from the group consisting of a promoter, an enhancer, an insulator, a silencer, a locus control region, or any known cis-regulatory element. In some embodiments of any of the aspects, the polynucleotide sequence with a known transcriptional regulatory functionality is a known enhancer (i.e., known in the art or readily identified by a skilled practitioner). In some embodiments of any of the aspects, the polynucleotide sequence with a known transcriptional regulatory functionality is a known promoter.

In some embodiments of any of the aspects, the known transcriptional regulatory functionality is in any given cell or tissue type. As a non-limiting example, the cell or tissue type can be any cell or tissue type within an organism. In some embodiments of any of the aspects, the known transcriptional regulatory functionality is in any given cell or tissue type selected from the group consisting of the nervous system, central nervous system, brain, cerebrum, cerebral hemispheres, diencephalon, the brainstem, midbrain, pons, medulla oblongata, cerebellum, the spinal cord, the ventricular system, choroid plexus, peripheral nervous system, nerves, cranial nerves, spinal nerves, ganglia, enteric nervous system, sensory organs, sensory system, eye, cornea, ins, ciliary body, lens, retina, ear, outer ear, earlobe, eardrum, middle ear, ossicles, inner ear, cochlea, vestibule of the ear, semicircular canals, olfactory epithelium, tongue, taste buds, integumentary system, mammary glands, skin, subcutaneous tissue, immune system, muscular system, musculoskeletal system, bone, human skeleton, joints, ligaments, tendons, digestive system, mouth, teeth, tongue, salivary glands, parotid glands, submandibular glands, sublingual glands, pharynx, esophagus, stomach, small intestine, duodenum, jejunum, ileum, large intestine, liver, gallbladder, mesentery, pancreas, anal canal and anus, blood cells, respiratory system, nasal cavity, pharynx, larynx, trachea, bronchi, lungs, diaphragm, urinary system, kidneys, ureter, bladder, urethra, reproductive organs, female reproductive system, internal reproductive organs, ovaries, fallopian tubes, uterus, vagina, external reproductive organs, vulva, clitoris, placenta, male reproductive system, internal reproductive organs, testes, epididymis, vas deferens, seminal vesicles, prostate, bulbourethral glands, external reproductive organs, penis, scrotum, endocrine system, pituitary gland, pineal gland, thyroid gland, parathyroid glands, adrenal glands, pancreas, circulatory system, heart, patent foramen ovale, arteries, veins, capillaries, lymphatic system, lymphatic vessel, lymph node, bone marrow, thymus, spleen, gut-associated lymphoid tissue, tonsils, interstitium, skeletal muscle, cardiac muscle, smooth muscle, epithelium, epidermis, dermis, hypodermis, connective tissue, adipose tissue, areolar tissue, and cartilage.

In some embodiments of any of the aspects, the known transcriptional regulatory functionality is in liver cells. In some embodiments of any of the aspects, the known transcriptional regulatory functionality is in cardiac muscle cells. In some embodiments of any of the aspects, the known transcriptional regulatory functionality is in skeletal muscle cells. In some embodiments of any of the aspects, the known transcriptional regulatory functionality is in cardiac muscle cells and skeletal muscle cells.

In some embodiments of any of the aspects, the known transcriptional regulatory functionality is specific to a tissue or cell type. In some embodiments of any of the aspects, the polynucleotide sequences with known transcriptional regulatory functionality are differentially (e.g., increased) accessible in a tissue or cell type compared to other tissue or cell types (see e.g., Example 5, FIG. 25-29). Chromatin accessibility can be determined using assays including DNase I hypersensitive site (DHS) assay, Assay for Transposase-Accessible Chromatin using sequencing (ATAC-seq), or other chromatin accessibility detection methods known in the art.

In some embodiments of any of the aspects, the polynucleotide sequence(s) with known transcriptional regulatory functionality are accessible or have increased accessibility in the tissue or cell type of interest compared to tissue or cell types not of interest. In some embodiments of any of the aspects, the polynucleotide sequence(s) with known transcriptional regulatory functionality are inaccessible or have decreased accessibility in tissue or cell types not of interest compared to the tissue or cell type of interest. In some embodiments of any of the aspects, the known transcriptional regulatory functionality of the polynucleotide sequence is present or increased in the tissue or cell type of interest compared to tissue or cell types not of interest. In some embodiments of any of the aspects, the known transcriptional regulatory functionality of the polynucleotide sequence is absent or decreased in tissue or cell types not of interest compared to the tissue or cell type of interest.

K-mers

In some embodiments of any of the aspects, methods of designing or synthesizing a synthetic polynucleotide with transcriptional regulatory functionality comprise processing a set of genetic data into a set of sequence elements that each comprise a portion of the polynucleotide sequence. In some embodiments of any of the aspects, methods of designing or synthesizing a synthetic polynucleotide with transcriptional regulatory functionality comprise identifying an enhancer portion of the polynucleotide sequence and processing the enhancer portion into a set of sequence elements. In some embodiments of any of the aspects, a sequence element comprises a k-mer fragment of the enhancer portion of the polynucleotide sequence.

As used herein, the term "k-mer" (also referred to interchangeably as kmer, K-mer, k-mer fragment, etc.) refers to a nucleotide sequence of a specified length, denoted by k. As a non-limiting example, k can equal 2, 3, 4, 5, 6, 7, 8, 9, 10, 11, 12, 13, 14, 15, 16, 17, 18, 19, 20, 21, 22, 23, 24, 25, 26, 27, 28, 29, or 30. As another non-limiting example, the k-mer can be a 2-mer, 3-mer, 4-mer, 5-mer, 6-mer, 7-mer, 8-mer, 9-mer, 10-mer, 11-mer, 12-mer, 13-mer, 14-mer, 15-mer, 16-mer, 17-mer, 18-mer, 19-mer, 20-mer, 21-mer, 22-mer, 23-mer, 24-mer, 25-mer, 26-mer, 27-mer, 28-mer, 29-mer, or 30-mer. In certain preferred embodiments of any of the aspects, the k-mer is a 10-mer (i.e., a nucleotide sequence that is 10 nucleotides long). In some embodiments of any of the aspects, the k-mer is a fragment (i.e., shortened portion) of a longer nucleotide sequence and can thus be referred to as a k-mer fragment.

In some embodiments of any of the aspects, a machine learning model as described herein comprises a gapped k-mer kernel. In some embodiments of any of the aspects, a k-mer fragment comprises a gapped k-mer fragment. In some embodiments of any of the aspects, a kernel as described herein implicitly maps the gapped k-mer fragments. As used herein in the context of k-mers, the term "gap" refers to a position in the k-mer that can match any nucleotide (see e.g., FIG. 1). In some embodiments of any of the aspects, the gapped k-mer fragment comprises 1, 2, 3, 4, 5, 6, 7, 8, 9, or at least 10 gaps. In some embodiments of any of the aspects, 2 gaps can be adjacent. In some embodiments of any of the aspects, 2 gaps can be separated by 1, 2, 3, 4, 5, 6, 7, 8, 9, or at least 10 nucleotides. In certain preferred embodiments of any of the aspects, the gapped k-mer fragment comprises 4 gaps.

In some embodiments of any of the aspects, a machine learning model as described herein comprises a k-DNF k-mer kernel. In some embodiments of any of the aspects, the k-DNF k-mer kernel described herein works with DNA sequences of different lengths, and allows the number of gaps to range from L−1 to L-k, wherein L is the length of the k-mers and k is a model parameter. The parameter k is an integer such that k>0 and k<L. As a non-limiting example, for 10-mers using a given value of k in the k-DNF k-mer kernel, the number of gaps is 10-k+n where n is each integer in the range [0, k−1]. As such, the k-DNF k-mer kernel defines gapped k-mers with 10-k+n gaps where the non-gapped positions are all possible combinations of (k-n) positions in the original 10-mer. As a non-limiting example, with a set of 10-mers using a k-DNF k-mer kernel and k=3, the number of gaps in any gapped k-mer derived from one 10-mer selected from the set can be 7, 8, or 9 gaps.

First Set of Sequence Elements

In some embodiments of any of the aspects, methods of designing or synthesizing a synthetic polynucleotide with transcriptional regulatory functionality comprise receiving a set of genetic data comprising a regulatory polynucleotide sequence, optionally having a known transcriptional regulatory functionality. In some embodiments of any of the aspects, the method comprises processing the polynucleotide sequence into a first set of sequence elements. In some embodiments of any of the aspects, the first set of sequence elements comprises at least one subset of sequence elements corresponding to all k-mer fragments comprising a selected nucleotide position of the polynucleotide sequence.

In some embodiments of any of the aspects, each of the k-mer fragments of the first set of sequence elements comprises a gapped k-mer fragment. In some embodiments of any of the aspects, the first set of sequence elements comprises all possible 10-mers of a regulatory polynucleotide sequence, optionally having a known transcriptional regulatory functionality. In some embodiments of any of the aspects, each gapped k-mer fragment of the first set of sequence elements comprises a 10 nucleotide-long fragment comprising 4 gaps.

In some embodiments of any of the aspects, the step of processing the polynucleotide sequence comprises processing the polynucleotide sequence into subsets of sequence elements. In some embodiments of any of the aspects, the step of processing the polynucleotide sequence into subsets of sequence elements comprises selecting a nucleotide position of the polynucleotide sequence and generating all k-mer fragments comprising the nucleotide position (see e.g., FIG. 3). In some embodiments of any of the aspects, a subset of sequence elements is produced for each nucleotide position of the polynucleotide sequence. In some embodiments of any of the aspects, a subset of sequence elements is produced for specific nucleotide positions of the polynucleotide sequence.

In some embodiments of any of the aspects, the first set of sequence elements comprises at least two subsets of sequence elements. As a non-limiting example, the first set of sequence elements comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, or at least 100 subsets of sequence elements. In some embodiments of any of the aspects, the first set of sequence elements comprises a subset of sequence elements corresponding to each nucleotide position of the polynucleotide sequence. In some embodiments of any of the aspects, the first set of sequence elements comprises a subset of sequence elements corresponding to specific nucleotide positions of the polynucleotide sequence.

Second Set of Sequence Elements

In some embodiments of any of the aspects, methods of designing or synthesizing a synthetic polynucleotide with transcriptional regulatory functionality comprise training a machine learning model using a second set of sequence elements. In some embodiments of any of the aspects, the second set of sequence elements comprise portions of transcriptional regulatory elements and non-regulatory elements. In some embodiments of any of the aspects, the transcriptional regulatory elements are labeled as "active" (or an equivalent) and such an "active" label is provided to the machine learning model during training. In some embodiments of any of the aspects, the non-transcriptional-elements are labeled as "inactive" (or an equivalent) and such an "inactive" label is provided to the machine learning model during training.

In some embodiments of any of the aspects, the portions of transcriptional regulatory elements of the second set of sequence elements comprise regions identified or known to those of skill in the art to be regulatory sequences (e.g., promoters, enhancers, etc.). In some embodiments of any of the aspects, the portions of transcriptional regulatory elements of the second set of sequence elements comprise regions identified as accessible chromatin. In some embodiments of any of the aspects, the regions identified as accessible chromatin comprise regions detected by DNase I hypersensitive site (DHS) assay, Assay for Transposase-Accessible Chromatin using sequencing (ATAC-seq), or other chromatin accessibility detection methods (e.g., DNase-seq, FAIRE-seq, MNase-seq, CHiP-seq).

DNase I hypersensitive sites (DHSs) are regions of chromatin that are sensitive to cleavage by the DNase I enzyme. In these specific regions of the genome, chromatin has lost its condensed structure, exposing the DNA and making it accessible. This increases the availability of DNA to degradation by enzymes, such as DNase I. These accessible chromatin zones are functionally related to transcriptional activity, since this remodeled state is necessary for the binding of proteins such as transcription factors. Since the discovery of DHSs, they have been used as markers of regulatory DNA regions. These regions have been shown to map many types of cis-regulatory elements including promoters, enhancers, insulators, silencers and locus control regions. Methods of determining DHSs, e.g., using DHS assays are well known in the art. See e.g., Wang et al., (2012) PLoS One 7: e42414.

A high-throughput measure of accessible chromatin regions is available through sequencing methods such as DNase-seq. DNase-seq (DNase I hypersensitive sites sequencing) is a method in molecular biology used to identify the location of regulatory regions, based on the genome-wide sequencing of regions sensitive to cleavage by DNase I. See e.g., Boyle et al. (2008) Cell 132 (2): 311-22; Crawford et al. (2006) Genome Research 16 (1): 230; Madrigal et al. (2012) Front Genet. 3: 230). FAIRE-Seq (Formaldehyde-Assisted Isolation of Regulatory Elements) is an alternative of DNase-seq for the genome-wide identification of accessible DNA regions in the genome; see e.g., Giresi et al. (2007). Genome Research. 17 (6): 877-85. Another alternative method for identifying accessible chromatin is MNase-seq (sequencing of micrococcal nuclease sensitive sites); see e.g., Pajoro et al., Methods Mol Biol. 2018; 1675:167-181.

Another method to identify accessible chromatin or regulatory regions is ChIP-sequencing, also known as ChIP-seq, which is a method used to analyze protein interactions with DNA. ChIP-seq combines chromatin immunoprecipitation (ChIP) with massively parallel DNA sequencing to identify the binding sites of DNA-associated proteins. It can be used to map global binding sites precisely for any protein of interest. See e.g., Johnson et al. (2007). "Genome-wide mapping of in vivo protein-DNA interactions" (PDF). Science. 316 (5830): 1497-1502.

ATAC-seq is a technique used in molecular biology to assess genome-wide chromatin accessibility. ATAC-seq identifies accessible DNA regions by probing open chromatin with hyperactive mutant Tn5 Transposase that inserts sequencing adapters into open regions of the genome. While naturally occurring transposases have a low level of activity, ATAC-seq employs the mutated hyperactive transposase. In a process called "tagmentation", Tn5 transposase cleaves and tags double-stranded DNA with sequencing adaptors. The tagged DNA fragments are then purified, PCR-amplified, and sequenced using next-generation sequencing. Sequencing reads can then be used to infer regions of increased accessibility as well as to map regions of transcription factor binding sites and nucleosome positions. The number of reads for a region correlate with how open that chromatin is, at single nucleotide resolution. Methods of ATAC-seq are well-known in the art; see e.g., Buenrostro et al. (2013), Nature Methods. 10 (12): 1213-8.; Buenrostro et al. (2015) Current Protocols in Molecular Biology. 109: 21.29.1-21.29.9.

In some embodiments of any of the aspects, the portions of transcriptional regulatory elements of the second set of sequence elements do not comprise core promoter regions or are not within 2 kilobases of a transcriptional start site (TSS). In some embodiments of any of the aspects, the portions of transcriptional regulatory elements of the second set of sequence elements do not comprise core promoter regions. Core promoter sequences are known to those of skill in the art or identifiable to those of skill in the art using methods as described herein and elsewhere. In some embodiments of any of the aspects, the portions of transcriptional regulatory elements of the second set of sequence elements are not within 2 kilobases (kb) of a transcriptional start site (TSS). As a non-limiting example, the portions of transcriptional regulatory elements of the second set of sequence elements are not within 0.5 kb, 1.0 kb, 1.5 kb, 2.0 kb, 2.5 kb, 3 kb, 3.5 kb, 4.0 kb, 4.5 kb, 5.0 kb, 5.5 kb, 6.0 kb, 6.5 kb, 7.0 kb, 7.5 kb, 8 kb, 8.5 kb, 9.0 kb, 9.5 kb, or at least 10.0 kb of a transcriptional start site (TSS). In some embodiments of any of the aspects, the portions of transcriptional regulatory elements of the second set of sequence elements do not comprise promoter regions and are not within 2 kilobases of a transcriptional start site (TSS).

In some embodiments of any of the aspects, the portions of transcriptional regulatory elements of the second set of sequence elements do not comprise regions detected by a chromatin accessibility assay (e.g., DHS assay, ATAC-seq, etc.) in greater than 30% of known sequences, e.g., sequences of human ENCODE cell lines. Such a constraint can allow for the selection of tissue-specific or cell-specific transcriptional regulatory elements, as opposed to transcriptional regulatory elements that are active in a majority of an organism. As a non-limiting example, the portions of transcriptional regulatory elements of the second set of sequence elements do not comprise regions detected by a chromatin accessibility assay (e.g., DHS assay, ATAC-seq, etc.) in greater than 1%, 5%, 10%, 15%, 20%, 25%, 30%, 35%, 40%, 45%, or 50% of known sequences, e.g., sequences of human ENCODE cell lines In some embodiments of any of the aspects, the portions of non-regulatory elements of the second set of sequence elements comprises shuffled sequences of the portions of transcriptional regulatory elements of the second set of sequence elements. In some embodiments of any of the aspects, the portions of non-regulatory elements of the second set of sequence elements comprises random nucleotide sequences. In some embodiments of any of the aspects, the portions of non-regulatory elements of the second set of sequence elements is generated using the genNullSeqs function (see e.g., Lee et al., 2015; Ghandi et al. 2014; Ghandi et al. 2016); uShuffle (see e.g., Jiang et al. (2008) BMC bioinformatics, 9, 192); BiasAway (see e.g., Worsley-Hunt et al. BMC Genomics. 2014 Jun. 13; 15:472); the code described in Altschul et al. Molecular Biology and Evolution, Volume 2, Issue 6, Nov. 1985, Pages 526-538; or any other method known the art that generates a set of random control sequence elements; the contents of each reference are incorporated herein by reference in their entireties.

In some embodiments of any of the aspects, the portions of transcriptional regulatory elements and non-regulatory elements of the second set of sequence elements are adjusted to 250 to 750 base pairs long. As a non-limiting example, the portions of transcriptional regulatory elements and non-regulatory elements of the second set of sequence elements are adjusted to approximately 250 bp, 300 bp, 350 bp, 400 bp, 450 bp, 460 bp, 470 bp, 480 bp, 490 bp, 500 bp, 510 bp, 520 bp, 530 bp, 540 bp, 550 bp, 600 bp, 700 bp or 750 bp long. In a preferred embodiment of any of the aspects, the portions of transcriptional regulatory elements and non-regulatory elements of the second set of sequence elements are adjusted to 500 base pairs long, e.g., by taking the midpoint of the sequence and including sequence comprising 250 nucleotides on both sides of the midpoint.

In some embodiments of any of the aspects, the portions of transcriptional regulatory elements comprise a similar GC content or similar nucleotide repeat composition as the portions of non-regulatory elements of the second set of sequence elements. In some embodiments of any of the aspects, the portions of transcriptional regulatory elements comprise a similar GC content as the portions of non-regulatory elements of the second set of sequence elements. As used herein, the term "GC content" refers (or guanine-cytosine content) refers to the percentage of nitrogenous bases in a DNA or RNA molecule that are either guanine (G) or cytosine (C). This measure indicates the proportion of G and C bases out of an implied four total bases, also including adenine and thymine in DNA and adenine and uracil in RNA. In some embodiments of any of the aspects, the GC content of the regulatory and non-regulatory elements of the second set of sequence elements is the same or similar (e.g., within +/−5%) and is approximately 5%, 10%, 15%, 20%, 25%, 30%, 35%, 40%, 45%, 50%, 55%, 60%, 65%, 70%, 75%, 80%, 85%, 90%, or 95%.

In some embodiments of any of the aspects, the portions of transcriptional regulatory elements comprise a similar nucleotide repeat composition as the portions of non-regulatory elements of the second set of sequence elements. As used herein, the term "nucleotide repeat composition" refers to a measurement of the number and length of sequences each comprising the same nucleotide (e.g., A, G, T, or C) or short nucleotide motif (e.g., repeating dinucleotide or repeating trinucleotide). In some embodiments of any of the aspects, the portions of transcriptional regulatory elements comprise a similar GC content and similar nucleotide repeat composition as the portions of non-regulatory elements of the second set of sequence elements.

Third Set of Sequence Elements

In some embodiments of any of the aspects, methods of designing or synthesizing a synthetic polynucleotide with transcriptional regulatory functionality comprise generating a third set of sequence elements. In some embodiments of any of the aspects, the third set of sequence elements comprises all k-mer fragments of the same length as the k-mer fragments of the first set of sequence elements. As a non-limiting example, with a first set of sequence elements comprising 10-mers, the third set of sequence elements comprises all possible 10-mers, i.e., 4^10 10-mers. As a non-limiting example, with a first set of sequence elements comprising 10-mers with 4 gaps, the third set of sequence elements comprises all possible 10-mers with 4 gaps.

Machine Learning Model

In some embodiments of any of the aspects, methods of designing or synthesizing a synthetic polynucleotide with transcriptional regulatory functionality comprise processing a set of sequence elements with a machine learning model to determine a transcriptional regulatory score associated with each of the set of sequence elements.

In some embodiments of any of the aspects, the machine learning model comprises a support vector machine. In machine learning, support-vector machines (SVMs, also referred to as support-vector networks) are supervised learning models with associated learning algorithms that analyze data used for classification and regression analysis. In some embodiments of any of the aspects, given a set of training examples each marked as belonging to one or the other of two categories, an SVM training algorithm builds a model that assigns new examples to one category or the other, making it a non-probabilistic binary linear classifier. In some embodiments of any of the aspects, given a set of training examples each marked as belonging to one or the other of two categories (e.g., transcriptional regulatory elements and non-regulatory elements), an SVM training algorithm builds a model that assigns a new example a non-binary score representing the model's confidence that the example falls into one or other of the two categories. In some embodiments of any of the aspects, an SVM model comprises a representation of the examples as points in space, mapped so that the examples of the separate categories are divided by a hyperplane such that the gap between points in different categories is maximized; new examples are then mapped into that same space and predicted to belong to a category based on the side of the hyperplane on which they fall. As used herein, the term "hyperplane" refers to a subspace whose dimension is one less than that of its ambient space, and the hyperplane separates the space into two half spaces; as a non-limiting example, if a space is 3-dimensional then its hyperplanes are the 2-dimensional planes, while if the space is 2-dimensional, its hyperplanes are the 1-dimensional lines. Examples of methods comprising SVM are known in the art. See e.g., Cortes et al (1995). "Support-vector networks" Machine Learning. 20 (3): 273-297; Ben-Hur et al. "Support vector clustering" (2001) Journal of Machine Learning Research. 2: 125-137.

In addition to performing linear classification, in some embodiments SVMs can efficiently perform a non-linear classification using what is referred to as a "kernel" (or a "kernel function"), implicitly mapping their inputs into high-dimensional feature spaces. As used herein, the term "kernel" refers a function permitting a pattern analysis method (e.g., SVM) to operate in a high-dimensional, implicit feature space without ever computing the coordinates of the data in that space, but rather by simply computing the inner products between the images of all pairs of data in the feature space. Methods comprising a kernel are typically computationally cheaper than the explicit computation of the coordinates. In some embodiments of any of the aspects, some form of kernel is can be used to allow the machine learning model (e.g., SVM, voted perceptron, etc.) to work with nucleic acid sequences.

In some embodiments of any of the aspects, the machine learning model (e.g., support vector machine) comprises a gapped k-mer kernel. As used herein, the term "gapped k-mer kernel" refers to a kernel that implicitly maps input sequence elements into a space of gapped k-mers comprising specific characteristics (e.g., 10-mer with 4 gaps). The gapped k-mer kernel does not explicitly convert the input k-mers into gapped k-mers; rather, the gapped k-mer kernel can compute the same value dot product value as done without the kernel, but using less computational power. In some embodiments of any of the aspects, the machine learning model comprises a gapped-k-mer kernel model SVM (gkm-SVM). In some embodiments of any of the aspects, the set of sequence elements are input into the support vector machine. In some embodiments of any of the aspects, the input into the SVM comprises each sequence element encoded as a vector of values (e.g., the values {1,2,3,4}; corresponding to the 4 nucleotide base values (e.g., A, G, T, C); any four values can be used in the vector as long as they correspond to the 4 nucleotide base values. As a non-limiting example, the specific k-mer fragments input into the support vector machine can comprise the first, second, or third set of sequence elements as described herein. See e.g., Ghandi et al. (2014) Enhanced regulatory sequence prediction using gapped k-mer features. PloS Computational Biology 10(7): e1003711, code available on the world wide web at github.com/mghandi/gkmSVM; Lee et al. (2015) A method to predict the impact of regulatory variants from DNA sequence. Nature Genetics 47(8):955-61, code available on the world wide web at beerlab.org/deltasvm/; Leslie C., Kuang R. (2004) Fast String Kernels using inexact matching for protein sequences. J. Mach. Learn. Res., 5, 1435-1455; WO 2016/183348A1; the contents of each of which are incorporated herein by reference in their entireties.

In some embodiments of any of the aspects, the machine learning model (e.g., support vector machine) comprises a k-DNF k-mer kernel, which is related to the k-DNF kernel. The k-DNF kernel (see e.g., Sadohara, 2001; Khardon et al., 2005) takes as input 2 vectors of the same length. The k-DNF kernel was originally defined so that each element of an input vector is a Boolean-valued feature, i.e. either 0 or 1, and a conjunction of length k is a logical conjunction (logical and) of k values selected from the vector. In this case the k-DNF kernel calculates the value of the dot product of its inputs when they are mapped into the space of all possible conjunctions of length k or less. That is, it counts the number of conjunctions of length k or less which are true in both input vectors x and y, which amounts to calculating $$\sum_{i=1}^{k} \binom{\text{same}(x, y)}{i}$$

where same(x,y)=number of original features that have the same value in x and y, i.e. the number of bit positions j which have $x_j = y_j$.

The k-DNF kernel generalizes to operate on vectors whose values range across more than 2 integers (see e.g., Mourão et al., 2012, Learning STRIPS operators from noisy and incomplete observations. In Proceedings of the Twenty Eighth Conference on Uncertainty in Artificial Intelligence (UAI 2012) (pp. 614-623)), in particular to vectors with 4 values as in the case of DNA sequences. In this case the k-DNF kernel counts the number of combinations of k or fewer vector elements which have the same values in both input vectors x and y, which as before means calculating Formula 1, where same(x,y) equals the number of original features that have the same value in x and y, i.e. the number of positions j which have $x_j = y_j$.

$$\sum_{i=1}^{k} \binom{\text{same}(x, y)}{i} \tag{1}$$

The k-DNF kmer kernel is a generalization of both the k-DNF kernel approach (which works with single binary vectors), and the gapped kmer kernel approach (which specifies only one value for the number of gaps in the kmer). The k-DNF kmer kernel employs the same tactic the gapped-kmer kernel uses to work with input vectors of different lengths, by repeating a calculation across all pairs of kmers where one kmer in each pair comes from one input vector, and the other kmer from the other input vector. The k-DNF kmer kernel calculates the k-DNF kernel for each pair of kmers, and then sums the results to produce a final value, i.e. for input vectors x and y it calculates Formula 2, where kmers(x)=the set of all kmers in x, and same(x,y) is as defined above.

$$\sum_{a \in kmers(x)} \sum_{b \in kmers(y)} \sum_{i=1}^{k} \binom{\text{same}(a, b)}{i} \tag{2}$$

Similar to the gapped kmer kernel, the k-DNF kmer kernel works with features which are likely to be relevant in determining whether or not a DNA sequence is an active promoter, namely combinations of subsequences of kmers, which should coincide with TFBSs.

In terms of computation the k-DNF kmer kernel is not much more demanding than the gapped kmer kernel (which calculates Formula 3 for parameters kmer length=l, number of gaps=k) as the calculation of same(a,b) is common to both and dominates the calculation time. However, as it has more features than the gapped kmer kernel, the k-DNF kmer kernel may produce better results. Additionally, previous work (see e.g., Mourão et al., 2012) showed that in some domains the k-DNF kernel does not produce increasingly better results with higher values of k, so the k-DNF kernel model may produce better results with longer kmers (e.g. length=20), by working with shorter conjunctions (e.g. k=3).

$$\sum_{a \in kmers(x)} \sum_{b \in kmers(y)} \binom{\text{same}(a, b)}{l - k} \tag{3}$$

The k-DNF k-mer kernel described herein works with DNA sequences of different lengths, and given a chosen value k<L allows the number of gaps to range from L-k to L-l, wherein L is the length of the k-mers. Accordingly, in some embodiments of any of the aspects, the support vector machine comprises a k-DNF k-mer kernel.

In some embodiments of any of the aspects, the machine learning model can be modified. In some embodiments of any of the aspects, the machine learning model can comprise a voted perceptron as, without wishing to be bound by theory, it is expected to produce similar results, e.g., in combination with the gapped k-mer kernel or k-DNF k-mer kernel as described further herein. In some embodiments of any of the aspects, the machine learning model can comprise any kernelizable model as known in the art, e.g., in combination with the gapped k-mer kernel or k-DNF k-mer kernel as described further herein. In some embodiments of any of the aspects, the kernel functions (e.g., k-mer kernel or gapped k-mer kernel) can be replaced with, as a non-limiting example, combinations of string kernels, spectrum kernel etc., or with another kernel as known in the art.

Processing Sequence Elements

In some embodiments of any of the aspects, processing a set of sequence elements comprises training a machine learning model, i.e., processing the machine learning model with a training data set. During training, the machine learning model learns parameters of a calculation whose result can be used to classify sequences as a regulatory element or as a non-regulatory element. In some embodiments of any of the aspects, the training data set comprises the second set of sequence elements (e.g., comprising portions of transcriptional regulatory elements and non-regulatory elements). In some embodiments of any of the aspects, training a machine learning model comprises inputting the second set of sequence elements to generate, e.g., to generate a set of rules or value functions. After the machine learning model has processed the training data set (e.g., the second set of sequence elements), it can be referred to as a trained model (e.g., a trained SVM). In some embodiments of any of the aspects, the trained machine learning model is configured to return a transcriptional regulatory score (e.g., as opposed to a binary classification).

As used herein, the term "transcriptional regulatory score" (also referred to as a score or a "decision function") refers to a positive or negative value, corresponding to the distance between an element in the test data set (e.g., the third set of sequence elements) and the trained model's hyperplane separating the two training groups (e.g., the portions of transcriptional regulatory elements and non-regulatory elements of the second set of sequence elements). The transcriptional regulatory score corresponds to the degree of confidence the model has that the tested point (e.g., sequence) is in one or the other category. The sign of the score has no bearing on the degree of similarity. In some embodiments of any of the elements, the transcriptional regulatory score can be any positive or negative number. As a non-limiting example, the greater in value a score is for a sequence element of the third set, the greater the model's confidence that it belongs to a specific category (e.g., transcriptional regulatory elements), and, e.g., the higher its predicted transcriptional regulatory function. As another non-limiting example, the lesser in value a score is for a sequence element of the third set, the lesser the model's confidence that it belongs to a specific category (e.g., transcriptional regulatory elements), and, e.g., the lower its predicted transcriptional regulatory function.

In some embodiments of any of the aspects, processing a set of sequence elements comprises outputting scores for a test data set based on the trained machine learning model. In some embodiments of any of the aspects, the test data set comprises the third set of sequence elements (e.g., comprising all possible k-mers of a specific length or gap frequency). In some embodiments of any of the aspects, the method comprises processing the third set of sequence elements with the machine learning model to determine a transcriptional regulatory score associated with each sequence element of the third set of sequence elements. In some embodiments of any of the aspects, the transcriptional regulatory score (e.g., of each k-mer in the third set of sequence elements) is stored in a database referenced to a k-mer fragment. As a non-limiting example, the database can comprise a look-up table.

In some embodiments of any of the aspects, the method of designing or synthesizing a synthetic polynucleotide with transcriptional regulatory function comprises determining the transcriptional regulatory score of each k-mer fragment in a subset, e.g., a subset of the first set of sequence elements. In some embodiments of any of the aspects, the transcriptional regulatory score of each k-mer fragment in a subset is determined by assigning the transcriptional regulatory score of the matching k-mer fragment (e.g., from the third set of sequence elements) from the database (e.g., look-up table).

In some embodiments of any of the aspects, a transcriptional regulatory score is determined for each nucleotide position corresponding to each subset of sequence elements (e.g., of the first set of sequence elements; e.g., from the polynucleotide, optionally having known transcriptional regulatory function). In some embodiments of any of the aspects, the method of designing or synthesizing a synthetic polynucleotide comprises determining the transcriptional regulatory score of at least one nucleotide position in the original polynucleotide sequence. In some embodiments of any of the aspects, determining the transcriptional regulatory score of at least one nucleotide position in the original polynucleotide sequence comprises averaging all transcriptional regulatory scores of all sequence elements (e.g., k-mer fragments) in the subset corresponding to that specific nucleotide position (see e.g., FIG. 3). In some embodiments of any of the aspects, determining the transcriptional regulatory score of at least one nucleotide position in the original polynucleotide sequence comprises summing all transcriptional regulatory scores of all sequence elements (e.g., k-mers fragments) in the subset corresponding to that specific nucleotide position.

In some embodiments of any of the aspects, a transcriptional regulatory score is determined for at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 125, at least 150, at least 200, at least 250, at least 300, at least 350, at least 400, at least 450, or least 500 nucleotide positions in the original polynucleotide sequence. In some embodiments of any of the aspects, the transcriptional regulatory score for each nucleotide position of the polynucleotide sequence is plotted (see e.g., FIG. 4A, "SVM scores").

In some embodiments of any of the aspects, a transcriptional regulatory score is determined for each possible mutation (e.g., single-nucleotide point mutation) of at least one nucleotide position in the original polynucleotide sequence. In some embodiments of any of the aspects, the transcriptional regulatory score for each nucleotide position and each mutation of the polynucleotide sequence is plotted (see e.g., FIG. 4B, "Model scores").

In some embodiments of any of the aspects, the method of designing or synthesizing a synthetic polynucleotide sequence comprises identifying at least one region of nucleotide positions (e.g., of the original polynucleotide sequence) comprising transcriptional regulatory scores at or above a threshold. In some embodiments of any of the aspects, the at least one region of nucleotide positions comprising transcriptional regulatory scores at or above a threshold is identified as a regulatory sequence element. In some embodiments of any of the aspects, all of the transcriptional regulatory scores of a regulatory sequence element are at or above the threshold.

In some embodiments of any of the aspects, the method of designing or synthesizing a synthetic polynucleotide sequence comprises identifying at least one region of nucleotide positions that is not a regulatory sequence element as a non-regulatory sequence element. In some embodiments of any of the aspects, at least one region of nucleotide positions comprising transcriptional regulatory scores below a threshold is identified as a non-regulatory sequence element. In some embodiments of any of the aspects, all of the transcriptional regulatory scores of a non-regulatory sequence element are below the threshold.

In some embodiments of any of the aspects, the threshold is the average of all transcriptional regulatory scores for each k-mer fragment of the third set of sequence elements plus a variable value. In some embodiments of any of the aspects, the average corresponds to the mean value of all transcriptional regulatory scores for each k-mer fragment of the third set of sequence elements. In some embodiments of any of the aspects, the variable value is at least 1.2 times the standard deviation of the transcriptional regulatory score for each k-mer fragment of the third set of sequence elements. As a non-limiting example, the variable value is at least 1.0, 1.1, 1.2, 1.3, 1.4, 1.5, 1.6, 1.7, 1.8, 1.9, 2.0, 2.5, or 3.0 times the standard deviation of the transcriptional regulatory score for each k-mer fragment of the third set of sequence elements. In some embodiments of any of the aspects, the threshold is the mean of all transcriptional regulatory scores for each k-mer fragment of the third set of sequence elements plus 1.2 times the standard deviation of the transcriptional regulatory score for each k-mer fragment of the third set of sequence elements.

In some embodiments of any of the aspects, the average corresponds to the median value of all transcriptional regulatory scores for each k-mer fragment of the third set of sequence elements. In some embodiments of any of the aspects, the variable value is user-selected; as a non-limiting example, the variable value can be at least 0.05, 0.1, 0.2, 0.3, 0.4, 0.5, 0.6, 0.7, 0.8, 0.9, or at least 1. In some embodiments of any of the aspects, the threshold is the median value of all transcriptional regulatory scores for each k-mer fragment of the third set of sequence elements plus a user-determined value.

In some embodiments of any of the aspects, the regulatory sequence element is at least as long as one k-mer fragment of the first set of sequence elements. In some embodiments of any of the aspects, the regulatory sequence element is at least 10 nucleotides long. As a non-limiting example, the regulatory sequence element is at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleotides long.

In some embodiments of any of the aspects, the non-regulatory sequence element is at least as long as one k-mer fragment of the first set of sequence elements. In some embodiments of any of the aspects, the non-regulatory sequence element is at least 10 nucleotides long. As a non-limiting example, the non-regulatory sequence element is at least 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 nucleotides long.

In some embodiments of any of the aspects, the method comprises designing a modified polynucleotide molecule based on the determined transcriptional regulatory scores of the sequence elements. In some embodiments of any of the aspects, the method comprises designing a modified polynucleotide molecule based on the identified non-regulatory sequence elements. In some embodiments of any of the aspects, the modified polynucleotide sequence is designed based on the polynucleotide sequence with the at least one non-regulatory sequence element removed (i.e., a shortened polynucleotide). In some embodiments of any of the aspects, the modified polynucleotide sequence is designed based on the polynucleotide sequence with the at least one non-regulatory sequence element replaced (i.e., a replaced polynucleotide). In some embodiments of any of the aspects, the modified polynucleotide sequence is designed based on at least one mutation of nucleotide position(s) to alter a transcriptional regulatory score (i.e., a mutated polynucleotide). In some embodiments of any of the aspects, the method comprises shortening, replacing, or mutating at least one portion of a polynucleotide sequence, or any combination thereof.

In some embodiments of any of the aspects, the method comprises designing a shortened polynucleotide molecule based on the polynucleotide sequence with the at least one non-regulatory sequence element removed. In some embodiments of any of the aspects, at least 1, 2, 3, 4, 5, 6, 7, 8, 9, or 10 non-regulatory sequence elements are removed. In some embodiments of any of the aspects, the method comprises designing a shortened polynucleotide molecule based on the polynucleotide sequence with a portion of at least one non-regulatory sequence element removed. In some embodiments of any of the aspects, the portion of the non-regulatory sequence element comprises at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of the non-regulatory region. In some embodiments of any of the aspects, the portion of the non-regulatory sequence element comprises at most 1%, at most 5%, at most 10%, at most 15%, at most 20%, at most 25%, at most 30%, at most 35%, at most 40%, at most 45%, at most 50%, at most 55%, at most 60%, at most 65%, at most 70%, at most 75%, at most 80%, at most 85%, at most 90%, at most 95%, at most 96%, at most 97%, at most 98%, or at most 99% of the non-regulatory region. In some embodiments of any of the aspects, the portion of the non-regulatory sequence element does not comprise 1, 2, 3, 4, 5, 6, 7, 8, 9, 10, 11, 12, 13, 14, 15, 16, 17, 18, 19, or at least 20 nucleotides on the 5' end or 3' end of the non-regulatory region.

In some embodiments of any of the aspects, the designed shortened polynucleotide molecule is synthesized. In some embodiments of any of the aspects, the shortened polynucleotide is approximately 10%, 15%, 20%, 25%, 30%, 35%, 40%, 45%, 50%, 55%, 60%, 65%, 70%, 75%, 80%, 90%, 91%, 92%, 93%, 94%, 95%, 96%, 97%, 98%, or 99% the length of the parent polynucleotide. In some embodiments of any of the aspects, the shortened polynucleotide molecule is no more than 100 nucleotides long. As a non-limiting example, the shortened polynucleotide molecule is at most 25, at most 50, at most 100, at most 125, at most 150, at most 200, at most 250, at most 300, at most 350, at most 400, at most 450, or at most 500 nucleotides long. In some embodiments of any of the aspects, the shortened polynucleotide molecule is approximately 25, 50, 100, 125, 150, 200, 250, 300, 350, 400, 450, or 500 nucleotides long.

In some embodiments of any of the aspects, the method comprises designing a replaced polynucleotide molecule based on the polynucleotide sequence with the at least one non-regulatory sequence element replaced with a new sequence. In some embodiments, the new sequence can be the same or similar length (e.g., +/−1, 2, 3, 4, 5, 6, 7, 8, 9, or at least 10 nucleotide length difference) as the replaced sequence. In some embodiments of any of the aspects, the non-regulatory sequence element is replaced with an inactive or neutral sequence (e.g., with no known transcriptional regulatory function; see e.g., FIGS. 30 and 31). In some embodiments of any of the aspects, the non-regulatory sequence element is replaced with an active sequence (e.g., with a known transcriptional regulatory function; see e.g., FIGS. 30 and 31). In some embodiments of any of the aspects, at least 1, 2, 3, 4, 5, 6, 7, 8, 9, or 10 non-regulatory sequence elements are replaced. In some embodiments of any of the aspects, the method comprises designing a replaced polynucleotide molecule based on the polynucleotide sequence with a portion (e.g., as described further herein) of at least one non-regulatory sequence element replaced.

In some embodiments of any of the aspects, the designed replaced polynucleotide molecule is the same or similar (+/−5%) length as the original polynucleotide sequence. In some embodiments of any of the aspects, the shortened polynucleotide is approximately 80%, 85%, 90%, 91%, 92%, 93%, 94%, 95%, 96%, 97%, 98%, 99%, 100%, 101%, 102%, 103%, 104%, 105%, 106%, 107%, 108%, 109%, 110%, 115%, or 120% the length of the parent polynucleotide. In some embodiments of any of the aspects, the replaced polynucleotide molecule is no more than 100 nucleotides long. In some embodiments of any of the aspects, the replaced polynucleotide molecule is at most 25, at most 50, at most 100, at most 125, at most 150, at most 200, at most 250, at most 300, at most 350, at most 400, at most 450, or at most 500 nucleotides long. In some embodiments of any of the aspects, the replaced polynucleotide molecule is approximately 25, 50, 100, 125, 150, 200, 250, 300, 350, 400, 450, or 500 nucleotides long. In some embodiments of any of the aspects, the designed replaced polynucleotide molecule is synthesized using methods as described further herein.

In some embodiments of any of the aspects, the modified polynucleotide sequence is designed based on at least one mutation of nucleotide position(s) to alter the transcriptional regulatory score(s) (i.e., a mutated polynucleotide). As described herein, a transcriptional regulatory score can be calculated for each nucleotide (e.g., A, C, G, T) in a specific position (see e.g., FIG. 4B, FIG. 4C, FIG. 5A, FIG. 24). In some embodiments of any of the aspects, the mutated polynucleotide comprises at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or at least 50 mutations of nucleotide positions. In some embodiments of any of the aspects, the nucleotide position is mutated to a nucleotide with an increased transcriptional regulatory score. In some embodiments of any of the aspects, the nucleotide position is mutated to a nucleotide with a minimally altered, unaltered, or decreased transcriptional regulatory score.

In some embodiments of any of the aspects, the mutated polynucleotide comprises at least one mutation of nucleotide position(s) corresponding to a transcriptional regulatory score below the pre-determined threshold, for example in order to increase the transcriptional regulatory score of the mutated position above the threshold. In some embodiments of any of the aspects, the mutated polynucleotide comprises at least one mutation of nucleotide position(s) corresponding to a transcriptional regulatory score at or above the pre-determined threshold, for example if the mutation results in an increased transcriptional regulatory score for the mutated nucleotide position. In some embodiments of any the aspects, the mutated nucleotide position comprises a transcriptional regulatory score that is at least 1%, at least 5%, at least 10%, at least 15%, or at least 20% greater than the transcriptional regulatory score of the original nucleotide position. In some embodiments of any the aspects, the mutated nucleotide position comprises a transcriptional regulatory score that is at most 1%, at most 5%, at most 10%, at most 15%, or at most 20% greater than the transcriptional regulatory score of the original nucleotide position. In some embodiments of any of the aspects, the mutated polynucleotide comprises at least one mutation of nucleotide position(s) in a regulatory sequence element or a non-regulatory sequence element that results in a higher score for the nucleotide position.

In some embodiments of any of the aspects, the mutation comprises a nucleotide substitution, nucleotide insertion, or nucleotide deletion. In a preferred embodiment, the mutation comprises a substitution. In a mutated polynucleotide comprising at least two mutations, the mutations can be sequential or non-sequential. In some embodiments of any of the aspects, the mutation(s) can be in a regulatory sequence element, as determined using the methods described herein. In some embodiments of any of the aspects, the mutation(s) can be in a non-regulatory sequence element, as determined using the methods described herein.

In some embodiments of any of the aspects, the mutated polynucleotide molecule is the same or similar (+/−5%) length as the original polynucleotide sequence with transcriptional regulatory function. In some embodiments of any of the aspects, the mutated polynucleotide is approximately 80%, 85%, 90%, 91%, 92%, 93%, 94%, 95%, 96%, 97%, 98%, 99%, 100%, 101%, 102%, 103%, 104%, 105%, 106%, 107%, 108%, 109%, 110%, 115%, or 120% the length of the parent polynucleotide. In some embodiments of any of the aspects, the mutated polynucleotide molecule is no more than 100 nucleotides long. In some embodiments of any of the aspects, the mutated polynucleotide molecule is at most 25, at most 50, at most 100, at most 125, at most 150, at most 200, at most 250, at most 300, at most 350, at most 400, at most 450, or at most 500 nucleotides long. In some embodiments of any of the aspects, the mutated polynucleotide molecule is approximately 25, 50, 100, 125, 150, 200, 250, 300, 350, 400, 450, or 500 nucleotides long. In some embodiments of any of the aspects, the designed mutated polynucleotide molecule is synthesized using methods as described further herein.

In some embodiments of any of the aspects, the method of designing or synthesizing a synthetic polynucleotide sequence further comprises re-processing the modified (e.g., shortened, replaced, mutated) polynucleotide sequence using the machine learning model. In some embodiments of any of the aspects, re-processing the modified (e.g., shortened, replaced, mutated) polynucleotide sequence comprises repeating the machine learning processing steps as described herein using the modified (e.g., shortened, replaced, mutated) polynucleotide sequence in place of the polynucleotide sequence.

In some embodiments of any of the aspects, the method of re-processing the modified (e.g., shortened, replaced, mutated) polynucleotide sequence comprises: (a) processing the modified (e.g., shortened, replaced, mutated) polynucleotide sequence into a first set of sequence elements, wherein the first set of sequence elements comprises at least one subset of sequence elements corresponding to all k-mer fragments comprising a selected nucleotide position of the polynucleotide sequence; (b) determining the transcriptional regulatory score of each k-mer fragment in a subset by assigning the transcriptional regulatory score of the matching k-mer fragment from the database (as described further herein, e.g., a look-up table); (c) identifying at least one region of nucleotide positions comprising transcriptional regulatory scores at or above a threshold as a regulatory sequence element; and (d) identifying at least one region of nucleotide positions that is not a regulatory sequence element as a non-regulatory sequence element.

In some embodiments of any of the aspects, the modified (e.g., shortened, replaced, mutated) polynucleotide molecule based on the modified (e.g., shortened, replaced, mutated) polynucleotide sequence is determined to be a satisfactory design if, after the method of re-processing, the length of the at least one regulatory sequence element identified is at least the same length as the corresponding regulatory sequence element identified in the parent (i.e., original) polynucleotide sequence. In some embodiments of any of the aspects, the modified (e.g., shortened, replaced, mutated) polynucleotide molecule based on the modified (e.g., shortened, replaced, mutated) polynucleotide sequence is synthesized if, the modified (e.g., shortened, replaced, mutated) polynucleotide molecule is determined to be a satisfactory design.

In some embodiments of any of the aspects, the modified (e.g., shortened, replaced, mutated) polynucleotide molecule based on the modified (e.g., shortened, replaced, mutated) polynucleotide sequence determined to be a non-satisfactory design if, after the method of re-processing, the length of the at least one regulatory sequence element identified is less than the length of the regulatory sequence element identified in the parent polynucleotide sequence. In some embodiments of any of the aspects, the modified (e.g., shortened, replaced, mutated) polynucleotide molecule based on the modified (e.g., shortened, replaced, mutated) polynucleotide sequence is not synthesized if, the modified (e.g., shortened, replaced, mutated) polynucleotide molecule is determined to be a non-satisfactory design.

Synthesizing Polynucleotides

In several aspects, described herein are methods of synthesizing a synthetic polynucleotide with transcriptional regulatory functionality. In some embodiments of any of the aspects, a synthetic polynucleotide with transcriptional regulatory functionality comprises a modified (e.g., shortened, replaced, mutated) polynucleotide molecule designed using methods as described further herein. In some embodiments of any of the aspects, synthesizing the modified (e.g., shortened, replaced, mutated) polynucleotide molecule comprises de novo DNA synthesis.

Methods of de novo DNA synthesis are well known to those of skill in the art. As used herein, "de novo DNA synthesis" refers to synthesis of DNA from nucleotides without the need for precursor template DNA; it can also be referred to as artificial gene synthesis. As used herein, "polynucleotide synthesis" refers to the chemical synthesis of relatively long fragments of nucleic acids with defined chemical structure. As a non-limiting example, methods of DNA synthesis include phosphoramidite solid-phase synthesis, phosphoramidite synthesis, phosphodiester synthesis, phosphotriester synthesis, or phosphite triester synthesis. See e.g., Beaucage et al. Tetrahedron Volume 48, Issue 12, 20 Mar. 1992, Pages 2223-2311; Caruthers, J Biol Chem. 2013 Jan. 11, 288(2):1420-7. Any other method of DNA synthesis known to those of skill in the art can also be used.

In some embodiments of any of the aspects, synthesizing the modified (e.g., shortened, replaced, mutated) polynucleotide molecule comprises recombining or performing mutagenesis on one or more nucleic acid molecules. In some embodiments of any of the aspects, the one or more nucleic acid molecules comprise overlapping portions of the modified (e.g., shortened, replaced, mutated) polynucleotide molecule, that are for example synthesized using de novo DNA synthesis, and then recombined into a longer polynucleotide. In some embodiments of any of the aspects, synthesizing the modified (e.g., shortened, replaced, mutated) polynucleotide molecule comprises amplifying the sequence in a vector and isolating the amplified modified (e.g., shortened, replaced, mutated) polynucleotide molecule.

The nucleic acids described herein may be synthesized and/or modified by methods well established in the art, such as those described in "Current protocols in nucleic acid chemistry," Beaucage, S. L. et al. (Edrs.), John Wiley & Sons, Inc., New York, NY, USA, which is hereby incorporated herein by reference.

In some embodiments of any of the aspects, the transcriptional regulatory functionality of the modified (e.g., shortened, replaced, mutated) polynucleotide molecule is compared against the parent polynucleotide molecule. The transcriptional regulatory function can be measured using methods as described herein. As a non-limiting example, a vector or viral vector comprising a synthetic polynucleotide as designed herein and a detectable marker (e.g., fluorescent protein, luciferase, etc.) can be used to test the transcriptional regulatory function of a synthetic polynucleotide as described herein, compared to a vector or viral vector comprising the parent polynucleotide and a detectable marker.

In some embodiments of any of the aspects, the transcriptional regulatory functionality of the modified (e.g., shortened, replaced, mutated) polynucleotide molecule is at least 10% that of the parent polynucleotide molecule. As a non-limiting example, the transcriptional regulatory functionality of the modified (e.g., shortened, replaced, mutated) polynucleotide molecule is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190, at least 200%, at least 210%, at least 220%, at least 230%, at least 240%, at least 250%, at least 260%, at least 270%, at least 280%, or at least 290, at least 300% that of the parent polynucleotide molecule.

In some embodiments of any of the aspects, the transcriptional regulatory functionality of the modified (e.g., shortened, replaced, mutated) polynucleotide molecule is increased in a specific tissue or cell type (e.g., corresponding to the specific tissue or cell type of the polynucleotide sequence and/or sequence elements used to design the modified polynucleotide molecule) compared to the parent polynucleotide molecule. In some embodiments of any of the aspects, the transcriptional regulatory functionality of the modified (e.g., shortened, replaced, mutated) polynucleotide molecule is increased at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190, at least 200%, at least 210%, at least 220%, at least 230%, at least 240%, at least 250%, at least 260%, at least 270%, at least 280%, or at least 290, or at least 300% in the same tissue or cell type compared to the parent polynucleotide molecule. In some embodiments of any of the aspects, the increased transcriptional regulatory functionality of the modified (e.g., shortened, replaced, mutated) polynucleotide molecule is in any given cell or tissue type, e.g., liver tissue or cells, cardiac muscle tissue or cells, and/or skeletal muscle tissue or cells.

In another aspect, described herein is a method of designing a polynucleotide sequence with transcriptional regulatory functionality that is altered in size without losing transcriptional regulatory functionality comprising: (a) using a machine to process a set of genetic data comprising polynucleotide sequences to identify putative promoter sequences or putative enhancer sequences; (b) processing the set of putative promoter sequences with a machine learning model to determine a transcriptional regulatory score associated with each of the nucleotides within the putative promoter sequences to identify peaks and troughs based upon the scores provided to each nucleotide within the putative promoter sequences; (c) identifying at least one member of the set of putative promoter sequences where there is a trough of at least 20 nucleotides between peaks, wherein the score for members of the trough is below a pre-determined threshold; and (d) designing a shortened polynucleotide molecule, wherein at least 10% of the nucleotides within a trough has been removed as compared to the selected identified putative promoter sequence of step (c). In some embodiments of any of the aspects, the designed shortened polynucleotide molecule is synthesized.

In another aspect, described herein is a method of synthesizing a polynucleotide sequence with transcriptional regulatory functionality that is altered in size without losing transcriptional regulatory functionality comprising: (a) using a machine to process a set of genetic data comprising polynucleotide sequences to identify putative promoter sequences or putative enhancer sequences; (b) processing the set of putative promoter sequences with a machine learning model to determine a transcriptional regulatory score associated with each of the nucleotides within the putative promoter sequences to identify peaks and troughs based upon the scores provided to each nucleotide within the putative promoter sequences; (c) identifying at least one member of the set of putative promoter sequences where there is a trough of at least 20 nucleotides between peaks, wherein the scores for members of the trough is below a pre-determined threshold; and (d) synthesizing a shortened polynucleotide molecule, wherein at least 10% of the nucleotides within a trough has been removed as compared to the selected identified putative promoter sequence of step (c).

In some embodiments of any of the aspects, the nucleotide sequences are scored using k-mer methodology, as described further herein, for example methods comprising gapped k-mers, SVM, and/or k-DNF k-mer kernel. In some embodiments of any of the aspects, the k-mer methodology outputs a transcriptional regulatory score associated with each of the nucleotides in the putative promoter sequence.

As used herein, the term "trough" refers to a portion of the putative promoter sequence comprising transcriptional regulatory scores below a pre-determined threshold, as described further herein. As used herein, the term "peak" refers to a portion of the putative promoter sequence comprising transcriptional regulatory scores at or above a pre-determined threshold, as described further herein. In some embodiments of any of the aspects, at least one trough within a putative promoter sequence are identified. In some embodiments of any of the aspects, at least two troughs within a putative promoter sequence are identified. As a non-limiting example, at least 2, at least 3, at least 4, at least 5, at least 6, at least 7, at least 8, at least 9, or at least 10 troughs within the putative promoter sequence are identified.

In some embodiments of any of the aspects, at least one trough is removed from the putative promoter sequence. In some embodiments of any of the aspects, at least two troughs are removed are from the putative promoter sequence. As a non-limiting example, at least 2, at least 3, at least 4, at least 5, at least 6, at least 7, at least 8, at least 9, or at least 10 troughs within the putative promoter sequence are removed from the polynucleotide sequence.

In some embodiments of any of the aspects, at least one trough is replaced in the putative promoter sequence, for example a sequence with known transcriptional regulatory function. In some embodiments of any of the aspects, at least two troughs are replaced in the putative promoter sequence. As a non-limiting example, at least 2, at least 3, at least 4, at least 5, at least 6, at least 7, at least 8, at least 9, or at least 10 troughs within a putative promoter sequence are replaced in the putative promoter sequence.

In some embodiments of any of the aspects, at least 10% of the nucleotides within a trough is removed or replaced. As a non-limiting example, at least 1%, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of the nucleotides within a trough is removed or replaced.

In some embodiments of any of the aspects, the transcriptional regulatory functionality of the shortened polynucleotide molecule is compared against the parent putative promoter sequence and is at least 35% that of the parent putative promoter sequence. As a non-limiting example, the transcriptional regulatory functionality of the shortened polynucleotide molecule is at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% that of the parent putative promoter sequence.

Nucleic Acids

Described in several aspects herein are methods of designed or synthesizing a synthetic polynucleotide with transcriptional regulatory functionality. In some embodiments of any of the aspects, the synthetic polynucleotide sequence is optionally isolated from the cellular (or viral) materials with which it is naturally associated. In some embodiments of any of the aspects, an isolated nucleic acid module comprises one or more of the polynucleotides (e.g., synthetic regulatory sequence) described herein. As used herein, the term "isolated nucleic acid module", which can be used interchangeable with "isolated nucleic acid", refers to a nucleic acid separated or substantially free from at least some of the other components of the naturally occurring organism, for example, the cell structural components commonly found associated with nucleic acids in a cellular environment and/or other nucleic acids.

In some embodiments of any of the aspects, an isolated nucleic acid comprising a synthetic polynucleotide with transcriptional regulatory functionality can be designed or synthesized using any method of designing said synthetic polynucleotide with transcriptional regulatory functionality, as described further herein. Included below are non-limiting examples of isolated nucleic acids comprising a synthetic polynucleotide with transcriptional regulatory functionality.

Accordingly, in one aspect described herein is an isolated nucleic acid module comprising a polynucleotide that was synthesized using a process comprising: (a) receiving a set of genetic data comprising a regulatory polynucleotide sequence, optionally having a known transcriptional regulatory functionality; (b) processing the set of genetic data into a set of sequence elements that each comprise a portion of the polynucleotide sequence; (c) processing the set of sequence elements with a machine learning model to determine a transcriptional regulatory score associated with each of the set of sequence elements; (d) identifying at least one sequence element of the set of sequence elements comprising a transcriptional regulatory score below a threshold as a non-regulatory sequence element; (e) designing a modified polynucleotide molecule based on the determined transcriptional regulatory scores and/or identified non-regulatory sequence elements; and (f) synthesizing a shortened polynucleotide molecule based on the modified polynucleotide sequence.

In some embodiments of any of the aspects, each of the set of sequence elements is a k-mer fragment of the polynucleotide sequence. In some embodiments of any of the aspects, each of the k-mer fragments comprises a gapped k-mer fragment, as described further herein. In some embodiments of any of the aspects, the gapped k-mer fragment comprises a 10 nucleotide-long fragment comprising 4 gaps.

In some embodiments of any of the aspects, the machine learning model is a support vector machine. In some embodiments of any of the aspects, the set of sequence elements are input into the support vector machine. In some embodiments of any of the aspects, the support vector machine comprises a gapped k-mer kernel. In some embodiments of any of the aspects, the support vector machine comprises a k-DNF k-mer kernel. In some embodiments of any of the aspects, the machine learning model is trained using a second set of genetic data comprising a second set of sequence elements that comprise portions of transcriptional regulatory elements and non-regulatory elements. In some embodiments of any of the aspects, synthesizing the shortened polynucleotide molecule comprises de novo DNA synthesis.

In some embodiments of any of the aspects, the known transcriptional regulatory functionality comprises transcriptional activation and/or transcriptional repression. In some embodiments of any of the aspects, the known transcriptional regulatory functionality is in any given cell or tissue type. In some embodiments of any of the aspects, the known transcriptional regulatory functionality is in liver cells, cardiac muscle cells, and/or skeletal muscle cells. In some embodiments of any of the aspects, the known transcriptional regulatory functionality comprises promoter activity. In some embodiments of any of the aspects, promoter activity comprises a level of expression of a particular set of genes.

In some embodiments of any of the aspects, the modified polynucleotide sequence is designed based on the polynucleotide sequence with the at least one non-regulatory sequence element removed (i.e., a shortened polynucleotide). In some embodiments of any of the aspects, the modified polynucleotide sequence is designed based on the polynucleotide sequence with the at least one non-regulatory sequence element replaced (i.e., a replaced polynucleotide). In some embodiments of any of the aspects, the modified polynucleotide sequence is designed based on at least one mutation of nucleotide position(s) to alter the transcriptional regulatory score(s) (i.e., a mutated polynucleotide).

Non-limiting examples are disclosed herein of modified polynucleotide sequences designed or synthesized using the methods described herein (e.g., SEQ ID NO: 1-33). In some embodiments of any of the aspects, a modified polynucleotide sequence comprises SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33 that maintains the same functions as any one of SEQ ID NO: 1-33 (e.g., transcriptional regulatory functionality).

In some embodiments of any of the aspects, a modified polynucleotide sequence comprises a combination of at least 2 (e.g., 2, 3, 4, at least 5) modifications (e.g., deletion(s), replacement(s), mutation(s)) described herein or a sequence that is at least 70% identical to such a combination sequence that maintains the same function (e.g., transcriptional regulatory functionality). As a non-limiting example, described herein are two specific deletions of the original SYNP_LVR_SP0257 parent sequence (SEQ ID NO: 31): a 105 bp deletion (SEQ ID NO: 20) and a 56 bp deletion (SEQ ID NO: 22); in some embodiments of any of the aspects, a modified SYNP_LVR_SP0257 polynucleotide sequence comprises both deletions described herein (SEQ ID NO: 20 and SEQ ID NO: 22). Accordingly, in some embodiments of any of the aspects, a modified polynucleotide sequence comprises a combination of modifications comprised by SEQ ID NO: 1-27, that maintains the same functions as any one of SEQ ID NO: 1-33 (e.g., transcriptional regulatory functionality).

SEQ ID NO: 1-4 correspond to variants of SYN-P_LVR_SP0155 (SEQ ID NO: 28). SEQ ID NO: 5-10 correspond to variants of SYNP_LVR_SP0239 (SEQ ID NO: 29). SEQ ID NO: 11-18 correspond to variants of SYNP_LVR_SP0247 (SEQ ID NO: 30). SEQ ID NO: 19-22 correspond to variants of SYNP_LVR_SP0257 (SEQ ID NO: 31). SEQ ID NO: 23-25 correspond to variants of SYNP_LVR_SP0259 (SEQ ID NO: 32). SEQ ID NO: 26-27 correspond to variants of SYNP_LVR_SP0264 (SEQ ID NO: 33).

In some embodiments of any of the aspects, a modified nucleotide comprises SYNP_LVR_SP0155 (SEQ ID NO: 28) comprising at least two modifications comprised by SEQ ID NO: 1-4 or a sequence that is at least 70% identical to such a combination sequence that maintains the same function (e.g., transcriptional regulatory functionality).

In some embodiments of any of the aspects, a modified nucleotide comprises SYNP_LVR_SP0239 (SEQ ID NO: 29) comprising at least two modifications comprised by SEQ ID NO: 5-10 or a sequence that is at least 70% identical to such a combination sequence that maintains the same function (e.g., transcriptional regulatory functionality).

In some embodiments of any of the aspects, a modified nucleotide comprises SYNP_LVR_SP0247 (SEQ ID NO: 30) comprising at least two modifications comprised by SEQ ID NO: 11-18 or a sequence that is at least 70% identical to such a combination sequence that maintains the same function (e.g., transcriptional regulatory functionality).

In some embodiments of any of the aspects, a modified nucleotide comprises SYNP_LVR_SP0257 (SEQ ID NO: 31) comprising at least two modifications comprised by SEQ ID NO: 19-22 or a sequence that is at least 70% identical to such a combination sequence that maintains the same function (e.g., transcriptional regulatory functionality).

In some embodiments of any of the aspects, a modified nucleotide comprises SYNP_LVR_SP0259 (SEQ ID NO: 32) comprising at least two modifications comprised by SEQ ID NO: 23-25 or a sequence that is at least 70% identical to such a combination sequence that maintains the same function (e.g., transcriptional regulatory functionality).

In some embodiments of any of the aspects, a modified nucleotide comprises SYNP_LVR_SP0264 (SEQ ID NO: 33) comprising at least two modifications comprised by SEQ ID NO: 26-27 or a sequence that is at least 70% identical to such a combination sequence that maintains the same function (e.g., transcriptional regulatory functionality).

In any of the above embodiments or examples, the modified polynucleotide designed or synthesized using the methods described herein may be a promoter, suitably a synthetic promoter.

Therefore, in a further aspect of the invention, there is provided a synthetic promoter comprising or consisting of any one of SEQ ID NO: 1-33 or a functional variant thereof. In some embodiments, the synthetic promoter is a liver-specific promoter. In some embodiments, the synthetic promoter is a muscle-specific promoter.

In some embodiments, the synthetic promoter comprises a sequence at least 70%, 75%, 80%, 85%, 90%, 91%, 92%, 93% 94%, 95%, 96%, 97%, 98% or 99% identical to any one of SEQ ID NO: 1-33. Suitably in such embodiments, the synthetic promoter retains the same functions as any one of SEQ ID NO:1-33.

In some embodiments, a synthetic promoter may comprise a combination of at least 2 (e.g., 2, 3, 4, at least 5) modifications (e.g., deletion(s), replacement(s), mutation(s)) described herein or a sequence that is at least 70% identical to such a combination sequence that maintains the same function.

Accordingly, in some embodiments, a synthetic promoter sequence comprises a combination of modifications comprised by SEQ ID NO: 1-27, that maintains the same functions as any one of SEQ ID NO: 1-33.

In one embodiment, a synthetic promoter comprises SYNP_LVR_SP0155 (SEQ ID NO: 28) comprising at least two modifications comprised by SEQ ID NO: 1-4 or a sequence that is at least 70% identical to such a combination sequence that maintains the same function.

In one embodiment, a synthetic promoter comprises SYNP_LVR_SP0239 (SEQ ID NO: 29) comprising at least two modifications comprised by SEQ ID NO: 5-10 or a sequence that is at least 70% identical to such a combination sequence that maintains the same function.

In one embodiment, a synthetic promoter comprises SYNP_LVR_SP0247 (SEQ ID NO: 30) comprising at least two modifications comprised by SEQ ID NO: 11-18 or a sequence that is at least 70% identical to such a combination sequence that maintains the same function In one embodiment, a synthetic promoter comprises SYNP_LVR_SP0257 (SEQ ID NO: 31) comprising at least two modifications comprised by SEQ ID NO: 19-22 or a sequence that is at least 70% identical to such a combination sequence that maintains the same function In one embodiment, a synthetic promoter comprises SYNP_LVR_SP0259 (SEQ ID NO: 32) comprising at least two modifications comprised by SEQ ID NO: 23-25 or a sequence that is at least 70% identical to such a combination sequence that maintains the same function.

In one embodiment, a synthetic promoter comprises SYNP_LVR_SP0264 (SEQ ID NO: 33) comprising at least two modifications comprised by SEQ ID NO: 26-27 or a sequence that is at least 70% identical to such a combination sequence that maintains the same function.

A functional variant of a reference synthetic promoter is a promoter which comprises a sequence which varies from the reference synthetic promoter, but which substantially retains promoter activity, i.e. a variant of a reference sequence that retains the ability to function in the same way as the reference sequence.

It will be appreciated by the skilled person that ability of a given synthetic promoter to act like a promoter, for example a liver-specific promoter, is determined principally by the ability of the sequence to bind transcription factors (TFs) i.e. transcriptional regulatory functionality. It will also be appreciated that is possible to vary the sequence of a synthetic promoter while retaining its ability to recruit suitable TFs and to recruit RNA polymerase II to provide expression of an operably linked sequence. A functional variant of a synthetic promoter can comprise substitutions, deletions and/or insertions compared to a reference promoter, provided such substitutions, deletions and/or insertions do not render the synthetic promoter substantially non-functional compared to the reference promoter.

Accordingly, in most cases, a functional variant of a synthetic promoter will contain transcription factor binding sites (TFBS) for most or all of the same transcription factors as the reference sequence. Therefore, it will retain transcriptional regulatory functionality. It is also preferred, but not essential, that the TFBS of a functional variant are in the same orientation as the reference sequence (it will be noted that TFBS can in some cases be present in reverse orientation, e.g. as the reverse complement vis-i-vis the sequence in the reference sequence). It is also preferred, but not essential, that the TFBS of a functional variant are on the same strand as the reference sequence. Thus, in preferred embodiments, the functional variant comprises TFBS for the same TFs, in the same order, the same position, in the same orientation and on the same strand as the reference sequence. It will also be appreciated that the sequences lying between TFBS (referred to in some cases as spacer sequences, or suchlike) are of less consequence to the function of the synthetic promoter. Such sequences can typically be varied considerably, and their lengths can be altered. However, in preferred embodiments the spacing (i.e. the distance between adjacent TFBS) is substantially the same (e.g. it does not vary by more than 20%, preferably by not more than 10%, and more preferably it is approximately the same) in a functional variant as it is in the reference sequence.

In some embodiments, a functional variant of a synthetic promoter is a variant which substantially retains the promoter activity of the reference promoter. Suitably a functional variant of a synthetic promoter retains at least 25%, 50%, 75%, 80%, 85%, 90%, 95% or 100% of the activity of the reference promoter. Suitably said activity is assessed using one of the examples as described herein, but other methods can be used.

Functional variants of a synthetic promoter often retain a significant level of sequence similarity to the reference synthetic promoter. In some embodiments, functional variants of the synthetic promoter comprise a sequence that is at least 70% identical to the reference synthetic promoter, more preferably at least 80%, 90%, 95% or 99% identical to the reference synthetic promoter. Activity in a functional variant can be assessed by comparing expression of a suitable reporter under the control of the reference synthetic promoter with the putative functional variant under equivalent conditions. Suitable assays for assessing promoter activity are disclosed herein, e.g. in the examples.

SEQ ID NO: 1, SYNP_LVR_SP0328
SYNP_LVR_SP0155_140
TAAAGAACTGTTTGCATGTTGCAAATGATGTCCAAAGTCCAAACATTGT

TAATAATTAATACTCCAATAAACATCATGTCAGAATTTCTGTTTTCTTT

TCCCTTTGAACCTTTGCAGGATTGCCACATCATCAGGACCACACCTTCA

TCAGGAATGAATATCCGATGACCTAATGATTCTGAGCTTGGCAAAGGTC

TTATCTCCCAGCTCGCCCAGGCCCAGTGTTCCAGGAATGTGACCTTTGC

TGCAGCAGCCGCTGGAGGGGGCAGAGGGGATGGGCTGGAGGTTGAGCAA

ACAGAGCAGCAGAAAAGGCAGTTCCTCTTCTCCAGTGCCCTCCTTCCCT

GTCTCTGCCTCTCCCTCCCTTCCTCAGGCATCAGAGCGGAGACTTCAGG

GAGACCAGAGCCCAGCTTGCCAGGCACTGAGCTAGAAGCCCTGCC

SEQ ID NO: 2, SYNP_LVR_SP0329 SYNP_LVR_SP0155_140r
TGATGTCCTGATTGGAAGGACCGTTGGCCCCCCACCCTTATAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

-continued

AATATCCGATGACCTAATGATTCTGAGCTTGGCAAAGGTCTTATCTCCC

AGCTCGCCCAGGCCCAGTGTTCCAGGAATGTGACCTTTGCTGCAGCAGC

CGCTGGAGGGGGCAGAGGGGATGGGCTGGAGGTTGAGCAAACAGAGCAG

CAGAAAAGGCAGTTCCTCTTCTCCAGTGCCCTCCTTCCCTGTCTCTGCC

TCTCCCTCCCTTCCTCAGGCATCAGAGCGGAGACTTCAGGGAGACCAGA

GCCCAGCTTGCCAGGCACTGAGCTAGAAGCCCTGCC

SEQ ID NO: 3, SYNP_LVR_SP0330
SYNP_LVR_SP0155_167216
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACTTCTGAGCTTGGCAAAGGTCTTATCTCCCA

GCTCGCCCAGGCCCAGTGTTCCAGGAATGTGACCTTTGCTGCAGCAGCC

GCTGGAGGGGGCAGAGGGGATGGGCTGGAGGTTGAGCAAACAGAGCAGC

AGAAAAGGCAGTTCCTCTTCTCCAGTGCCCTCCTTCCCTGTCTCTGCCT

CTCCCTCCCTTCCTCAGGCATCAGAGCGGAGACTTCAGGGAGACCAGAG

CCCAGCTTGCCAGGCACTGAGCTAGAAGCCCTGCC

SEQ ID NO: 4, SYNP_LVR_SP0331
SYNP_LVR_SP0155_167216r
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACTGATGTCCTGATTGGAAGGACCGTTGGCCC

CCCACCCTTAGGCAGTGTATTTCTGAGCTTGGCAAAGGTCTTATCTCCC

AGCTCGCCCAGGCCCAGTGTTCCAGGAATGTGACCTTTGCTGCAGCAGC

CGCTGGAGGGGGCAGAGGGGATGGGCTGGAGGTTGAGCAAACAGAGCAG

CAGAAAAGGCAGTTCCTCTTCTCCAGTGCCCTCCTTCCCTGTCTCTGCC

TCTCCCTCCCTTCCTCAGGCATCAGAGCGGAGACTTCAGGGAGACCAGA

GCCCAGCTTGCCAGGCACTGAGCTAGAAGCCCTGCC

SEQ ID NO: 5, SYNP_LVR_SP0332
SYNP_LVR_SP0239_46A
CAGGCTTTCACTTTCTCGCCAACTTACAAGGCCTTTCTGTGTAAAAAT

ACCTGAACCTTTACCCCGTTGCCCGGCAACGGCCAGGTCTGTGCCAAGT

GTTTGAGGTTAATTTTTAAAAAGCAGTCAAAAGTCCAAGTGGCCCTTGG

CAGCATTTACTCTCTCTGTTTGCTCTGGTTAATAATCTCAGGAGCACAA

ACATTCCGGCCCGGGAGGCGCCCTTTGGACCTTTTGCAATCCTGGCGCA

CTGAACCCTTGACCCCTGCCCTGCAGCCCCCGCAGCTTGCTGTTTGCCC

ACTCTATTTGCCCAGCCCCAGCCCTGGAGAGTCCTTTAGCAGGGCAAAG

TGCAACATAGGCAGACCTTAAGGGATGACTCAGTAACAGATAAGCTTTG

TGTGCCTGCAGGGCATATAAAACAGGGGCAAGGCACAGACTCATAGCAG

AGCAATCACCACCAAGCCTGGAATAACTGCAGCCACC

-continued

SEQ ID NO: 6, SYNP_LVR_SP0333
SYNP_LVR_SP0239_127C
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGAGGTTAATTTTTAAAAAGCAGTCCAAAGTCCAAGTGGCCCTTGG

CAGCATTTACTCTCTCTGTTTGCTCTGGTTAATAATCTCAGGAGCACAA

ACATTCCGGCCCGGGAGGCGCCCTTTGGACCTTTTGCAATCCTGGCGCA

CTGAACCCTTGACCCCTGCCCTGCAGCCCCCGCAGCTTGCTGTTTGCCC

ACTCTATTTGCCCAGCCCCAGCCCTGGAGAGTCCTTTAGCAGGGCAAAG

TGCAACATAGGCAGACCTTAAGGGATGACTCAGTAACAGATAAGCTTTG

TGTGCCTGCAGGGCATATAAAACAGGGGCAAGGCACAGACTCATAGCAG

AGCAATCACCACCAAGCCTGGAATAACTGCAGCCACC

SEQ ID NO: 7, SYNP_LVR_SP0334
SYNP_LVR_SP0239_132
CTTTCTGTGTAAACAATACCTGAACCTTTACCCCGTTGCCCGGCAACGG

CCAGGTCTGTGCCAAGTGTTTGAGGTTAATTTTTAAAAAGCAGTCAAAA

GTCCAAGTGGCCCTTGGCAGCATTTACTCTCTCTGTTTGCTCTGGTTAA

TAATCTCAGGAGCACAAACATTCCGGCCCGGGAGGCGCCCTTTGGACCT

TTTGCAATCCTGGCGCACTGAACCCTTGACCCCTGCCCTGCAGCCCCCG

CAGCTTGCTGTTTGCCCACTCTATTTGCCCAGCCCCAGCCCTGGAGAGT

CCTTTAGCAGGGCAAAGTGCAACATAGGCAGACCTTAAGGGATGACTCA

GTAACAGATAAGCTTTGTGTGCCTGCAGGGCATATAAAACAGGGGCAAG

GCACAGACTCATAGCAGAGCAATCACCACCAAGCCTGGAATAACTGCAG

CCACC

SEQ ID NO: 8, SYNP_LVR_SP0335
SYNP_LVR_SP0239_132r
TGATGTCCTGATTGGAAGGACCGTTGGCCCCCCTTTCTGTGTAAACAAT

ACCTGAACCTTTACCCCGTTGCCCGGCAACGGCCAGGTCTGTGCCAAGT

GTTTGAGGTTAATTTTTAAAAAGCAGTCAAAAGTCCAAGTGGCCCTTGG

CAGCATTTACTCTCTCTGTTTGCTCTGGTTAATAATCTCAGGAGCACAA

ACATTCCGGCCCGGGAGGCGCCCTTTGGACCTTTTGCAATCCTGGCGCA

CTGAACCCTTGACCCCTGCCCTGCAGCCCCCGCAGCTTGCTGTTTGCCC

ACTCTATTTGCCCAGCCCCAGCCCTGGAGAGTCCTTTAGCAGGGCAAAG

TGCAACATAGGCAGACCTTAAGGGATGACTCAGTAACAGATAAGCTTTG

TGTGCCTGCAGGGCATATAAAACAGGGGCAAGGCACAGACTCATAGCAG

AGCAATCACCACCAAGCCTGGAATAACTGCAGCCACC

SEQ ID NO: 9, SYNP_LVR_SP0336
SYNP_LVR_SP0239_138
GTGTAAACAATACCTGAACCTTTACCCCGTTGCCCGGCAACGGCCAGGT

CTGTGCCAAGTGTTTGAGGTTAATTTTTAAAAAGCAGTCAAAAGTCCAA

GTGGCCCTTGGCAGCATTTACTCTCTCTGTTTGCTCTGGTTAATAATCT

CAGGAGCACAAACATTCCGGCCCGGGAGGCGCCCTTTGGACCTTTTGCA

ATCCTGGCGCACTGAACCCTTGACCCCTGCCCTGCAGCCCCCGCAGCTT

GCTGTTTGCCCACTCTATTTGCCCAGCCCCAGCCCTGGAGAGTCCTTTA

-continued

GCAGGGCAAAGTGCAACATAGGCAGACCTTAAGGGATGACTCAGTAACA

GATAAGCTTTGTGTGCCTGCAGGGCATATAAAACAGGGGCAAGGCACAG

ACTCATAGCAGAGCAATCACCACCAAGCCTGGAATAACTGCAGCCACC

SEQ ID NO: 10, SYNP_LVR_SP0337
SYNP_LVR_SP0239_230246
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGAGGTTAATTTTTAAAAAGCAGTCAAAAGTCCAAGTGGCCCTTGG

CAGCATTTACTCTCTCTGTTTGCTCTGGTTAATAATCTCAGGAGCACAA

ACATTCCGGCCCGGGAGGCGCCCTTTGGACCTTTGAACCCTTGACCCCT

GCCCTGCAGCCCCCGCAGCTTGCTGTTTGCCCACTCTATTTGCCCAGCC

CCAGCCCTGGAGAGTCCTTTAGCAGGGCAAAGTGCAACATAGGCAGACC

TTAAGGGATGACTCAGTAACAGATAAGCTTTGTGTGCCTGCAGGGCATA

TAAAACAGGGGCAAGGCACAGACTCATAGCAGAGCAATCACCACCAAGC

CTGGAATAACTGCAGCCACC

SEQ ID NO: 11, SYNP_LVR_SP0338
SYNP_LVR_SP0247_77A
GCTGGTTTCTTATAAAACTGATGGAAGATACAAACACTATTAAAGAACT

GTTTGCATGTTGCAAATGATGTCCAAAATCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCAGGCTTTCACTTTCTCGCCAACTTACAAGGCCTTTCTGTGTAA

ACAATACCTGAACCTTTACCCCGTTGCCCGGCAACGGCCAGGTCTGTGC

CAAGTGTTTGCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC

SEQ ID NO: 12, SYNP_LVR_SP0339
SYNP_LVR_SP0247_94G
GCTGGTTTCTTATAAAACTGATGGAAGATACAAACACTATTAAAGAACT

GTTTGCATGTTGCAAATGATGTCCAAAGTCCAAACATTGTTAATGATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCAGGCTTTCACTTTCTCGCCAACTTACAAGGCCTTTCTGTGTAA

ACAATACCTGAACCTTTACCCCGTTGCCCGGCAACGGCCAGGTCTGTGC

CAAGTGTTTGCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC

-continued

SEQ ID NO: 13, SYNP_LVR_SP0340
SYNP_LVR_SP0247_145
GAACTGTTTGCATGTTGCAAATGATGTCCAAAGTCCAAACATTGTTAAT

AATTAATACTCCAATAAACATCATGTCAGAATTTCTGTTTTCTTTTCCC

TTTGAACCTTTGCAGGATTGCCACATCATCAGGACCACACCTTCATCAG

GAATGAATATCAGGCTTTCACTTTCTCGCCAACTTACAAGGCCTTTCTG

TGTAAACAATACCTGAACCTTTACCCCGTTGCCCGGCAACGGCCAGGTC

TGTGCCAAGTGTTTGCCGATGACCTAATGATTCTGAGCTTGGCAAAGGT

CTTATCTCCCAGCTCGCCCAGGCCCAGTGTTCCAGGAATGTGACCTTTG

CTGCAGCAGCCGCTGGAGGGGGCAGAGGGGATGGGCTGGAGGTTGAGCA

AACAGAGCAGCAGAAAAGGCAGTTCCTCTTCTCCAGTGCCCTCCTTCCC

TGTCTCTGCCTCTCCCTCCCTTCCTCAGGCATCAGAGCGGAGACTTCAG

GGAGACCAGAGCCCAGCTTGCCAGGCACTGAGCTAGAAGCCCTGCC

SEQ ID NO: 14, SYNP_LVR_SP0341
SYNP_LVR_SP0247_167
ATGTCCAAAGTCCAAACATTGTTAATAATTAATACTCCAATAAACATCA

TGTCAGAATTTCTGTTTTCTTTTCCCTTTGAACCTTTGCAGGATTGCCA

CATCATCAGGACCACACCTTCATCAGGAATGAATATCAGGCTTTCACTT

TCTCGCCAACTTACAAGGCCTTTCTGTGTAAACAATACCTGAACCTTTA

CCCCGTTGCCCGGCAACGGCCAGGTCTGTGCCAAGTGTTTGCCGATGAC

CTAATGATTCTGAGCTTGGCAAAGGTCTTATCTCCCAGCTCGCCCAGGC

CCAGTGTTCCAGGAATGTGACCTTTGCTGCAGCAGCCGCTGGAGGGGGC

AGAGGGGATGGGCTGGAGGTTGAGCAAACAGAGCAGCAGAAAAGGCAGT

TCCTCTTCTCCAGTGCCCTCCTTCCCTGTCTCTGCCTCTCCCTCCCTTC

CTCAGGCATCAGAGCGGAGACTTCAGGGAGACCAGAGCCCAGCTTGCCA

GGCACTGAGCTAGAAGCCCTGCC

SEQ ID NO: 15, SYNP_LVR_SP0342
SYNP_LVR_SP0247_156233
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCCTTTCTGTGTAAACAATACCTGAACCTTTACCCCGTTGCCC

GGCAACGGCCAGGTCTGTGCCAAGTGTTTGCCGATGACCTAATGATTCT

GAGCTTGGCAAAGGTCTTATCTCCCAGCTCGCCCAGGCCCAGTGTTCCA

GGAATGTGACCTTTGCTGCAGCAGCCGCTGGAGGGGGCAGAGGGGATGG

GCTGGAGGTTGAGCAAACAGAGCAGCAGAAAAGGCAGTTCCTCTTCTCC

AGTGCCCTCCTTCCCTGTCTCTGCCTCTCCCTCCCTTCCTCAGGCATCA

GAGCGGAGACTTCAGGGAGACCAGAGCCCAGCTTGCCAGGCACTGAGCT

AGAAGCCCTGCC

SEQ ID NO: 16, SYNP_LVR_SP0343
SYNP_LVR_SP0247_156233r
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

-continued

```
ACCTTTGCTGATGTCCTGATTGGAAGGACCGTTGGCCCCCCACCCTTAG

GCAGTGTATACTCTTCCATAAACGAGCTATTAGTTATCTTTCTGTGTAA

ACAATACCTGAACCTTTACCCCGTTGCCCGGCAACGGCCAGGTCTGTGC

CAAGTGTTTGCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC
```

SEQ ID NO: 17, SYNP_LVR_SP0344
SYNP_LVR_SP0247_250328
```
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCAGGCTTTCACTTTCTCGCCAACTTACAAGGCCTTTCTGTGTAA

ACAATGGCAAAGGTCTTATCTCCCAGCTCGCCCAGGCCCAGTGTTCCAG

GAATGTGACCTTTGCTGCAGCAGCCGCTGGAGGGGGCAGAGGGGATGGG

CTGGAGGTTGAGCAAACAGAGCAGCAGAAAAGGCAGTTCCTCTTCTCCA

GTGCCCTCCTTCCCTGTCTCTGCCTCTCCCTCCCTTCCTCAGGCATCAG

AGCGGAGACTTCAGGGAGACCAGAGCCCAGCTTGCCAGGCACTGAGCTA

GAAGCCCTGCC
```

SEQ ID NO: 18, SYNP_LVR_SP0345
SYNP_LVR_SP0247_270325
```
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCAGGCTTTCACTTTCTCGCCAACTTACAAGGCCTTTCTGTGTAA

ACAATACCTGAACCTTTACCCCGTGCTTGGCAAAGGTCTTATCTCCCAG

CTCGCCCAGGCCCAGTGTTCCAGGAATGTGACCTTTGCTGCAGCAGCCG

CTGGAGGGGGCAGAGGGGATGGGCTGGAGGTTGAGCAAACAGAGCAGCA

GAAAAGGCAGTTCCTCTTCTCCAGTGCCCTCCTTCCCTGTCTCTGCCTC

TCCCTCCCTTCCTCAGGCATCAGAGCGGAGACTTCAGGGAGACCAGAGC

CCAGCTTGCCAGGCACTGAGCTAGAAGCCCTGCC
```

SEQ ID NO: 19, SYNP_LVR_SP0346
SYNP_LVR_SP0257_122
```
CTTACAAGGCCTTTCTGTGTAAACAATACCTGAACCTTTACCCCGTTGC

CCGGCAACGGCCAGGTCTGTGCCAAGTGTTTGGCTGGTTTCTTATAAAA

CTGATGGAAGATACAAACACTATTAAAGAACTGTTTGCATGTTGCAAAT

GATGTCCAAAGTCCAAACATTGTTAATAATTAATACTCCAATAAACATC

ATGTCAGAATTTCTGTTTTCTTTTCCCTTTGAACCTTTGCAGGATTGCC

ACATCATCAGGACCACACCTTCATCAGGAATGAATATCCGATGACCTAA

TGATTCTGAGCTTGGCAAAGGTCTTATCTCCCAGCTCGCCCAGGCCCAG
```

-continued

```
TGTTCCAGGAATGTGACCTTTGCTGCAGCAGCCGCTGGAGGGGGCAGAG

GGGATGGGCTGGAGGTTGAGCAAACAGAGCAGCAGAAAAGGCAGTTCCT

CTTCTCCAGTGCCCTCCTTCCCTGTCTCTGCCTCTCCCTCCCTTCCTCA

GGCATCAGAGCGGAGACTTCAGGGAGACCAGAGCCCAGCTTGCCAGGCA

CTGAGCTAGAAGCCCTGCC
```

SEQ ID NO: 20, SYNP_LVR_SP0347
SYNP_LVR_SP0257_66170
```
CAGGCTTTCACTTTCTCGCCAACTTACAAGGCCTTTCTGTGTAAACAAT

ACCTGAACCTTTACCCATGTCCAAAGTCCAAACATTGTTAATAATTAAT

ACTCCAATAAACATCATGTCAGAATTTCTGTTTTCTTTTCCCTTTGAAC

CTTTGCAGGATTGCCACATCATCAGGACCACACCTTCATCAGGAATGAA

TATCCGATGACCTAATGATTCTGAGCTTGGCAAAGGTCTTATCTCCCAG

CTCGCCCAGGCCCAGTGTTCCAGGAATGTGACCTTTGCTGCAGCAGCCG

CTGGAGGGGGCAGAGGGGATGGGCTGGAGGTTGAGCAAACAGAGCAGCA

GAAAAGGCAGTTCCTCTTCTCCAGTGCCCTCCTTCCCTGTCTCTGCCTC

TCCCTCCCTTCCTCAGGCATCAGAGCGGAGACTTCAGGGAGACCAGAGC

CCAGCTTGCCAGGCACTGAGCTAGAAGCCCTGCC
```

SEQ ID NO: 21, SYNP_LVR_SP0348
SYNP_LVR_SP0257_66170r
```
CAGGCTTTCACTTTCTCGCCAACTTACAAGGCCTTTCTGTGTAAACAAT

ACCTGAACCTTTACCCTGATGTCCTGATTGGAAGGACCGTTGGCCCCCC

ACCCTTAGGCAGTGTATACTCTTCCATAAACGAGCTATTAGTTATGAGG

TCCGTAGATTGAAAAGGGTGACGATGTCCAAAGTCCAAACATTGTTAAT

AATTAATACTCCAATAAACATCATGTCAGAATTTCTGTTTTCTTTTCCC

TTTGAACCTTTGCAGGATTGCCACATCATCAGGACCACACCTTCATCAG

GAATGAATATCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC
```

SEQ ID NO: 22, SYNP_LVR_SP0349
SYNP_LVR_SP0257_263319
```
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGGCTGGTTTCTTATAAAACTGATGGAAGATACAAACACTATTAAA

GAACTGTTTGCATGTTGCAAATGATGTCCAAAGTCCAAACATTGTTAAT

AATTAATACTCCAATAAACATCATGTCAGAATTTCTGTTTTCTTTTCCC

TTTGAACCTTTGCAGGATTCTGAGCTTGGCAAAGGTCTTATCTCCCAGC

TCGCCCAGGCCCAGTGTTCCAGGAATGTGACCTTTGCTGCAGCAGCCGC

TGGAGGGGGCAGAGGGGATGGGCTGGAGGTTGAGCAAACAGAGCAGCAG
```

-continued

AAAAGGCAGTTCCTCTTCTCCAGTGCCCTCCTTCCCTGTCTCTGCCTCT

CCCTCCCTTCCTCAGGCATCAGAGCGGAGACTTCAGGGAGACCAGAGCC

CAGCTTGCCAGGCACTGAGCTAGAAGCCCTGCC

SEQ ID NO: 23, SYNP_LVR_SP0350
SYNP_LVR_SP0259_23104
CTGTTTGCTGCTTGCAATGTTTGTCCAAAGTCCAAACATTGTTAATAAT

TAATACTCCAATAAACATCATGTCAGAATTTCTGTTTTCTTTTCCCTTT

GAACCTTTGCAGGATTGCCACATCATCAGGACCACACCTTCATCAGGAA

TGAATATCCGATGACCTAATGATTCTGAGCTTGGCAAAGGTCTTATCTC

CCAGCTCGCCCAGGCCCAGTGTTCCAGGAATGTGACCTTTGCTGCAGCA

GCCGCTGGAGGGGGCAGAGGGGATGGGCTGGAGGTTGAGCAAACAGAGC

AGCAGAAAGGCAGTTCCTCTTCTCCAGTGCCCTCCTTCCCTGTCTCTG

CCTCTCCCTCCCTTCCTCAGGCATCAGAGCGGAGACTTCAGGGAGACCA

GAGCCCAGCTTGCCAGGCACTGAGCTAGAAGCCCTGCC

SEQ ID NO: 24, SYNP_LVR_SP0351
SYNP_LVR_SP0259_23104r
CTGTTTGCTGCTTGCAATGTTTTGATGTCCTGATTGGAAGGACCGTTGG

CCCCCCACCCTTAGGCAGTGTATACTCTTCCATAAACGAGCTATTAGTT

ATGAGGGTCCAAAGTCCAAACATTGTTAATAATTAATACTCCAATAAAC

ATCATGTCAGAATTTCTGTTTTCTTTTCCCTTTGAACCTTTGCAGGATT

GCCACATCATCAGGACCACACCTTCATCAGGAATGAATATCCGATGACC

TAATGATTCTGAGCTTGGCAAAGGTCTTATCTCCCAGCTCGCCCAGGCC

CAGTGTTCCAGGAATGTGACCTTTGCTGCAGCAGCCGCTGGAGGGGGCA

GAGGGGATGGGCTGGAGGTTGAGCAAACAGAGCAGCAGAAAAGGCAGTT

CCTCTTCTCCAGTGCCCTCCTTCCCTGTCTCTGCCTCTCCCTCCCTTCC

TCAGGCATCAGAGCGGAGACTTCAGGGAGACCAGAGCCCAGCTTGCCAG

GCACTGAGCTAGAAGCCCTGCC

SEQ ID NO: 25, SYNP_LVR_SP0352
SYNP_LVR_SP0259_202260
CTGTTTGCTGCTTGCAATGTTTGCCCATTTTAGGGGCTGGTTTCTTATA

AAACTGATGGAAGATACAAACACTATTAAAGAACTGTTTGCATGTTGCA

AATGATGTCCAAAGTCCAAACATTGTTAATAATTAATACTCCAATAAAC

ATCATGTCAGAATTTCTGTTTTCTTTTCCCTTTGAACCTTTGCAGGATT

GCCACTGGCAAAGGTCTTATCTCCCAGCTCGCCCAGGCCCAGTGTTCCA

GGAATGTGACCTTTGCTGCAGCAGCCGCTGGAGGGGGCAGAGGGGATGG

GCTGGAGGTTGAGCAAACAGAGCAGCAGAAAAGGCAGTTCCTCTTCTCC

AGTGCCCTCCTTCCCTGTCTCTGCCTCTCCCTCCCTTCCTCAGGCATCA

GAGCGGAGACTTCAGGGAGACCAGAGCCCAGCTTGCCAGGCACTGAGCT

AGAAGCCCTGCC

SEQ ID NO: 26, SYNP_LVR_SP0353
SYNP_LVR_SP0264_61G_58T
CAGGCTTTCACTTTCTCGCCAACTTACAAGGCCTTTCTGTGTAAACAAT

ACCTGAACTTTGACCCCGTTGCCCGGCAACGGCCAGGTCTGTGCCAAGT

GTTTGCCTTTGCAACAGCTTATCGGAAGCAAACAAGCTGAGGGGAATTG

AGCAAGAATTTCTGGGATACCAACAGCATAGGAGGAACAAAGGACGTAG

AGGGAGGGTTGACTGTCTACACAGGACAAAGCCAATGATTAACCAAACC

TCTTGCAGATTTAAATAGGATGGGAACTAGGAGTGGCAGCAATCCTTTC

TTTCAGCTGGAGTGCTCCTCAGGAGCCAGCCCCACCCTTAGAAAAGCCA

CC

SEQ ID NO: 27, SYNP_LVR_SP0354
SYNP_LVR_SP0264_213T
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGCCTTTGCAACAGCTTATCGGAAGCAAACAAGCTGAGGGGAATTG

AGCAAGAATTTCTGGGATACCAACAGCATAGGAGGAACAAAGGACGTAG

AGGGAGGGTTGACTGTTTACACAGGACAAAGCCAATGATTAACCAAACC

TCTTGCAGATTTAAATAGGATGGGAACTAGGAGTGGCAGCAATCCTTTC

TTTCAGCTGGAGTGCTCCTCAGGAGCCAGCCCCACCCTTAGAAAAGCCA

CC

SEQ ID NO: 28, SYNP_LVR_SP0155
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCCGATGACCTAATGATTCTGAGCTTGGCAAAGGTCTTATCTCCC

AGCTCGCCCAGGCCCAGTGTTCCAGGAATGTGACCTTTGCTGCAGCAGC

CGCTGGAGGGGGCAGAGGGGATGGGCTGGAGGTTGAGCAAACAGAGCAG

CAGAAAAGGCAGTTCCTCTTCTCCAGTGCCCTCCTTCCCTGTCTCTGCC

TCTCCCTCCCTTCCTCAGGCATCAGAGCGGAGACTTCAGGGAGACCAGA

GCCCAGCTTGCCAGGCACTGAGCTAGAAGCCCTGCCATG

SEQ ID NO: 29, SYNP_LVR_SP0239
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGAGGTTAATTTTTAAAAAGCAGTCAAAAGTCCAAGTGGCCCTTGG

CAGCATTTACTCTCTCTGTTTGCTCTGGTTAATAATCTCAGGAGCACAA

ACATTCCGGCCCGGGAGGCGCCCTTTGGACCTTTTGCAATCCTGGCGCA

CTGAACCCTTGACCCCTGCCCTGCAGCCCCCGCAGCTTGCTGTTTGCCC

ACTCTATTTGCCCAGCCCCAGCCCTGGAGAGTCCTTTAGCAGGGCAAAG

TGCAACATAGGCAGACCTTAAGGGATGACTCAGTAACAGATAAGCTTTG

TGTGCCTGCAGGGCATATAAAACAGGGGCAAGGCACAGACTCATAGCAG

AGCAATCACCACCAAGCCTGGAATAACTGCAGCCACC

SEQ ID NO: 30, SYNP_LVR_SP0247
GCTGGTTTCTTATAAAACTGATGGAAGATACAAACACTATTAAAGAACT

GTTTGCATGTTGCAAATGATGTCCAAAGTCCAAACATTGTTAATAATTA

ATACTCCAATAAACATCATGTCAGAATTTCTGTTTTCTTTTCCCTTTGA

ACCTTTGCAGGATTGCCACATCATCAGGACCACACCTTCATCAGGAATG

AATATCAGGCTTTCACTTTCTCGCCAACTTACAAGGCCTTTCTGTGTAA

-continued

ACAATACCTGAACCTTTACCCCGTTGCCCGGCAACGGCCAGGTCTGTGC

CAAGTGTTTGCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC

SEQ ID NO: 31, SYNP_LVR_SP0257
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGGCTGGTTTCTTATAAAACTGATGGAAGATACAAACACTATTAAA

GAACTGTTTGCATGTTGCAAATGATGTCCAAAGTCCAAACATTGTTAAT

AATTAATACTCCAATAAACATCATGTCAGAATTTCTGTTTTCTTTTCCC

TTTGAACCTTTGCAGGATTGCCACATCATCAGGACCACACCTTCATCAG

GAATGAATATCCGATGACCTAATGATTCTGAGCTTGGCAAAGGTCTTAT

CTCCCAGCTCGCCCAGGCCCAGTGTTCCAGGAATGTGACCTTTGCTGCA

GCAGCCGCTGGAGGGGGCAGAGGGGATGGGCTGGAGGTTGAGCAAACAG

AGCAGCAGAAAGGCAGTTCCTCTTCTCCAGTGCCCTCCTTCCCTGTCT

CTGCCTCTCCCTCCCTTCCTCAGGCATCAGAGCGGAGACTTCAGGGAGA

CCAGAGCCCAGCTTGCCAGGCACTGAGCTAGAAGCCCTGCC

SEQ ID NO: 32, SYNP_LVR_SP0259
CTGTTTGCTGCTTGCAATGTTTGCCCATTTTAGGGGCTGGTTTCTTATA

AAACTGATGGAAGATACAAACACTATTAAAGAACTGTTTGCATGTTGCA

AATGATGTCCAAAGTCCAAACATTGTTAATAATTAATACTCCAATAAAC

ATCATGTCAGAATTTCTGTTTTCTTTTCCCTTTGAACCTTTGCAGGATT

GCCACATCATCAGGACCACACCTTCATCAGGAATGAATATCCGATGACC

TAATGATTCTGAGCTTGGCAAAGGTCTTATCTCCCAGCTCGCCCAGGCC

CAGTGTTCCAGGAATGTGACCTTTGCTGCAGCAGCCGCTGGAGGGGGCA

GAGGGGATGGGCTGGAGGTTGAGCAAACAGAGCAGCAGAAAAGGCAGTT

CCTCTTCTCCAGTGCCCTCCTTCCCTGTCTCTGCCTCTCCCTCCCTTCC

TCAGGCATCAGAGCGGAGACTTCAGGGAGACCAGAGCCCAGCTTGCCAG

GCACTGAGCTAGAAGCCCTGCC

SEQ ID NO: 33, SYNP_LVR_SP0264
CAGGCTTTCACTTTCTCGCCAACTTACAAGGCCTTTCTGTGTAAACAAT

ACCTGAACCTTTACCCCGTTGCCCGGCAACGGCCAGGTCTGTGCCAAGT

GTTTGCCTTTGCAACAGCTTATCGGAAGCAAACAAGCTGAGGGGAATTG

AGCAAGAATTTCTGGGATACCAACAGCATAGGAGGAACAAAGGACGTAG

AGGGAGGGTTGACTGTCTACACAGGACAAAGCCAATGATTAACCAAACC

TCTTGCAGATTTAAATAGGATGGGAACTAGGAGTGGCAGCAATCCTTTC

TTTCAGCTGGAGTGCTCCTCAGGAGCCAGCCCCACCCTTAGAAAAGCCA

CC

In some embodiments of any of the aspects, the isolation of nucleic acids is optionally accomplished by techniques such as cell lysis followed by phenol plus chloroform extraction, followed by ethanol precipitation of the nucleic acids. The nucleic acids of this invention can be isolated from cells according to methods well known in the art for isolating nucleic acids. Alternatively, the nucleic acids of the present invention can be synthesized according to standard protocols well described in the literature for synthesizing nucleic acids.

Numerous methods are known in the art for the synthesis and production of nucleic acid sequences illustratively including cloning and expression in cells such as *E. coli*, insect cells such as Sf9 cells, yeast, and mammalian cell types such as Hela cells, Chinese hamster ovary cells, or other cells systems known in the art as amendable to transfection and nucleic acid and/or protein expression. Methods of nucleic acid isolation are similarly recognized in the art. Illustratively, plasmid DNA amplified in E. co/i is cleaved by suitable restriction enzymes such as NdeI and XhoI to linearize PA DNA. The PA DNA is subsequently isolated following gel electrophoresis using a S.N.A.P.™ UV-Free Gel Purification Kit (Invitrogen, Carlsbad, Calif) as per the manufacturer's instructions.

In some embodiments of any of the aspects, the isolated nucleic acid is transfected into a cell. Numerous agents are amenable to facilitate cell transfection illustratively including synthetic or natural transfection agents such as LIPO-FECTIN, LIPOFECTAMINE, baculovirus, naked plasmid or other DNA, or other systems known in the art.

The nucleic acid sequences of the invention may be isolated or amplified by conventional uses of polymerase chain reaction or cloning techniques such as those described in conventional texts. For example, the nucleic acid sequences of this invention may be prepared or isolated from DNA using DNA primers and PCR techniques. Alternatively, the inventive nucleic acid sequence may be obtained from gene banks derived from whole genomic DNA. These sequences, fragments thereof, modifications thereto and the full-length sequences may be constructed recombinantly using conventional genetic engineering or chemical synthesis techniques or PCR, and the like.

Modifications to the nucleic acids of the invention are also contemplated, provided that the essential structure and function of the peptide encoded by the nucleic acid are maintained. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of nucleic acid compounds useful in the embodiments described herein include, but are not limited to nucleic acids containing modified backbones or no natural internucleoside linkages. nucleic acids having modified backbones include, among others, those that do not have a phosphorus atom in the backbone. For the purposes of this specification, and as sometimes referenced in the art, modified nucleic acids that do not have a phosphorus atom in their internucleoside backbone can also be considered to be oligonucleosides. In some embodiments of any of the aspects, the modified nucleic acid will have a phosphorus atom in its internucleoside backbone.

Modified nucleic acid backbones can include, for example, phosphorothioates, chiral phosphorothioates, phosphorodithioates, phosphotriesters, aminoalkylphospho-triesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; others having mixed N, O, S and CH2 component parts, and oligonucleosides with heteroatom backbones, and in particular —CH2-NH—CH2-, —CH2-N(CH3)-O—CH2-[known as a methylene (methylimino) or MMI backbone], —CH2-O—N(CH3)-CH2-, —CH2-N(CH3)-N(CH3)-CH2- and —N(CH3)-CH2-CH2-[wherein the native phosphodiester backbone is represented as —O—P—O—CH2-].

Modified nucleic acids can also contain one or more substituted sugar moieties. The nucleic acids described herein can include one of the following at the 2' position: OH; F; O—, S—, or N-alkyl; O—, S—, or N-alkenyl; O—, S- or N-alkynyl; or O-alkyl-O-alkyl, wherein the alkyl, alkenyl and alkynyl may be substituted or unsubstituted C1 to C10 alkyl or C2 to C10 alkenyl and alkynyl. Exemplary suitable modifications include O[(CH2)nO]mCH3, O(CH2) nOCH3, O(CH2)nNH2, O(CH2)nCH3, O(CH2)nONH2, and O(CH2)nON[(CH2)nCH3)]2, where n and m are from 1 to about 10. In some embodiments of any of the aspects, nucleic acids include one of the following at the 2' position: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a nucleic acid, or a group for improving the pharmacodynamic properties of a nucleic acid, and other substituents having similar properties. In some embodiments of any of the aspects, the modification includes a 2' methoxyethoxy (2'-O—CH$_2$CH$_2$OCH$_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O(CH2)20N(CH3)2 group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH2-O—CH2-N(CH2)2, also described in examples herein below.

Other modifications include 2'-methoxy (2'-OCH3), 2'-aminopropoxy (2'-OCH2CH2CH2NH2) and 2'-fluoro (2'-F). Similar modifications can also be made at other positions on the nucleic acid, particularly the 3' position of the sugar on the 3' terminal nucleotide or in 2'-5' linked dsRNAs and the 5' position of 5' terminal nucleotide. Nucleic acids may also have sugar mimetics such as cyclobutyl moieties in place of the pentofuranosyl sugar.

A nucleic acid can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases can include other synthetic and natural nucleobases including but not limited to as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Certain of these nucleobases are particularly useful for increasing the binding affinity of the inhibitory nucleic acids featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications. In some embodiments of any of the aspects, modified nucleobases can include d5SICS and dNAM, which are a non-limiting example of unnatural nucleobases that can be used separately or together as base pairs (see e.g., Leconte et. al. J. Am. Chem. Soc. 2008, 130, 7, 2336-2343; Malyshev et. al. PNAS. 2012. 109 (30) 12005-12010). In some embodiments of any of the aspects, oligonucleotide tags (e.g., Oligopaint) comprise any modified nucleobases known in the art, i.e., any nucleobase that is modified from an unmodified and/or natural nucleobase.

The preparation of the modified nucleic acids, backbones, and nucleobases described above are well known in the art.

Vectors

Described in several aspects herein are methods of designed or synthesizing a synthetic polynucleotide with transcriptional regulatory functionality. In some embodiments, a recombinant expression vector or plasmid comprises one or more of the polynucleotides (e.g., synthetic regulatory sequence) described herein. In some embodiments of any of the aspects, a vector comprising a synthetic polynucleotide with transcriptional regulatory functionality can be designed or synthesized using any method of designing said synthetic polynucleotide with transcriptional regulatory functionality, as described further herein. In some embodiments of any of the aspects, a vector comprises SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33, or to a sequence comprising a combination of modifications comprised by SEQ ID NO: 1-27, that maintains the same functions as any one of SEQ ID NO: 1-33 (e.g., transcriptional regulatory functionality).

In a further aspect of the invention, there is provided an expression cassette comprising a synthetic promoter comprising or containing any one of SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33, or to a sequence comprising a combination of modifications comprised by SEQ ID NO: 1-27, or a functional variant thereof, operably linked to a sequence encoding an expression product, suitably a gene, e.g. a transgene. In some embodiments the expression product is a therapeutic expression product.

In a further aspect, there is provided a vector comprising a synthetic promoter comprising or containing any one of SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33, or to a sequence comprising a combination of modifications comprised by SEQ ID NO: 1-27, or a functional variant thereof, or an expression cassette comprising a synthetic promoter comprising or containing any one of SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33, or to a sequence comprising a combination of modifications comprised by SEQ ID NO: 1-27, or a functional variant thereof. In some embodiments the vector is an expression vector. In some embodiments the vector is a viral vector. In some embodiments the vector is a gene therapy vector, suitably an AAV vector, an adenoviral vector, a retroviral vector or a lentiviral vector. AAV vectors are of particular interest.

In a further aspect, there is provided a virion (viral particle) comprising a vector, suitably a viral vector, according to the present invention. In some embodiments the virion is an AAV virion.

In a further aspect, there is provided a pharmaceutical composition comprising a synthetic promoter, expression cassette, vector or virion according to the present invention.

In a further aspect, there is provided a synthetic promoter, expression cassette, vector, virion or pharmaceutical composition according to the present invention for use in therapy, i.e. the prevention or treatment of a medical condition or disease. In a further aspect, there is provided a synthetic promoter, expression cassette, vector, virion or pharmaceutical composition according to the present invention for use in in the manufacture of a pharmaceutical composition for the treatment of a medical condition or disease.

As used herein, the term "vector" refers to a polynucleotide sequence suitable for transferring transgenes into a host cell. The term "vector" includes plasmids, mini-chromosomes, phage, naked DNA and the like. See, for example, U.S. Pat. Nos. 4,980,285; 5,631,150; 5,707,828; 5,759,828; 5,888,783 and, 5,919,670, and, Sambrook et al, Molecular Cloning: A Laboratory Manual, 2nd Ed., Cold Spring Harbor Press (1989). One type of vector is a "plasmid," which refers to a circular double stranded DNA loop into which additional DNA segments are ligated. Another type of vector is a viral vector, wherein additional DNA segments are ligated into the viral genome, as described further herein. Certain vectors are capable of autonomous replication in a host cell into which they are introduced (e.g., bacterial vectors having a bacterial origin of replication and episomal mammalian vectors). Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" is used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

A cloning vector is one which is able to replicate autonomously or integrated in the genome in a host cell, and which is further characterized by one or more endonuclease restriction sites at which the vector may be cut in a determinable fashion and into which a desired DNA sequence can be ligated such that the new recombinant vector retains its ability to replicate in the host cell. In the case of plasmids, replication of the desired sequence can occur many times as the plasmid increases in copy number within the host cell such as a host bacterium or just a single time per host before the host reproduces by mitosis. In the case of phage, replication can occur actively during a lytic phase or passively during a lysogenic phase.

An expression vector is one into which a desired DNA sequence can be inserted by restriction and ligation such that it is operably joined to regulatory sequences and can be expressed as an RNA transcript. Vectors can further contain one or more marker sequences suitable for use in the identification of cells which have or have not been transformed or transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). In certain embodiments, the vectors used herein are capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript can be translated into the desired protein or polypeptide.

Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA). That heterologous DNA (RNA) is placed under operable control of transcriptional elements to permit the expression of the heterologous DNA in the host cell.

In some embodiments, one or more of the recombinantly expressed gene can be integrated into the genome of the cell.

Viral Vectors

Described in several aspects herein are methods of designed or synthesizing a synthetic polynucleotide with transcriptional regulatory functionality. In some embodiments of any of the aspects, the synthetic polynucleotide comprises a shortened polynucleotide with transcriptional regulatory functionality. Said shortened polynucleotide can be of particular use in applications with size restrictions, such as viral vectors. As a non-limiting example, the packaging capacity of AAV vectors is generally considered to be 4.5 kb or less. Accordingly, various aspects of the invention relate to methods of designing or synthesizing a viral vector comprising a synthetic regulatory sequence (e.g., promoter, enhancer, etc.) designed and/or synthesized using methods as described herein. In some embodiments of any of the aspects, a viral vector comprising a synthetic polynucleotide with transcriptional regulatory functionality can be designed or synthesized using any method of designing said synthetic polynucleotide with transcriptional regulatory functionality, as described further herein. Included below are non-limiting examples of methods of designing or synthesizing viral vectors, as well as corresponding aspects directed at viral vectors.

In some embodiments of any of the aspects, a viral vector (e.g., AAV) comprises SEQ ID NO: 1-33 or a sequence that is at least 70% (e.g., at least 70%, at least 75%, at least 80%, at least 85%, at least 90%, at least 91%, at least 92%, at least 93%, at least 94%, at least 95%, at least 96%, at least 97%, at least 98%, or at least 99%) identical to the sequence of any one of SEQ ID NO: 1-33, or to a sequence comprising a combination of modifications comprised by SEQ ID NO: 1-27, that maintains the same functions as any one of SEQ ID NO: 1-33 (e.g., transcriptional regulatory functionality).

In one aspect, described herein is a method of designing a viral vector comprising a synthetic polynucleotide with transcriptional regulatory functionality, the method comprising: (a) receiving a set of genetic data comprising a polynucleotide sequence; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; and (f) designing a modified polynucleotide molecule based on the determined transcriptional regulatory scores and/or identified non-regulatory sequence elements. In some embodiments of any of the aspects, the designed viral vector is synthesized or manufactured, using methods as described further herein or otherwise known in the art.

In another aspect, described herein is a method of synthesizing a viral vector comprising a synthetic polynucleotide with transcriptional regulatory functionality, the method comprising: (a) receiving a set of genetic data comprising a polynucleotide sequence; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (g) synthesizing a viral vector comprising the modified polynucleotide molecule.

In one aspect, described herein is a viral vector comprising a synthetic regulatory sequence designed or synthesized using methods as described herein. As a non-limiting example, described herein is a viral vector comprising a shortened polynucleotide that was designed or synthesized using a process comprising: (a) receiving a set of genetic data comprising a polynucleotide sequence; (b) identifying an enhancer portion of the polynucleotide sequence using a machine learning model based on k-mers; (c) processing the enhancer portion into a set of sequence elements that each comprise a k-mer fragment of the enhancer portion of the polynucleotide sequence; (d) processing the set of sequence elements with a machine learning model to determine a transcriptional regulatory score associated with each sequence element of the set of sequence elements; (e) identifying at least one sequence element of the set of sequence elements comprising a transcriptional regulatory score below a threshold as a non-regulatory sequence element; (f) designing a modified polynucleotide molecule based on the determined transcriptional regulatory scores and/or identified non-regulatory sequence elements; and (f) synthesizing a viral vector comprising the modified polynucleotide molecule.

In some embodiments of any of the aspects, the modified polynucleotide sequence is designed based on the polynucleotide sequence with the at least one non-regulatory sequence element removed (i.e., a shortened polynucleotide). In some embodiments of any of the aspects, the modified polynucleotide sequence is designed based on the polynucleotide sequence with the at least one non-regulatory sequence element replaced (i.e., a replaced polynucleotide). In some embodiments of any of the aspects, the modified polynucleotide sequence is designed based on at least one mutation of nucleotide position(s) to alter the transcriptional regulatory score(s) (i.e., a mutated polynucleotide).

In some embodiments of any of the aspects, the modified polynucleotide is preferably a shortened polynucleotide (e.g., in order to accommodate length restrictions). In some embodiments of any of the aspects, the shortened polynucleotide is approximately 10%, 15%, 20%, 25%, 30%, 35%, 40%, 45%, 50%, 55%, 60%, 65%, 70%, 75%, 80%, 90%, 91%, 92%, 93%, 94%, 95%, 96%, 97%, 98%, or 99% the length of the parent polynucleotide. In some embodiments of any of the aspects, the shortened polynucleotide molecule is no more than 100 nucleotides long. As a non-limiting example, the shortened polynucleotide molecule is at most 25, at most 50, at most 100, at most 125, at most 150, at most 200, at most 250, at most 300, at most 350, at most 400, at most 450, or at most 500 nucleotides long. In some embodiments of any of the aspects, the shortened polynucleotide molecule is approximately 25, 50, 100, 125, 150, 200, 250, 300, 350, 400, 450, or 500 nucleotides long.

In some embodiments of any of the aspects, the shortened polynucleotide is approximately 80%, 85%, 90%, 91%, 92%, 93%, 94%, 95%, 96%, 97%, 98%, 99%, 100%, 101%, 102%, 103%, 104%, 105%, 106%, 107%, 108%, 109%, 110%, 115%, or 120% the length of the parent polynucleotide. In some embodiments of any of the aspects, the viral vector comprises a synthetic replaced polynucleotide molecule based on the polynucleotide sequence with the at least one non-regulatory sequence element replaced. In some embodiments of any of the aspects, the replaced polynucleotide molecule is at most 25, at most 50, at most 100, at most 125, at most 150, at most 200, at most 250, at most 300, at most 350, at most 400, at most 450, or at most 500 nucleotides long. In some embodiments of any of the aspects, the replaced polynucleotide molecule is approximately 25, 50, 100, 125, 150, 200, 250, 300, 350, 400, 450, or 500 nucleotides long.

In some embodiments of any of the aspects, the transcriptional regulatory functionality of the shortened polynucleotide molecule is compared against the parent polynucleotide molecule, as described further herein. In some embodiments of any of the aspects, the transcriptional regulatory functionality of the shortened polynucleotide molecule is at least 10% that of the parent polynucleotide molecule. As a non-limiting example, the transcriptional regulatory functionality of the modified (e.g., shortened, replaced, mutated) polynucleotide molecule (e.g., in a viral vector as described herein) is at least 10%, at least 20%, at least 30%, at least 40%, at least 50%, at least 60%, at least 70%, at least 80%, at least 90%, at least 100%, at least 110%, at least 120%, at least 130%, at least 140%, at least 150%, at least 160%, at least 170%, at least 180%, at least 190, at least 200%, at least 210%, at least 220%, at least 230%, at least 240%, at least 250%, at least 260%, at least 270%, at least 280%, or at least 290, at least 300% that of the parent polynucleotide molecule.

In some embodiments of any of the aspects, each of the set of sequence elements is a k-mer fragment of the polynucleotide sequence. In some embodiments of any of the aspects, each of the k-mer fragments comprises a gapped k-mer fragment, as described further herein. In some embodiments of any of the aspects, the gapped k-mer fragment comprises a 10 nucleotide-long fragment comprising 4 gaps.

In some embodiments of any of the aspects, the machine learning model is a support vector machine. In some embodiments of any of the aspects, the set of sequence elements are input into the support vector machine. In some embodiments of any of the aspects, the support vector machine comprises a gapped k-mer kernel. In some embodiments of any of the aspects, the support vector machine comprises a k-DNF k-mer kernel. In some embodiments of any of the aspects, the machine learning model is trained using a second set of genetic data comprising a second set of sequence elements that comprise portions of transcriptional regulatory elements and non-regulatory elements. In some embodiments of any of the aspects, synthesizing the shortened polynucleotide molecule comprises de novo DNA synthesis.

In some embodiments of any of the aspects, the known transcriptional regulatory functionality comprises transcriptional activation and/or transcriptional repression. In some embodiments of any of the aspects, the known transcriptional regulatory functionality is in any given cell or tissue type. In some embodiments of any of the aspects, the known transcriptional regulatory functionality is in liver cells, cardiac muscle cells, and/or skeletal muscle cells. In some embodiments of any of the aspects, the known transcriptional regulatory functionality comprises promoter activity. In some embodiments of any of the aspects, promoter activity comprises a level of expression of a particular set of genes.

Synthetic nucleic acids described herein can be used in the production of recombinant vectors, e.g., a recombinant AAV vector. Protocols for producing recombinant vectors and for using vectors for nucleic acid delivery can be found, e.g., in Current Protocols in Molecular Biology, Ausubel, F. M. et al. (eds.) Greene Publishing Associates, (1989) and other standard laboratory manuals (e.g., Vectors for Gene Therapy. In: Current Protocols in Human Genetics. John Wiley and Sons, Inc.: 1997). Further, production of AAV vectors is further described, e.g., in U.S. Pat. No. 9,441,206, the contents of which is incorporated herein by reference in its entirety.

Non-limiting examples of vectors employed in the methods of this invention include any nucleotide construct used to deliver nucleic acid into cells, e.g., a plasmid, an expression vector, a template, a non-viral vector or a viral vector, such as a retroviral vector which can package a recombinant retroviral genome (see e.g., Pastan et al., Proc. Natl. Acad. Sci. U.S.A. 85:4486 (1988); Miller et al., Mol. Cell. Biol. 6:2895 (1986)). For example, the recombinant retrovirus vector can then be administered in vivo and thereby deliver a synthetic nucleic acid of the invention in vivo. The exact method of introducing the synthetic nucleic acids into mammalian cells is, of course, not limited to the use of retroviral vectors. Other techniques are widely available for this procedure including the use of adenoviral vectors (Mitani et al., Hum. Gene Ther. 5:941-948, 1994), adeno-associated viral (AAV) vectors (Goodman et al., Blood 84:1492-1500, 1994), lentiviral vectors (Naldini et al., Science 272:263-267, 1996), pseudotyped retroviral vectors (Agrawal et al., Exper. Hematol. 24:738-747, 1996), and any other vector system now known or later identified.

Also included are chimeric viral particles, which are well known in the art and which can comprise viral proteins and/or nucleic acids from two or more different viruses in any combination to produce a functional viral vector. Chimeric viral particles of this invention can also comprise amino acid and/or nucleotide sequence of non-viral origin (e.g., to facilitate targeting of vectors to specific cells or tissues and/or to induce a specific immune response). Incubation conditions (e.g., timing, climate, medium, etc.) for a given condition are known in the art and can be readily identified by a skilled practitioner.

Viral vectors produced in a cell can be released (i.e. set free from the cell that produced the vector) using any standard technique. For example, viral vectors can be released via mechanical methods, for example microfluidization, centrifugation, or sonication, or chemical methods, for example using lysis buffers and detergents. Released viral vectors are then recovered (i.e., collected) and purified to obtain a pure population using standard methods in the art. For example, viral vectors can be recovered from a buffer they were released into via purification methods, including a clarification step using depth filtration or Tangential Flow Filtration (TFF). Viral vectors can be released from the cell via sonication and recovered via purification of clarified lysate using column chromatography.

In one embodiment, the viral vector is a DNA or RNA virus. Non-limiting examples of a viral vector of this invention include an AAV vector, an adenovirus vector, a lentivirus vector, a retrovirus vector, a herpesvirus vector, an alphavirus vector, a poxvirus vector, a baculovirus vector, and a chimeric virus vector.

Any viral vector that is known in the art can be used in the present invention. Examples of such viral vectors include, but are not limited to vectors derived from: Adenoviridae; Birnaviridae; Bunyaviridae; Caliciviridae; Capillovirus group; Carlavirus group; Carmovirus virus group; Group Caulimovirus; Closterovirus Group; *Commelina* yellow mottle virus group; Comovirus virus group; Coronaviridae; PM2 phage group; Corcicoviridae; Group Cryptic virus; group Cryptovirus; Cucumovirus virus group Family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Peaenation mosaic virus group; Phycodnaviridae; Picornaviridae; Plasmaviridae; Prodoviridae; Polydnaviridae; Potexvirus group; Potyvirus; Poxviridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and Plant virus satellites.

Viral vectors of the invention may comprise the genome, in part or entirety, of any naturally occurring and/or recombinant viral vector nucleotide sequence (e.g., AAV, AV, LV, etc.) or variant. Viral vector variants may have genomic sequences of significant homology at the nucleic acid and amino acid levels, produce viral vector which are generally physical and functional equivalents, replicate by similar mechanisms, and assemble by similar mechanisms.

Variant viral vector sequences can be used to deliver a therapeutic nucleic acid in vivo as described herein. For example, one or more sequences having at least about 70%, at least about 75%, at least about 80%, at least about 85%, at least about 90%, at least about 95%, at least about 99%, or more nucleotide and/or amino acid sequence identity (e.g., a sequence having about 75-99% nucleotide sequence identity) to a given vector (for example, AAV, AV, LV, etc.).

It is understood that a viral vector would further comprise components necessary for a given vector. For example, production of an AAV requires the presence of at least one Replication (Rep) genes and/or at least Capsid (Cap) genes. On the left side of the AAV genome there are two promoters called p5 and p19, from which two overlapping messenger ribonucleic acids (mRNAs) of different length can be produced. Each of these contains an intron which can be either spliced out or not, resulting in four potential Rep genes; Rep78, Rep68, Rep52 and Rep40. Rep genes (specifically Rep 78 and Rep 68) bind the hairpin formed by the ITR in the self-priming act and cleave at the designated terminal resolution site, within the hairpin. They are necessary for the AAVS1-specific integration of the AAV genome. All four Rep proteins were shown to bind ATP and to possess helicase activity. The right side of a positive-sensed AAV genome encodes overlapping sequences of three capsid proteins, VP1, VP2 and VP3, which start from one promoter, designated p40. The cap gene produces an additional, non-structural protein called the Assembly-Activating Protein (AAP). This protein is produced from ORF2 and is essential for the capsid-assembly process. Necessary elements for manufacturing AAV vectors are known in the art, and can further be reviewed, e.g., in U.S. Patent Numbers U.S. Pat. Nos. 5,478,745A; 5,622,856A; 5,658,776A; 6,440,742B1; 6,632,670B1; 6,156,303A; 8,007,780B2; 6,521,225B1; 7,629,322B2; 6,943,019B2; 5,872,005A; and U.S. Patent Application Numbers US 2017/0130245; US20050266567A1; US20050287122A1; the contents of each are incorporated herein by reference in their entireties. In various embodiments, nucleic acids expressing Rep and/or Cap genes are transformed using standard methods, for example, by a plasmid, a virus, a liposome, a microcapsule, a non-viral vector, or as naked DNA.

In some embodiments of any of the aspects, the viral vector comprises at least one inverted terminal repeat (ITR). In one embodiment, the synthetic nucleic acid comprises at least 2, 3, 4, 5, 6, 7, 8, 9, 10, or more ITRs. In one embodiment, the synthetic nucleic acid described herein comprises at least one terminal repeat (TR).

In various embodiments, the TR is an ITR. An ITR includes any viral terminal repeat or synthetic sequence that forms a hairpin structure and functions as an inverted terminal repeat (i.e., mediates the desired functions such as replication, integration and/or provirus rescue, and the like). The ITR can be an AAV ITR or a non-AAV ITR. For example, a non-AAV ITR sequence such as those of other parvoviruses (e.g., canine parvovirus, bovine parvovirus, mouse parvovirus, porcine parvovirus, human parvovirus B-19) or the SV40 hairpin that serves as the origin of SV40 replication can be used as an ITR, which can further be modified by truncation, substitution, deletion, insertion and/or addition. Further, the ITR can be partially or completely synthetic, e.g., as described in U.S. Pat. No. 9,169,494, the contents of which are incorporated by reference in their entirety. Typically, the ITR is 145 nucleotides. The terminal 125 nucleotides form a palindromic double stranded T-shaped hairpin structure. In the structure the A-A' palindrome forms the stem, and the two smaller palindromes B-B' and C-C' form the cross-arms of the T. The other 20 nucleotides in the D sequence remain single-stranded. In the context of an AAV genome, there would be two ITR's, one at each end of the genome.

In some embodiments of any of the aspects, the viral vector is AAV. An AAV ITR may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered. An AAV ITR need not have the native terminal repeat sequence (e.g., a native AAV ITR sequence may be altered by insertion, deletion, truncation and/or missense mutations), as long as the terminal repeat mediates the desired functions, e.g., replication, or, integration.

In one embodiment, the ITR is a wild-type ITR. In another embodiment, the ITR is a mutant ITR. A mutant ITR can be a functional or non-functional ITR. For example, a non-functional ITR would have reduced or a complete loss of the function of a wild-type ITR, e.g., mediates replication, integration and/or provirus rescue.

Figure 1:
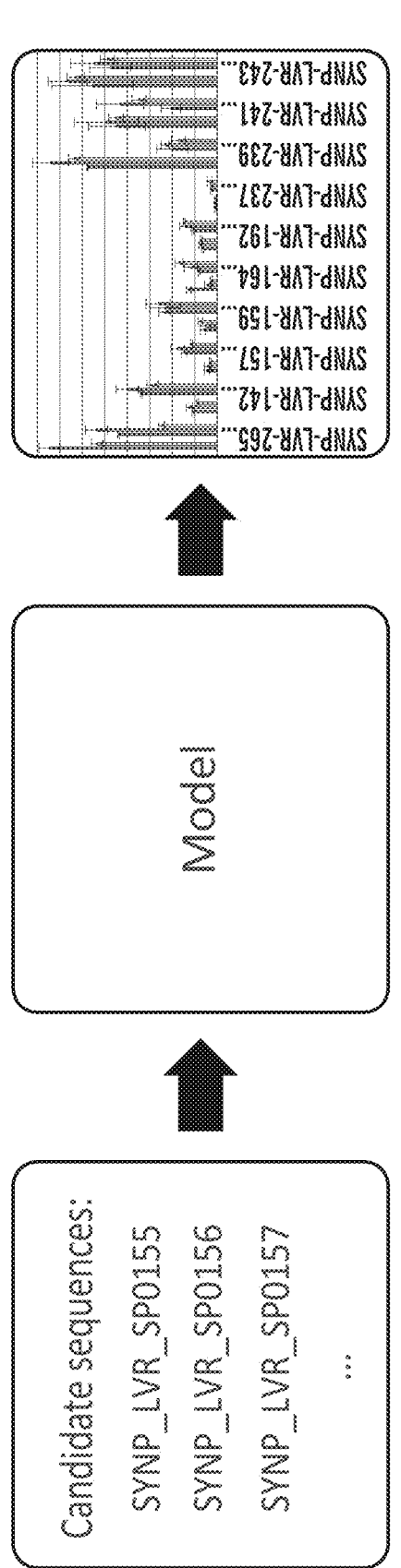
FIG. 1 is a schematic showing the gapped k-mer model. SEQ ID NOs: 34-40 are also indicated in grey. Asterisks (*) indicate that the position can be any nucleotide (e.g., A, T, G, or C)
Figure 1:
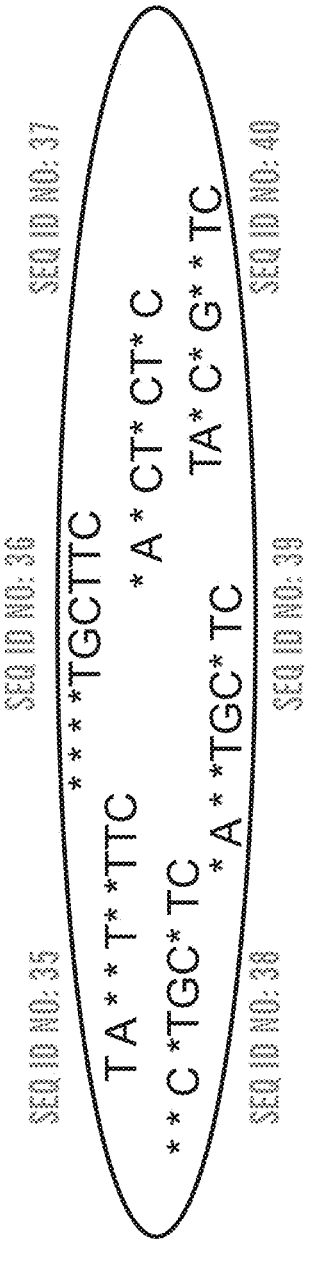

In one embodiment, the mutant ITR is a DD mutant ITR (DD-ITR). A DD-ITR has the same sequence the ITR from which it is derived, but includes a second D sequence adjacent the A sequence, so there are D and D'. The D and D' can anneal (e.g., as described in U.S. Pat. No. 5,478,745, the contents of which are incorporated herein by reference). Each D is typically about 20 nt in length, but can be as small as 5 nucleotides. Shorter D regions preserve the A-D junction (e.g., are generated by deletions at the 3' end that preserve the A-D junction). Preferably the D region retains the nicking site and/or the A-D junction. The DD-ITR is typically about 165 nucleotides. The DD-ITR has the ability to provide information in cis for replication of the DNA construct. Thus, a DD-ITR has an inverted palindromic sequence with flanking D and D' elements, e.g. a (+) strand 5'to 3' sequence of 5'-DABB'CC'A'D'-3' and a (−) strand complimentary to the (+) strand that has a 5' to 3' sequence of 5'-DACC'BB'A'D'-3' that can form a Holiday structure, e.g. as illustrated in FIG. 1. In certain embodiments, the DD-ITR may have deletions in its components (e.g. A-C), while still retaining the D and D' element. In certain embodiments, the ITR comprises deletions while still retaining the ability to form a Holliday structure and retaining two copies of the D element (D and D'). The DD-ITR may be generated from a native AAV ITR or from a synthetic ITR. In certain embodiments, the deletion is in the B region element. In certain embodiments, the deletion is in the C region element. In certain embodiments, a deletion within both the B and C element of the ITR. In one embodiment, the entire B and/or C element is deleted, and e.g. replaced with a single hairpin element. In one embodiment, the template comprises at least two DD-ITRs.

A synthetic ITR can also be used. The synthetic ITR refers to a non-naturally occurring ITR that differs in nucleotide sequence from wild-type ITRs, e.g., the AAV serotype 2 ITR (ITR2) sequence due to one or more deletions, additions, substitutions, or any combination thereof. The difference between the synthetic and wild-type ITR (e.g., ITR2) sequences may be as little as a single nucleotide change, e.g., a change in 1, 2, 3, 4, 5, 6, 7, 8, 9, 10, 15, 20, 25, 30, 35, 40, 45, 50, 60, 60, 70, 80, 90, or 100 or more nucleotides or any range therein. In some embodiments, the difference between, the synthetic and wild-type ITR (e.g., ITR2) sequences may be no more than about 100, 90, 80, 70, 60, 50, 45, 40, 35, 30, 25, 20, 15, 10, 9, 8, 7, 6, 5, 4, 3, 2, or 1 nucleotide or any range therein. Additional TRs can be used in the current invention, for example a long terminal repeat (LTR). Systems FIG. 23 illustrates an example overview of a system for implementing the current disclosure. The system includes genetic data 400 (e.g., genetic data 100, 130, or 200; see e.g., FIG. 15-17) that can be input into a machine learning model that may be stored in a database 460.

The computing device 430 and server 450 may be connected by a network 410, and the network 410 may be connected to various other devices, servers or network equipment for implementing the present disclosure. A computing device 430 may be connected to a display 440. Computing device 430 may be any suitable computing device, including a desktop computer, server (including remote servers), mobile device, or other suitable computing device. In some examples, algorithms, and other software may be stored in database 460 and run on server 450 including the machine learning model. Additionally, genetic data 400, machine learning model, and other genetic information (e.g., scores 150 or plot 250; see e.g., FIG. 15-17) may be stored in database 460.

It should initially be understood that the disclosure herein may be implemented with any type of hardware and/or software, and may be a pre-programmed general purpose computing device. For example, the system may be implemented using a server, a personal computer, a portable computer, a thin client, or any suitable device or devices. The disclosure and/or components thereof may be a single device at a single location, or multiple devices at a single, or multiple, locations that are connected together using any appropriate communication protocols over any communication medium such as electric cable, fiber optic cable, or in a wireless manner.

It should also be noted that the disclosure is illustrated and discussed herein as having a plurality of modules which perform particular functions. It should be understood that these modules are merely schematically illustrated based on their function for clarity purposes only, and do not necessary represent specific hardware or software. In this regard, these modules may be hardware and/or software implemented to substantially perform the particular functions discussed. Moreover, the modules may be combined together within the disclosure, or divided into additional modules based on the particular function desired. Thus, the disclosure should not be construed to limit the present technology as disclosed herein, but merely be understood to illustrate one example implementation thereof.

The computing system can include clients and servers. A client and server may be remote from each other and typically interact through a communication network. The relationship of client and server arises by virtue of computer programs running on the respective computers and having a client-server relationship to each other. In some implementations, a server transmits data (e.g., an HTML page) to a client device (e.g., for purposes of displaying data to and receiving user input from a user interacting with the client device). Data generated at the client device (e.g., a result of the user interaction) can be received from the client device at the server.

Implementations of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer to-peer networks).

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively, or in addition, the program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a "data processing apparatus" on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array), a GPU (graphics processing unit), or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable DNA can include, e.g., genomic DNA or cDNA. Suitable RNA can include, e.g., mRNA.

A variant DNA (or amino acid) sequence can be at least 30%, at least 40%, at least 50%, at least 60%, at least 70%, at least 80%, at least 90%, at least 91%, at least 92%, at least 93%, at least 94%, at least 95%, at least 96%, at least 97%, at least 98%, at least 99%, or more, identical to a native or reference sequence. The degree of homology (percent identity) between a native and a mutant sequence can be determined, for example, by comparing the two sequences using freely available computer programs commonly employed for this purpose on the world wide web (e.g. BLASTn or BLASTp with default settings).

As used herein, "synthetic" refers to a continuous sequence of nucleotides that is not naturally occurring. Synthetic nucleic acid expression constructs of the present invention are produced artificially, typically by de novo synthesis or recombinant technologies. Such synthetic nucleic acids may contain naturally occurring sequences (e.g. promoter, enhancer, intron, and other such regulatory sequences), but these are present in a non-naturally occurring context. As a non-limiting example, portions of an enhancer or promoter sequence (e.g., non-regulatory sequence elements as detected using methods described herein) can be removed or replaced in the enhancer or promoter sequence, producing a synthetic polynucleotide.

The term "regulatory element" refers to a nucleic acid sequence which functions alone or in combination with other regulatory elements to regulate the expression of a gene. Exemplary regulatory elements include, without limitation, a promoter, a transcription factor binding site, an enhancer, a silencer, a boundary control element, an insulator, a locus control region, a response element, a binding site, a segment of a terminal repeat, a responsive site, a stabilizing element, a destabilizing element, a splicing element, a cis- or trans-regulatory element, a trans-activator, an inducible element, and a repressible element. Such regulatory elements are, in general, but not without exceptions, located 5' to the coding sequence of the gene it controls, in an intron, or 3' to the coding sequence of a gene, either in the untranslated or untranscribed region. As used herein, "strength of a regulatory element" refers to, the amount of mRNA expression of, e.g., an ORF resulting from the regulatory element being operatively connected to the ORF in the context of, e.g., an expression vector, plasmid, or viral vector.

The term "cis-regulatory element" or "CRE", is a term well-known to the skilled person, and means a nucleic acid sequence such as an enhancer, promoter, insulator, or silencer, that can regulate or modulate the transcription of a neighbouring gene (i.e. in cis). CREs are found in the vicinity of the genes that they regulate. CREs typically regulate gene transcription by binding to TFs, i.e. they include TFBS. A single TF may bind to many CREs, and hence control the expression of many genes (pleiotropy). CREs are usually, but not always, located upstream of the transcription start site (TSS) of the gene that they regulate. "Enhancers" are CREs that enhance (i.e. upregulate) the transcription of genes that they are operably associated with, and can be found upstream, downstream, and even within the introns of the gene that they regulate. Multiple enhancers can act in a coordinated fashion to regulate transcription of one gene. "Silencers" in this context relates to CREs that bind TFs called repressors, which act to prevent or down-regulate transcription of a gene. The term "silencer" can also refer to a region in the 3' untranslated region of messenger RNA, that bind proteins which suppress translation of that mRNA molecule, but this usage is distinct from its use in describing a CRE. In the present context, it is preferred that the CRE is located 1500 nucleotides or less from the transcription start site (TSS), more preferably 1000 nucleotides or less from the TSS, more preferably 500 nucleotides or less from the TSS, and suitably 250, 200, 150, or 100 nucleotides or less from the TSS. CREs of the present invention are preferably comparatively short in length, preferably 250 nucleotides or less in length, for example they may be 200, 175, 150, 90, 80, 70, 60 or 50 nucleotides or less in length. The CREs of the present invention are typically provided in combination with an operably linked promoter element, which can be a minimal promoter or proximal promoter; the CREs of the present invention enhance liver-specific activity or muscle-specific activity of the promoter element; however, the CREs can enhance any tissue-specific activity.

As used herein, "Cis-regulatory module" or "CRM" refers to a stretch of DNA, for example, a stretch of 100-1000 base pairs comprising at least 1, 2, 3, 4, 5, or more CREs (e.g., a combination of CREs), or wherein at least 1, 2, 3, 4, 5, or more transcription factors bind and regulate expression of nearby genes, and/or regulate their transcription rates.

As used herein, "trans-regulatory element" or "TRE", as used herein, is a term known to the skilled person as it relates to a regulatory element, and refers to a regulatory element which regulates the transcription of an ORF that is on a different nucleic acid construct. Trans-regulatory elements include proteins that interact with, e.g., bind to, a nucleic acid. A trans-acting regulatory element can be located on a distinct vector or synthetic nucleic acid construct that does not comprise a transcription start site (TSS) of the gene which it regulates.

As used herein, the phrase "transcription factor target sequence" or "TFBS" or "transcription factor binding site" or "TFTS" or "TFBS motif" or "TFBM" refers to a region of DNA that generally contains specific sequences that are recognized and bound by transcription factors. Transcription factors bind to the TFBS and result in the recruitment of RNA polymerase, an enzyme that synthesizes RNA from the coding region of the gene.

As used herein, the phrase "promoter" refers to a region of DNA that generally is located upstream of a nucleic acid sequence to be transcribed that is needed for transcription to occur. Promoters permit the proper activation or repression of transcription of sequence under their control. A promoter typically contains specific sequences that are recognized and bound by transcription factors. Transcription factors bind to the promoter DNA sequences and result in the recruitment of RNA polymerase, an enzyme that synthesizes RNA from the coding region of the gene. A great many promoters are known in the art. Synthetic promoters typically comprise one or more enhancers linked to a core/minimal promoter or a proximal promoter.

As used herein, "minimal promoter" (also known as the "core promoter") refers to a short DNA segment which is inactive or largely inactive by itself, but can mediate transcription when combined with other transcription regulatory elements. Minimum promoter sequence can be derived from various different sources, including prokaryotic and eukaryotic genes. Examples of minimal promoters are discussed above, and include the dopamine beta-hydroxylase gene minimum promoter, cytomegalovirus (CMV) immediate early gene minimum promoter (CMV-MP), and the herpes thymidine kinase minimal promoter (MinTK). A minimal promoter typically comprises the transcription start site (TSS) and elements directly upstream, a binding site for RNA polymerase II, and general transcription factor binding sites (often a TATA box). A minimal promoter may also include some elements downstream of the TSS, but these typically have little functionality absent additional regulatory elements.

As used herein, "proximal promoter" relates to the minimal promoter plus the proximal sequence upstream of the gene that tends to contain primary regulatory elements. It often extends approximately 250 base pairs upstream of the TSS, and includes specific TFBS. A proximal promoter may also include one or more regulatory elements downstream of the TSS, for example an untranslated region (UTR) or an intron. In the present case, the proximal promoter may suitably be a naturally occurring liver-specific proximal promoter that can be combined with one or more CREs or CRMs of the present invention. However, the proximal promoter can be synthetic.

As used herein, the term "insulator" refers to a genetic boundary element that can block the interaction between enhancers and promoters, so that expression of a gene (including induction or repression of the expression of the gene) does not interfere with that of the neighboring gene.

As used herein, "open reading frame", refers to a sequence of nucleotides that, when read in a particular frame, do not contain any stop codons over the stretch of the open reading frame.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment or agent) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

The sequences as described herein can comprise nucleic acid sequences of a subject. As used herein, a "subject" means a human or animal. Usually the animal is a vertebrate such as a primate, rodent, domestic animal or game animal. Primates include chimpanzees, cynomolgus monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein. Preferably, the subject is a mammal. The mammal can be a human, non-human primate, mouse, rat, dog, cat, horse, or cow, but is not limited to these examples. Mammals other than humans can be advantageously used as subjects that represent animal models. A subject can be male or female.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The term "expression" refers to the cellular processes involved in producing RNA and proteins and as appropriate, secreting proteins, including where applicable, but not limited to, for example, transcription, transcript processing, translation and protein folding, modification and processing. Expression can refer to the transcription and stable accumulation of sense (mRNA) or antisense RNA derived from a nucleic acid fragment or fragments of the invention and/or to the translation of mRNA into a polypeptide.

In some embodiments, the methods described herein relate to measuring, detecting, or determining the level of at least one marker. As used herein, the term "detecting" or "measuring" refers to observing a signal from, e.g. a probe, label, or target molecule to indicate the presence of an analyte in a sample. Any method known in the art for detecting a particular label moiety can be used for detection. Exemplary detection methods include, but are not limited to, spectroscopic, fluorescent, photochemical, biochemical, immunochemical, electrical, optical or chemical methods. In some embodiments of any of the aspects, measuring can be a quantitative observation.

In some embodiments of any of the aspects, a polypeptide, nucleic acid, or cell as described herein can be engineered. As used herein, "engineered" refers to the aspect of having been manipulated by the hand of man. For example, a polypeptide is considered to be "engineered" when at least one aspect of the polypeptide, e.g., its sequence, has been manipulated by the hand of man to differ from the aspect as it exists in nature. As is common practice and is understood by those in the art, progeny of an engineered cell are typically still referred to as "engineered" even though the actual manipulation was performed on a prior entity.

In some embodiments of any of the aspects, the synthetic polynucleotide described herein is exogenous. In some embodiments of any of the aspects, the synthetic polynucleotide described herein is ectopic. In some embodiments of any of the aspects, the synthetic polynucleotide described herein is not endogenous.

The term "exogenous" refers to a substance present in a cell other than its native source. The term "exogenous" when used herein can refer to a nucleic acid (e.g. a nucleic acid encoding a polypeptide) or a polypeptide that has been introduced by a process involving the hand of man into a biological system such as a cell or organism in which it is not normally found and one wishes to introduce the nucleic acid or polypeptide into such a cell or organism. Alternatively, "exogenous" can refer to a nucleic acid or a polypeptide that has been introduced by a process involving the hand of man into a biological system such as a cell or organism in which it is found in relatively low amounts and one wishes to increase the amount of the nucleic acid or polypeptide in the cell or organism, e.g., to create ectopic expression or levels. In contrast, the term "endogenous" refers to a substance that is native to the biological system or cell. As used herein, "ectopic" refers to a substance that is found in an unusual location and/or amount. An ectopic substance can be one that is normally found in a given cell, but at a much lower amount and/or at a different time. Ectopic also includes substance, such as a polypeptide or nucleic acid that is not naturally found or expressed in a given cell in its natural environment.

In some embodiments, a nucleic acid encoding a synthetic polynucleotide as described herein is comprised by a vector. In some of the aspects described herein, a nucleic acid sequence encoding a given polypeptide (e.g., a therapeutic product or therapeutic protein), or any module thereof, is operably linked to a vector. The term "vector", as used herein, refers to a nucleic acid construct designed for delivery to a host cell or for transfer between different host cells. As used herein, a vector can be viral or non-viral. The term "vector" encompasses any genetic element that is capable of replication when associated with the proper control elements and that can transfer gene sequences to cells. A vector can include, but is not limited to, a cloning vector, an expression vector, a plasmid, phage, transposon, cosmid, chromosome, virus, virion, etc.

In some embodiments of any of the aspects, the vector is recombinant, e.g., it comprises sequences originating from at least two different sources. In some embodiments of any of the aspects, the vector comprises sequences originating from at least two different species. In some embodiments of any of the aspects, the vector comprises sequences originating from at least two different genes, e.g., it comprises a fusion protein or a nucleic acid encoding an expression product which is operably linked to at least one non-native (e.g., heterologous) genetic control element (e.g., a promoter, suppressor, activator, enhancer, response element, or the like).

In some embodiments of any of the aspects, the vector or nucleic acid described herein is codon-optimized, e.g., the native or wild-type sequence of the nucleic acid sequence has been altered or engineered to include alternative codons such that altered or engineered nucleic acid encodes the same polypeptide expression product as the native/wild-type sequence, but will be transcribed and/or translated at an improved efficiency in a desired expression system. In some embodiments of any of the aspects, the expression system is an organism other than the source of the native/wild-type sequence (or a cell obtained from such organism). In some embodiments of any of the aspects, the vector and/or nucleic acid sequence described herein is codon-optimized for expression in a mammal or mammalian cell, e.g., a mouse, a murine cell, or a human cell. In some embodiments of any of the aspects, the vector and/or nucleic acid sequence described herein is codon-optimized for expression in a human cell. In some embodiments of any of the aspects, the vector and/or nucleic acid sequence described herein is codon-optimized for expression in a yeast or yeast cell. In some embodiments of any of the aspects, the vector and/or nucleic acid sequence described herein is codon-optimized for expression in a bacterial cell. In some embodiments of any of the aspects, the vector and/or nucleic acid sequence described herein is codon-optimized for expression in an *E. coli* cell.

As used herein, the term "expression vector" refers to a vector that directs expression of an RNA or polypeptide from sequences linked to transcriptional regulatory sequences on the vector. The sequences expressed will often, but not necessarily, be heterologous to the cell. An expression vector may comprise additional elements, for example, the expression vector may have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the nucleic acid encoding a polypeptide as described herein in place of non-essential viral genes. The vector and/or particle may be utilized for the purpose of transferring any nucleic acids into cells either in vitro or in vivo. Numerous forms of viral vectors are known in the art. Non-limiting examples of a viral vector of this invention include an AAV vector, an adenovirus vector, a lentivirus vector, a retrovirus vector, a herpesvirus vector, an alphavirus vector, a poxvirus vector a baculovirus vector, and a chimeric virus vector.

It should be understood that the vectors described herein can, in some embodiments, be combined with other suitable compositions and therapies. In some embodiments, the vector is episomal. The use of a suitable episomal vector provides a means of maintaining the nucleotide of interest in the subject in high copy number extra chromosomal DNA thereby eliminating potential effects of chromosomal integration.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean ±1%.

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of additional elements that do not materially affect the basic and novel or functional characteristic(s) of that embodiment of the invention.

As used herein, the term "corresponding to" refers to an amino acid or nucleotide at the enumerated position in a first polypeptide or nucleic acid, or an amino acid or nucleotide that is equivalent to an enumerated amino acid or nucleotide in a second polypeptide or nucleic acid. Equivalent enumerated amino acids or nucleotides can be determined by alignment of candidate sequences using degree of homology programs known in the art, e.g., BLAST.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology and molecular biology can be found in The Merck Manual of Diagnosis and Therapy, 20th Edition, published by Merck Sharp & Dohme Corp., 2018 (ISBN 0911910190, 978-0911910421); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Janeway's Immunobiology, Kenneth Murphy, Allan Mowat, Casey Weaver (eds.), W. W. Norton & Company, 2016 (ISBN 0815345054, 978-0815345053); Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), Current Protocols in Protein Science (CPPS), John E. Coligan (ed.), John Wiley and Sons, Inc., 2005; and Current Protocols in Immunology (CPI) (John E. Coligan, A D A M Kruisbeek, David H Margulies, Ethan M Shevach, Warren Strobe, (eds.) John Wiley and Sons, Inc., 2003 (ISBN 0471142735, 9780471142737), the contents of which are all incorporated by reference herein in their entireties.

In some embodiments of any of the aspects, the disclosure described herein does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of designing or synthesizing a synthetic polynucleotide with transcriptional regulatory functionality, the method comprising:
   a) receiving a set of genetic data comprising a regulatory polynucleotide sequence, optionally having a known transcriptional regulatory functionality;
   b) processing the set of genetic data into a set of sequence elements that each comprise a portion of the polynucleotide sequence;

c) processing the set of sequence elements with a machine learning model to determine a transcriptional regulatory score associated with each of the set of sequence elements;

d) identifying at least one sequence element of the set of sequence elements comprising a transcriptional regulatory score below a threshold as a non-regulatory sequence element;

e) designing a modified polynucleotide molecule based on the determined transcriptional regulatory scores and/or identified non-regulatory sequence elements; and f) optionally synthesizing the modified polynucleotide molecule.

2. The method of paragraph 1, wherein each of the set of sequence elements is a k-mer fragment of the polynucleotide sequence.

3. The method of paragraph 2, wherein each of the k-mer fragments comprises a gapped k-mer fragment.

4. The method of paragraph 3, wherein the gapped k-mer fragment comprises a 10 nucleotide-long fragment comprising 4 gaps.

5. The method of paragraph 1, wherein the machine learning model is a support vector machine.

6. The method of paragraph 5, wherein the set of sequence elements are input into the support vector machine.

7. The method of paragraph 5, wherein the support vector machine comprises a gapped k-mer kernel.

8. The method of paragraph 5, wherein the support vector machine comprises a k-DNF k-mer kernel.

9. The method of paragraph 1, wherein the machine learning model is trained using a second set of genetic data comprising a second set of sequence elements that comprise portions of transcriptional regulatory elements and non-regulatory elements.

10. The method of paragraph 1, wherein the modified polynucleotide sequence is designed based on the polynucleotide sequence with the at least one non-regulatory sequence element removed.

11. The method of paragraph 1, wherein the modified polynucleotide sequence is designed based on the polynucleotide sequence with the at least one non-regulatory sequence element replaced.

12. The method of paragraph 1, wherein the modified polynucleotide sequence is designed based on at least one mutation of nucleotide position(s) to alter a transcriptional regulatory score.

13. The method of paragraph 1, wherein synthesizing the shortened modified polynucleotide molecule comprises de novo DNA synthesis 14. The method of paragraph 1, wherein the known transcriptional regulatory functionality comprises transcriptional activation and/or transcriptional repression.

15. The method of paragraph 1, wherein the known transcriptional regulatory functionality is in any given cell or tissue type.

16. The method of paragraph 1, wherein the known transcriptional regulatory functionality is in liver cells, cardiac muscle cells, and/or skeletal muscle cells.

17. The method of paragraph 1, wherein the known transcriptional regulatory functionality comprises promoter activity.

18. The method of paragraph 17, wherein promoter activity comprises a level of expression of a particular set of genes.

19. An isolated nucleic acid module comprising a polynucleotide that was synthesized using a process comprising:

a) receiving a set of genetic data comprising a regulatory polynucleotide sequence, optionally having a known transcriptional regulatory functionality;

b) processing the set of genetic data into a set of sequence elements that each comprise a portion of the polynucleotide sequence;

c) processing the set of sequence elements with a machine learning model to determine a transcriptional regulatory score associated with each of the set of sequence elements;

d) identifying at least one sequence element of the set of sequence elements comprising a transcriptional regulatory score below a threshold as a non-regulatory sequence element;

e) designing a modified polynucleotide molecule based on the determined transcriptional regulatory scores and/or identified non-regulatory sequence elements; and f) synthesizing the modified polynucleotide molecule.

20. The isolated nucleic acid module of paragraph 19, wherein each of the set of sequence elements is a k-mer fragment of the polynucleotide sequence.

21. The isolated nucleic acid module of paragraph 20, wherein each of the k-mer fragments comprises a gapped k-mer fragment.

22. The isolated nucleic acid module of paragraph 21, wherein the gapped k-mer fragment comprises a 10 nucleotide-long fragment comprising 4 gaps.

23. The isolated nucleic acid module of paragraph 19, wherein the machine learning model is a support vector machine.

24. The isolated nucleic acid module of paragraph 23, wherein the set of sequence elements are input into the support vector machine.

25. The isolated nucleic acid of paragraph 24, wherein the support vector machine comprises a gapped k-mer kernel.

26. The isolated nucleic acid module of paragraph 24, wherein the support vector machine comprises a k-DNF k-mer kernel.

27. The isolated nucleic acid module of paragraph 19, wherein the machine learning model is trained using a second set of genetic data comprising a second set of sequence elements that comprise portions of transcriptional regulatory elements and non-regulatory elements.

28. The isolated nucleic acid module of paragraph 19, wherein synthesizing the modified polynucleotide molecule comprises de novo DNA synthesis.

29. The isolated nucleic acid module of paragraph 19, wherein the known transcriptional regulatory functionality comprises transcriptional activation and/or transcriptional repression.

30. The isolated nucleic acid module of paragraph 19, wherein the known transcriptional regulatory functionality is in any given cell or tissue type.

31. The isolated nucleic acid module of paragraph 19, wherein the known transcriptional regulatory functionality is in liver cells, cardiac muscle cells, and/or skeletal muscle cells.

32. The isolated nucleic acid module of paragraph 19, wherein the known transcriptional regulatory functionality comprises promoter activity.

33. The isolated nucleic acid module of paragraph 33, wherein promoter activity comprises a level of expression of a particular set of genes.

34. The isolated nucleic acid module of paragraph 19, wherein the modified polynucleotide sequence is designed based on the polynucleotide sequence with the at least one non-regulatory sequence element removed.

35. The isolated nucleic acid module of paragraph 19, wherein the modified polynucleotide sequence is designed based on the polynucleotide sequence with the at least one non-regulatory sequence element replaced.

36. The isolated nucleic acid module of paragraph 19, wherein the modified polynucleotide sequence is designed based on at least one mutation of nucleotide position(s) to alter a transcriptional regulatory score.

37. A method of designing or synthesizing a synthetic polynucleotide with transcriptional regulatory functionality, the method comprising:
   a) receiving a set of genetic data comprising a regulatory polynucleotide sequence, optionally having a known transcriptional regulatory functionality;
   b) identifying an enhancer portion of the polynucleotide sequence using a machine learning model based on k-mers;
   c) processing the enhancer portion into a set of sequence elements that each comprise a k-mer fragment of the enhancer portion of the polynucleotide sequence;
   d) processing the set of sequence elements with a machine learning model to determine a transcriptional regulatory score associated with each sequence element of the set of sequence elements;
   e) identifying at least one sequence element of the set of sequence elements comprising a transcriptional regulatory score below a threshold as a non-regulatory sequence element;
   f) designing a modified polynucleotide molecule based on the determined transcriptional regulatory scores and/or identified non-regulatory sequence elements; and
   g) optionally synthesizing the modified polynucleotide molecule.

38. The method of paragraph 37, wherein each of the k-mer fragments comprises a gapped k-mer fragment.

39. The method of paragraph 38, wherein the gapped k-mer fragment comprises a 10 nucleotide-long fragment comprising 4 gaps.

40. The method of paragraph 37, wherein the machine learning model is a support vector machine.

41. The method of paragraph 40, wherein the set of sequence elements are input into the support vector machine.

42. The method of paragraph 41, wherein the support vector machine comprises a gapped k-mer kernel.

43. The method of paragraph 41, wherein the support vector machine comprises a k-DNF k-mer kernel.

44. The method of paragraph 37, wherein the machine learning model is trained using a second set of genetic data comprising a second set of sequence elements that comprise portions of transcriptional regulatory elements and non-regulatory elements.

45. The method of paragraph 37, wherein synthesizing the modified polynucleotide molecule comprises de novo DNA synthesis.

46. The method of paragraph 37, wherein the known transcriptional regulatory functionality comprises transcriptional activation and/or transcriptional repression.

47. The method of paragraph 37, wherein the known transcriptional regulatory functionality is in any given cell or tissue type.

48. The method of paragraph 37, wherein the known transcriptional regulatory functionality is in liver cells, cardiac muscle cells, and/or skeletal muscle cells.

49. The method of paragraph 37, wherein the known transcriptional regulatory functionality comprises promoter activity.

50. The method of paragraph 49, wherein promoter activity comprises a level of expression of a particular set of genes.

51. A method of designing or synthesizing a polynucleotide sequence with transcriptional regulatory functionality that is altered in size without losing transcriptional regulatory functionality comprising:
   a) using a machine to process a set of genetic data comprising polynucleotide sequences to identify putative promoter sequences or putative enhancer sequences;
   b) processing the set of putative promoter sequences with a machine learning model to determine a transcriptional regulatory score associated with each of the nucleotides within the putative promoter sequences to identify peaks and troughs based upon the scores provided to each nucleotide within the putative promoter sequences;
   c) identifying at least one member of the set of putative promoter sequences where there is a trough of at least 20 nucleotides between peaks, wherein the scores for members of the trough is below a predetermined threshold; and
   d) optionally synthesizing a shortened polynucleotide molecule, wherein at least 10% of the nucleotides within a trough has been removed as compared to the selected identified putative promoter sequence of step (c).

52. The method of paragraph 51, wherein the nucleotide sequences are scored using k-mer methodology.

53. The method of paragraph 51, wherein at least one trough within a putative promoter sequence are identified.

54. The method of paragraph 51, wherein at least one trough is removed.

55. The method of paragraph 51, wherein the transcriptional regulatory functionality of the shortened polynucleotide molecule is compared against the parent putative promoter sequence and is at least 35% that of the parent putative promoter sequence.

56. A method of designing or synthesizing a synthetic polynucleotide with transcriptional regulatory functionality, the method comprising:
   a) receiving a set of genetic data comprising a regulatory polynucleotide sequence, optionally having a known transcriptional regulatory functionality;
   b) processing the polynucleotide sequence into a first set of sequence elements, wherein the first set of sequence elements comprises at least one subset of sequence elements corresponding to all k-mer fragments comprising a selected nucleotide position of the polynucleotide sequence;

c) training a machine learning model using a second set of sequence elements that comprise portions of transcriptional regulatory elements and non-regulatory elements;

d) generating a third set of sequence elements comprising all k-mer fragments of the same length as the k-mer fragments of the first set of sequence elements;

e) processing the third set of sequence elements with the machine learning model to determine a transcriptional regulatory score associated with each sequence element of the third set of sequence elements, wherein the transcriptional regulatory score is stored in a database referenced to a k-mer fragment;

f) determining the transcriptional regulatory score of each k-mer fragment in a subset by assigning the transcriptional regulatory score of the matching k-mer fragment from the database;

g) determining the transcriptional regulatory score of at least one nucleotide position comprising averaging all transcriptional regulatory scores of all k-mer fragments in the corresponding subset;

h) identifying at least one region of nucleotide positions comprising transcriptional regulatory scores at or above a threshold as a regulatory sequence element;

i) identifying at least one region of nucleotide positions that is not a regulatory sequence element as a non-regulatory sequence element;

j) designing a modified polynucleotide molecule based on the determined transcriptional regulatory scores and/or identified non-regulatory sequence elements; and k) optionally synthesizing the modified polynucleotide molecule.

57. The method of paragraph 56, wherein each of the k-mer fragments of the first set of sequence elements comprises a gapped k-mer fragment.

58. The method of paragraph 57, wherein each gapped k-mer fragment of the first set of sequence elements comprises a 10 nucleotide-long fragment comprising 4 gaps.

59. The method of paragraph 56, wherein processing the polynucleotide sequence of step (b) comprises processing the polynucleotide sequence into subsets of sequence elements.

60. The method of paragraph 59, wherein processing the polynucleotide sequence into subsets of sequence elements comprises selecting a nucleotide position of the polynucleotide sequence and generating all k-mer fragments comprising the nucleotide position.

61. The method of paragraph 59, wherein a subset of sequence elements is produced for each nucleotide position of the polynucleotide sequence.

62. The method of paragraph 56, wherein the first set of sequence elements comprises at least two subsets of sequence elements.

63. The method of paragraph 56, wherein the first set of sequence elements comprises a subset of sequence elements corresponding to each nucleotide position of the polynucleotide sequence.

64. The method of paragraph 56, wherein the portions of transcriptional regulatory elements of the second set of sequence elements comprise regions identified as accessible chromatin.

65. The method of paragraph 64, wherein the regions identified as accessible chromatin comprise regions detected by DNase I hypersensitive site (DHS) assay, Assay for Transposase-Accessible Chromatin using sequencing (ATAC-seq), or other chromatin accessibility detection methods.

66. The method of paragraph 64, wherein the portions of transcriptional regulatory elements of the second set of sequence elements do not comprise promoter regions or are not within 2 kilobases of a transcriptional start site (TSS).

67. The method of paragraph 64, wherein the portions of transcriptional regulatory elements of the second set of sequence elements do not comprise regions detected by DHS assay in greater than 30% of human ENCODE cell lines.

68. The method of paragraph 56, wherein the portions of non-regulatory elements of the second set of sequence elements comprises shuffled sequences of the portions of transcriptional regulatory elements of the second set of sequence elements.

69. The method of paragraph 56, wherein the portions of transcriptional regulatory elements and non-regulatory elements of the second set of sequence elements are adjusted to 250 to 750 base pairs long.

70. The method of paragraph 56, wherein the portions of transcriptional regulatory elements comprise a similar GC content and/or similar nucleotide repeat composition as the portions of non-regulatory elements of the second set of sequence elements.

71. The method of paragraph 56, wherein the machine learning model is configured to return a transcriptional regulatory score.

72. The method of paragraph 56, wherein the transcriptional regulatory score comprises a positive or negative value, corresponding to the degree of confidence the model has that the sequence element is in a group comprising the portions of transcriptional regulatory elements or non-regulatory sequence elements of the second set of sequence elements.

73. The method of paragraph 56, wherein a transcriptional regulatory score is determined for each nucleotide position corresponding to each subset of sequence elements.

74. The method of paragraph 56, wherein the transcriptional regulatory score for each nucleotide position of the polynucleotide sequence is plotted.

75. The method of paragraph 56, wherein the threshold is the average of all transcriptional regulatory scores for each k-mer fragment of the third set of sequence elements plus a variable value.

76. The method of paragraph 56, wherein the variable value is at least 1.2 times the standard deviation of the transcriptional regulatory score for each k-mer fragment of the third set of sequence elements.

77. The method of paragraph 56, wherein the regulatory sequence element is at least as long as one k-mer fragment of the first set of sequence elements.

78. The method of paragraph 56, wherein the regulatory sequence element is at least 10 nucleotides long.

79. The method of paragraph 56, wherein the non-regulatory sequence element is at least as long as one k-mer fragment of the first set of sequence elements.

80. The method of paragraph 56, wherein the non-regulatory sequence element is at least 10 nucleotides long.

81. The method of paragraph 56, further comprising after step (i), re-processing a modified polynucleotide sequence using the machine learning model, wherein the modified polynucleotide sequence comprises the polynucleotide sequence with the at least one non-regulatory sequence element removed.

82. The method of paragraph 81, wherein re-processing the modified polynucleotide sequence comprises repeating steps b, f, g, h, and i of paragraph 56 using the modified polynucleotide sequence in place of the polynucleotide sequence.

83. The method of paragraph 82, wherein the modified polynucleotide molecule based on the modified polynucleotide sequence is synthesized if, after the step of re-processing, the length of the at least one regulatory sequence element identified is at least the same length as the corresponding regulatory sequence element identified in the parent polynucleotide sequence.

84. The method of paragraph 82, wherein the modified polynucleotide molecule based on the modified polynucleotide sequence is not synthesized if, after the step of re-processing, the length of the at least one regulatory sequence element identified is less than the length of the regulatory sequence element identified in the parent polynucleotide sequence.

85. The method of paragraph 56, wherein the machine learning model is a support vector machine.

86. The method of paragraph 85, wherein the set of sequence elements are input into the support vector machine.

87. The method of paragraph 85, wherein the support vector machine comprises a gapped k-mer kernel.

88. The method of paragraph 85, wherein the support vector machine comprises a k-DNF k-mer kernel.

89. The method of paragraph 56, wherein synthesizing the modified polynucleotide molecule comprises de novo DNA synthesis.

90. The method of paragraph 56, wherein the known transcriptional regulatory functionality comprises transcriptional activation and/or transcriptional repression.

91. The method of paragraph 56, wherein the known transcriptional regulatory functionality is in any given cell or tissue type.

92. The method of paragraph 56, wherein the known transcriptional regulatory functionality is in liver cells, cardiac muscle cells, and/or skeletal muscle cells.

93. The method of paragraph 56, wherein the known transcriptional regulatory functionality comprises promoter activity.

94. The method of paragraph 93, wherein promoter activity comprises a level of expression of a particular set of genes.

95. A method of designing or synthesizing a viral vector comprising a synthetic polynucleotide with transcriptional regulatory functionality, the method comprising:

a) receiving a set of genetic data comprising a regulatory polynucleotide sequence, optionally having a known transcriptional regulatory activity;

b) identifying an enhancer portion of the polynucleotide sequence using a machine learning model based on k-mers;

c) processing the enhancer portion into a set of sequence elements that each comprise a k-mer fragment of the enhancer portion of the polynucleotide sequence;

d) processing the set of sequence elements with a machine learning model to determine a transcriptional regulatory score associated with each sequence element of the set of sequence elements;

e) identifying at least one sequence element of the set of sequence elements comprising a transcriptional regulatory score below a threshold as a non-regulatory sequence element;

f) designing a modified polynucleotide molecule based on the determined transcriptional regulatory scores and/or identified non-regulatory sequence elements; and g) optionally synthesizing a viral vector comprising the modified polynucleotide molecule.

96. The method of paragraph 95, wherein the viral vector is an AAV vector.

97. The method of paragraph 95, wherein the modified polynucleotide molecule is no more than 100 nucleotides long.

98. The method of paragraph 95, wherein the transcriptional regulatory functionality of the modified polynucleotide molecule is compared against the parent polynucleotide molecule and is at least 10% that of the parent polynucleotide molecule.

99. The method of paragraph 95, wherein each of the k-mer fragments comprises a gapped k-mer fragment.

100. The method of paragraph 99, wherein the gapped k-mer fragment comprises a 10 nucleotide-long fragment comprising 4 gaps.

101. The method of paragraph 95, wherein the machine learning model is a support vector machine.

102. The method of paragraph 95, wherein the set of sequence elements are input into the support vector machine.

103. The method of paragraph 102, wherein the support vector machine comprises a gapped k-mer kernel.

104. The method of paragraph 102, wherein the support vector machine comprises a k-DNF k-mer kernel.

105. The method of paragraph 95, wherein the machine learning model is trained using a second set of genetic data comprising a second set of sequence elements that comprise portions of transcriptional regulatory elements and non-regulatory elements.

106. The method of paragraph 95, wherein synthesizing the modified polynucleotide molecule comprises de novo DNA synthesis.

107. The method of paragraph 95, wherein the known transcriptional regulatory functionality comprises transcriptional activation and/or transcriptional repression.

108. The method of paragraph 95, wherein the known transcriptional regulatory functionality is in any given cell or tissue type.

109. The method of paragraph 95, wherein the known transcriptional regulatory functionality is in liver cells, cardiac muscle cells, and/or skeletal muscle cells.

110. The method of paragraph 95, wherein the known transcriptional regulatory functionality comprises promoter activity.

111. The method of paragraph 110, wherein promoter activity comprises a level of expression of a particular set of genes.

112. The method of paragraph 95, wherein the modified polynucleotide sequence is designed based on the polynucleotide sequence with the at least one non-regulatory sequence element removed.

113. The method of paragraph 95, wherein the modified polynucleotide sequence is designed based on the polynucleotide sequence with the at least one non-regulatory sequence element replaced.

114. The method of paragraph 86, wherein the modified polynucleotide sequence is designed based on at least one mutation of nucleotide position(s) corresponding to a transcriptional regulatory score below the pre-determined threshold.

115. A viral vector comprising a modified polynucleotide that was synthesized using a process comprising:
    a) receiving a set of genetic data comprising a regulatory polynucleotide sequence, optionally having a known transcriptional regulatory activity;
    b) identifying an enhancer portion of the polynucleotide sequence using a machine learning model based on k-mers;
    c) processing the enhancer portion into a set of sequence elements that each comprise a k-mer fragment of the enhancer portion of the polynucleotide sequence;
    d) processing the set of sequence elements with a machine learning model to determine a transcriptional regulatory score associated with each sequence element of the set of sequence elements;
    e) identifying at least one sequence element of the set of sequence elements comprising a transcriptional regulatory score below a threshold as a non-regulatory sequence element;
    f) designing a modified polynucleotide molecule based on the determined transcriptional regulatory scores and/or identified non-regulatory sequence elements; and
    g) synthesizing a viral vector comprising the modified polynucleotide molecule.

116. The viral vector of paragraph 115, wherein the viral vector is an AAV vector.

117. The viral vector of paragraph 115, wherein the modified polynucleotide molecule is no more than 100 nucleotides long.

118. The viral vector of paragraph 115, wherein the transcriptional regulatory functionality of the modified polynucleotide molecule is compared against the parent polynucleotide molecule and is at least 10% that of the parent polynucleotide molecule.

119. The viral vector of paragraph 115, wherein each of the k-mer fragments comprises a gapped k-mer fragment.

120. The viral vector of paragraph 119, wherein the gapped k-mer fragment comprises a 10 nucleotide-long fragment comprising 4 gaps.

121. The viral vector of paragraph 115, wherein the machine learning model is a support vector machine.

122. The viral vector of paragraph 121, wherein the set of sequence elements are input into the support vector machine.

123. The viral vector of paragraph 121, wherein the support vector machine comprises a gapped k-mer kernel.

124. The viral vector of paragraph 121, wherein the support vector machine comprises a k-DNF k-mer kernel.

125. The viral vector of paragraph 115, wherein the machine learning model is trained using a second set of genetic data comprising a second set of sequence elements that comprise portions of transcriptional regulatory elements and non-regulatory elements.

126. The viral vector of paragraph 115, wherein synthesizing the modified polynucleotide molecule comprises de novo DNA synthesis.

127. The viral vector of paragraph 115, wherein the transcriptional regulatory functionality comprises transcriptional activation and/or transcriptional repression.

128. The viral vector of paragraph 115, wherein the transcriptional regulatory functionality is in any given cell or tissue type.

129. The viral vector of paragraph 115, wherein the transcriptional regulatory functionality is in liver cells, cardiac muscle cells, and/or skeletal muscle cells.

130. The viral vector of paragraph 115, wherein the transcriptional regulatory functionality comprises promoter activity.

131. The viral vector of paragraph 130, wherein promoter activity comprises a level of expression of a particular set of genes.

132. The viral vector of paragraph 115, wherein the modified polynucleotide sequence is designed based on the polynucleotide sequence with the at least one non-regulatory sequence element removed.

133. The viral vector of paragraph 115, wherein the modified polynucleotide sequence is designed based on the polynucleotide sequence with the at least one non-regulatory sequence element replaced.

134. The viral vector of paragraph 115, wherein the modified polynucleotide sequence is designed based on at least one mutation of nucleotide position(s) corresponding to a transcriptional regulatory score below the pre-determined threshold.

135. The viral vector of paragraph 115, wherein the modified polynucleotide sequence is designed based on one mutation of a nucleotide position.

EXAMPLES

Example 1

Use of Gapped-k-Mer Models

As described herein, the gapped-k-mer model can use a standard SVM model with a gapped-k-mer kernel (see e.g., FIG. 1). The kernel defines the model's representation of sequences as a collection of all of the gapped-k-mers found in each sequence (e.g., 10 mers with 4 gaps). In some embodiments of any of the aspects, SVM model can further comprise the k-DNF k-mer kernel described herein. Given a trained model, sequence regions with low model scores can be identified as more likely to be non-functional and deleted or replaced. Similarly, sequences with overall low scores can be identified as more likely to have low expression and screened out of further testing.

Described herein are data comprising in vitro Huh7 data, as well as in vivo cardiac and quadriceps data. Also described herein are models comprising a liver model (e.g., 10 mer/4 gaps), and two muscle models (e.g., cardiac and skeletal muscle gapped k-mer, e.g., 10 mer/4gaps). The models be trained on different tissues, and can generate results which apply to different tissues, or experimental data can be generated using different tissues.

Described herein is a gapped-k-mer model, wherein the model is provided training data in the form of DNA sequences (e.g., a set of candidate CREs), labelled as either positive example sequences or negative background sequences. The gapped k-mer model is an SVM with a gapped-kmer kernel. The gapped-kmer kernel allows the SVM to internally represent each input sequence as a collection of gapped k-mers where the k-mers are of a fixed length and there are a fixed number of gaps e.g. 10 bp in length with 4 gaps. The SVM calculates the maximum margin hyperplane separating the positive and negative training datasets when mapped into the space of gapped k-mers. Once trained the model uses the distance from the maximum margin hyperplane as a prediction of the expected activity level of a sequence provided to it.

Liver Models

Figure 2:
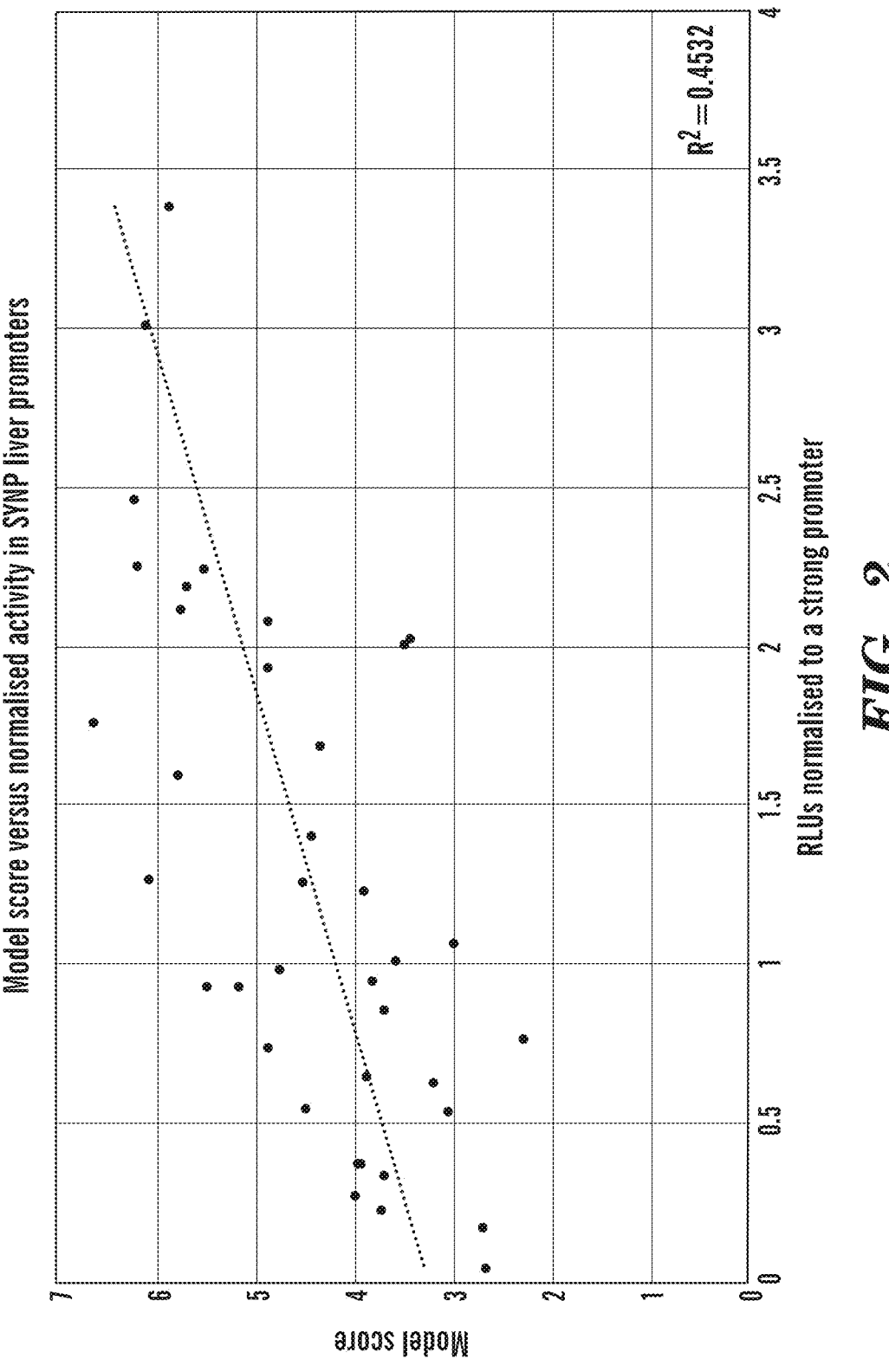
FIG. 2 is a graph showing model scores of tested liver promoters. Note that the sequences with higher model scores are more likely to exhibit transcriptional activity. Sequence scores depend on the model scores for localized regions of each sequence.

The gapped-k-mer SVM model was trained on 10,000 DHS sequences selected from DHS regions in HepG2 cells, excluding regions which were DHS in more than 30% of human ENCODE cell lines, or near promoters (<2kb from TSS; see e.g., Lee et al. 2015, supra). A further 10,000 background sequences were matched in size, GC content, and repeats to the DHS sequence training set (see e.g., Lee et al. 2015, supra). Over 20 liver promoters were tested, corresponding to SYNP_LVR_SP0236-264, alongside controls. As shown in FIG. 2, the model score was plotted compared to the experimental result (RLUs normalized to a strong liver promoter control). There was a positive correlation of 0.45 between the scores and experimental results.

In some embodiments of any of the aspects, the model score is calculated for a specific position in the sequence using the scores of multiple k-mers (see e.g., FIG. 3). A model score is calculated at each base in a sequence. FIG. 3 shows an exemplary score calculation for highlighted base C. First, every k-mer in the sequence that contains C was selected. Then, the model score for each of those k-mers was calculated. These results were averaged to obtain the score for base C. Such a method is repeated for every base in the sequence.

Figure 4A:
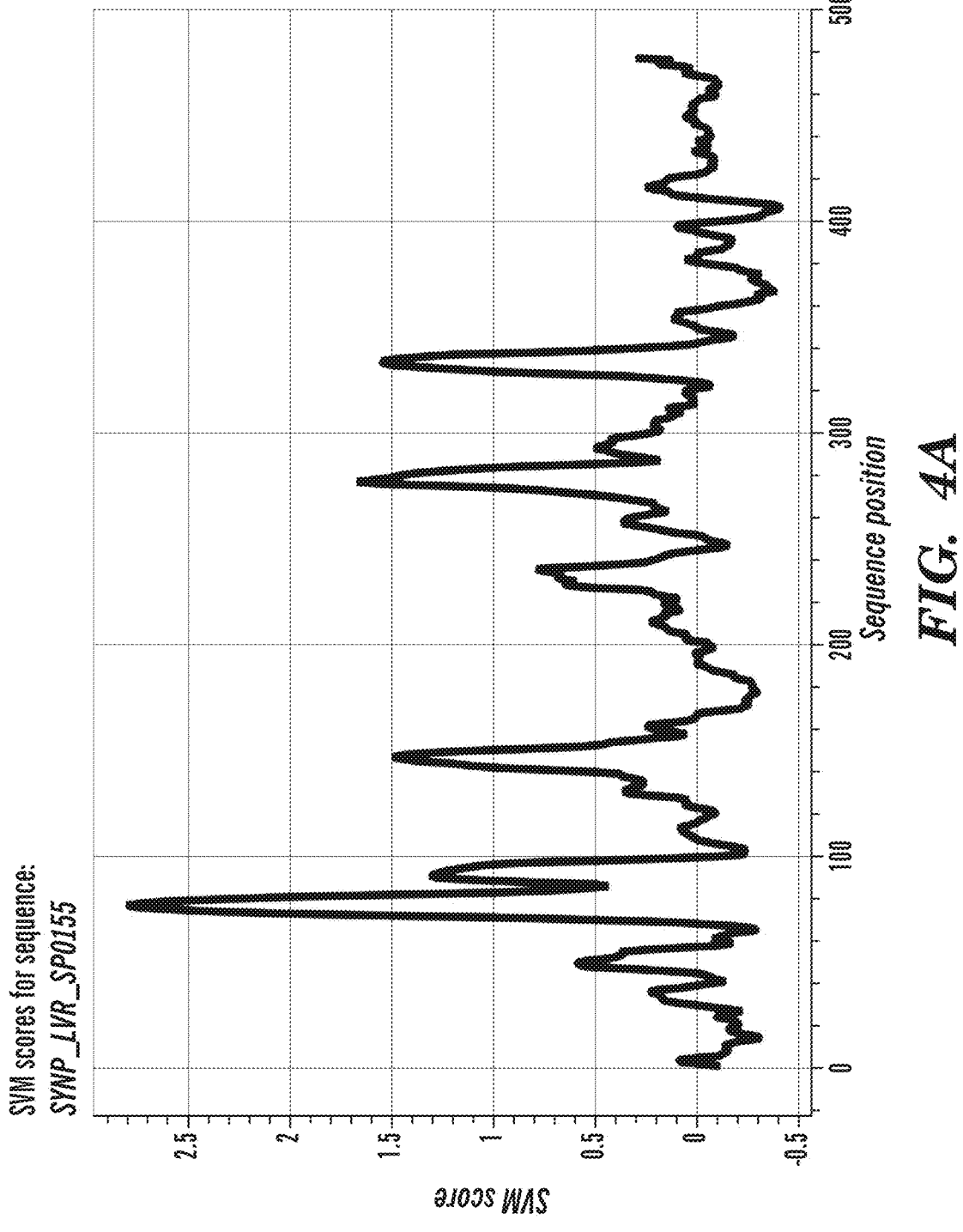
FIG. 4A-4C is a series of graphs showing use of machine learning models to analyze the SYNP_LVR_SP0155 promoter sequence.
Figure 4B:
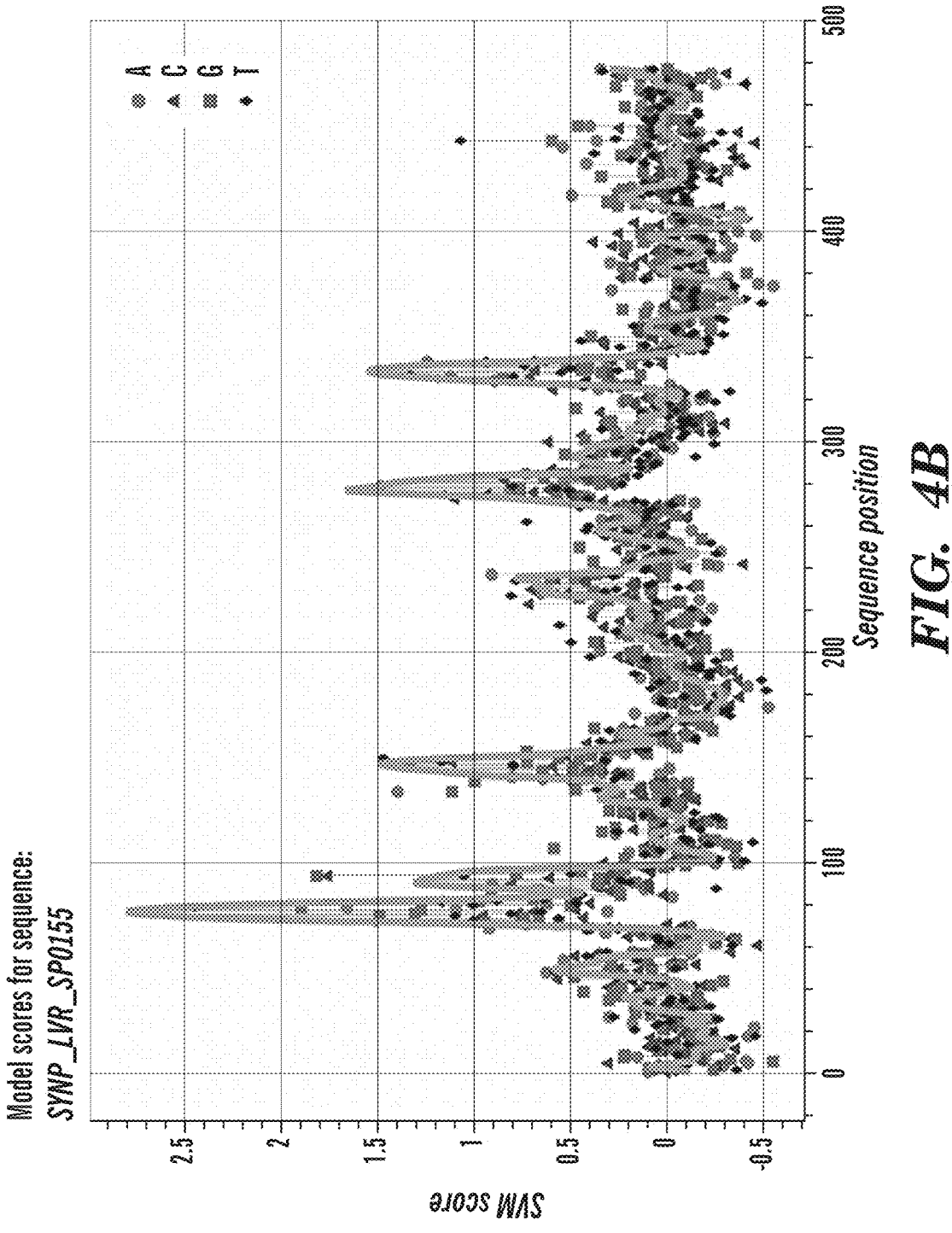
Figure 4C:
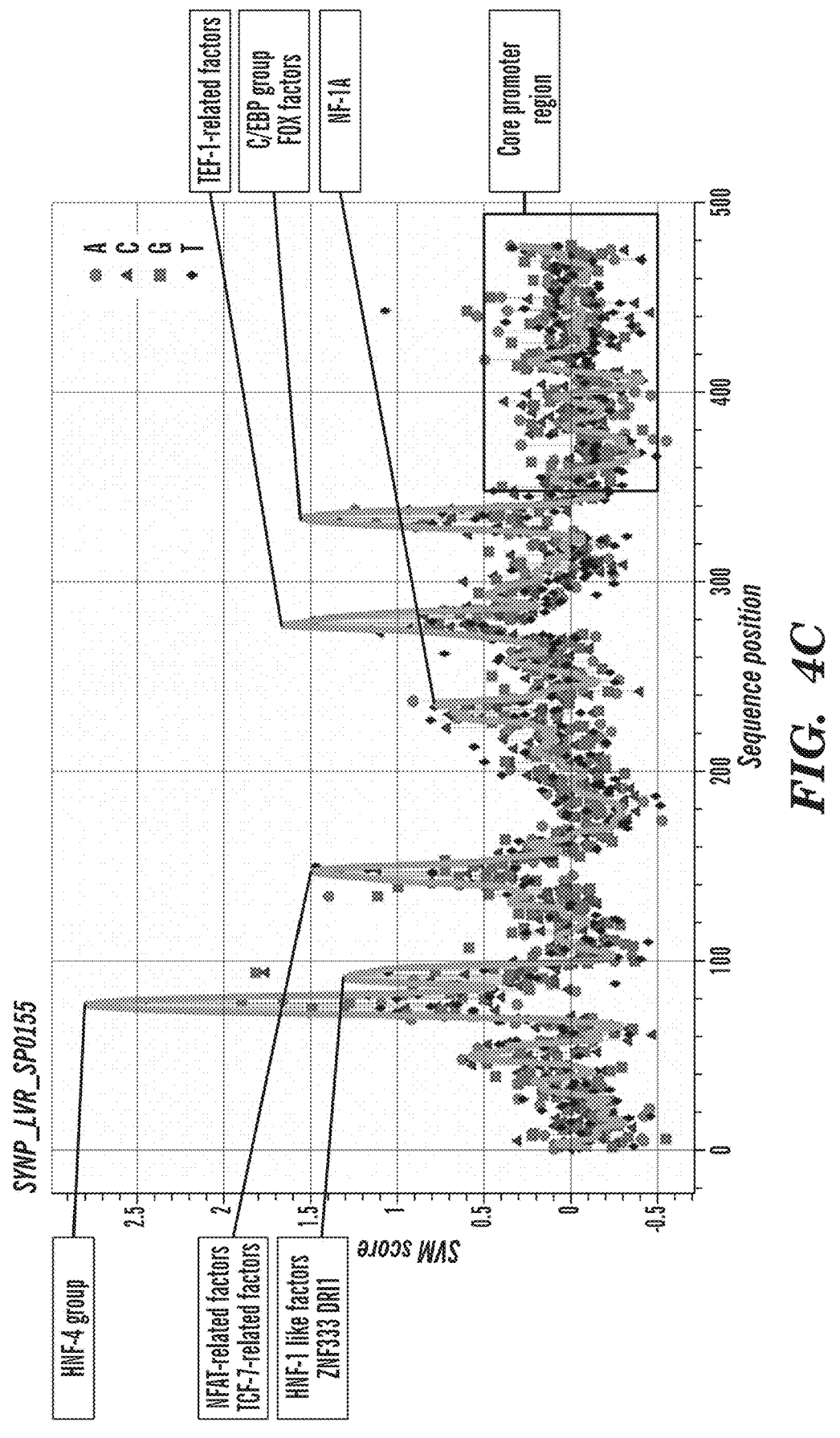

The gapped k-mer SVM model was used to generate a profile for the SYNP_LVR_SP0155 promoter sequence (see e.g., FIG. 4A). The model can be used to calculate a score for every possible mutation at every position in the sequence (see e.g., FIG. 4B). As seen with the SYNP_LVR_SP0155 liver promoter sequence scores, the peaks correspond to TFBSs important for liver promoter sequences (see e.g., FIG. 4C).

Figure 5A:
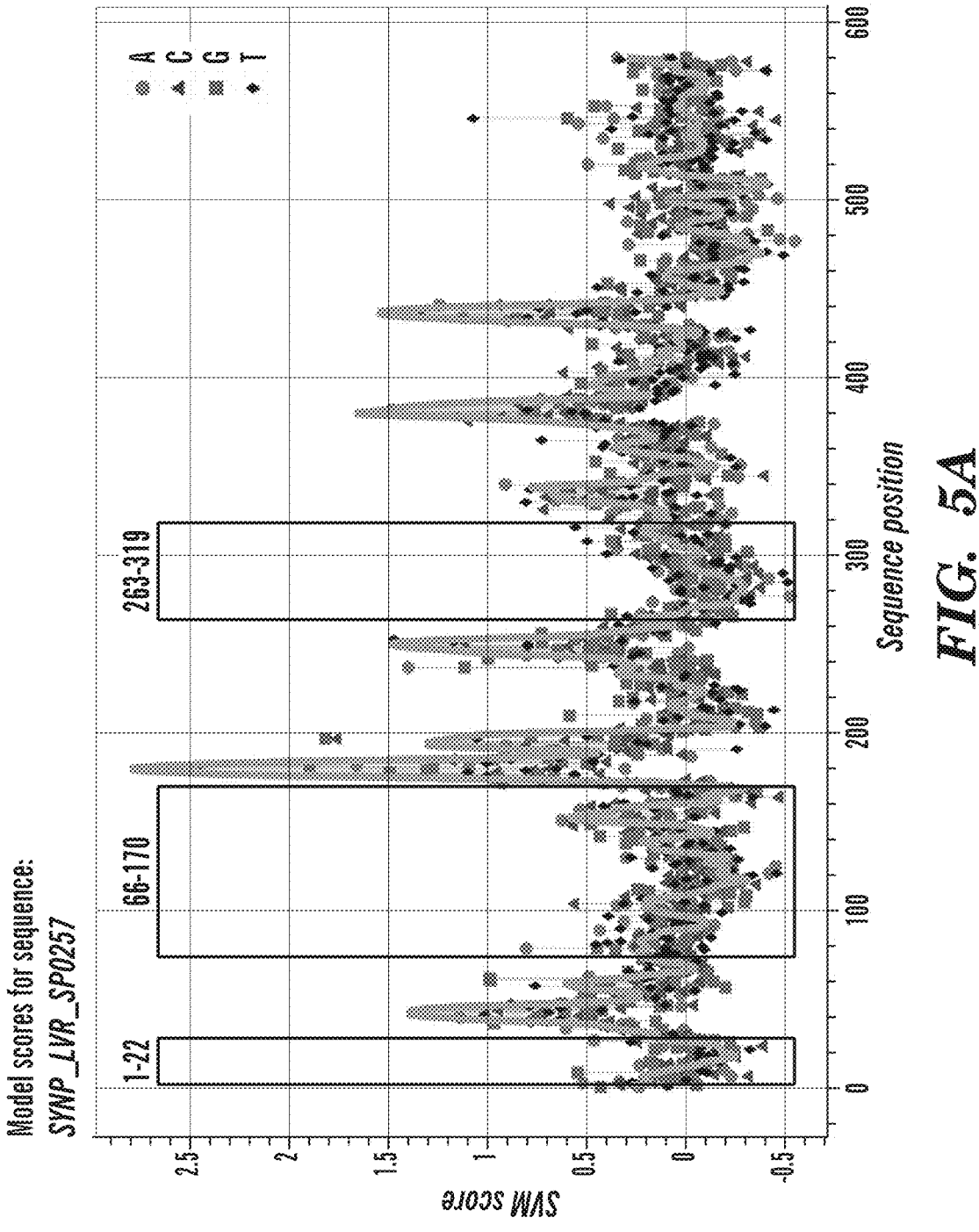
FIG. 5A-5B is a series of graphs showing use of the model score to define promoter region deletion or replacement in the liver.

One use for the methods described herein is to delete regions with low model scores, on the basis that these were unlikely to be contributing to the promoter's activity. For example, the SYNP_LVR_SP0257 sequence was tested using the gapped k-mer SVM model. As shown in FIG. 5A, there were a number of low-score troughs in the 0257 sequence, and specific deletion of these regions was tested.

For example, regions were selected to be deleted on the basis of the model scores (e.g., a score below a certain threshold), but said selection was conservative (e.g., erring on the side of smaller or fewer regions; e.g., having a lower threshold score value). Furthermore, the selection of regions coincided with the boundaries of the CREs (cis-regulatory elements) from which the promoters were constructed. In other words, most deletion regions included or straddled a CRE boundary.

Figure 5B:
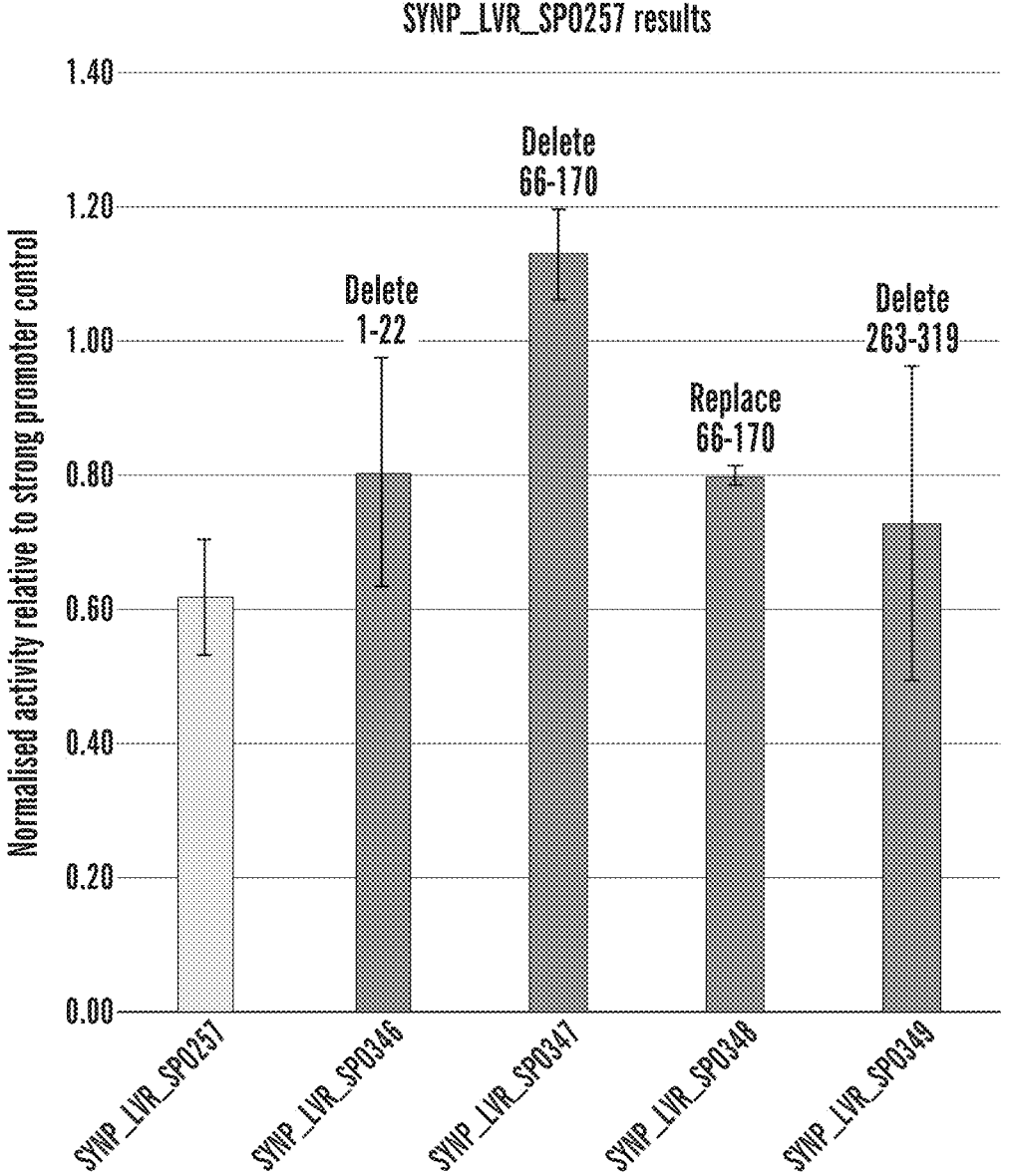

Each region was deleted separately, and the resulting promoter was tested (see e.g., FIG. 5B). In some cases, more or less conservative versions of the region were tested. As a non-limiting example, having selected shorter more conservative regions, some regions were extended, especially where a CRE-CRE boundary existed in more than one of the tested sequences. Extensions were up to 20 base pairs, depending on the plot. In some cases, the deleted region was replaced with a section of control sequence known not to have activity. Such deletions or replacements were performed with several promoters. In some embodiments, promoters were created with mutations (e.g., in the low-score regions).

FIG. 6 show a plot of the activity (normalized to a control promoter) for each of the original promoter sequences in light grey. The dark grey points are the new promoter sequences, arranged above or below their parent sequence.

The full set of promoter results is shown in FIG. 7A, as well as a demonstration of liver specificity (see e.g., FIG. 7B). Results for each promoter are also shown (see e.g., FIGS. 8-12).

Cardiac and Skeletal Muscle Models

As shown in FIG. 13A, mouse ATAC-seq data of regions differentially expressed in cardiac muscle (see e.g., Cusanovich et al., 2018, supra) were analyzed to output a model score. The sequences were first filtered to remove promoter regions. The sequences were then adjusted to 500 bp (e.g., sequences <200 bp and >3000 bp were removed; for the remaining sequences between 200 bp and 3000 bp, the midpoint was found and 250 bp of sequence was include from both sides of the midpoint). The top 2500 sequences by fold change in expression were chosen for further analysis using the methods as described herein. The 2500 background sequences were generated using the genNullSeqs function that were GC content and repeat matched. Note the positive correlation between the model score and the experimental activity (expressed in log(RLUs)).

As shown in FIG. 13B, data from DHS regions in human psoas cells (see e.g., Lee et al., 2015, supra; Ghandi et al. 2014, supra; Ghandi et al. 2016, supra) were analyzed using the methods as described herein to output a model score. Regions that were DHS in more than 30% of human ENCODE cell lines or regions that were near promoters (e.g., <2kb from a transcriptional start site (TSS)) were excluded. The background was generated using equal size GC and repeat matched training set from genNullSeqs, as in FIG. 13A.

The experimental results in FIG. 13A-13B represent in vivo results for five selected sequences. The experimental results in FIG. 13A show normalized AAV9-LUC expression in heart, and FIG. 13B shows normalized AAV9-LUC expression in quadriceps.

SPc5-12 Promoter

System and methods utilizing machine learning were next used to re-engineer the SPc5-12 promoter, which is a strong synthetic muscle promoter (see e.g., Li et al. Nat Biotechnol. 1999; 17:241-245). The skeletal muscle model and cardiac muscle model were used to identify potential sites in the SPc5-12 promoter that are not functional. Several regions were predicted to be non-functional (see e.g., FIG. 14). Modified sequences were produced from the original SPc5-12 promoter, including but not limited to deletion of each region or replacement of each region with a random sequence or a functional motif cluster. It is expected that each of these modified sequences demonstrate maintained activity level compared to the original promoter sequence.

As shown herein, a liver model was used to test and modify liver enhancer sequences, and muscle sequences were designed based on cardiac/skm models (e.g., Spc5-12 variants).

In some embodiments of any of the aspects, the SVM model (e.g., comprising a gapped-k-mer kernel) can be modified. As a non-limiting example, the SVM model can be replaced with a voted perceptron (as it is expected to produce similar results) or with another model which can be kernelized or a model which works directly with gapped k-mers. In some embodiments of any of the aspects, the kernel functions can be replaced with, as a non-limiting example, combinations of string kernels, spectrum kernel etc., or with a new kernel. In some embodiments of any of the aspects, the k-DNF k-mer kernel can be used. Without wishing to be bound by theory, the k-DNF k-mer kernel comprises parameter settings which can perform similarly or better than the gapped-k-mer kernel. Furthermore, the k-DNF k-mer kernel has not previously been used in genomic contexts, and it is computationally intensive.

The methods as described herein can be used in a variety of experimental setups. For example, the methods as described herein can be used to explore the performance of deletion and/or mutation predictions. Furthermore, multiplex screening of 5000-10,000 training data points can be used to increase the accuracy of models.

Example 2

Described herein are exemplary methods of setting up, training, and running a model. First the model was set up using a set of "active" and "inactive" sequences (see e.g., FIG. 15). The set of "active" sequences comprised data from assays used to detect accessible chromatin e.g. DHS, ATAC-seq. The set of "inactive" sequences can comprise as a non-limiting example shuffled versions of the active sequences. The model (e.g., gapped-k-mer SVM model) was then trained using the "active" and "inactive" sequences, using the following parameters: k-mer length=10; gaps=4. The model was set up to return the decision function value for predictions (instead of more standard binary classification). Classification is related to the SVM's (learnt) decision function f and a (learnt) bias term, as given some input x, the classification is sign(f(x)-bias). After training the model, all k-mers of length 10 were generated. The decision function value (also referred to herein as a "score") was determined for each k-mer of length 10, and these values were stored in a lookup table (see e.g., FIG. 15).

Next, the score was determined for a specific sequence (see e.g., FIG. 16). A candidate sequence was selected to process. A specific position was selected in the sequence. All k-mers (e.g., 10mers) which overlapped this position were generated. The score was determined for each k-mer by referencing the lookup table, and all the scores were averaged. The averaged score is thus the score for the specific position in the sequence. Such a method was repeated for each position in the sequence, and the scores were plotted (see e.g., FIG. 16).

Then, the functional and non-functional regions of the sequence were identified (see e.g., FIG. 17). A threshold was set, e.g., (((the average score of all the k-mer scores from the look-up table) +(1.2*SD of k-mer scores)), wherein SD stands for standard deviation. A window was also set, corresponding to the minimum size of the functional region. The length of the window was at least the length of the k-mer (e.g., 10 nucleotides). For each position in the sequence, it was determined if the position was associated with a score that was greater than the threshold. All regions with a length longer than the window where all scores were above the threshold were identified and marked as functional regions. Any region that was outside of a functional region was defined as a non-functional region. In some embodiments, for each position in the sequence, it was determined if the position was associated with a score that was less than the threshold. All regions with a length longer than the window where all scores were less the threshold were identified and marked as non-functional regions.

At least one non-functional region was then deleted or replaced (e.g., with a neutral sequence) in the original sequence to create an altered sequence. The functional region identification (see e.g., FIG. 17) was then repeated for this altered sequence. If the functional regions in the altered sequence decreased in size compared to the original sequence, then the altered sequence was rejected. In this case, a new altered sequence could be produced by deleting or replacing at least one different non-functional region in the original sequence. If the functional regions in the altered sequence were the same size or increased in size compared to the original sequence, then the altered sequence was accepted.

The following relates to a comparison between using a model trained with the original gkmSVM gapped k-mer code (which has an approximation to the kernel calculation)—the "approximate" model—and a model trained without this approximation—the "naive" model (see e.g., Ghandi et al. 2016, supra). The approximate liver model was used to identify functional and non-functional regions of two sequences. The threshold value was determined to be 0.38, and the window was chosen as size 10 (i.e., 10 nucleotides long; see e.g., FIG. 18). Next, the regions of the SYN-P_LVR_SP0257 sequence that were above the threshold and greater in length than the window (referred to herein as peaks) were identified. The following peaks were identified: positions 34-48, 172-200, 242-256, 329-340, 372-387, and 430-441 (see e.g., FIG. 19). A second sequence (SYN-P_LVR_SP0155) was also analyzed using the same threshold, and the following peaks were identified: positions 69-97, 139-153, 226-237, 269-284, and 327-338 (see e.g., FIG. 20).

The naive liver model was used to identify functional and non-functional regions of a sequence. The threshold value was determined to be −1.06, and the window was chosen as size 10 (i.e., 10 nucleotides long; see e.g., FIG. 21). Next, the regions of the SYNP_LVR_SP0257 sequence that were above the threshold and greater in length than the window (i.e., peaks) were identified. The following peaks were identified: positions 37-46, 173-184, 190-199, 243-253, 375-386, and 430-440 (see e.g., FIG. 22). Note that similar peaks were identified for SYNP_LVR_SP0257 using the approximate liver model (see e.g., FIG. 19) and the naive liver model (see e.g., FIG. 22).

Example 3 k-DNF k-mer Kernel

Described herein are methods and systems of synthetic regulatory sequence design and/or production. In some embodiments of any of the aspects, the methods and systems comprise the use of the k-DNF kernel in combination with k-mers (e.g., k-DNF k-mer kernel) to modify promoter sequences.

The training dataset for the model is 10,000 DHS sequences selected from DHS regions in HepG2 cells, excluding regions which were DHS in more than 30% of human ENCODE cell lines, or near promoters (<2kb from TSS). A further 10,000 background sequences are matched in size, GC content, and repeats to the DHS sequence training set. The test dataset for the model consists of over 20 liver promoters, corresponding to SYNP_LVR_SP0236-264, alongside controls.

Using the training dataset, an SVM model is trained with a k-DNF kmer kernel, where the parameter k is set to 3 and the length of kmers used is set to 20. Model scores are calculated for each sequence and plotted against the experimental results. Without wishing to be bound by theory, it is expected that the correlation between model scores and experimental results will be higher than for the (e.g., 10mer/4 gaps) gapped-kmer model, as the k-DNF kmer model is expected to produce better results.

The model score for a specific position in each test sequence can be calculated using the scores of multiple k-mers (see e.g., FIG. 3). In this case it is better not to calculate every possible kmer score and use a lookup process (as the number of possible 20-mers is infeasibly large); however, each kmer score can be calculated as required by inputting it into the trained model. The k-DNF k-mer SVM model is used to generate a profile for the SYNP_LVR_SP0155promoter sequence. The model can be used to calculate a score for every possible mutation at every position in the sequence. The peaks correspond to TFBSs important for liver enhancer sequences. As before the profile can be used to identify low-scoring regions which are unlikely to be contributing to a promoter's activity and which can be deleted.

By permitting the use of longer kmers (e.g., 20mers), the k-DNF kmer kernel can be used to identify cases where an interaction between two separated TFBSs is an important determinant of the activity of the sequence.

Example 4

Point Mutations

FIG. 24 illustrates the disclosed systems and methods of synthetic regulatory sequence design applied to point mutations. Accordingly, the disclosed technology may be used to predict individual nucleotides within a promoter sequence that can be mutated or changed and have a positive or negative impact of overall promoter activity. FIG. 24 (left panel) shows model scores across a liver-selective synthetic promoter, indicating the impact of changing individual nucleotides on an example model score for each individual nucleotide position within the promoter sequence. At position 94, the parent sequence contains an A. The example model predicts that by changing that to a C or G there may be an increase in activity. Likewise, at position 77 the example model predicts that by changing the existing base G to an A there would potentially be a decrease in promoter activity.

FIG. 24 (right panel) depicts a graph showing the impact on promoter activity of making single base pair substitutions as suggested by the ML model. As predicted, by changing nucleotide 94 from an A to a G resulted in a slight increase in promoter activity. Whereas changing the nucleotide 77 from a G to and A had a substantial negative impact on promoter activity. This data suggests that the model may be used to further improve on transcriptional activity by suggesting single base pair modifications that can be made to promoters or enhancers.

Example 5

Liver Model

The gapped-kmer SVM model was trained on 2000 differentially expressed liver sequences extracted from the mouse-derived dataset of Cusanovich et al. 2018, supra. The liver sequences were differentially accessible relative to the 10 tissues most correlated with liver in the Cusanovich et al. dataset. Without wishing to be bound by theory, the choice of these tissues for comparison is motivated by the expectation that locating regions which are differentially accessible in liver relative to very similar tissues will drive tissue-specificity in the resulting model. For all sequences, the original data is processed so that only cells with at least 3000 peaks, and peaks present in at least 10 cells are used. Counts are normalised and a ranking of differentially accessible regions is determined by applying a t-test with Benjamini-Hochberg correction and ranking by adjusted p-value. The top ranked 2000 sequences were used as positive training examples. An additional 2000 background sequences were matched in size, GC content and repeats to the positive training set.

The scores from this "differentially accessible" model were calculated for the experimentally tested liver promoters used in Example 1. As shown in FIG. 25 the model score was plotted compared to the experimental result (RLUs normalized to a strong liver promoter control). There was a positive correlation of 0.66 between the scores and experimental results.

The gapped k-mer SVM model was used to generate a profile for the SYNP_LVR_SP0155 promoter sequence. The threshold to determine whether a region was active was calculated as described in Example 2, with the threshold value determined to be −0.136. Four of six regions identified as active by the "approximate" model (see e.g., Examples 1-2) are also identified as active by the "differentially accessible" model, with the remaining two regions hosting peaks close to the threshold (see e.g., FIG. 26). The two regions at CRE boundaries identified as inactive are also below threshold in this model (see e.g., FIG. 27).

Similarly, the "differentially accessible" and "approximate" models were used to generate a profile for the SYNP_LVR_SP0257 promoter sequence. Five of seven regions identified as active by the "approximate" model are also identified as active by the "differentially accessible" model, with the remaining two regions hosting peaks close to threshold (see e.g., FIG. 28). The two regions at CRE boundaries identified as inactive are also below threshold in the "differentially accessible" model (see e.g., FIG. 29).

SPc5-12

Sequences resulting from the modifications to SPc5-12 in Example 1 (see e.g., FIG. 14) were experimentally tested in vitro in H9C2 (heart) and H2K (skeletal muscle) cell lines. The activity for the original SPc5-12 promoter and each modified sequence is plotted in FIG. 30 (H9C2) and FIG. 31 (H2K), normalised to a strong muscle promoter control.

This example demonstrates the utility of the model as a rational guide to identify regions which can be modified without complete loss of activity (e.g., deleting region 1, replacing region 3 with neutral sequence). Additionally, the relatively lower activity in H2K for deleting region 1 is consistent with the higher scoring profile in the skeletal muscle model for this region (see e.g., FIG. 14). The rise in activity as a result of replacing region 2 demonstrates that the models identify non-functional or inhibitory regions. Finally, replacing region 3 with a known active sequence recovers activity relative to neutral sequence, demonstrating the utility of the model as a guide to successful combination of active sequences.

---

What is claimed herein is:

1. A method of synthesizing an adeno-associated virus (AAV) viral vector comprising a synthetic polynucleotide with transcriptional regulatory functionality, the method comprising the steps of:

a) receiving a set of genetic data comprising a regulatory polynucleotide sequence, optionally having a known transcriptional regulatory functionality;

b) processing the set of genetic data into a set of sequence elements that each comprise a portion of the polynucleotide sequence; wherein each of the set of sequence elements is a k-mer fragment of the polynucleotide sequence;

c) processing the set of sequence elements with a machine learning model to determine a transcriptional regulatory score associated with each of the set of sequence elements;

d) identifying at least one sequence element of the set of sequence elements comprising a trough of at least 20 nucleotides between peaks with a transcriptional regulatory score below a threshold as a non-regulatory sequence element;

e) designing a modified polynucleotide molecule based on the determined transcriptional regulatory scores and/or identified non-regulatory sequence elements; wherein at least 10% of the nucleotides within the trough have been removed in the modified polynucleotide molecule; and f) synthesizing an AAV viral vector comprising the modified polynucleotide molecule.

2. The method of claim 1, wherein each of the k-mer fragments comprises a gapped k-mer fragment.

3. The method of claim 2, wherein the gapped k-mer fragment comprises a 10 nucleotide-long fragment comprising 4 gaps.

4. The method of claim 1, wherein the machine learning model is produced by a support vector machine.

5. The method of claim 4, wherein the set of sequence elements are input into the support vector machine.

6. The method of claim 4, wherein the support vector machine comprises a gapped k-mer kernel.

7. The method of claim 4, wherein the support vector machine comprises a k-DNF k-mer kernel.

8. The method of claim 1, wherein the machine learning model is trained using a second set of genetic data comprising a second set of sequence elements that comprise portions of transcriptional regulatory elements and non-regulatory elements.

9. The method of claim 1, wherein the modified polynucleotide sequence is designed based on the polynucleotide sequence with the at least one non-regulatory sequence element removed.

10. The method of claim 1, wherein the modified polynucleotide sequence is designed based on the polynucleotide sequence with the at least one non-regulatory sequence element replaced.

11. The method of claim 1, wherein the modified polynucleotide sequence is designed based on at least one mutation of nucleotide position(s) to alter a transcriptional regulatory score.

12. The method of claim 1, wherein synthesizing the shortened modified polynucleotide molecule comprises de novo DNA synthesis.

13. The method of claim 1, wherein the known transcriptional regulatory functionality:

comprises transcriptional activation and/or transcriptional repression;

is in any given cell or tissue type;

is in liver cells, cardiac muscle cells, and/or skeletal muscle cells; or comprises promoter activity.

14. The method of claim 13, wherein promoter activity comprises a level of expression of a particular set of genes.

15. An AAV viral vector comprising a modified polynucleotide molecule that was synthesized using a method comprising the steps of:

a) receiving a set of genetic data comprising a regulatory polynucleotide sequence, optionally having a known transcriptional regulatory functionality;

b) processing the set of genetic data into a set of sequence elements that each comprise a portion of the polynucleotide sequence, wherein each of the set of sequence elements is a k-mer fragment of the polynucleotide sequence;

c) processing the set of sequence elements with a machine learning model to determine a transcriptional regulatory score associated with each of the set of sequence elements;

d) identifying at least one sequence element of the set of sequence elements comprising a trough of at least 20 nucleotides between peaks with a transcriptional regulatory score below a threshold as a non-regulatory sequence element;

e) designing a modified polynucleotide molecule based on the determined transcriptional regulatory scores and/or identified non-regulatory sequence elements; wherein at least 10% of the nucleotides within the trough have been removed in the modified polynucleotide molecule; and f) synthesizing an AAV viral vector comprising the modified polynucleotide molecule.

16. A method of synthesizing an AAV viral vector comprising a polynucleotide sequence with transcriptional regulatory functionality that is altered in size without losing transcriptional regulatory functionality comprising the steps of:

a) using a machine to process a set of genetic data comprising polynucleotide sequences to identify putative promoter sequences or putative enhancer sequences;

b) processing the set of putative promoter sequences into a set of sequence elements that each comprise a portion of the putative promoter sequences with a machine learning model to determine a transcriptional regulatory score associated with each of the nucleotides within the putative promoter sequences to identify peaks and troughs based upon the scores provided to each nucleotide within the putative promoter sequences; wherein each of the set of sequence elements is a k-mer fragment of the polynucleotide sequence;

c) identifying at least one member of the set of putative promoter sequences where there is a trough of at least 20 nucleotides between peaks, wherein the scores for members of the trough are below a pre-determined threshold; and d) synthesizing an AAV viral vector comprising a shortened polynucleotide molecule, wherein at least 10% of the nucleotides within the trough have been removed as compared to the selected identified putative promoter sequence of step (c).

17. A method of synthesizing an AAV viral vector comprising a synthetic polynucleotide with transcriptional regulatory functionality, the method comprising the steps of:

a) receiving a set of genetic data comprising a regulatory polynucleotide sequence, optionally having a known transcriptional regulatory activity;

b) identifying an enhancer portion of the polynucleotide sequence using a machine learning model based on k-mers;

c) processing the enhancer portion into a set of sequence elements that each comprise a k-mer fragment of the enhancer portion of the polynucleotide sequence;

d) processing the set of sequence elements with a machine learning model to determine a transcriptional regulatory score associated with each sequence element of the set of sequence elements;

e) identifying at least one sequence element of the set of sequence elements comprising a trough of at least 20 nucleotides between peaks with a transcriptional regulatory score below a threshold as a non-regulatory sequence element;

f) designing a modified polynucleotide molecule based on the determined transcriptional regulatory scores and/or identified non-regulatory sequence elements; wherein at least 10% of the nucleotides within the trough have been removed in the modified polynucleotide molecule; and g) synthesizing an AAV viral vector comprising the modified polynucleotide molecule.

18. An AAV viral vector comprising a modified polynucleotide that was synthesized using a method comprising the steps of:

a) receiving a set of genetic data comprising a regulatory polynucleotide sequence, optionally having a known transcriptional regulatory activity;

b) identifying an enhancer portion of the polynucleotide sequence using a machine learning model based on k-mers;

c) processing the enhancer portion into a set of sequence elements that each comprise a k-mer fragment of the enhancer portion of the polynucleotide sequence;

d) processing the set of sequence elements with a machine learning model to determine a transcriptional regulatory score associated with each sequence element of the set of sequence elements;

e) identifying at least one sequence element of the set of sequence elements comprising a trough of at least 20 nucleotides between peaks with a transcriptional regulatory score below a threshold as a non-regulatory sequence element;

f) designing a modified polynucleotide molecule based on the determined transcriptional regulatory scores and/or identified non-regulatory sequence elements; wherein at least 10% of the nucleotides within the trough have been removed in the modified polynucleotide molecule; and g) synthesizing an AAV viral vector comprising the modified polynucleotide molecule.

\*    \*    \*    \*    \*

SEQUENCE LISTING

<160> NUMBER OF SEQ ID NOS: 51

<210> SEQ ID NO 1
<211> LENGTH: 437
<212> TYPE: DNA

<213> ORGANISM: Artificial Sequence
<220> FEATURE:
<223> OTHER INFORMATION: synthetic polynucleotide

<400> SEQUENCE: 1

```
taaagaactg tttgcatgtt gcaaatgatg tccaaagtcc aaacattgtt aataattaat     60
actccaataa acatcatgtc agaatttctg ttttcttttc cctttgaacc tttgcaggat    120
tgccacatca tcaggaccac accttcatca ggaatgaata tccgatgacc taatgattct    180
gagcttggca aaggtcttat ctcccagctc gcccaggccc agtgttccag gaatgtgacc    240
tttgctgcag cagccgctgg aggggggcaga ggggatgggc tggaggttga gcaaacagag    300
cagcagaaaa ggcagttcct cttctccagt gccctccttc cctgtctctg cctctccctc    360
ccttcctcag gcatcagagc ggagacttca gggagaccag agcccagctt gccaggcact    420
gagctagaag ccctgcc                                                   437
```

<210> SEQ ID NO 2
<211> LENGTH: 477
<212> TYPE: DNA
<213> ORGANISM: Artificial Sequence
<220> FEATURE:
<223> OTHER INFORMATION: synthetic polynucleotide

<400> SEQUENCE: 2

```
tgatgtcctg attggaagga ccgttggccc cccacccctta taaagaactg tttgcatgtt     60
gcaaatgatg tccaaagtcc aaacattgtt aataattaat actccaataa acatcatgtc    120
agaatttctg ttttcttttc cctttgaacc tttgcaggat tgccacatca tcaggaccac    180
accttcatca ggaatgaata tccgatgacc taatgattct gagcttggca aaggtcttat    240
ctcccagctc gcccaggccc agtgttccag gaatgtgacc tttgctgcag cagccgctgg    300 aggggggcaga ggggatgggc tggaggttga gcaaacagag cagcagaaaa ggcagttcct    360
cttctccagt gccctccttc cctgtctctg cctctccctc ccttcctcag gcatcagagc    420
ggagacttca gggagaccag agcccagctt gccaggcact gagctagaag ccctgcc       477
```

<210> SEQ ID NO 3
<211> LENGTH: 427
<212> TYPE: DNA
<213> ORGANISM: Artificial Sequence
<220> FEATURE:
<223> OTHER INFORMATION: synthetic polynucleotide

<400> SEQUENCE: 3

```
gctggtttct tataaaactg atggaagata caaacactat taaagaactg tttgcatgtt     60
gcaaatgatg tccaaagtcc aaacattgtt aataattaat actccaataa acatcatgtc    120
agaatttctg ttttcttttc cctttgaacc tttgcaggat tgccacttct gagcttggca    180
aaggtcttat ctcccagctc gcccaggccc agtgttccag gaatgtgacc tttgctgcag    240
cagccgctgg aggggggcaga ggggatgggc tggaggttga gcaaacagag cagcagaaaa    300
ggcagttcct cttctccagt gccctccttc cctgtctctg cctctccctc ccttcctcag    360
gcatcagagc ggagacttca gggagaccag agcccagctt gccaggcact gagctagaag    420
ccctgcc                                                              427
```

<210> SEQ ID NO 4
<211> LENGTH: 477
<212> TYPE: DNA
<213> ORGANISM: Artificial Sequence

```
<220> FEATURE:
<223> OTHER INFORMATION: synthetic polynucleotide

<400> SEQUENCE: 4
gctggtttct tataaaactg atggaagata caaacactat taaagaactg tttgcatgtt      60
gcaaatgatg tccaaagtcc aaacattgtt aataattaat actccaataa acatcatgtc     120
agaatttctg ttttctttc cctttgaacc tttgcaggat tgccactgat gtcctgattg      180
gaaggaccgt tggcccccca cccttaggca gtgtatttct gagcttggca aaggtcttat      240
ctcccagctc gcccaggccc agtgttccag gaatgtgacc tttgctgcag cagccgctgg     300
agggggcaga ggggatgggc tggaggttga gcaaacagag cagcagaaaa ggcagttcct     360
cttctccagt gccctccttc cctgtctctg cctctccctc ccttcctcag gcatcagagc     420
ggagacttca gggagaccag agcccagctt gccaggcact gagctagaag ccctgcc       477

<210> SEQ ID NO 5
<211> LENGTH: 478
<212> TYPE: DNA
<213> ORGANISM: Artificial Sequence
<220> FEATURE:
<223> OTHER INFORMATION: synthetic polynucleotide

<400> SEQUENCE: 5
caggctttca ctttctcgcc aacttacaag gcctttctgt gtaaaaaata cctgaacctt      60
taccccgttg cccggcaacg gccaggtctg tgccaagtgt ttgaggttaa tttttaaaaa     120
gcagtcaaaa gtccaagtgg cccttggcag catttactct ctctgtttgc tctggttaat     180
aatctcagga gcacaaacat tccggcccgg gaggcgccct ttggaccttt tgcaatcctg     240
gcgcactgaa cccttgaccc ctgccctgca gcccccgcag cttgctgttt gcccactcta     300
tttgcccagc cccagccctg gagagtcctt tagcagggca aagtgcaaca taggcagacc     360
ttaagggatg actcagtaac agataagctt tgtgtgcctg cagggcatat aaaacagggg     420
caaggcacag actcatagca gagcaatcac caccaagcct ggaataactg cagccacc     478

<210> SEQ ID NO 6
<211> LENGTH: 478
<212> TYPE: DNA
<213> ORGANISM: Artificial Sequence
<220> FEATURE:
<223> OTHER INFORMATION: synthetic polynucleotide

<400> SEQUENCE: 6
caggctttca ctttctcgcc aacttacaag gcctttctgt gtaaacaata cctgaacctt      60
taccccgttg cccggcaacg gccaggtctg tgccaagtgt ttgaggttaa tttttaaaaa     120
gcagtccaaa gtccaagtgg cccttggcag catttactct ctctgtttgc tctggttaat     180
aatctcagga gcacaaacat tccggcccgg gaggcgccct ttggaccttt tgcaatcctg     240
gcgcactgaa cccttgaccc ctgccctgca gcccccgcag cttgctgttt gcccactcta     300
tttgcccagc cccagccctg gagagtcctt tagcagggca aagtgcaaca taggcagacc     360
ttaagggatg actcagtaac agataagctt tgtgtgcctg cagggcatat aaaacagggg     420
caaggcacag actcatagca gagcaatcac caccaagcct ggaataactg cagccacc     478

<210> SEQ ID NO 7
<211> LENGTH: 446
<212> TYPE: DNA
<213> ORGANISM: Artificial Sequence
<220> FEATURE:
```

<223> OTHER INFORMATION: synthetic polynucleotide

<400> SEQUENCE: 7
ctttctgtgt aaacaatacc tgaacctta ccccgttgcc cggcaacggc caggtctgtg        60
ccaagtgttt gaggttaatt tttaaaaagc agtcaaaagt ccaagtggcc cttggcagca       120
tttactctct ctgtttgctc tggttaataa tctcaggagc acaaacattc cggcccggga       180 ggcgccttt ggacctttg caatcctggc gcactgaacc cttgacccct gccctgcagc         240
ccccgcagct tgctgtttgc ccactctatt tgcccagccc cagccctgga gagtccttta       300
gcagggcaaa gtgcaacata ggcagacctt aagggatgac tcagtaacag ataagctttg       360
tgtgcctgca gggcatataa aacaggggca aggcacagac tcatagcaga gcaatcacca       420
ccaagcctgg aataactgca gccacc                                          446

<210> SEQ ID NO 8
<211> LENGTH: 478
<212> TYPE: DNA
<213> ORGANISM: Artificial Sequence
<220> FEATURE:
<223> OTHER INFORMATION: synthetic polynucleotide

<400> SEQUENCE: 8
tgatgtcctg attggaagga ccgttggccc ccctttctgt gtaaacaata cctgaacctt        60
taccccgttg cccggcaacg gccaggtctg tgccaagtgt ttgaggttaa tttttaaaaa       120
gcagtcaaaa gtccaagtgg cccttggcag catttactct ctctgtttgc tctggttaat       180
aatctcagga gcacaaacat tccggcccgg gaggcgccct ttggaccttt tgcaatcctg       240
gcgcactgaa cccttgaccc ctgccctgca gccccgcag cttgctgttt gcccactcta        300
tttgcccagc cccagccctg gagagtcctt tagcagggca aagtgcaaca taggcagacc       360
ttaagggatg actcagtaac agataagctt tgtgtgcctg cagggcatat aaaacagggg       420
caaggcacag actcatagca gagcaatcac caccaagcct ggaataactg cagccacc        478

<210> SEQ ID NO 9
<211> LENGTH: 440
<212> TYPE: DNA
<213> ORGANISM: Artificial Sequence
<220> FEATURE:
<223> OTHER INFORMATION: synthetic polynucleotide

<400> SEQUENCE: 9
gtgtaaacaa tacctgaacc tttaccccgt tgcccggcaa cggccaggtc tgtgccaagt        60
gtttgaggtt aattttttaaa aagcagtcaa aagtccaagt ggcccttggc agcatttact       120
ctctctgttt gctctggtta ataatctcag gagcacaaac attccggccc gggaggcgcc       180
ctttggacct tttgcaatcc tggcgcactg aacccttgac ccctgccctg cagcccccgc       240
agcttgctgt ttgcccactc tatttgccca gccccagccc tggagagtcc tttagcaggg       300
caaagtgcaa cataggcaga ccttaaggga tgactcagta acagataagc tttgtgtgcc       360
tgcagggcat ataaaacagg ggcaaggcac agactcatag cagagcaatc accaccaagc       420
ctggaataac tgcagccacc                                                 440

<210> SEQ ID NO 10
<211> LENGTH: 461
<212> TYPE: DNA
<213> ORGANISM: Artificial Sequence
<220> FEATURE:
<223> OTHER INFORMATION: synthetic polynucleotide -continued

<400> SEQUENCE: 10

```
caggctttca ctttctcgcc aacttacaag gcctttctgt gtaaacaata cctgaacctt        60 tacccgttg cccggcaacg gccaggtctg tgccaagtgt ttgaggttaa tttttaaaaa       120
gcagtcaaaa gtccaagtgg cccttggcag catttactct ctctgtttgc tctggttaat       180
aatctcagga gcacaaacat tccggcccgg gaggcgccct ttggaccttt gaacccttga       240
cccctgccct gcagccccg cagcttgctg tttgcccact ctatttgccc agccccagcc       300
ctggagagtc ctttagcagg gcaaagtgca acataggcag accttaaggg atgactcagt       360
aacagataag ctttgtgtgc ctgcagggca tataaaacag gggcaaggca cagactcata       420
gcagagcaat caccaccaag cctggaataa ctgcagccac c                         461
```

<210> SEQ ID NO 11
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 11

```
gctggtttct tataaaactg atggaagata caaacactat taaagaactg tttgcatgtt        60
gcaaatgatg tccaaaatcc aaacattgtt aataattaat actccaataa acatcatgtc       120
agaatttctg ttttctttc cctttgaacc tttgcaggat tgccacatca tcaggaccac       180
accttcatca ggaatgaata tcaggctttc actttctcgc caacttacaa ggcctttctg       240
tgtaaacaat acctgaacct ttaccccgtt gcccggcaac ggccaggtct gtgccaagtg       300
tttgccgatg acctaatgat tctgagcttg gcaaaggtct tatctcccag ctcgcccagg       360
cccagtgttc caggaatgtg accttgctg cagcagccgc tggagggggc agaggggatg       420
ggctggaggt tgagcaaaca gagcagcaga aaaggcagtt cctcttctcc agtgccctcc       480
ttccctgtct ctgcctctcc ctcccttcct caggcatcag agcggagact tcagggagac       540
cagagcccag cttgccaggc actgagctag aagccctgcc                            580
```

<210> SEQ ID NO 12
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 12

```
gctggtttct tataaaactg atggaagata caaacactat taaagaactg tttgcatgtt        60
gcaaatgatg tccaaagtcc aaacattgtt aatgattaat actccaataa acatcatgtc       120
agaatttctg ttttctttc cctttgaacc tttgcaggat tgccacatca tcaggaccac       180
accttcatca ggaatgaata tcaggctttc actttctcgc caacttacaa ggcctttctg       240
tgtaaacaat acctgaacct ttaccccgtt gcccggcaac ggccaggtct gtgccaagtg       300
tttgccgatg acctaatgat tctgagcttg gcaaaggtct tatctcccag ctcgcccagg       360
cccagtgttc caggaatgtg accttgctg cagcagccgc tggagggggc agaggggatg       420
ggctggaggt tgagcaaaca gagcagcaga aaaggcagtt cctcttctcc agtgccctcc       480
ttccctgtct ctgcctctcc ctcccttcct caggcatcag agcggagact tcagggagac       540
cagagcccag cttgccaggc actgagctag aagccctgcc                            580
```

<210> SEQ ID NO 13
<211> LENGTH: 536
<212> TYPE: DNA
<213> ORGANISM: Artificial Sequence
<220> FEATURE:
<223> OTHER INFORMATION: synthetic polynucleotide

<400> SEQUENCE: 13

```
gaactgtttg catgttgcaa atgatgtcca aagtccaaac attgttaata attaatactc        60
caataaacat catgtcagaa tttctgtttt cttttccctt tgaacctttg caggattgcc       120
acatcatcag gaccacacct tcatcaggaa tgaatatcag gctttcactt tctcgccaac       180
ttacaaggcc tttctgtgta aacaatacct gaacctttac cccgttgccc ggcaacggcc       240
aggtctgtgc caagtgtttg ccgatgacct aatgattctg agcttggcaa aggtcttatc       300
tcccagctcg cccaggccca gtgttccagg aatgtgacct ttgctgcagc agccgctgga       360
gggggcagag gggatgggct ggaggttgag caaacagagc agcagaaaag gcagttcctc       420
ttctccagtg ccctccttcc ctgtctctgc ctctccctcc cttcctcagg catcagagcg       480
gagacttcag ggagaccaga gcccagcttg ccaggcactg agctagaagc cctgcc        536
```

<210> SEQ ID NO 14
<211> LENGTH: 513
<212> TYPE: DNA
<213> ORGANISM: Artificial Sequence
<220> FEATURE:
<223> OTHER INFORMATION: synthetic polynucleotide

<400> SEQUENCE: 14

```
atgtccaaag tccaaacatt gttaataatt aatactccaa taaacatcat gtcagaattt        60
ctgttttctt ttccctttga acctttgcag gattgccaca tcatcaggac cacaccttca       120
tcaggaatga atatcaggct ttcactttct cgccaactta caaggccttt ctgtgtaaac       180
aatacctgaa cctttacccc gttgcccggc aacggccagg tctgtgccaa gtgtttgccg       240
atgacctaat gattctgagc ttggcaaagg tcttatctcc cagctcgccc aggcccagtg       300
ttccaggaat gtgacctttg ctgcagcagc cgctggaggg ggcagagggg atgggctgga       360
ggttgagcaa acagagcagc agaaaaggca gttcctcttc tccagtgccc tccttccctg       420
tctctgcctc tccctccctt cctcaggcat cagagcggag acttcaggga gaccagagcc       480
cagcttgcca ggcactgagc tagaagccct gcc                                   513
```

<210> SEQ ID NO 15
<211> LENGTH: 502
<212> TYPE: DNA
<213> ORGANISM: Artificial Sequence
<220> FEATURE:
<223> OTHER INFORMATION: synthetic polynucleotide

<400> SEQUENCE: 15

```
gctggtttct tataaaactg atggaagata caaacactat taaagaactg tttgcatgtt        60
gcaaatgatg tccaaagtcc aaacattgtt aataattaat actccaataa acatcatgtc       120
agaatttctg ttttctttc cctttgaacc tttgcctttc tgtgtaaaca atacctgaac       180
ctttaccccg ttgcccggca acggccaggt ctgtgccaag tgtttgccga tgacctaatg       240
attctgagct tggcaaaggt cttatctccc agctcgccca ggcccagtgt tccaggaatg       300
tgacctttgc tgcagcagcc gctggagggg cagaggggga tgggctggag gttgagcaaa       360
cagagcagca gaaaaggcag ttcctcttct ccagtgccct ccttccctgt ctctgcctct       420
```

-continued

```
ccctcccttc ctcaggcatc agagcggaga cttcagggag accagagccc agcttgccag        480
gcactgagct agaagccctg cc                                                  502

<210> SEQ ID NO 16
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 16
gctggtttct tataaaactg atggaagata caaacactat taaagaactg tttgcatgtt         60
gcaaatgatg tccaaagtcc aaacattgtt aataattaat actccaataa acatcatgtc        120
agaatttctg ttttcttttc cctttgaacc tttgctgatg tcctgattgg aaggaccgtt        180
ggccccccac ccttaggcag tgtatactct tccataaacg agctattagt tatctttctg        240
tgtaaacaat acctgaacct ttaccccgtt gcccggcaac ggccaggtct gtgccaagtg        300
tttgccgatg acctaatgat tctgagcttg gcaaaggtct tatctcccag ctcgcccagg        360
cccagtgttc caggaatgtg acctttgctg cagcagccgc tggagggggc agaggggatg        420
ggctggaggt tgagcaaaca gagcagcaga aaaggcagtt cctcttctcc agtgccctcc        480
ttccctgtct ctgcctctcc ctcccttcct caggcatcag agcggagact tcagggagac        540
cagagcccag cttgccaggc actgagctag aagccctgcc                              580

<210> SEQ ID NO 17
<211> LENGTH: 501
<212> TYPE: DNA
<213> ORGANISM: Artificial Sequence
<220> FEATURE:
<223> OTHER INFORMATION: synthetic polynucleotide

<400> SEQUENCE: 17
gctggtttct tataaaactg atggaagata caaacactat taaagaactg tttgcatgtt         60
gcaaatgatg tccaaagtcc aaacattgtt aataattaat actccaataa acatcatgtc        120
agaatttctg ttttcttttc cctttgaacc tttgcaggat tgccacatca tcaggaccac        180
accttcatca ggaatgaata tcaggctttc actttctcgc caacttacaa ggcctttctg        240
tgtaaacaat ggcaaaggtc ttatctccca gctcgcccag gcccagtgtt ccaggaatgt        300
gacctttgct gcagcagccg ctggagggggg cagaggggat gggctggagg ttgagcaaac        360
agagcagcag aaaaggcagt tcctcttctc cagtgccctc cttccctgtc tctgcctctc        420
cctcccttcc tcaggcatca gagcggagac ttcagggaga ccagagccca gcttgccagg        480
cactgagcta gaagccctgc c                                                  501

<210> SEQ ID NO 18
<211> LENGTH: 524
<212> TYPE: DNA
<213> ORGANISM: Artificial Sequence
<220> FEATURE:
<223> OTHER INFORMATION: synthetic polynucleotide

<400> SEQUENCE: 18
gctggtttct tataaaactg atggaagata caaacactat taaagaactg tttgcatgtt         60
gcaaatgatg tccaaagtcc aaacattgtt aataattaat actccaataa acatcatgtc        120
agaatttctg ttttcttttc cctttgaacc tttgcaggat tgccacatca tcaggaccac        180
```

```
accttcatca ggaatgaata tcaggctttc actttctcgc caacttacaa ggcctttctg        240
tgtaaacaat acctgaacct ttaccccgtg cttggcaaag gtcttatctc ccagctcgcc        300
caggcccagt gttccaggaa tgtgaccttt gctgcagcag ccgctggagg gggcagaggg        360
gatgggctgg aggttgagca aacagagcag cagaaaaggc agttcctctt ctccagtgcc        420
ctccttccct gtctctgcct ctccctccct tcctcaggca tcagagcgga gacttcaggg        480
agaccagagc ccagcttgcc aggcactgag ctagaagccc tgcc                         524
```

```
<210> SEQ ID NO 19
<211> LENGTH: 558
<212> TYPE: DNA
<213> ORGANISM: Artificial Sequence
<220> FEATURE:
<223> OTHER INFORMATION: synthetic polynucleotide

<400> SEQUENCE: 19
cttacaaggc ctttctgtgt aaacaatacc tgaacctttta ccccgttgcc cggcaacggc         60
caggtctgtg ccaagtgttt ggctggtttc ttataaaact gatggaagat acaaacacta        120
ttaaagaact gtttgcatgt tgcaaatgat gtccaaagtc caaacattgt taataattaa        180
tactccaata aacatcatgt cagaatttct gtttttctttt ccctttgaac ctttgcagga        240
ttgccacatc atcaggacca caccttcatc aggaatgaat atccgatgac ctaatgattc        300
tgagcttggc aaaggtctta tctcccagct cgcccaggcc cagtgttcca ggaatgtgac        360
ctttgctgca gcagccgctg gaggggcag aggggatggg ctggaggttg agcaaacaga        420
gcagcagaaa aggcagttcc tcttctccag tgccctcctt ccctgtctct gcctctccct        480
cccttcctca ggcatcagag cggagacttc agggagacca gagcccagct tgccaggcac        540
tgagctagaa gccctgcc                                                      558
```

```
<210> SEQ ID NO 20
<211> LENGTH: 475
<212> TYPE: DNA
<213> ORGANISM: Artificial Sequence
<220> FEATURE:
<223> OTHER INFORMATION: synthetic polynucleotide

<400> SEQUENCE: 20
caggctttca ctttctcgcc aacttacaag gcctttctgt gtaaacaata cctgaacctt         60
tacccatgtc caaagtccaa acattgttaa taattaatac tccaataaac atcatgtcag        120
aatttctgtt ttcttttccc tttgaacctt gcaggattg ccacatcatc aggaccacac        180
cttcatcagg aatgaatatc cgatgaccta atgattctga gcttggcaaa ggtcttatct        240
cccagctcgc ccaggcccag tgttccagga atgtgacctt tgctgcagca gccgctggag        300
ggggcagagg ggatgggctg gaggttgagc aaacagagca gcagaaaagg cagttcctct        360
tctccagtgc cctccttccc tgtctctgcc tctccctccc ttcctcaggc atcagagcgg        420
agacttcagg gagaccagag cccagcttgc caggcactga gctagaagcc ctgcc             475
```

```
<210> SEQ ID NO 21
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 21
caggctttca ctttctcgcc aacttacaag gcctttctgt gtaaacaata cctgaacctt         60
```

```
taccctgatg tcctgattgg aaggaccgtt ggcccccac ccttaggcag tgtatactct       120
tccataaacg agctattagt tatgaggtcc gtagattgaa aagggtgacg atgtccaaag      180
tccaaacatt gttaataatt aatactccaa taaacatcat gtcagaattt ctgttttctt      240
ttccctttga acctttgcag gattgccaca tcatcaggac cacaccttca tcaggaatga      300
atatccgatg acctaatgat tctgagcttg gcaaaggtct tatctcccag ctcgcccagg      360
cccagtgttc caggaatgtg acctttgctg cagcagccgc tggaggggc agaggggatg       420 ggctggaggt tgagcaaaca gagcagcaga aaaggcagtt cctcttctcc agtgccctcc      480
ttccctgtct ctgcctctcc ctcccttcct caggcatcag agcggagact tcagggagac      540
cagagcccag cttgccaggc actgagctag aagccctgcc                            580
```

```
<210> SEQ ID NO 22
<211> LENGTH: 523
<212> TYPE: DNA
<213> ORGANISM: Artificial Sequence
<220> FEATURE:
<223> OTHER INFORMATION: synthetic polynucleotide

<400> SEQUENCE: 22
caggctttca ctttctcgcc aacttacaag gcctttctgt gtaaacaata cctgaacctt        60
taccccgttg cccggcaacg gccaggtctg tgccaagtgt ttggctggtt tcttataaaa       120
ctgatggaag atacaaacac tattaaagaa ctgtttgcat gttgcaaatg atgtccaaag      180
tccaaacatt gttaataatt aatactccaa taaacatcat gtcagaattt ctgttttctt      240
ttccctttga acctttgcag gattctgagc ttggcaaagg tcttatctcc cagctcgccc      300
aggcccagtg ttccaggaat gtgacctttg ctgcagcagc cgctggaggg ggcagagggg      360
atgggctgga ggttgagcaa acagagcagc agaaaaggca gttcctcttc tccagtgccc      420
tccttccctg tctctgcctc tccctcccctt cctcaggcat cagagcggag acttcaggga      480
gaccagagcc cagcttgcca ggcactgagc tagaagccct gcc                        523
```

```
<210> SEQ ID NO 23
<211> LENGTH: 430
<212> TYPE: DNA
<213> ORGANISM: Artificial Sequence
<220> FEATURE:
<223> OTHER INFORMATION: synthetic polynucleotide

<400> SEQUENCE: 23
ctgtttgctg cttgcaatgt ttgtccaaag tccaaacatt gttaataatt aatactccaa        60
taaacatcat gtcagaattt ctgttttctt ttccctttga acctttgcag gattgccaca      120
tcatcaggac cacaccttca tcaggaatga atatccgatg acctaatgat tctgagcttg      180
gcaaaggtct tatctcccag ctcgcccagg cccagtgttc caggaatgtg acctttgctg      240
cagcagccgc tggaggggc agaggggatg ggctggaggt tgagcaaaca gagcagcaga       300
aaaggcagtt cctcttctcc agtgccctcc ttccctgtct ctgcctctcc ctcccttcct      360
caggcatcag agcggagact tcagggagac cagagcccag cttgccaggc actgagctag      420
aagccctgcc                                                             430
```

```
<210> SEQ ID NO 24
<211> LENGTH: 512
<212> TYPE: DNA
<213> ORGANISM: Artificial Sequence
<220> FEATURE:
```

<223> OTHER INFORMATION: synthetic polynucleotide

<400> SEQUENCE: 24
ctgtttgctg cttgcaatgt tttgatgtcc tgattggaag gaccgttggc cccccaccct      60
taggcagtgt atactcttcc ataaacgagc tattagttat gagggtccaa agtccaaaca     120
ttgttaataa ttaatactcc aataaacatc atgtcagaat ttctgttttc ttttcccttt     180
gaacctttgc aggattgcca catcatcagg accacacctt catcaggaat gaatatccga     240
tgacctaatg attctgagct tggcaaaggt cttatctccc agctcgccca ggcccagtgt     300
tccaggaatg tgacctttgc tgcagcagcc gctggagggg gcagagggga tgggctggag     360
gttgagcaaa cagagcagca gaaaaggcag ttcctcttct ccagtgccct ccttccctgt     420
ctctgcctct ccctcccttc ctcaggcatc agagcggaga cttcagggag accagagccc     480
agcttgccag gcactgagct agaagccctg cc                                     512

<210> SEQ ID NO 25
<211> LENGTH: 453
<212> TYPE: DNA
<213> ORGANISM: Artificial Sequence
<220> FEATURE:
<223> OTHER INFORMATION: synthetic polynucleotide

<400> SEQUENCE: 25
ctgtttgctg cttgcaatgt ttgcccattt taggggctgg tttcttataa aactgatgga      60
agatacaaac actattaaag aactgtttgc atgttgcaaa tgatgtccaa agtccaaaca     120
ttgttaataa ttaatactcc aataaacatc atgtcagaat ttctgttttc ttttcccttt     180
gaacctttgc aggattgcca ctggcaaagg tcttatctcc cagctcgccc aggcccagtg     240
ttccaggaat gtgacctttg ctgcagcagc cgctggaggg ggcagagggg atgggctgga     300
ggttgagcaa acagagcagc agaaaaggca gttcctcttc tccagtgccc tccttccctg     360
tctctgcctc tccctccctt cctcaggcat cagagcggag acttcaggga accagagcc     420 cagcttgcca ggcactgagc tagaagccct gcc                                     453

<210> SEQ ID NO 26
<211> LENGTH: 345
<212> TYPE: DNA
<213> ORGANISM: Artificial Sequence
<220> FEATURE:
<223> OTHER INFORMATION: synthetic polynucleotide

<400> SEQUENCE: 26
caggctttca ctttctcgcc aacttacaag gcctttctgt gtaaacaata cctgaacttt      60
gaccccgttg cccggcaacg gccaggtctg tgccaagtgt ttgcctttgc aacagcttat     120
cggaagcaaa caagctgagg ggaattgagc aagaatttct gggataccaa cagcatagga     180
ggaacaaagg acgtagaggg agggttgact gtctacacag gacaaagcca atgattaacc     240
aaacctcttg cagatttaaa taggatggga actaggagtg gcagcaatcc tttctttcag     300
ctggagtgct cctcaggagc cagccccacc cttagaaaag ccacc                       345

<210> SEQ ID NO 27
<211> LENGTH: 345
<212> TYPE: DNA
<213> ORGANISM: Artificial Sequence
<220> FEATURE:
<223> OTHER INFORMATION: synthetic polynucleotide

<400> SEQUENCE: 27

-continued

```
caggctttca ctttctcgcc aacttacaag gcctttctgt gtaaacaata cctgaacctt        60 tacccgttg cccggcaacg gccaggtctg tgccaagtgt ttgcctttgc aacagcttat        120
cggaagcaaa caagctgagg ggaattgagc aagaatttct gggataccaa cagcatagga       180
ggaacaaagg acgtagaggg agggttgact gtttacacag gacaaagcca atgattaacc       240
aaacctcttg cagatttaaa taggatggga actaggagtg gcagcaatcc tttctttcag       300
ctggagtgct cctcaggagc cagccccacc cttagaaaag ccacc                       345
```

```
<210> SEQ ID NO 28
<211> LENGTH: 480
<212> TYPE: DNA
<213> ORGANISM: Artificial Sequence
<220> FEATURE:
<223> OTHER INFORMATION: synthetic polynucleotide

<400> SEQUENCE: 28
gctggtttct tataaaactg atggaagata caaacactat taaagaactg tttgcatgtt        60
gcaaatgatg tccaaagtcc aaacattgtt aataattaat actccaataa acatcatgtc       120
agaatttctg ttttcttttc cctttgaacc tttgcaggat tgccacatca tcaggaccac       180
accttcatca ggaatgaata tccgatgacc taatgattct gagcttggca aaggtcttat       240
ctcccagctc gcccaggccc agtgttccag gaatgtgacc tttgctgcag cagccgctgg       300 aggggcaga ggggatgggc tggaggttga gcaaacagag cagcagaaaa ggcagttcct        360
cttctccagt gccctccttc cctgtctctg cctctccctc ccttcctcag gcatcagagc       420
ggagacttca gggagaccag agcccagctt gccaggcact gagctagaag ccctgccatg       480
```

```
<210> SEQ ID NO 29
<211> LENGTH: 478
<212> TYPE: DNA
<213> ORGANISM: Artificial Sequence
<220> FEATURE:
<223> OTHER INFORMATION: synthetic polynucleotide

<400> SEQUENCE: 29
caggctttca ctttctcgcc aacttacaag gcctttctgt gtaaacaata cctgaacctt        60 tacccgttg cccggcaacg gccaggtctg tgccaagtgt ttgaggttaa ttttaaaaa        120 gcagtcaaaa gtccaagtgg cccttggcag catttactct ctctgtttgc tctggttaat      180
aatctcagga gcacaaacat tccggcccgg gaggcgccct ttggaccttt tgcaatcctg       240
gcgcactgaa cccttgaccc ctgccctgca gcccccgcag cttgctgttt gcccactcta       300
tttgcccagc cccagccctg gagagtcctt tagcagggca aagtgcaaca taggcagacc       360
ttaagggatg actcagtaac agataagctt tgtgtgcctg cagggcatat aaaacagggg       420
caaggcacag actcatagca gagcaatcac caccaagcct ggaataactg cagccacc        478
```

```
<210> SEQ ID NO 30
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 30
gctggtttct tataaaactg atggaagata caaacactat taaagaactg tttgcatgtt        60
gcaaatgatg tccaaagtcc aaacattgtt aataattaat actccaataa acatcatgtc       120
```

-continued

```
agaatttctg ttttctttc cctttgaacc tttgcaggat tgccacatca tcaggaccac      180
accttcatca ggaatgaata tcaggctttc actttctcgc caacttacaa ggcctttctg      240
tgtaaacaat acctgaacct ttaccccgtt gcccggcaac ggccaggtct gtgccaagtg      300
tttgccgatg acctaatgat tctgagcttg gcaaaggtct tatctcccag ctcgcccagg      360
cccagtgttc caggaatgtg acctttgctg cagcagccgc tggaggggc agaggggatg       420 ggctggaggt tgagcaaaca gagcagcaga aaaggcagtt cctcttctcc agtgccctcc      480
ttccctgtct ctgcctctcc ctcccttcct caggcatcag agcggagact tcagggagac      540
cagagcccag cttgccaggc actgagctag aagccctgcc                            580
```

<210> SEQ ID NO 31
<211> LENGTH: 580
<212> TYPE: DNA
<213> ORGANISM: Artificial Sequence
<220> FEATURE:
<223> OTHER INFORMATION: synthetic polynucleotide

<400> SEQUENCE: 31

```
caggctttca ctttctcgcc aacttacaag gcctttctgt gtaaacaata cctgaacctt      60
taccccgttg cccggcaacg gccaggtctg tgccaagtgt ttggctggtt tcttataaaa      120
ctgatggaag atacaaacac tattaaagaa ctgtttgcat gttgcaaatg atgtccaaag      180
tccaaacatt gttaataatt aatactccaa taaacatcat gtcagaattt ctgttttctt      240
ttccctttga acctttgcag gattgccaca tcatcaggac cacccttca tcaggaatga       300 atatccgatg acctaatgat tctgagcttg gcaaaggtct tatctcccag ctcgcccagg      360
cccagtgttc caggaatgtg acctttgctg cagcagccgc tggaggggc agaggggatg       420 ggctggaggt tgagcaaaca gagcagcaga aaaggcagtt cctcttctcc agtgccctcc      480
ttccctgtct ctgcctctcc ctcccttcct caggcatcag agcggagact tcagggagac      540
cagagcccag cttgccaggc actgagctag aagccctgcc                            580
```

<210> SEQ ID NO 32
<211> LENGTH: 512
<212> TYPE: DNA
<213> ORGANISM: Artificial Sequence
<220> FEATURE:
<223> OTHER INFORMATION: synthetic polynucleotide

<400> SEQUENCE: 32

```
ctgtttgctg cttgcaatgt ttgcccattt taggggctgg tttcttataa aactgatgga      60
agatacaaac actattaaag aactgtttgc atgttgcaaa tgatgtccaa agtccaaaca      120
ttgttaataa ttaatactcc aataaacatc atgtcagaat ttctgttttc ttttcccttt      180
gaacctttgc aggattgcca catcatcagg accacacctt catcaggaat gaatatccga      240
tgacctaatg attctgagct tggcaaaggt cttatctccc agctcgccca ggcccagtgt      300
tccaggaatg tgacctttgc tgcagcagcc gctggagggg gcagagggga tgggctggag      360
gttgagcaaa cagagcagca gaaaaggcag ttcctcttct ccagtgccct ccttccctgt      420
ctctgcctct ccctcccttc ctcaggcatc agagcggaga cttcagggag accagagccc      480
agcttgccag gcactgagct agaagccctg cc                                    512
```

<210> SEQ ID NO 33
<211> LENGTH: 345
<212> TYPE: DNA
<213> ORGANISM: Artificial Sequence

```
<220> FEATURE:
<223> OTHER INFORMATION: synthetic polynucleotide

<400> SEQUENCE: 33
caggctttca ctttctcgcc aacttacaag gcctttctgt gtaaacaata cctgaacctt        60
taccccgttg cccggcaacg gccaggtctg tgccaagtgt ttgcctttgc aacagcttat       120
cggaagcaaa caagctgagg ggaattgagc aagaatttct gggataccaa cagcatagga       180
ggaacaaagg acgtagaggg agggttgact gtctacacag gacaaagcca atgattaacc       240
aaacctcttg cagatttaaa taggatggga actaggagtg gcagcaatcc tttctttcag       300
ctggagtgct cctcaggagc cagccccacc cttagaaaag ccacc                      345

<210> SEQ ID NO 34
<211> LENGTH: 38
<212> TYPE: DNA
<213> ORGANISM: Artificial Sequence
<220> FEATURE:
<223> OTHER INFORMATION: synthetic polynucleotide

<400> SEQUENCE: 34
ctatgtcgta cgtagtacct gcttcgaata ttcatcga                               38

<210> SEQ ID NO 35
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 35 tanntnnttc                                                              10

<210> SEQ ID NO 36
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(4)
<223> OTHER INFORMATION: n is a, c, g, or t

<400> SEQUENCE: 36 nnnntgcttc                                                              10

<210> SEQ ID NO 37
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(3)
```

-continued

```
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 37 nanctnctnc                                                        10

<210> SEQ ID NO 38
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 38 nncntgcntc                                                        10

<210> SEQ ID NO 39
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t

<400> SEQUENCE: 39 nanntgcntc                                                        10

<210> SEQ ID NO 40
<211> LENGTH: 10
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
```

-continued

<222> LOCATION: (7)..(8)
<223> OTHER INFORMATION: n is a, c, g, or t

<400> SEQUENCE: 40 tancngnntc                                                                                                   10

<210> SEQ ID NO 41
<211> LENGTH: 37
<212> TYPE: DNA
<213> ORGANISM: Artificial Sequence
<220> FEATURE:
<223> OTHER INFORMATION: synthetic polynucleotide

<400> SEQUENCE: 41
gcaactgcag atgtgtgacc atcgctagct gatcttc                                                                     37

<210> SEQ ID NO 42
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 42
gatgtgtgac                                                                                                   10

<210> SEQ ID NO 43
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 43
atgtgtgacc                                                                                                   10

<210> SEQ ID NO 44
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 44
tgtgtgacca                                                                                                   10

<210> SEQ ID NO 45
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 45
gtgtgaccat                                                                                                   10

<210> SEQ ID NO 46
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 46
tgtgaccatc                                                                                                   10

-continued

```
<210> SEQ ID NO 47
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 47
gtgaccatcg                                                          10

<210> SEQ ID NO 48
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 48
tgaccatcgc                                                          10

<210> SEQ ID NO 49
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 49
gaccatcgct                                                          10

<210> SEQ ID NO 50
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 50
accatcgcta                                                          10

<210> SEQ ID NO 51
<211> LENGTH: 10
<212> TYPE: DNA
<213> ORGANISM: Artificial Sequence
<220> FEATURE:
<223> OTHER INFORMATION: synthetic polynucleotide

<400> SEQUENCE: 51
ccatcgctag                                                          10
```